United States Patent
Kwok et al.

(10) Patent No.: US 11,174,491 B2
(45) Date of Patent: Nov. 16, 2021

(54) MODULATING LIGHT RESPONSE PATHWAYS IN PLANTS, INCREASING LIGHT-RELATED TOLERANCES IN PLANTS, AND INCREASING BIOMASS IN PLANTS

(71) Applicant: Ceres, Inc., Thousand Oaks, CA (US)

(72) Inventors: Shing Kwok, Alexandria, VA (US); Kenneth Bounds, Tarzana, CA (US); Ryan Miller, Sacramento, CA (US); Sam Harris, Newbury Park, CA (US); James Burns, Valley Village, CA (US); Roger I. Pennell, Malibu, CA (US); Vijay Sharma, Wildwood, MO (US); Michael F. Portereiko, Thousand Oaks, CA (US); Han-Suk Kim, Pinole, CA (US); Gerard Magpantay, Woodland Hills, CA (US)

(73) Assignee: Ceres, Inc., Thousand Oaks, CA (US)

( * ) Notice: Subject to any disclaimer, the term of this patent is extended or adjusted under 35 U.S.C. 154(b) by 41 days.

(21) Appl. No.: 16/045,503

(22) Filed: Jul. 25, 2018

(65) Prior Publication Data

US 2019/0055571 A1 Feb. 21, 2019
US 2021/0214735 A9 Jul. 15, 2021

Related U.S. Application Data

(60) Division of application No. 13/630,902, filed on Sep. 28, 2012, now abandoned, which is a continuation-in-part of application No. 12/863,102, filed as application No. PCT/US2009/031292 on Jan. 16, 2009, now abandoned, said application No. 13/630,902 is a continuation-in-part of application No. 12/373,134, filed as application No. PCT/US2007/073154 on Jul. 10, 2007, now abandoned, said application No. 13/630,902 is a continuation-in-part of application No. 12/513,086, filed as application No. PCT/US2007/083495 on Nov. 2, 2007, now abandoned, said application No. 13/630,902 is a continuation-in-part of application No. 12/515,687, filed as application No. PCT/US2007/085237 on Nov. 20, 2007, now abandoned, said application No. 13/630,902 is a continuation-in-part of application No. 12/307,561, filed as application No. PCT/US2007/072877 on Jul. 5, 2007, now Pat. No. 8,344,210, said application No. 13/630,902 is a continuation-in-part of application No. 13/119,572, filed as application No. PCT/US2009/057116 on Sep. 16, 2009, now abandoned.

(60) Provisional application No. 61/021,943, filed on Jan. 18, 2008, provisional application No. 60/819,763, filed on Jul. 10, 2006, provisional application No. 60/856,613, filed on Nov. 3, 2006, provisional application No. 60/860,145, filed on Nov. 20, 2006, provisional application No. 60/818,569, filed on Jul. 5, 2006, provisional application No. 61/097,789, filed on Sep. 17, 2008.

(51) Int. Cl.
*C12N 15/82* (2006.01)
*C07K 14/415* (2006.01)

(52) U.S. Cl.
CPC ........ *C12N 15/8271* (2013.01); *C07K 14/415* (2013.01); *C12N 15/82* (2013.01); *C12N 15/8261* (2013.01); *Y02A 40/146* (2018.01)

(58) Field of Classification Search
None
See application file for complete search history.

(56) References Cited

U.S. PATENT DOCUMENTS

| | | |
|---|---|---|
| 4,987,071 A | 1/1991 | Cech et al. |
| 5,034,323 A | 7/1991 | Jorgensen et al. |
| 5,204,253 A | 4/1993 | Sanford et al. |
| 5,231,020 A | 7/1993 | Jorgensen et al. |
| 5,254,678 A | 10/1993 | Haseloff et al. |
| 5,538,880 A | 7/1996 | Lundquist et al. |
| 5,766,847 A | 6/1998 | Jackle et al. |
| 5,878,215 A | 3/1999 | Kling et al. |
| 6,013,863 A | 1/2000 | Lundquist et al. |
| 6,326,527 B1 | 12/2001 | Kirihara et al. |

(Continued)

FOREIGN PATENT DOCUMENTS

| | | |
|---|---|---|
| EP | 0 534 858 | 3/1993 |
| WO | WO 97/01952 | 1/1997 |

(Continued)

OTHER PUBLICATIONS

Jiang et al. Assessment of low light tolerance of seashore paspalum and bermudagrass. Crop Science. 2004. 44:587-594.*

(Continued)

*Primary Examiner* — Ashley K Buran
(74) *Attorney, Agent, or Firm* — Dentons US LLP

(57) ABSTRACT

Methods and materials for modulating low light and/or shade tolerance, and red light specific responses in plants are disclosed. For example, nucleic acids encoding low light and/or SD+EODFR-tolerance polypeptides are disclosed as well as methods for using such nucleic acids to transform plant cells. Also disclosed are plants having increased low light and/or SD+EODFR tolerance. In addition, methods and materials involved in increasing UV-B tolerance in plants and methods and materials involved in modulating biomass levels in plants are provided.

5 Claims, 79 Drawing Sheets
Specification includes a Sequence Listing.

(56) References Cited

U.S. PATENT DOCUMENTS

| | | | |
|---|---|---|---|
| 6,329,571 B1 | 12/2001 | Hiei | |
| 6,423,885 B1 | 7/2002 | Waterhouse et al. | |
| 6,452,067 B1 | 9/2002 | Bedbrook et al. | |
| 6,573,099 B2 | 6/2003 | Graham | |
| 6,753,139 B1 | 6/2004 | Baulcombe et al. | |
| 6,777,588 B2 | 8/2004 | Waterhouse et al. | |
| 6,906,244 B2 | 6/2005 | Fischer et al. | |
| 7,173,121 B2 | 2/2007 | Fang | |
| 7,214,789 B2 | 5/2007 | Pennell | |
| 7,265,263 B1* | 9/2007 | Hannapel | C07K 14/415 800/278 |
| 7,312,376 B2 | 12/2007 | Apuya et al. | |
| 7,378,571 B2 | 5/2008 | Apuya et al. | |
| 7,402,667 B2 | 7/2008 | Cook et al. | |
| 7,429,692 B2 | 9/2008 | Dang | |
| 7,445,654 B2 | 11/2008 | Wong | |
| 7,598,367 B2 | 10/2009 | Cook et al. | |
| 8,344,210 B2 | 1/2013 | Kwok et al. | |
| 2003/0175783 A1 | 9/2003 | Waterhouse et al. | |
| 2003/0175965 A1 | 9/2003 | Lowe et al. | |
| 2003/0180945 A1 | 9/2003 | Wang et al. | |
| 2004/0214330 A1 | 10/2004 | Waterhouse et al. | |
| 2005/0009187 A1* | 1/2005 | Shinozaki | C07K 14/415 435/468 |
| 2005/0032221 A1 | 2/2005 | Chang et al. | |
| 2005/0160493 A9* | 7/2005 | Ratcliffe | C07K 14/415 800/281 |
| 2006/0021083 A1 | 1/2006 | Cook et al. | |
| 2006/0021088 A1 | 1/2006 | Inze et al. | |
| 2006/0041952 A1 | 2/2006 | Cook | |
| 2006/0260004 A1 | 11/2006 | Fang et al. | |
| 2006/0265788 A1 | 11/2006 | Rommens | |
| 2006/0272060 A1* | 11/2006 | Heard | C12N 15/8273 800/289 |
| 2007/0006335 A1 | 1/2007 | Cook et al. | |
| 2007/0033671 A1* | 2/2007 | Jiang | C12N 15/827 800/278 |
| 2007/0056058 A1 | 3/2007 | Olivier et al. | |
| 2009/0094717 A1 | 4/2009 | Troukhan et al. | |
| 2010/0119688 A1 | 5/2010 | Kwok et al. | |
| 2010/0192261 A1 | 7/2010 | Kwok et al. | |
| 2010/0199378 A1 | 8/2010 | Kwok et al. | |
| 2010/0205688 A1 | 8/2010 | Kwok et al. | |
| 2011/0214199 A1* | 9/2011 | Coffin | C12N 15/1079 800/275 |
| 2013/0014292 A1 | 1/2013 | Pennell et al. | |
| 2013/0117886 A1 | 5/2013 | Troukhan et al. | |

FOREIGN PATENT DOCUMENTS

| | | |
|---|---|---|
| WO | WO 98/36083 | 8/1998 |
| WO | WO 98/53083 | 11/1998 |
| WO | WO 99/32619 | 7/1999 |
| WO | WO 02/046449 | 6/2002 |
| WO | WO 05/011105 | 2/2005 |
| WO | WO 05/023639 | 3/2005 |
| WO | WO 05/034308 | 4/2005 |
| WO | WO 05/034343 | 4/2005 |
| WO | WO 2005/098007 | 10/2005 |
| WO | WO 2006/034479 | 3/2006 |
| WO | WO 06/038236 | 4/2006 |
| WO | WO 06/040572 | 4/2006 |
| WO | WO 2006/036864 | 4/2006 |
| WO | WO 2007/044988 | 4/2007 |
| WO | WO 2007/055826 | 5/2007 |
| WO | WO 07/062762 | 6/2007 |
| WO | WO 2007/0072877 | 6/2007 |
| WO | WO 2007/083495 | 7/2007 |
| WO | WO 2007/085237 | 8/2007 |
| WO | WO 07/103956 | 9/2007 |
| WO | WO 2007/120989 | 10/2007 |
| WO | WO 2008/008779 | 1/2008 |
| WO | WO 2009/057116 | 5/2009 |
| WO | WO 2009/092009 | 7/2009 |
| WO | WO 2010/033564 | 3/2010 |

OTHER PUBLICATIONS

Smith et al. The shade avoidance syndrome: multiple responses mediated by multiple phytochromes. Plant, Cell, and Environment. 1997. 20:840-844.*
Genbank Accession No. NM_001036413. *Arabidopsis thaliana* BLH1 (BEL1-like homeodomain 1) AT2G35940 (BLH1) transcript variant AT2G35940.3 mRNA, complete cds. Published Nov. 3, 2005. pp. 1-2.*
GenBank Accession No. AAK43836. BEL1-like homeodomain 1 [*Arabidopsis thaliana*]. Published Apr. 30, 2001. pp. 1.*
U.S. Appl. No. 60/505,689, Cook et al.
U.S. Appl. No. 60/518,075, Pennell et al.
U.S. Appl. No. 60/544,771, Cook et al.
U.S. Appl. No. 60/558,869, Cook et al.
U.S. Appl. No. 60/583,609, Alexandrov.
U.S. Appl. No. 60/583,691, Alexandrov et al.
U.S. Appl. No. 60/612,891, Kwok.
U.S. Appl. No. 60/637,140, Feldman.
U.S. Appl. No. 60/757,544, Dang.
U.S. Appl. No. 60/766,307, Kwok.
U.S. Appl. No. 61/097,789, Pennell.
Abler et al. "Isolation and characterization of a genomic sequence encoding the maize Cat3 catalase gene" *Plant Mol. Biol.*, 22:1031-1038 (1993).
Akashi et al., "Gene discovery by ribozyme and siRNA libraries," *Nature Reviews Mol. Cell Biology*, 2005, 6:413-422.
Alonso-Blanco et al., "The use of recombinant inbred lines (RILs) for genetic mapping," In *Methods in Molecular Biology* (J.M. Martinez-Zapater and J. Salinas, Humana Press, Totowa, NJ., 1998), 2: 137-146.
Baerson et al., "Developmental regulation of an acyl carrier protein gene promoter in vegetative and reproductive tissues" *Plant Mol. Biol.*, 22(2):255-267 (1993).
Bateman et al., "Pfam 3.1: 1313 multiple alignments and profile HMMs match the majority of proteins" *Nucl. Acids Res.*, 27(1):260-262 (1999).
Bechtold et al., "In planta Agrobacterium mediated gene transfer by infiltration of adult *Arabidopsis thaliana* plants" *C.R. Acad. Sci. Paris*, 316:1194-1199 (1993).
Burr et al., "Gene mapping with recombinant inbreds in maize," *Genetics*, 1988, 118:519-526.
Burr et al., "Mapping Genes with Recombinant Inbreds," In Freeling and Walbot (Ed.), *The Maize Handbook*, (New York, Springer-Verlag, 1994), pp. 249-254.
Bustos et al., "Regulation of b-glucuronidase expression in transgenic tobacco plants by an A/T-rich, cis-acting sequence found upstream of a French bean b-phaseolin gene" *Plant Cell*, 1(9):839-854.
Cerdan and Chory, "Regulation of flowering time by light quality," *Nature*, 2003, 423:881-885.
Cerdan et al., "A 146 bp fragment of the tobacco Lhcb1 *2 promoter confers very-low-fluence, low-fluence and high-irradiance responses of phytochrom to a minimal CaMV 35S promoter" *Plant Mol. Biol.*, 33:245-255 (1997).
Chen et al., "Functional analysis of regulatory elements in a plant embryo-specific gene" *Proc. Natl. Acad. Sci. USA*, 83:8560-8564 (1986).
Chenna et al., "Multiple sequence alignment with the Clustal series of programs" *Nucleic Acids Res.*, 31(13):3497-3500 (2003).
Conceicao, "A cotyledon regulatory region is responsible for the different spatial expression patterns of *Arabidopsis* 2S albumin genes" *The Plant Journal*, 1994, 5(4):493-505.
Conkling et al. "Isolation of transcriptionally regulated root-specific genes from tobacco" *Plant Physiol.*, 93:1203-1211, (1990).
Dai et al., "RF2b, a rice bZIP transcription activator, interacts with RF2a and is involved in symptom development of rice tungro disease" *Proc. Natl. Acad. Sci. USA*, 101 (2):687-692 (2004).

(56) References Cited

OTHER PUBLICATIONS

De FEYTER et al., Methods in Molecular Biology, vol. 74, Chapter 43, "Expressing Ribozymes in Plants", Edited by Turner, P.C., *Humana Press Inc.*, Totowa, NJ, 1997, pp. 403-415.
Do et al., "ProbCons: Probabilistic consistency-based multiple sequence alignment," *Genome Res.*, 2005, 15(2): 330-340.
Durbin et al., "3-Markov chains and hidden Markov models; 4-Pairwise alignment using HMMS; 5-Profile HMMs for sequence families" In Biological Sequence Analysis: Probabilistic Models of Proteins and Nucleic Acids, (Cambridge University Press, Cambridge, UK, 1998), pp. 47-134.
Fejes et al., "A 268 bp upstream sequence mediates the circadian clock-regulated transcription of the wheat Cab-1 gene in transgenic plants" *Plant Mol. Biol.*, 15:921-932 (1990).
Fromm et al., "An octopine synthase enhancer element directs tissue-specific expression and binds ASF-1, a factor from tobacco nuclear extracts" *The Plant Cell*, 1:977-984 (1989).
Gardiner et al., "Development of a core RFLP map in maize using an immortalized F2 population," *Genetics*, 1993, 134: 917-930.
GenBank Accession No. AF096096, dated Jan. 25, 1999, 2 pages.
GenBank Accession No. AF129516, dated Apr. 6, 1999, 2 pages.
GenBank Accession No. L05934, dated Oct. 22, 1993, 3 pages.
GenBank Accession No. U93215, dated Feb. 27, 2002, 42 pages.
Green et al., "Binding site requirements for pea nuclear protein factor GT-1 correlate with sequences required for light-dependent transcriptional activation of the rbcS-3A gene" *EMBO J.*, 7:4035-4044.
Guerois, Raphael, "Predicting Changes in the Stability of Proteins and Protein Complexes: A Study of More Than 1000 Mutations," J. Mol. Biol. (2002) 320, 369-387.
Hong et al., "Promoter sequences from two different *Brassica napus* tapetal oleosin-like genes direct tapetal expression of β-glucuronidase in transgenic *Brassica* plants" *Plant Mol Biol.*, 1997. 34(3):549-555.
Hwang et al., "Aleurone- and embryo-specific expression of the β-glucuronidase gene controlled by the barley Chi26 and Ltp1 promoters in transgenic rice" *Plant Cell Rep.* 20(7):647-654 (2001).
Hyrup et al., Peptide nucleic acids (PNA): synthesis, properties and potential applications *Bioorgan. Med. Chem.*, 4:5-23 (1996).
Jordano et al., "A sunflower helianthinin gene upstream sequence ensemble contains an enhancer and sites of nuclear protein interaction" *Plant Cell*, 1:855-866 (1989).
Kasuga et al., "Improving plant drought, salt, and freezing tolerance by gene transfer of a single stress-inducible transcription factor," *Nature Biotech*, 1999, 17: 287-291.
Kebrom et al., "The molecular analysis of the shade avoidance syndrome in the grasses has begun," *J. Exp. Bot.*, 2007, 58: 3079-3089.
Keller et al., "Vascular-specific expression of the bean GRP 1.8 gene is negatively regulated" *Plant Cell*, 3(10):1051-1061 (1991).
Kumar, Prateek, et al., "Predicting the effects of coding non-synonymous variants on protein function using the SIFT algorithm," Nature Publishing Group, vol. 4, No. 8, 2009, pp. 1073-1082.
Lam et al., "Site-specific mutations in alter in vitro factor binding and change promoter expression pattern in transgenic plants" *Proc. Natl. Acad. Sci.* USA, 86:7890-7894 (1989).
Luan et al., "A rice cab gene promoter contains separate cis-acting elements that regulate expression in dicot and monocot plants" *The Plant Cell*, 4:971-981 (1992).
Lubberstedt et al., "Promoters from genes for plastid proteins possess regions with different sensitivities toward red and blue light" *Plant Physiol.*, 104:997-1006 (1994).
Matsuoka et al., "Tissue-specific light-regulated expression directed by the promoter of a C4 gene, maize pyruvate, orthophosphate dikinase, in a C3 plant, rice" *Proc. Natl. Acad. Sci.* USA, 90:9586-9590 (1993).
Matzke et al., "RNAi-mediated pathways in the nucleus," *Nature Reviews Genetics*, 2005, 6:24-35.

Medberry et al., "The Commelina yellow mottle virus promoter is a strong promoter in vascular and reproductive tissues" *Plant Cell*, 4(2):185-192 (1992).
Meier et al., "Elicitor-inducible and constitutive in vivo DNA footprints indicate novel cis-acting elements in the promoter of a parsley gene encoding pathogenesis-related protein 1" *Plant Cell*, 3:309-316 (1991).
Mittal, "Improving the efficiency of RNA interference in mammals," Nature Reviews *Genetics*, 2004, 5: 355-365.
Nature reviews RNA interference collection' [online]. Nature publishing group, 2005, [retrieved on Apr. 12, 2012]. Retrieved from the Internet: <URL: ttp://www.nature.com/focus/rnai/index.html>, 2 pages.
Ng, Pauline C., et al., "Predicting the Effects off Amino Acid Substitutions on Protein Function," Annu. Rev. Genomics Hum. Genet. 2006, pp. 61-80.
Parks et al., "Sequential and coordinated action of phytochromes A and B during *Arabidopsis* stem growth revealed by kinetic analysis," *Proc. Natl. Acad. Sci.*, 1999, 96:14142-14146.
Perriman et al., "Effective ribozyme delivery in plant cells" Proc. Natl. Acad. Sci. USA, 92(13):6175-6179 (1995).
Refseth et al., "Hybridization capture of microsatellites directly from genomic DNA" *Electrophoresis*, 18:1519-1523 (1997).
Reva, Boris, et al., "Predicting the functional impact of protein mutations: application to cancer genomics," Nucleic Acids Research, 2011, vol. 39, No. 17, pp. 1-14.
Riggs et al., "Cotyledon nuclear proteins bind to DNA fragments harboring regulatory elements of phytohemagglutinin genes" *Plant Cell*, 1(6):609-621 (1989).
Rivera et al., "Genomic evidence for two functionally distinct gene classes" Proc. Natl. Acad. Sci. USA,95:6239-6244 (1998).
Sandhya, Sankaran, "CUSP: an algorithm to distinguish structurally conserved and unconserved regions in protein domain alignments and its application in the study of large length variations," BioMed Central, May 2008, pp. 1-14.
Sheridan, "The mac1 Gene: Controlling the commitment to the meiotic pathway in Maize" *Genetics*, 142:1009-1020 (1996).
Slocombe et al., "Temporal and tissue-specific regulation of a *Brassica napus* stearoyl-acyl carrier protein desaturase gene" *Plant Physiol.*, 104(4):1167-1176 (1994).
Sonnhammer et al., "Pfam: A comprehensive database of protein domain families based on seed alignments" *Proteins*, 28:405-420 (1997).
Sonnhammer et al., "Pfam: multiple sequence alignments and HMM-profiles of protein domains" *Nucl. Acids Res.*, 26:320-322 (1998).
Summerton et al., "Morpholino antisense oligomers: design, preparation, and properties" *Antisense Nucleic Acid Drug Dev.*, 7:187-195 (1997).
Truernit et al., "The promoter of the *Arabidopsis thaliana* SUC2 sucrose-H+ symporter gene directs expression of β-glucuronidase to the phloem: Evidence for phloem loading and unloading by SUC2" *Planta*. 196:564-570 (1995).
Urao et al. "Molecular cloning and characterization of a gene that encodes a MYC-related protein in *Arabidopsis*" *Plant Mol. Biol.*, 32:571-576 (1996).
Wagner et al., "Overexpression of phytochrome B induces a short hypocotyl phenotype in transgenic *Arabidopsis*," *Plant Cell*, 1991,3: 1275-1288.
Yamamoto et al., "The promoter of a pine photosynthetic gene allows expression of a βglucuronidase reporter gene in transgenic rice plants in a light-independent but tissue-specific manner" *Plant Cell Physiol.*, 1994, 35:773-778.
Yan et al., "New construct approaches for efficient gene silencing in plants," *Plant Physiology*, 2006,141: 1508-1518.
Zhang et al., "DNA sequences that activate isocitrate lyase gene expression during late embryogenesis and during postgerminative growth," *Plant Physiology*, 110:1069-1079 (1996).
Zheng et al., "SPK1 Is an Essential S-Phase-Specific Gene of *Saccharomyces cerevisiae* that encodes a nuclear serine/threonine/tyrosine kinase" *Mol. Cell Biol.*, 1993, 13:5829-5842.
International Preliminary Report on Patentability in PCT/US2009/031292 dated Jul. 20, 2010, 5 pages.

(56) References Cited

OTHER PUBLICATIONS

International Search Report and Written Opinion in International Application No. PCT/US2009/031292, dated Sep. 1, 2009, 8 pages.
Tiwari et al., The flowering time regulator CONSTANS is recruited to the Flowering Locus T promoter via a unique cis-elememt. *New Phytologist*. 2010. 187:57-66.
GenBank Accession No. NP_5683001.1. Unknown Protein. Published Apr. 24, 2008. pp. 1 -2.
GenBank Accession No. NP_5683001.1. CCT motif family protein. Published May 26, 2011. pp. 1-2.

* cited by examiner

| SEQ ID NO | Sequence | | | | | Length |
|---|---|---|---|---|---|---|
| SEQ-ID-NO-93 | MGKYMKKSKV | --TN------ | ---------- | TEPTEP---- | --TSLGVRTR | 28 |
| SEQ-ID-NO-70 | MGKYIRKSKI | DGAGAGAGGG | GGGGGGGESS | ND-ALMDVVSPS | SSSSLGVLTR | 50 |
| SEQ-ID-NO-80 | --MRKAKT-- | --TN------ | ---------- | ---LTVVDL-- | ---SCGVRTR | 22 |
| SEQ-ID-NO-99 | MGKYIRKTRK | -TE------- | ---------- | ---VL------ | --SPLGVLTR | 22 |
| SEQ-ID-NO-72 | MGKYIRKAKT | -AG------- | ---------- | D--VAVMEL-- | SQAAPLGVRTR | 29 |
| SEQ-ID-NO-105 | MGKYMRKPKV | -SG------- | ---------- | E--VAVMEV-- | AAAPLGVRTR | 29 |
| SEQ-ID-NO-119 | MGKYMRKGKV | -SG------- | ---------- | E--VAVMEV-P | CGALLGVRTR | 29 |
| SEQ-ID-NO-115 | MGKYMRKCKV | -SG------- | ---------- | E--VAVMEV-P | CGALLGVRTR | 30 |
| SEQ-ID-NO-103 | MGKYMRKGKV | -SG------- | ---------- | E--VAVMEV-P | CGALLGVRTR | 30 |
| SEQ-ID-NO-109 | MGKYMRKGKV | -SG------- | ---------- | E--VAVMEV-A | MAASASSRKR | 30 |
| SEQ-ID-NO-96 | MAQVKARART | -AL------- | ---------- | D--VDLDVP-- | ---TTT-K | 23 |
| SEQ-ID-NO-101 | ---MEV---- | -SD------- | ---------- | ---------- | ---TTTTK | 17 |
| SEQ-ID-NO-102 | --MRKCKG-- | -IE------- | ---------- | E--VTIMEV-SD | VDLEVPTTTK | 27 |

| SEQ ID NO | Sequence | | | | | Length |
|---|---|---|---|---|---|---|
| SEQ-ID-NO-93 | AAKTLALK-- | ---------- | SSASDSALAG | DSS------- | KKKQQQMNDC | 52 |
| SEQ-ID-NO-70 | AKSLALQQQ- | QQRCLLQKPS | SPSSLPPTSA | SPNPPSKQKM | ---------- | 99 |
| SEQ-ID-NO-80 | AKTLALKKQ- | QA--LRLH-- | ASSASPPPPS | SPA------- | ---------- | 50 |
| SEQ-ID-NO-99 | AKALALN--- | -G-------- | ---------G | DGG------- | ---------- | 34 |
| SEQ-ID-NO-72 | AKTLALQ--- | RLQ------- | KSSTSSPPTV | VSAPATCDG- | ---------- | 58 |
| SEQ-ID-NO-105 | ARALAMQ--- | ROP------- | QGAAVAKDQG | ---------- | ---------- | 49 |
| SEQ-ID-NO-119 | SRTLALQ--- | R-T------- | TSSQKPPEKG | EGDPGAGAGA | GA-------- | 60 |
| SEQ-ID-NO-115 | SRTLALQ--- | R--------- | AQRPPDKG-- | EAGEAAG--- | ---------- | 53 |
| SEQ-ID-NO-103 | SRTLALQ--- | R--------- | AQRPLDKG-- | DAEDAAA--- | ---------- | 53 |
| SEQ-ID-NO-109 | SRTLALQ--- | R--------- | AQRPLDKG-- | DAEDAAA--- | ---------- | 53 |
| SEQ-ID-NO-96 | -RKISIN--- | -N-------- | ---------- | ---------- | ---------- | 30 |
| SEQ-ID-NO-101 | -KRKISSD-- | ---------- | ---------- | ---------- | ---------- | 24 |
| SEQ-ID-NO-102 | -KRKISSD-- | ---------- | ---------- | ---------- | ---------- | 34 |

Figure 2 (continued)

[Sequence alignment figure showing multiple protein sequences labeled SEQ-ID-NO-93, SEQ-ID-NO-70, SEQ-ID-NO-80, SEQ-ID-NO-99, SEQ-ID-NO-72, SEQ-ID-NO-105, SEQ-ID-NO-119, SEQ-ID-NO-115, SEQ-ID-NO-103, SEQ-ID-NO-109, SEQ-ID-NO-96, SEQ-ID-NO-101, and SEQ-ID-NO-102, with residue position numbers on the right.]

| | | | |
|---|---|---|---|
| SEQ-ID-NO-93 | PLT | GRYEWVQ | VSP | 207 |
| SEQ-ID-NO-70 | PLPG | RFEWTK | VDD | 289 |
| SEQ-ID-NO-80 | PLPG | RYEWEK | LDP | 240 |
| SEQ-ID-NO-99 | PLPG | RYEWVK | VNH | 210 |
| SEQ-ID-NO-72 | PLPG | RYQWEK | MDP | 258 |
| SEQ-ID-NO-105 | PLPG | RYEWVK | LD- | 190 |
| SEQ-ID-NO-119 | PLPG | RYEWTR | LDC | 221 |
| SEQ-ID-NO-115 | PLPG | RYEWTR | LGC | 206 |
| SEQ-ID-NO-103 | PLPG | RYEWAR | LDC | 213 |
| SEQ-ID-NO-109 | PLPG | RYEWAR | LGC | 212 |
| SEQ-ID-NO-96 | SLE | GRYEWVK | L-- | 180 |
| SEQ-ID-NO-101 | PSE | GRYEWVR | LGS | 156 |
| SEQ-ID-NO-102 | PLE | GRYEWVR | LGS | 163 |

Figure 3

| SEQ-ID-NO | Sequence | # |
|---|---|---|
| SEQ-ID-NO-129 | MGRGRSSSSS SIESSSKSNP FGASSSTRNL SL--TDLRLG LSFGTSS--- | 44 |
| SEQ-ID-NO-247 | -------MS PPLELDYICL SAAAGGRPDD DLKGTELRLG LP-GCESPDR | 41 |
| SEQ-ID-NO-302 | ---------- ----MSTDTGR SSTESEVSGL DYEETELKLG LP-GGSRTAG | 36 |
| SEQ-ID-NO-270 | ---------- ----MDGGVG- ---YA---DMD ALKATELRLG LP-GSHPPEK | 30 |
| SEQ-ID-NO-236 | ---------- ----MERTAT- ---YE----- NLKATELRLG LP-GI DEPEK | 30 |
| SEQ-ID-NO-137 | ---------- ------MV--- ---FE----- NLDATELRLG LP-ASSKESL | 26 |
| SEQ-ID-NO-300 | ---------- ------ME--- ---FE----- NLDATELRLG LP-GTATRQS | 26 |
| SEQ-ID-NO-303 | ---------- ------ME--- ---RDL---- NLEATELRLG LP-GTATQQL | 26 |
| SEQ-ID-NO-133 | ---------- ----MEGSVG- ---YD----- NLRATELRLG LP-GTEPVSI | 30 |
| SEQ-ID-NO-209 | ---------- ----MENSLGK ---YG----- NLEATELRLG LP-GSDEPEK | 31 |
| SEQ-ID-NO-201 | ---------- ------MEK-- ---DGL---- ELE-TELRLG LP-GRDVTEK | 25 |
| SEQ-ID-NO-231 | ---------- ------MAR-- ---EGL---- GLE-TELRLG LSCGEPK--- | 23 |
| SEQ-ID-NO-234 | ---------- ------MEK-- ---EDL---- GLE-TELRLG LP-GAGGENN | 25 |

| SEQ-ID-NO | Sequence | # |
|---|---|---|
| SEQ-ID-NO-129 | RPVAATTTLE LLPAKGAKRG ---------- ISAACGKGKEA -GTQYFNGGY | 53 |
| SEQ-ID-NO-247 | S--------- -ETEKKKRG FSDEVVPPAP ---------- SGDEKDKKVA | 91 |
| SEQ-ID-NO-302 | PLPTTTTT-- --ARPTKRS FAETVDLSLG AESRSGDLGD RSTCDFGSGA | 74 |
| SEQ-ID-NO-270 | QSSSASTSA- --KYSKKRT LDEDRAA--- ---------- RRETSEGGR | 61 |
| SEQ-ID-NO-236 | ---------- --RISNKRA SSEMD----- ---------- NSSSGKENE | 60 |
| SEQ-ID-NO-137 | EKQTPNSNL- --AKSNKRS LPDMNDDS-- ---------- GVAAAKKCD | 50 |
| SEQ-ID-NO-300 | EKQTPSSNV- --TKSNKRS LPDMNEDPAG SSRENSSTVS SNEEKSHDQ | 71 |
| SEQ-ID-NO-303 | ---------- --VRSNKRS LPDMNEDSAG RSESSSV--- SSNDKKSDE | 68 |
| SEQ-ID-NO-133 | RSA------- --VRSNKRS LQQVADDDCG VN-------- GCRSDDQNE | 58 |
| SEQ-ID-NO-209 | M--------- ---MKKRG SPEASEEECI SKGNMNSSD- GSDITSDDQ | 69 |
| SEQ-ID-NO-201 | ---------- --KNEKKRM FTEMI MTSSG SHSEQCESSV VSSGVDVEKV | 61 |
| SEQ-ID-NO-231 | ---------- ---NKNKKRV FSEIDG---- ---------- GVEENGGSG | 45 |
| SEQ-ID-NO-234 | TDKDK----- ---------- FSDIE----- ---------- GENSSSEED | 51 |

| SEQ-ID-NO | | | | | | |
|---|---|---|---|---|---|---|
| SEQ-ID-NO-129 | CNEKSHVLTY | ADKEGDWMMV | GDVPWEMFLS | TVRRLKISRA | NYHY------ | 175 |
| SEQ-ID-NO-247 | RKDGEYVMTY | EDKDGDWMLV | GDVPWEMFTE | ACRRIRVMKS | SDV-VGLGVT | 235 |
| SEQ-ID-NO-302 | VNGTEYVPTY | EDKDGDWMLV | GDVPWKMFVA | SCKRLRLMKS | SEAINLAPRT | 203 |
| SEQ-ID-NO-270 | CKGSEYALTY | EDKDGDLMLV | GDVPWEMFTS | SCKKLRI-RG | AEAIRGLGSS | 187 |
| SEQ-ID-NO-236 | YNGSDYAPTY | EDKDGDWMLY | GDVPWDMFLN | SCRRLRIMKG | SEA-KGLHAY | 193 |
| SEQ-ID-NO-137 | YNGSEFVPTY | EDKDGDWMLV | GDVPWEMFIN | ACKRLRIVRG | SEA-RGLGCV | 182 |
| SEQ-ID-NO-300 | YNGSEHVPTY | EDKDGDWMLV | GDVPWEMFIN | SCKRLRIMKE | SEA-RGLGCA | 203 |
| SEQ-ID-NO-303 | YNGSEYVPTY | EDKDGDWMLV | GDVPWEMFIN | SCKRLRIMKE | SEA-RGLGCA | 200 |
| SEQ-ID-NO-133 | YKGSDYAPTY | EDKDGDWMLV | GDVPWEMFIN | SCKRLRIMKG | SEA-RGLGCG | 189 |
| SEQ-ID-NO-209 | YNGSEYAPTY | EDKDGDWMLA | GDVPWEMFIT | SCKRLRIMKG | SEA-KGLGCF | 202 |
| SEQ-ID-NO-201 | GDNCEYVITY | EDKDGDWMLV | GDVPWNMFVS | SCRRVRIMKR | SEX-TGFGLX | 191 |
| SEQ-ID-NO-231 | AENCEHVPIY | EDKDGDWMLA | GDVPWGMFIE | SCKRLRIMKR | SDA-KGFDLQ | 170 |
| SEQ-ID-NO-234 | AENAEHVPIY | EDKDGDWMLV | GDVPWEMFRE | SCKRLRIMKR | SDA-KGFDLQ | 174 |

| SEQ-ID-NO | | | |
|---|---|---|---|
| SEQ-ID-NO-129 | ---------- | ---------- | 175 |
| SEQ-ID-NO-247 | RAGVKSKNKN | ---------- | 245 |
| SEQ-ID-NO-302 | PQGSTRAR-- | ---------- | 211 |
| SEQ-ID-NO-270 | Q--------- | ---------- | 188 |
| SEQ-ID-NO-236 | RL-------- | ---------- | 195 |
| SEQ-ID-NO-137 | V--------- | ---------- | 183 |
| SEQ-ID-NO-300 | V--------- | ---------- | 204 |
| SEQ-ID-NO-303 | V--------- | ---------- | 201 |
| SEQ-ID-NO-133 | V--------- | ---------- | 190 |
| SEQ-ID-NO-209 | ---------- | ---------- | 202 |
| SEQ-ID-NO-201 | PXGLDE---- | ---------- | 197 |
| SEQ-ID-NO-231 | PKGSLKRFI- | ---------- | 179 |
| SEQ-ID-NO-234 | PKGSLKGFIE | GVRK       | 188 |

Figure 4

| | | | | | | | |
|---|---|---|---|---|---|---|---|
| SEQ-ID-NO-319 | ME AGSE--GE | NNRISN---- | ---------- | ---------- | --PNKNISS | SNEGNAKPKR | 31 |
| SEQ-ID-NO-331 | MDDGDGAAPA | EGSAASTPPP | APPAAAAAAA | ---------- | AAVSAGSTGA | SGSGEKTVKR | 50 |
| SEQ-ID-NO-317 | M--------- | ---------- | ---------- | ---------- | ---------- | ---------- | 1 |
| SEQ-ID-NO-321 | MEESSEVHFG | ENRVSP---- | ---------- | ---------- | ---------- | EKNLKR---- | 22 |
| SEQ-ID-NO-327 | MEEVTELQSE | ENKLSM---- | ---------- | ---------- | ---------- | EKNKKR---- | 22 |
| SEQ-ID-NO-330 | MEESSELQPE | ENKVSA---- | ---------- | ---------- | ---------- | EKFPKR---- | 22 |

| | | | | | | | |
|---|---|---|---|---|---|---|---|
| SEQ-ID-NO-319 | QMKTPFQLEA | LEKAYALETY | PSEATRAELS | EKICLSDRQL | ---------- | QMWFCHRRLK | 81 |
| SEQ-ID-NO-331 | MMKSPYQLEV | LEKITYAVEQY | PSETLRAELS | AKIGLSDRQL | ---------- | QMWFCHRRLK | 100 |
| SEQ-ID-NO-317 | --------A- | LENFYNEHKY | PTEEMKGKLA | EVGLIEKQV | ---------- | SGWFCHRRLK | 42 |
| SEQ-ID-NO-321 | TVKTPAQVVA | LENFYNEHKY | PTEEMKSELA | DQIGLIEKQI | ---------- | SSWFCHRRLK | 72 |
| SEQ-ID-NO-327 | RLKTPAQLKA | LEDFYNDNKY | PTEEMKSELA | DELELTEKQI | ---------- | SGWFCHRRLK | 72 |
| SEQ-ID-NO-330 | KLKTPAQLKG | LEKFYTEHKY | PTEELKLA-A | EELELTEKQV | ---------- | SGWFCHRRLK | 72 |

| | | | | | | | |
|---|---|---|---|---|---|---|---|
| SEQ-ID-NO-319 | E--------- | KKDN------ | PTKKQRKGAA | LPPESPVDEL | RAVPGPDYGS | GSGCSGSSPYM | 126 |
| SEQ-ID-NO-331 | DRKPPTKRQR | REEEAAVPL | MAPPPVLPPP | ALPLSSGELL | IGASSPYDEP | 150 |
| SEQ-ID-NO-317 | D--------- | KRHV------ | KEDGNALGSQ | DRSSVLQDR | GSGLRQDSCG | STKQTDYWNP | 87 |
| SEQ-ID-NO-321 | D--------- | KRL------- | RDEVCTNGRQ | DRSSGIIQDR | GSGLRQDSCG | STKQGDYRNL | 116 |
| SEQ-ID-NO-327 | D--------- | KKML------ | NDEVCANGRQ | DRSSGVIQDR | GSGLVQDSCG | STKHVHYRYL | 117 |
| SEQ-ID-NO-330 | D--------- | KRLL------ | KEEEANANGRQ | DRSSGVIQDR | GSGLGQDSCG | SSKHGDYKYL | 117 |

| | | | | | | | |
|---|---|---|---|---|---|---|---|
| SEQ-ID-NO-319 | DTRKLGGS-- | ---------- | ---------- | SSRGMMEDAP | TV-------- | 146 |
| SEQ-ID-NO-331 | PLPPVHSR-- | ---------- | ---------- | RGAGRSSAVP | RLSAPDIG-- | 176 |
| SEQ-ID-NO-317 | KPREVESQRL | Y--------- | ---------MG | NADG-EDSTS | SDRSSLRKN | 119 |
| SEQ-ID-NO-321 | DPREVESQRL | YGRDFHPADL | TYDRTSRYTG | NVTG-IDNS | SGSSSSLQDK | 165 |
| SEQ-ID-NO-327 | DPKEVESHGL | YNHCFSAADI | TYGHKNHRYA | ENDSATDNTS | SESSSLQDR | 167 |
| SEQ-ID-NO-330 | DPKEVESNGL | YNRDLSVADM | TYGRRNHFSE | NVSGMDDTS | SESSSYLQER | 167 |

| | | | | | | | |
|---|---|---|---|---|---|---|---|
| SEQ-ID-NO-319 | ---------- | ---RRYYESQ | QSIM------ | ---SMQL--- | ---MPS---- | E--------- | 158 |
| SEQ-ID-NO-331 | ---------- | ---RRYYEPL | PVMLPPPPVA | ---HPQF--- | MRSYGYNKPS | E--------- | 201 |
| SEQ-ID-NO-317 | LVSSKDGIRD | VESSRYVAHK | DVLQ------ | GAAMPLTPKG | TDSFGY-KPS | GYLKVKGESE | 167 |
| SEQ-ID-NO-321 | FVCQREDPYD | AETSKYLAQN | PVMLPPPVA-- | GSLLPPNT-KG | ANNMGH-KPS | GYLKVKGEIE | 214 |
| SEQ-ID-NO-327 | LLCQGQDPYD | MEPSSHVTPN | ---------- | KALPPLNPKG | AINMGY-KPS | GYLKVKGEIE | 216 |
| SEQ-ID-NO-330 | MYPQGQDPYE | MEPSRY---S | ---------- | ---------- | ---------- | GYLKVKGEIE | 213 |

Figure 4 (continued)

| | | | | | |
|---|---|---|---|---|---|
| SEQ-ID-NO-319 | LRAI ACVEAQ | LGEPLRDDGP | MLGIEFDPLP | PDAFIGA--- | ---------- | 194
| SEQ-ID-NO-331 | LRVI HSVESQ | LGEPLRDDGP | VLGIDFDPLP | PGSFGAPI-- | ---------- | 239
| SEQ-ID-NO-317 | NFAI TAVKRQ | LGRQYQEDGP | PLGVEFDPLP | PGAFEPQTNP | IVHEPI YVGN | 217
| SEQ-ID-NO-321 | NAAI TAVKKQ | LGRHYKEDGP | PLGVEFDPLP | PGAFASPSRD | PVSGPI YVGD | 264
| SEQ-ID-NO-327 | HAAI TAVKKQ | LCKHYREDGP | LLSVEFDTLP | PEAFECQLAD | LANEAYYAAN | 266
| SEQ-ID-NO-330 | HAAI TAVKKQ | LGRNYQEDGP | LLGVEFDPLP | PGAFECQTEE | AVHEPYHIAD | 263

| | | | | | |
|---|---|---|---|---|---|
| SEQ-ID-NO-319 | QRRPHL PHL | GTRKSFNPGP | ---------- | ---------- | ---------- | 194
| SEQ-ID-NO-331 | LAQMCSPDVS | GVRKQSSLGA | ---------- | ---------- | ---------- | 239
| SEQ-ID-NO-317 | PALPNSPEVS | AVKKQSSLSS | ---------- | ---------- | ---------- | 237
| SEQ-ID-NO-321 | PALLNSPEIS | TVKSRPGLSS | ---------- | ---------- | ---------- | 314
| SEQ-ID-NO-327 | | | FEAQVLLVHA | GNLYILQLSI | TSNDVCHPMF | 286
| SEQ-ID-NO-330 | | | | | | 283

| | | | | | |
|---|---|---|---|---|---|
| SEQ-ID-NO-319 | | | | | | 194
| SEQ-ID-NO-331 | | | | | | 239
| SEQ-ID-NO-317 | | | | | | 237
| SEQ-ID-NO-321 | ITTVTFTLLL | LPIYHQSCTG | TTSNYAHNMF | PSSFRYVPKK | GSVRPENVME | 364
| SEQ-ID-NO-327 | | | | | | 286
| SEQ-ID-NO-330 | | | | | | 283

| | | | | | |
|---|---|---|---|---|---|
| SEQ-ID-NO-319 | | | | | | 194
| SEQ-ID-NO-331 | | | | | | 239
| SEQ-ID-NO-317 | | | | | | 257
| SEQ-ID-NO-321 | QGIFLYDSSD | SIPPSSISCT | SNESLYILAV | SYEL ARKSKL | HSPDPDSEDD | 413
| SEQ-ID-NO-327 | | | | RYE- VYSTKM | SSHDSYTEGA | 300
| SEQ-ID-NO-330 | | | | RYD- SYFTKI | SSQDS----- | 302
| | | | | RYD- SYYTKH | GSQDTHMEGV |

| | | | | | |
|---|---|---|---|---|---|
| SEQ-ID-NO-319 | | | | | | 194
| SEQ-ID-NO-331 | EHDDDDNIMV | GMEPGLRDKK | SFGEPRLKSP | STSFYNSVPR | HKSFKETFKG | 239
| SEQ-ID-NO-317 | NCNPE----- | ---PSDSHDR | KSHHHLEQKP | TYNGSNSNAG | GNSAMDMPDD | 307
| SEQ-ID-NO-321 | | | | | QMVRD | 455
| SEQ-ID-NO-327 | DFGSLHDVHV | ---QDKQDKK | ALHGTKHRQT | FQSNAGRFPG | RNSLDLYED | 305
| SEQ-ID-NO-330 | | | | | | 349

Figure 4 (continued)

| SEQ-ID-NO-319 | ---------- | ---------- | ---------- | ---------- | 194 |
|---|---|---|---|---|---|
| SEQ-ID-NO-331 | SPREI PVTNS | ---------- | KKGW-I SSKS | ---------- | 239 |
| SEQ-ID-NO-317 | LAGET SAYVN | ---------- | KRHYRMSSKH | ---------- | 352 |
| SEQ-ID-NO-321 | STGEASAYNN | ---------- | TKNCRKGT KH | WAEGSRNHLV | 504 |
| SEQ-ID-NO-327 | STGEA-AYNL | ---------- | TKNHRKDAKR | ---------- | 355 |
| SEQ-ID-NO-330 | ---------- | ---------- | ---------- | ---------- | 397 |

| SEQ-ID-NO-319 | ---------- | ---------- | ---------- | ---------- | 194 |
|---|---|---|---|---|---|
| SEQ-ID-NO-331 | ---------- | ---------- | ---------- | ---------- | 239 |
| SEQ-ID-NO-317 | HDYDNNL SN | GGR------- | ---------- | ---------- | 380 |
| SEQ-ID-NO-321 | LHDCDNDNPK | IVQ------- | GFEERRSDSL | ANVQNL SGS- | 532 |
| SEQ-ID-NO-327 | LHGYENSNLK | NVQ------- | GFDGT RDSG | STHLGPSGR- | 384 |
| SEQ-ID-NO-330 | QYNYENTNQK | ---------- | GMEGI RSDST | SNPSDHYEEN | 447 |

| SEQ-ID | Block 1 | Block 2 | Block 3 | Block 4 | End |
|---|---|---|---|---|---|
| SEQ-ID-NO-319 | ---------- | ---------- | ---------- | ---------- | 194 |
| SEQ-ID-NO-331 | SPREI PVTNS | ---------- | KKGW-I SSKS | ---------- | 239 |
| SEQ-ID-NO-317 | LAGET SAYVN | ---------- | KRHYRMSSKH | ---------- | 352 |
| SEQ-ID-NO-321 | STGEASAYNN | ---------- | TKNCRKGT KH | WAEGSRNHLV | 504 |
| SEQ-ID-NO-327 | STGEA-AYNL | ---------- | TKNHRKDAKR | ---------- | 355 |
| SEQ-ID-NO-330 | ---------- | ---------- | ---------- | ---------- | 397 |

| SEQ-ID | Block 1 | Block 2 | Block 3 | Block 4 | End |
|---|---|---|---|---|---|
| SEQ-ID-NO-319 | ---------- | ---------- | ---------- | ---------- | 194 |
| SEQ-ID-NO-331 | ---------- | ---------- | ---------- | ---------- | 239 |
| SEQ-ID-NO-317 | HDYDNNL SN | GGR------- | ---------- | KTGYL T | 380 |
| SEQ-ID-NO-321 | LHDCDNDNPK | IVQ------- | ---------- | RNNYTS | 532 |
| SEQ-ID-NO-327 | LHGYENSNLK | NVQ------- | ---------- | RGEYAK | 384 |
| SEQ-ID-NO-330 | QYNYENTNQK | ---------- | LQYDYDNVNP | KKAPRSEHI K | 447 |

| SEQ-ID | Block 1 | Block 2 | Block 3 | Block 4 | End |
|---|---|---|---|---|---|
| SEQ-ID-NO-319 | ---------- | ---------- | ---------- | ---------- | 194 |
| SEQ-ID-NO-331 | ---------- | ---------- | ---------- | ---------- | 239 |
| SEQ-ID-NO-317 | SRSPESMD-R | GPSSGMA--G | YHGERNQMK | MQREK----- | 423 |
| SEQ-ID-NO-321 | GKSLDTEE-R | ARCT MEKED | KLHGEMKRMK | GSHDPVRVKR | 581 |
| SEQ-ID-NO-327 | QVYLDT GERR | GLNKRMAKEE | KFDGDRKI KK | QYRDPDEV-R | 433 |
| SEQ-ID-NO-330 | RGSVDTEE-R | GLSSRMT KDE | LFKGDRKSKK | QYRDAGGA-G | 495 |

| SEQ-ID | Block 1 | Block 2 | Block 3 | Block 4 | End |
|---|---|---|---|---|---|
| SEQ-ID-NO-319 | ---------- | IPE------- | PHNRT G | ---------- | 203 |
| SEQ-ID-NO-331 | ---------- | VVE------- | K------- | ---------- | 244 |
| SEQ-ID-NO-317 | RVKHGYI QQV | YAPKSSSYSE | LERKS----- | ---------- | 449 |
| SEQ-ID-NO-321 | RFRVDF PQQ- | EHVAKASFSE | RRRTNLTKR | LNPENMATGI | 630 |
| SEQ-ID-NO-327 | WAKVDPLEQ- | YDVKQSSVAE | LEPRKS---- | ---------- | 458 |
| SEQ-ID-NO-330 | RLKANT FQP- | YNMKQVPVAE | LEPRKT---- | AFTEVVGALD | 520 |

| SEQ-ID | Block 1 | Block 2 | End |
|---|---|---|---|
| SEQ-ID-NO-319 | ---------- | ---------- | 203 |
| SEQ-ID-NO-331 | ---------- | ---------- | 244 |
| SEQ-ID-NO-317 | QI NRSCV | ELPSSLSGDD ETDESSSSMD | 476 |
| SEQ-ID-NO-321 | VPI DI GRSAM | ERPSSFS--ED ETPET SSSAE | 659 |
| SEQ-ID-NO-327 | ---QRSAA | EMPSSFS--ED ETAETSSSAD | 482 |
| SEQ-ID-NO-330 | ---QRSAA | EMPSSFS--ED ETADT SSSLD | 544 |

| SEQ-ID | | | | | | |
|---|---|---|---|---|---|---|
| SEQ-ID-NO-401 | S--- | ---- | ---- | ---- | ---- | 134 |
| SEQ-ID-NO-370 | SRL- | LPAA- | AAADESWSPP | APTLT--AM | ---- | 161 |
| SEQ-ID-NO-409 | SRL- | LPAAT | TAADESWSPP | APTLT--AM | ---- | 164 |
| SEQ-ID-NO-349 | HRL- | LP--- | -ATTESPSPS | PATATPHFAR | I--- | 167 |
| SEQ-ID-NO-357 | LRL- | LP--- | PAADDYAAV | AAGLAARF- | ---- | 163 |
| SEQ-ID-NO-337 | TPL- | VVVP- | --EDHQLSSN | ---VM | ---- | 162 |
| SEQ-ID-NO-339 | TPL- | VVVA- | --ADDQLVSS | N---VM | ---- | 160 |
| SEQ-ID-NO-395 | TPL- | -MP-- | --EDDTPC-- | ---FQ- | ---- | 155 |
| SEQ-ID-NO-417 | TPL- | -LP-- | --EEEASC-- | ---FL- | ---- | 150 |
| SEQ-ID-NO-437 | TPL- | -LP-- | --EEDASC-- | ---FW- | ---- | 153 |
| SEQ-ID-NO-355 | THF- | VPYHK | MEDYNQRLWN | DAASEDDIDD | DVSLFSHRHD | YYYIANASL- | 180 |
| SEQ-ID-NO-393 | TPL- | VPGEM | PVAVDDQMWA | AAGVPDSYYD | DFFSFPFASA | SPPSPTLLLP | 191 |

| SEQ-ID | | |
|---|---|---|
| SEQ-ID-NO-401 | ---- | 134 |
| SEQ-ID-NO-370 | ---- | 161 |
| SEQ-ID-NO-409 | ---- | 164 |
| SEQ-ID-NO-349 | ---- | 167 |
| SEQ-ID-NO-357 | ---- | 163 |
| SEQ-ID-NO-337 | ---- | 162 |
| SEQ-ID-NO-339 | ---- | 160 |
| SEQ-ID-NO-395 | ---- | 155 |
| SEQ-ID-NO-417 | ---- | 150 |
| SEQ-ID-NO-437 | ---- | 153 |
| SEQ-ID-NO-355 | ---- | 180 |
| SEQ-ID-NO-393 | HQLFSAS | 198 |

Figure 6

| SEQ ID | Sequence | # |
|---|---|---|
| SEQ-ID-NO-1842 | MSSSCIPTGL RLDLDMVKAA ASPVCAHSSP LRPAHYSSPS STLSSEASNA | 50 |
| SEQ-ID-NO-456 | ---------- ----MCSNK ASPVVGEE-- ---------- KQSTRSSKR | 22 |
| SEQ-ID-NO-511 | ---------- ----MLMNC DFNCDLFE-- -QEAKRRS-- -YPWARPCDG | 29 |
| SEQ-ID-NO-498 | ---------- ----MFMNC NFNSNLLE-- -NEAGRIS-- -FPWARPCDG | 29 |
| SEQ-ID-NO-478 | ---------- ----MFKQE SNNICNRE-- -N-------- -NRGARACDT | 23 |
| SEQ-ID-NO-481 | ---------- ----MLKQE S--------- ---------- --NWAQACDT | 14 |
| SEQ-ID-NO-485 | ---------- ----MLKQE S--------- ---------- --NWAQTCDT | 14 |
| SEQ-ID-NO-496 | ---------- ----MLKKE NSN------- ------S--- --NWARVCDS | 16 |
| SEQ-ID-NO-510 | ---------- ----MLKKE KSGGFDRS-- ---------- -NNWARVCDS | 23 |
| SEQ-ID-NO-536 | ---------- ----MLKKE RTSGGETG-- ------E--- -NNWARICDT | 23 |
| SEQ-ID-NO-474 | ---------- ----MLKQE SSGGGGGD-- ---------- -NRARVCDT | 21 |
| SEQ-ID-NO-475 | ---------- ----MLKQE SSGSGGGD-- ---------- -NRARLCDT | 21 |
| SEQ-ID-NO-457 | ---------- ---------- ---------- ---------- -MPKPCDA | 7 |
| SEQ-ID-NO-532 | ---------- ----MKVEE QTVGGGG--- -GAGQGGAGF WGLAGRPCDT | 32 |
| SEQ-ID-NO-466 | ---------- ----MVIDT TNVKGLTG-- -R-------- WGMAAKTCDT | 24 |
| SEQ-ID-NO-508 | ---------- ----MGIER GGLKSLRG-- -G-------- WSVPPKLCDS | 24 |
| SEQ-ID-NO-488 | ---------- ---------- ---------- ---------- --MALKLCDS | 8 |
| SEQ-ID-NO-494 | ---------- ---------- ---------- ---------- --MATKLCDS | 8 |

| SEQ ID | Sequence | # |
|---|---|---|
| SEQ-ID-NO-1842 | SSSSATSVSL KRARAPRKRP NQAYNEAAL --LASLHPSV FPVNKSPKTA | 98 |
| SEQ-ID-NO-456 | -KKRKN REATTMEDK SSSNLDASRK --IRTKTKK- -P------- | 56 |
| SEQ-ID-NO-511 | CHAAPSAVYC HADAAYLCAS CDTQVHSANR --LASSHERV RVCVSCESAA | 77 |
| SEQ-ID-NO-498 | CHAAPSTVYC CADAAYLCAS CDLQVHSANR --LASSHERV RVCETCESAP | 77 |
| SEQ-ID-NO-478 | CGSTICTVYC HADSAYLCNS CDAQVHSANR --VASRHKRV RVCESCERAP | 77 |
| SEQ-ID-NO-481 | CRSAACTVYC RADSAYLCTS CDAQI HAANR --LASRHERV RVCESCERAP | 71 |
| SEQ-ID-NO-485 | CRSAACTVYC RADSAYLCTN CDAQVHAANR --LASRHERV RVCQSCERAP | 62 |
| SEQ-ID-NO-496 | CHSATCIVYC RADSAYLCAG CDARIHTASL --MASRHERV WVCEACERAP | 62 |
| SEQ-ID-NO-510 | CHSATCIVYC RADSAYLCAG CDSRIHAASL --MASRHERV WVCEACERAP | 64 |
| SEQ-ID-NO-536 | CRSAACTVYC RADSAYLCTS CDARVHAANR --VASRHERV WVCESCERAP | 71 |
| SEQ-ID-NO-474 | CRAAPCTVYC RADAAYLCVG CDARVHAANR --LASRHERV SVCEACERAP | 71 |
| SEQ-ID-NO-475 | CRAAACIVYC RADAAYLCVG CDGKVHGANK --VASRHERV WVCESCERAP | 69 |
| SEQ-ID-NO-457 | CHVSSAAVFC RLDGAYLCAG CDARAHGACS --RHARV--- WMCEVCEVAP | 69 |
| SEQ-ID-NO-532 | CAVDAARLYC RSDSAFMCLS CDSTIHSAND KLVSCRHERV WMCEVCEHAP | 55 |
| SEQ-ID-NO-466 | CKSAAAI FC RSDSAFLCIN CDSKIHAANK --LSSRHERV WMCEVCEQAP | 77 |
| SEQ-ID-NO-508 | CKLTPAALFC RSDSAFLCVN CDSNQAANK --LASRHARV WLCEVCEQAP | 74 |
| SEQ-ID-NO-488 | CKSATGTLFC RSDSAFLCIT ---------- --LASRHARV WMCEVCEQAP | 72 |
| SEQ-ID-NO-494 | CKSTKATLFC RSDSAFLCIT ---------- --LASRHHRV TLCEVCEQAP | 56 |

| | | | | | | |
|---|---|---|---|---|---|---|
| SEQ-ID-NO-1842 | DSLLDVGDAA | AGGLDGIMGS | LTVDVESGTA | ARSDDSILSS | SGIHPYLRRL | 243 |
| SEQ-ID-NO-456 | AAYLFNSATD | STISSIHDLL | PSS---AATD | VDCGGERNNL | ---SPYYDR- | 167 |
| SEQ-ID-NO-511 | DSWLLLERDS | DDNN------ | ------CTNN | IDQYXNLFGY | ---DMYYDKF | 180 |
| SEQ-ID-NO-498 | DSWLLRRNSD | ---------- | ---------- | ANKIDRYYNL | VGYNMYYDNI | 179 |
| SEQ-ID-NO-478 | ASWLFPKNSD | YH-------- | ---DNNC--- | NQNNELLFS- | ---DDYLDL- | 173 |
| SEQ-ID-NO-481 | ASWLLPSSVK | NC-------- | ---NNNN--- | NNTENNRFSV | G--EEYLDL- | 165 |
| SEQ-ID-NO-485 | ASWLLPSSLK | NSGDNN---- | ---GDNN--- | NNNSENRFSV | G--DEYVD-- | 167 |
| SEQ-ID-NO-496 | ASWLLLNPPV | K--------- | ---NNNN--- | NNNYGMLFGG | EVVDDYLDL- | 189 |
| SEQ-ID-NO-510 | ASWLLLNPPV | KNNNKNNI-- | N--NNNN--- | NNNYGMLFGG | EVVDEYLDL- | 206 |
| SEQ-ID-NO-536 | ASWLLLNPGK | NS-------- | ---GNNN--- | NQNNGFFFDG | EA-DEYLDL- | 185 |
| SEQ-ID-NO-474 | ASWLLLNPVK | ---------- | ---NSKN--- | QNNNGFLFGG | EV-DEYLDL- | 176 |
| SEQ-ID-NO-475 | ASWLLLNPVK | ---------- | ---NSKN--- | QNNNGFLFEG | EV-DEYLDL- | 179 |
| SEQ-ID-NO-457 | VSWLLLPHPKI | ---------- | ---SITNS-- | LIRGSAAADE | MGSSPFHD-- | 161 |
| SEQ-ID-NO-532 | ASWLLPEP-- | ---------- | ---GDSP--- | EDSAATFFAD | S--DAYLD-- | 176 |
| SEQ-ID-NO-466 | GSWLLPNPKL | TM-------- | ---ETNQ--- | VKTGDFFFSD | M--DPFID-- | 178 |
| SEQ-ID-NO-508 | AAWLIPNPNF | GSKLN----- | ---ETQD--- | IKTREMFFSD | M--DPFLD-- | 183 |
| SEQ-ID-NO-488 | ASWLLPNPKA | M--------- | ---ENPD--- | LNSGQYLFPE | M--DPYMD-- | 167 |
| SEQ-ID-NO-494 | ASWLLQTPAN | P--------- | ---KGPD--- | LNSSHYSFTE | IDATDL---- | 150 |

| | | | | | | |
|---|---|---|---|---|---|---|
| SEQ-ID-NO-1842 | MVVGLAGRFE | LGLGSQHGAR | PSLNRALKRR | DDDGAWWMWP | AVPVKDLTIA | 293 |
| SEQ-ID-NO-456 | S-----QD-- | HCSSSSLLR | TAMRKGASEE | E--------- | ---------- | 190 |
| SEQ-ID-NO-511 | S-----CN-- | PGPGEEYRLQ | EQDVQNMYRE | N--------- | ---------- | 204 |
| SEQ-ID-NO-498 | T-----CD-- | PRPEEQYRMQ | EQHVQNRYIE | K--------- | ---------- | 203 |
| SEQ-ID-NO-478 | ------AD-- | YNSSMDYKFT | SQYNQPRHKQ | D--------- | ---------- | 196 |
| SEQ-ID-NO-481 | ------VD-- | YSSSIDKRFX | GQ--TNQYQQ | D--------- | ---------- | 186 |
| SEQ-ID-NO-485 | ---------- | ---------- | -LVDYNKYQQ | D--------- | ---------- | 177 |
| SEQ-ID-NO-496 | ------AE-- | YGG------- | DQYSVNQQQQ | H--------- | ---------- | 210 |
| SEQ-ID-NO-510 | ------AE-- | YGG------- | DQYSVNQQQQ | H--------- | ---------- | 227 |
| SEQ-ID-NO-536 | ------VE-- | YNSSMENQFS | DQYSQ--YHQ | Q--------- | ---------- | 206 |
| SEQ-ID-NO-474 | ------VE-- | Y--------- | NQCSDQYNQQ | H--------- | ---------- | 195 |
| SEQ-ID-NO-475 | ------VE-- | Y--------- | NQCSDQYNQQ | H--------- | ---------- | 198 |
| SEQ-ID-NO-457 | ------RP-- | ESPKPKKQKV | ELPADLFSDV | M--------- | ---PFLDL-- | 189 |
| SEQ-ID-NO-532 | ---------- | ---------- | --LDFVRS-- | ---------- | ---------- | 183 |
| SEQ-ID-NO-466 | ---------- | ---------- | FEYQDSFQQH | D--------- | ---------- | 189 |
| SEQ-ID-NO-508 | ---------- | ---------- | FDYSNNFQNN | N--------- | ---------- | 194 |
| SEQ-ID-NO-488 | ---------- | LDYGHV---- | DPKLEDAQEQ | N--------- | ---------- | 184 |
| SEQ-ID-NO-494 | ---------- | NFVCV----- | DAKTDSPEQH | S--------- | ---------- | 166 |

| | | | | |
|---|---|---|---|---|
| SEQ-ID-NO-1842 | ---LR Q ALEEE T--------- | --------- | --------- | 485 |
| SEQ-ID-NO-456 | --------- | --------- | --------- | 339 |
| SEQ-ID-NO-511 | E--LDQML T I P ALP------ | --------- | WF------ | 369 |
| SEQ-ID-NO-498 | E--EDHML S PP ALP------ | D-SGHATVL | WF------ | 369 |
| SEQ-ID-NO-478 | E--DQEYNT M LMY------ | DT-SSYNT VP | SFYGQK | 366 |
| SEQ-ID-NO-481 | --ADHAL S TM VMF------ | CD-TGYGI VP | SFS--- | 342 |
| SEQ-ID-NO-485 | EEADKA F SSM VMF------ | D-TGYGI VP | SF---- | 335 |
| SEQ-ID-NO-496 | E--VDQMFSTQ LMT------ | D-TGYGI VP | SF---- | 391 |
| SEQ-ID-NO-510 | E--VDQMFSTQ LMT------ | D-SNYGI VP | SF---- | 413 |
| SEQ-ID-NO-536 | E--VDQ A FST T LMQ------ | D-SSYGI VP | SF---- | 381 |
| SEQ-ID-NO-474 | E--DDQMFSST LMA------ | E-TGYGI VP | SF---- | 369 |
| SEQ-ID-NO-475 | E--DDR T FSST LMA------ | E-SGYGI VP | SF---- | 372 |
| SEQ-ID-NO-457 | E--Q--- F GSV DSS------ | G--GCGI VP | SF---- | 358 |
| SEQ-ID-NO-532 | E--QDGPFSPA SSA----HLA | F-GVVP | SF---- | 325 |
| SEQ-ID-NO-466 | E--VDHMYNSA SSAATAAAFM | SD-GDYGVVP | SF---- | 368 |
| SEQ-ID-NO-508 | D--VDRLYNPA DPLSVPSSML | YD-NQYGI VP | SF---- | 375 |
| SEQ-ID-NO-488 | E--AE P M--------- | MD-CPYGVVP | TF---- | 340 |
| SEQ-ID-NO-494 | N-VN-L I GED ESY------ | ---CRYGI VP | SF---- | 312 |
| | | ---DGYGVVP | S C ---- | |

Figure 7

```
                                                                           20            70
                                                                           50           100
SEQ-ID-NO-634  ----------  --------  -MEESKKY-  --------  --------
SEQ-ID-NO-637  MHVKLSLWLK  HFVVTILIYK  YRPPSRPLHH  NSVFISKKAM  KSM
                                                              VKQTMNKKKK
                                                              EESRSNREQR

SEQ-ID-NO-634  NNNKKGHCSG  SRSGLLQMKV  RRLQILIPGG  QTCNHPDLLL  SKTVDYIVHL
SEQ-ID-NO-637  KQTKKKTGRG  SGSGSIQIKM  RKLRVLIPGG  RRLNQPDLLL  TKTADYIMHL 86
                           117
SEQ-ID-NO-634  KLKLRFLKAI  SEMYSL-
SEQ-ID-NO-637  ELRIRFLKAI  SDIYSLS
```

| SEQ ID | Sequence | # |
|---|---|---|
| SEQ-ID-NO-826 | LASSCPKKLA GRKKFRETRH PIYRGVRQRN SGKWVCEVRE PNKKSRI WLG | 81 |
| SEQ-ID-NO-813 | LAASCPKKPA GRKKFRETRH PVYRGVRLRN SGKWVCEVRE PNKKSRI WLG | 78 |
| SEQ-ID-NO-809 | LATSCPKKPA GRKKFRETRH PIYRGVRQRN SGKWVCEVRE PNKKSRI WLG | 78 |
| SEQ-ID-NO-811 | LATSCPKKPA GRKKFRETRH PVYRGVRQRN SGKWVSELRE PNKKTRI WLG | 78 |
| SEQ-ID-NO-808 | LATSCPKKPA GRKKFRETRH PIYRGVRQRN SGKWVSEVRE PNKKTRI WLG | 78 |
| SEQ-ID-NO-804 | LATSCPKKPA GRKKFRETRH PIYRGVRQRN SGKWVCELRE PNKKTRI WLG | 75 |
| SEQ-ID-NO-644 | LASSCPKKPA GRKKFRETRH PIYRGVRQRN SGKWVCEVRE PNKKTRI WLG | 78 |
| SEQ-ID-NO-796 | LASSCPKKPA GRKKFRETRH PIYRGVRRRS SGKWVCEVRE PNKKTRI WLG | 78 |
| SEQ-ID-NO-797 | LASSCPKKPA GRKKFRETRH PIYRGVRRRN SGKWVCEVRE PNKKTRI WLG | 78 |
| SEQ-ID-NO-645 | LASSCPKKPA GRKKFRETRH PIYRGVRRRN SCKWVCEVRE PNKKTRI WLG | 78 |
| SEQ-ID-NO-767 | LASSCPKKPA GRKKFRETRH PIYRGVRRRN SGKWVCEVRE PNKKTRI WLG | 78 |
| SEQ-ID-NO-1843 | LASCYPKKRA GRKKFRETRH PVFRGVRRRN SGKWVCEVRE PYKKSRI WLG | 86 |
| SEQ-ID-NO-834 | LASKNPKKRA CRKKFRETRH PIYRGVRRRD SGKWVCEVRE PNKKTRV WLG | 92 |
| SEQ-ID-NO-837 | LASTHPKKRA GRKKFRETRH PVYRGVRRRN SGKWVCEVRE PNKTSRI WLG | 84 |
| SEQ-ID-NO-838 | LASTRNPKKRA GRKKFRETRH PVYRGVRRRN SGKWVCEVRE PNKKSRI WLG | 93 |
| SEQ-ID-NO-830 | LASTCPKKRA GRKKFRETRH PVFRGVRRRN SCKWVCEVRE PNKKSRI WLG | 85 |
| SEQ-ID-NO-840 | LASNNPKKRPA GRKKFRETRH PIYRGIRKRN SGKWVCEVRE PNKKTRI WLG | 85 |
| SEQ-ID-NO-832 | LASNNPKKPA GRKKFRETRH PIYRGIRKRN SGKWVCEVRE PNKKKTRI WLG | 82 |
| SEQ-ID-NO-835 | LASNNPKKPA GRKKFRETRH PVYRGVRKRN SGKWVCEVRE PNKKSRI WLG | 88 |
| SEQ-ID-NO-831 | LASNNPKKRA GRKKFRETRH PVYRGVRKRN SDKWVCEVRE PNKKSRI WLG | 87 |
| SEQ-ID-NO-839 | LASNNPKKRA GRKKFRETRH PVYRGVRKRN SDKWVCELRE PNKKSRI WLG | 87 |

Figure 8 (continued)

| SEQ ID | Sequence | Length |
|---|---|---|
| SEQ-ID-NO-826 | TFPTVEMAAR AHDVAALALR GRSACLNFAD SAWRLRIPES TCPKEI QRAA | 131 |
| SEQ-ID-NO-813 | TFLLTAEIAAR AHDVAAIALR GKSACLNFAD SAWRLRIPET TCPKEI QKAA | 128 |
| SEQ-ID-NO-809 | TFPTAEMAAR AHDVAAIALR GRSACLNFAD SAWRLRIPES TCAKDI QKAA | 128 |
| SEQ-ID-NO-811 | TFPQTAEMAAR AHDVAALALR GRSACLNFAD SVWRLRIPES ACAKDI QKAA | 128 |
| SEQ-ID-NO-808 | TFPQTAEMAAR AHDVAAIALR GRSACLNFAD SAWRLRIPES TCAKEI QKAA | 125 |
| SEQ-ID-NO-804 | TFPQTAEMAAR AHDVAALALR DRSACLNFAD SAWRLRIPES TCAKEI QKAA | 128 |
| SEQ-ID-NO-644 | TFPQTAEMAAR AHDVAAIALR GRSACLNFAD SAWRLRIPES TCAKDI QKAA | 128 |
| SEQ-ID-NO-796 | TFPQTAEMAAR AHDVAAIALR GRSACLNFAD SAWRLRIPES TCAKDI QKAA | 128 |
| SEQ-ID-NO-797 | TFPQTAEMAAR AHDVAALALR GRSACLNFAD SAWRLRIPES TCAKDI QKAA | 128 |
| SEQ-ID-NO-645 | TFPTAEMAAR AHDVAALALR GRLACLNFAD SAWRLPVPAS TCAKDI QKAA | 128 |
| SEQ-ID-NO-767 | TFPTEEMAAR AHDVAALAMR GRGACLNFAD SLWRLPIPES TDPKDI QKAA | 136 |
| SEQ-ID-NO-1843 | TYPTADMAAR AHDVAALALR GRGACLNFAD SAWRLHVPSS SNVKDI QKAA | 142 |
| SEQ-ID-NO-834 | TFPTADMAAR AHDVAALALR GRSACLNFAD SAWRLPTPAS RDAKDI QKAA | 134 |
| SEQ-ID-NO-837 | TFPTAEMAAR AHDVAALALR GRSACLNFAD SARRLPVPAS SDAKDI QTAA | 143 |
| SEQ-ID-NO-838 | TFPTADMAAR AHDVAAIALR GRSACLNFSD SAWRLPIPAS SNAKDI QKAA | 135 |
| SEQ-ID-NO-830 | TFPTAEMAAR AHDVAALALR GRSACLNFSD SAWRLPVPAS SNSKDI QKAA | 135 |
| SEQ-ID-NO-840 | TFPTAEMAAR AHDVAAIALR GRSACLNFAD SAWRLPIPAS SDTKDI QKAA | 132 |
| SEQ-ID-NO-832 | TFPTAEMAAR AHDVAAIALR GRSACLNFAD SAWRLPVPAS SDTKDI QKAA | 138 |
| SEQ-ID-NO-835 | TFPSAEMAAR AHDVAAIALK GRSACLNFAD SAWKLLPIPAS SDTKDI QKAA | 138 |
| SEQ-ID-NO-831 | TFPSAEMAAR AHDVAAIALR GRSACLNFAD SAWKLPIPAS TDAKDI QKAA | 137 |
| SEQ-ID-NO-839 | TFPSAEMAAR AHDVAAIALR GRSACLNFAD SAWKLPIPAS TDAKDI QKAA | 137 |

| SEQ-ID-NO | | | | | | |
|---|---|---|---|---|---|---|
| SEQ-ID-NO:826 | LGMPRFLENM | GEEMLLPPPE | LGWNH | DLAG-DADV | SLWSF- | 220 |
| SEQ-ID-NO:813 | LEMPALLASM | AEGMLLPPPS | -VHFGH---N | YDFDG-DADV | SLWSY- | 214 |
| SEQ-ID-NO:809 | FGMPRLLANM | AEGMLLPPPS | -VQWGH---N | YDCDG-DADV | SLWSY- | 216 |
| SEQ-ID-NO:811 | FGMPSLMANM | AEGMLLPLPS | -IQWI-N | YDVEG-DADM | PLWSY- | 216 |
| SEQ-ID-NO:808 | FGMPTLLDNM | AEGMLLPPPS | -VQMNH---N | YDGEG-DGEV | PLWSY- | 213 |
| SEQ-ID-NO:804 | LGMSSLLDNM | AEGMLLPSPS | -VQMNH---N | FDVKG-DDDM | SLWSY- | 216 |
| SEQ-ID-NO:644 | FEMPSLLANM | AEGMLLPLPS | -VQMNY---N | HEVDGGDDDV | SLWSY- | 216 |
| SEQ-ID-NO:796 | FEMPSLLANM | AEGMLLPLPS | -VQMNH---N | HEVDGDDDDV | SLWSY- | 216 |
| SEQ-ID-NO:797 | FEMPSLLANM | AEGMLLPLPS | -VQMNH---N | HEVDGDDDDV | SLWSY- | 216 |
| SEQ-ID-NO:645 | FEMPSLLANM | AEGMLLPLPS | -VQMNH---N | HEVDGGDDDV | SLWSY- | 216 |
| SEQ-ID-NO:767 | FGREKFLANM | AAGMMMSPPH | -SGYEK---DE | QELEFVDDCV | QLWSYSI | 222 |
| SEQ-ID-NO:1843 | FEMQGFLADM | AEGMMLPPPR | TLEYDN---C | QDDLEFVDA | SLWSF- | 219 |
| SEQ-ID-NO:834 | FGMPGLLVNM | AEGLLMPPPH | SVADGY---G | GDDMAADADM | SLWSY- | 218 |
| SEQ-ID-NO:837 | FGMPGLLANI | AEGMLLPPPN | CCGYSGGDSL | DNMENNDTDM | SLWSFSV | 233 |
| SEQ-ID-NO:838 | FGMPGLLADM | AEGMLLPPPH | --YSD----D | DDVDV-CADV | PLWSF- | 219 |
| SEQ-ID-NO:830 | FFMPGLLANM | AEGLMLPPPQ | -CAEMG---D | HYVETDAYML | TLWNYSI | 222 |
| SEQ-ID-NO:840 | FFMPGLLANM | AEGLMLPPPQ | -CAEMG---D | HCVETDAYML | TLWNYSI | 210 |
| SEQ-ID-NO:832 | FCMPGLLANI | AEGLMLPPPQ | -CAEIG---D | HI-VETADADT | PLWSFSI | 215 |
| SEQ-ID-NO:835 | FCMPGLLADM | AEGLMLPPPQ | -CAEIG---D | HI-VETADADT | PLWSFSI | 215 |
| SEQ-ID-NO:831 | FCMPGLLTNM | AEGLMLPPPQ | -CSQIG---D | HMED-DFDM | PLWSYSI | 219 |
| SEQ-ID-NO:839 | FFMPGLLVNM | AEGLMLPPPQ | -CSQIG---D | HMEA-DVDM | PLWSYSI | 219 |

Figure 9

```
SEQ-ID-NO-850  ------MEKS--------------------------------------------PRYRD------------------------------------KA  11
SEQ-ID-NO-881  ------MEPCTKQ------FLPM--------------------------P-PQDPNSPSSSTSSSSSSSTSPSHPYHRA--------------  40
SEQ-ID-NO-895  ------MEVSTKQ------LLPM--------------------------PHQQDPNSPSSSTSSSSSSSTSPSHPHHRA--------------  41
SEQ-ID-NO-885  ------MEVAPAV------KQLL--------------------------PMARGPNSPSPSSTSSSSPSPSAA-------------------  34
SEQ-ID-NO-898  -----------------------------------------------------MAHDPNSPSSSTSSSSPSSAAAAASSSPS-----------  29
SEQ-ID-NO-876  ------MDSIS----------------------------------------PKPQENNNN-NNNI-------------------------S-  19
SEQ-ID-NO-877  ------MDSTSSMRYQ-EEQKSSLTSL----------------------PSPKTQSNGHNHSHNQIPSPRPISLPSPKT--------------  50
SEQ-ID-NO-853  ------METSPRQTT--NPN---FLAS----------------------PKSLSPNSSTSSTSGS--------------------NT------  35
SEQ-ID-NO-857  ------METSPRHRD--NQNPQSLFPS----------------------PTSYSSSSNSNSNSSTTATNNVALNNNI---------------  49

SEQ-ID-NO-850  -----------------------------------------------------------TTP----------YETTFIRTDP-----------  43
SEQ-ID-NO-881  -----------------KNL------LPSPSSCT---------------------PRPVPRTIETTPFPTTFVQADT---------------  73
SEQ-ID-NO-895  -----------------QPP------HPHNLPPS---------------------PRPIPRTIDTTPFPTTFVQADT---------------  71
SEQ-ID-NO-885  -----------------Q---------PHNLPPS---------------------QAPIPRTIDTTPFPTTFVQADT---------------  67
SEQ-ID-NO-898  -----------------APS------PPPRQQQS---------------------SPRTVVPRTIDTTPFPTTFVQADT-------------  72
SEQ-ID-NO-876  -----------------SHR------PPPPPPSSSS-------------QPALPPSPRTMTRSEPANSYPTTFVQADT--------------  41
SEQ-ID-NO-877  -----------------------------------------------------PKPTRSEPGNPYPTTFVQADT------------------  90
SEQ-ID-NO-853  -----------------QTQSNGHNHN------HNHNQIPS--------------PKPTRSESANPYPTTFVQADT----------------  68
SEQ-ID-NO-857  -----------------NHP------PPTPPPQQ---------------------PKPLSRSESTNPYPTTFVQADS---------------  79

SEQ-ID-NO-850  SSFKQVVQLL------TGIPK--------------------N---PTHQPDPRFPPFHSIPPIKA---------G-----------------  79
SEQ-ID-NO-881  TSFKQIVQML------TGSEQS-------------------S---KSAAAATTNGSAGNQAASGS--------------------------- 110
SEQ-ID-NO-895  TSFKQVVQML------TGAEQPTKND---------------A---TTAAAAPAGNGGGGQAA---G------------------------- 110
SEQ-ID-NO-885  ASFKQVVQRL------TGSD-----------------------T-PPPAQKPAKTHGHHHHH---G------------------------- 100
SEQ-ID-NO-898  ASFKQVVQML------TGSD---------------------A---TPPSQRPPAKSNHHQHHHSG-------------------------- 107
SEQ-ID-NO-876  TSFKQVVQML------GSSETAK------------QAAAAAA--AASSSSSSKKPANPIPPMKS-------------------------- 86
SEQ-ID-NO-877  TSFKQVVQML------GSSETAK------------LASSTK--AKQASTSTKANHNHNIPP----------------------------- 124
SEQ-ID-NO-853  SSFKQVVQML------GSSETAK--------TTTTTTTT----PTPSPLSDSNLKTHIPPIKS---------------------------- 112
SEQ-ID-NO-857  SSFKQVVQML------GSPKPKPTC------------------A-PNTSQVDPLPKTHNIPPIKS-------------------------- 129

SEQ-ID-NO-850  VTNKKQSSSF------RLSERRNS-------MKHYLNIN---PTH-------GP---SPRNAS------- 111
SEQ-ID-NO-881  GPCRPKKPSF------KLYERRSS-------LKNLKMA----PLA----M--GAPPSPRR--------- 150
SEQ-ID-NO-895  GPCRPKKPSF------KLYERRSS-------MKNLKMA----PLA----M--GPPPSPRK--------- 148
SEQ-ID-NO-885  GGVGKKPAF-------KLYERRLG-------KNLKMA-----PL-----A--CPSPSPRK--------- 137
SEQ-ID-NO-898  APCRPKKQAF------KLYERRSGV------HKNFKMA----PLAMAAAAAAGASSSPRK--------- 152
SEQ-ID-NO-876  IPNKKQQPHF------SKLYERRNS------LNRNSLHI---PLTSFF---S-NHTNSPRK--------- 131
SEQ-ID-NO-877  ---KKQQGF------KLYERRNS-------FHKNLNIN---PLLPPIF--S-NSTFSPRNK-------- 163
SEQ-ID-NO-853  IPKNKQNSGF------RLYERRSS-------LKNLK-I----PLNPAFGS--N-NSIGFSPRK------- 154
SEQ-ID-NO-857  MPKKNQSSGF------KLYERRNS-------LKNLK-N----PLNPIFAQ-P-SSGFSSRK-------- 171
```

Figure 9 (continued)

| SEQ ID | | | | | | | | | |
|---|---|---|---|---|---|---|---|---|---|
| SEQ-ID-NO-850 | ---------- | PEIL | TPTILNFPAL | DL-SPDTPLM | SDPFYRPGSF | SQSP--SDSK | 152 |
| SEQ-ID-NO-881 | AA------ | PEIL | SPSVLDFPSL | KLSSPVTPLT | GDPFFPSPAS | SSGD---- | 190 |
| SEQ-ID-NO-895 | AA------ | PEIL | SPSVLDFPSL | RLSSPVTPLT | GDPFNRSPAS | TSSS---- | 188 |
| SEQ-ID-NO-885 | AA------ | PEVL | SPSVLDFPSL | ALGSPVTPLL | ADPFNRSASA | SPGE---- | 177 |
| SEQ-ID-NO-898 | AAQHQQEAL | ---- | SPSVLDFPSL | AL-SPVTPLV | ADPFNRSPAS | ASSS---- | 195 |
| SEQ-ID-NO-876 | ---------- | ADIL | SPSILDFPSL | VL-SPVTPLI | PDPFDRSNAA | -DSE---- | 168 |
| SEQ-ID-NO-877 | ---------- | QEIL | SPSILDFPSL | VL-SPVTPLI | PDPFNRSGSS | SSSAARNGS | 206 |
| SEQ-ID-NO-853 | ---------- | PEIL | SPSILDFPSL | AL-SPVTPLI | PDPFDRSGSG | NYTNCINNNV | 197 |
| SEQ-ID-NO-857 | ---------- | KFIL | SPSILDFPAL | VL-SPVTPLI | PDPFDRSGSA | KYTN---- | 208 |

| SEQ ID | | | | | | | | | |
|---|---|---|---|---|---|---|---|---|---|
| SEQ-ID-NO-850 | PSFDDDQERS | KEKGFYLRP | SPST--TPRD | TEPRLISLFP | MTPIHSPAPS | 200 |
| SEQ-ID-NO-881 | -AAERAA-- | ADKGFFFHP | SPRGA-EP- | -PRLLPLFP | VSSPRMAAAS | 231 |
| SEQ-ID-NO-895 | -EEAERAA-- | AERGFFLHP | SPRGA-EP- | -PRLLPLFP | VTSPRMAAPA | 230 |
| SEQ-ID-NO-885 | ---------- | AQRGFFLHP | SPRGAVEP- | -PRLLPLFP | VTSPKMAQ-- | 219 |
| SEQ-ID-NO-898 | -QDEAEAAA- | AQKGFFLHP | SPRSA-EP- | -PRLLPLFP | VTSPRVASSS | 239 |
| SEQ-ID-NO-876 | -ASPE----- | AEVKA---- | SPRD----K | AQPLLPLFP | TTSPRASSGP | 208 |
| SEQ-ID-NO-877 | SLDSLAEDKA | REKGFFLHP | SPRAASTSRD | SEPRLLPLFP | TSSPRASGPS | 256 |
| SEQ-ID-NO-853 | NLDKEAEEKA | KEKGFYLHP | SPAS--TPRD | SEPRLLPLFP | VTSPRVSGSS | 245 |
| SEQ-ID-NO-857 | ---------- | KEKGFYLHP | SPGS--SPRE | TEPRLLPLFP | LTSPRISGSV | 250 |

| SEQ ID | | | |
|---|---|---|---|
| SEQ-ID-NO-850 | ----PHD--- | ---------- | -----H | 204 |
| SEQ-ID-NO-881 | AT-APAE--- | ---------- | ------ | 238 |
| SEQ-ID-NO-895 | AA--PSE--- | ---------- | ------ | 235 |
| SEQ-ID-NO-885 | ---------- | ---------- | ------ | 219 |
| SEQ-ID-NO-898 | SSSAAAVAV | ASPSFE---- | ------ | 255 |
| SEQ-ID-NO-876 | SSSAPPS-- | ---------- | ------ | 215 |
| SEQ-ID-NO-877 | SSSKYSAS-- | ---------- | ------ | 264 |
| SEQ-ID-NO-853 | TS-------- | ---------- | ------ | 247 |
| SEQ-ID-NO-857 | N---PSS--- | ---------- | ------ | 254 |

```
SEQ-ID-NO-948              GGLPVPVAKL  AGN-------  ----------  ----------  ----------   33
SEQ-ID-NO-950              GGLPVPLEKQ  LGD-------  ----------  ----------  ----------   33
SEQ-ID-NO-932              GGLPAVPLEK  MCN-------  ----------  ----------  RFSSASS---  132
SEQ-ID-NO-931              AGLCLLYQLP  NPNGVFTPAT  MNACATDSPS  TLLSITPYPH  RFSSASS---  144
SEQ-ID-NO-1844             EGLSHFYQLQ  NPSGIFG---  ---NSGDMV   NLYGTTSFPP  RFSSTAS---  139
SEQ-ID-NO-911              EGFSHFNQLQ  NPNGMFG---  ---NSSDMV   NFYGTTPFPS  NNLIEKSLNF  147
SEQ-ID-NO-907              EGLSHFYQLQ  NPNSMFG---  ---HSSDTV   NFYGSSSFPS  SNLPFSMLNS  160
SEQ-ID-NO-922              ARFFHNYPLL  EVE-------  ----------  ----------  SNLEFSLLNS  152
SEQ-ID-NO-923              TGVVVEDES   ATR-------  ----------  ----------  SNLDFSVLNS  156
SEQ-ID-NO-929              GARPRLEDAL  APE-------  ----------  ----------  PFHQLH----  126
SEQ-ID-NO-936              ----------  ----------  ----------  ----------  MMDKQKA---  118
SEQ-ID-NO-947              ----------  ----------  ----------  ----------  ----------  106

SEQ-ID-NO-948              ----------  ----------  ----------  TRQPYNCT--  ----------   50
SEQ-ID-NO-950              ----------  ----------  ----------  TRQPYNCT--  ----------   50
SEQ-ID-NO-932              SAA-------  -TKDV       EGKNLELRLG  ACSH-GDGAE  ERLDLQLRLG  168
SEQ-ID-NO-931              AAATN-----  -DYYS       EVKNLELRMG  ACSHGGDGTE  ERLDLQLRLG  183
SEQ-ID-NO-1844             AAT-------  -NDYS       EGKTLELRMG  ACSHGGDGTE  ERLDLELRLG  176
SEQ-ID-NO-911              LVAPPEINTS  HCYSIKAEPS  ASIDNSNN-N  SDNNFKELAH  EELDLELRLG  197
SEQ-ID-NO-907              PVEVPP----  ---RLIEYST  GDDESIGSMK  EATGTSVD--  ELDLELRLG-  200
SEQ-ID-NO-922              SVEVPP----  ---RLIQYPT  GDDEKAGSMK  ETILRTSVN-  EPDLELRLG-  192
SEQ-ID-NO-923              PVEVPP----  ---RFIEYST  GDDESIGSMK  ETKRTSVG--  EPDLELRLG-  196
SEQ-ID-NO-929              ----------  ---A        GTSISHEYD   TPPPAEPSDH  ANLDLTLRL-  156
SEQ-ID-NO-936              PAA-------  -DDDA       PATASSSNMK  RSSYGYG-V   EELDLSLRL-  153
SEQ-ID-NO-947              ----------  -RS         SRLLLRDKKG  SSEHGGVERA  DELDLSLRL-  137

SEQ-ID-NO-948              ----------  ----------  ----------  ----------  FCRRGFPTAQ   60
SEQ-ID-NO-950              ----------  ----------  ----------  ----------  FCRRGFPTAQ   60
SEQ-ID-NO-932              ----------  ----------  ----------  ----------  ----------  170
SEQ-ID-NO-931              YS--------  ----------  ----------  ----------  ----------  184
SEQ-ID-NO-1844             Y---------  ----------  ----------  ----------  ----------  177
SEQ-ID-NO-911              Y---------  ----------  ----------  ----------  ----------  200
SEQ-ID-NO-907              HRS-------  EDSKSSSEET  DKSEQSIDDM  RTGRRSYECV  FCKRGFSTAQ  250
SEQ-ID-NO-922              HHPPMEANHL  ----------  ----------  ----------  ----------  195
SEQ-ID-NO-923              HKP-------  ----------  ----------  ----------  ----------  199
SEQ-ID-NO-929              HNP-------  ----------  ----------  ----------  ----------  156
SEQ-ID-NO-936              ----------  ----------  ----------  ----------  ----------  153
SEQ-ID-NO-947              ----------  ----------  ----------  ----------  ----------  137
```

Figure 10 (continued)

```
SEQ-ID-NO-948   ALGGHMNVHR KDRVGRATPS SSSSTTAAAA RRSVSYDTLV GLFLPPASCG   110
SEQ-ID-NO-950   ALGGHMNVHR KDRVGRATPS SSSSTTAAAA RRSVSYDTLV RLFRPPASCG   110
SEQ-ID-NO-932   ---------- ---------- ---------- ---------- ----------   170
SEQ-ID-NO-931   ---------- ---------- ---------- ---------- ----------   184
SEQ-ID-NO-1844  ---------- ---------- ---------- ---------- ----------   177
SEQ-ID-NO-911   ---------- ---------- ---------- ---------- ----------   200
SEQ-ID-NO-907   ALGGHMNIHR KDRVKSRPSS VPIVSLSGNK ADDKNYPSFR PYSYPPIHSY   300
SEQ-ID-NO-922   ---------- ---------- ---------- ---------- ----------   195
SEQ-ID-NO-923   ---------- ---------- ---------- ---------- ----------   199
SEQ-ID-NO-929   ---------- ---------- ---------- ---------- ----------   156
SEQ-ID-NO-936   ---------- ---------- ---------- ---------- ----------   153
SEQ-ID-NO-947   ---------- ---------- ---------- ---------- ----------   137

SEQ-ID-NO-948   SEDAAASTAA GGGGSLRSRT AEPAPQELRL FGRGAGRREE GGGRDRRDRY   160
SEQ-ID-NO-950   SEDAAASTAA GGGASLRSRT AEPAPQELRL FGRGAGRREE GGGRDRRDRY   160
SEQ-ID-NO-932   ---------- ---------- ---------- ---------- ----------   170
SEQ-ID-NO-931   ---------- ---------- ---------- ---------- ----------   184
SEQ-ID-NO-1844  ---------- ---------- ---------- ---------- ----------   177
SEQ-ID-NO-911   ---------- ---------- ---------- ---------- ----------   200
SEQ-ID-NO-907   QPHYSIAPEV ------HV SYQAFLPVSG WGFRLPPHTA QLFVDNSKHR   342
SEQ-ID-NO-922   ---------- ---------- ---------- ---------- ----------   195
SEQ-ID-NO-923   ---------- ---------- ---------- ---------- ----------   199
SEQ-ID-NO-929   ---------- ---------- ---------- ---------- ----------   156
SEQ-ID-NO-936   ---------- ---------- ---------- ---------- ----------   153
SEQ-ID-NO-947   ---------- ---------- ---------- ---------- ----------   137

SEQ-ID-NO-948   GCCSKDGDGN GGHDHGEEEE LDLELRLGGS GSAGS   195
SEQ-ID-NO-950   GCCSKDGDGN GGHDHGEEEE LDLELRLGGS GSAGS   195
SEQ-ID-NO-932   ---------- ---------- ---------- -----   170
SEQ-ID-NO-931   ---------- ---------- ---------- -----   184
SEQ-ID-NO-1844  ---------- ---------- ----------TT -----   177
SEQ-ID-NO-911   ---------- ---------- ---------- PPPSS   207
SEQ-ID-NO-907   NPFGEDDHEN KKADGYNDKE DELDLELRLG HDP--   375
SEQ-ID-NO-922   ---------- ---------- ---------- --P--   196
SEQ-ID-NO-923   ---------- ---------- ---------- --P--   200
SEQ-ID-NO-929   ---------- ---------- ---------- -----   156
SEQ-ID-NO-936   ---------- ---------- ---------- -----   153
SEQ-ID-NO-947   ---------- ---------- ---------- -----   137
```

Figure 11

| SEQ:ID:NO:1005 | ME-S-L-S | --- | --- | --- | -SKKRV | RNSD--- | --- | SV-EAKRL | -RD | 26 |
|---|---|---|---|---|---|---|---|---|---|---|
| SEQ:ID:NO:953 | MEKKLLDITR | TDSA-EKKRV | RDE-SFD--- | -ESVVD | SPEVKRLR | -RD | 39 |
| SEQ:ID:NO:971 | MAEETLTRTD | SAEPTDKKRV | RDE-S-D--- | -EAVLD | SPEVKRLR | -RD | 39 |
| SEQ:ID:NO:963 | ME-LLN--- | --- | -HKKRV | RDG-S--N--- | -GAVLD | SPEVKKIR | -RD | 30 |
| SEQ:ID:NO:955 | MD-ELN--- | --- | -SKKRV | RDD-S-D--- | -ES-DLD | FPEVKKLR | -RD | 29 |
| SEQ:ID:NO:977 | MD-------- | --- | -CKKRV | RDD-S-D--- | -ES-GLD | SPDVKRLR | -RD | 26 |
| SEQ:ID:NO:979 | MD-------- | --- | -CKKRV | RDD-S-D--- | -ES-VLE | SPEAKRLR | -RD | 26 |
| SEQ:ID:NO:999 | MEDSR--- | --- | -DRKRR | RDEAE-E--- | -ES-I-LE | SPEAKRLR | -RD | 28 |
| SEQ:ID:NO:985 | MESSSSSLLL | SSYAGNNKRA | RDADLE--- | -QE--- | AEAAKRMRPE | 42 |
| SEQ:ID:NO:995 | MESSSSLLL | SSYTGGNKRA | READLD--- | -VC-SAE | AEAAKRI-RPE | 42 |
| SEQ:ID:NO:1015 | MDSSNNNN | --- | -SHKRA | RDAE--- | -VA-SSAE | ADEAKRLRAE | 29 |
| SEQ:ID:NO:1009 | MESS--- | --- | -SHKRA | REAA-D--- | -E-KRLRPE | 31 |
| SEQ:ID:NO:991 | METS--- | --- | -SHKRA | REAV-D--- | LAAAGDGALP | EADAKRLRPQ | 35 |
| SEQ:ID:NO:993 | METS--- | --- | -SHKRA | REAV-DLAAA | AAAAGEAVWP | ESDAKRLRPQ | 38 |

| SEQ:ID:NO:1005 | -LLDIL DDSD | VC-TPS-HDLD | SF-MKTFQDEI | SPSPAPEF--- | -TG--- | -SST- | 68 |
|---|---|---|---|---|---|---|---|
| SEQ:ID:NO:953 | DLFFDVLDDSD | PE-PVSQDLD | SVMKSFEDEL | STVTT-T-A--- | -QG--- | -SSTA | 82 |
| SEQ:ID:NO:971 | DLFFDVFDDSD | PE-PVSQDLD | SVMKSFEDEL | SS--- | --- | AQPR | 74 |
| SEQ:ID:NO:963 | DLFGLLDDSD | PD-SLGQDLD | SVMKSFEQEI | SASSSSPV--- | -PVVDLT-SES | 76 |
| SEQ:ID:NO:955 | DLF--LDDSD | SL-PLNQDLA | SVMKSFEEEI | SAVPSTSTES | MPVVDLTSDS | 76 |
| SEQ:ID:NO:977 | DLLEFFDDAD | DA-PISSQDLD | SVMKSLQEEI | SGV--- | --- | ASDS | 62 |
| SEQ:ID:NO:979 | DLLEFFDDAD | DA-ASTQDLD | SVMKSLQEEI | SGV--- | -TSPDY | 62 |
| SEQ:ID:NO:999 | LFDILDDDA | EA--GDQDIA | SVMRSLEEEI | ALSSPPPP--- | -RALV | 71 |
| SEQ:ID:NO:985 | DLLDLLDDDA | DA-AAAGDLA | SVMRSLEEEI | C--- | -PPT--- | ADEL | 76 |
| SEQ:ID:NO:995 | DLLDLLDDDA | DAGGAAGDLA | SVMRSLEEEI | C--- | --- | AGDL | 76 |
| SEQ:ID:NO:1015 | DLLDMLDDDT | DA-AAAGDLA | SVMRSFEEEL | VAGDVA--- | --- | GDVA | 69 |
| SEQ:ID:NO:1009 | DLLDMLDDDA | DAGGAAGDLA | SVMRSLEEEI | GSFDEAGA--- | -PDA--- | AAAP | 75 |
| SEQ:ID:NO:991 | DLLDMLDDDT | EA-AAAGDLA | SVMRSLEEEI | ASFDEA--- | --- | AEAA | 74 |
| SEQ:ID:NO:993 | DLLDMLEDDT | DA-AAAGDLA | SVMRSLEEEI | ASFDEA--- | --- | AEAA | 77 |

Figure 11 (continued)

| SEQ ID NO | | | | | | |
|---|---|---|---|---|---|---|
| SEQ-ID-NO-1005 | SGERPELGFL | FEASDDELGL | | | ERVLA---- | 99 |
| SEQ-ID-NO-953 | GETQPDLGYL | LEASDDELGL | PPTE------ | --TN------ | VTDLVRASS- | 131 |
| SEQ-ID-NO-971 | GETQPDLGYL | LEASDDELGL | PPPPSISPVP | VAKEEVTTET | VADLVRASS- | 121 |
| SEQ-ID-NO-963 | GESQPDLGFL | LEASDDELGL | PPPP---PPVS | VVEEVTTET | ETELARVDSA | 122 |
| SEQ-ID-NO-955 | CDSQPDLGYL | LEASDDELGL | PPVS----IN | LSSGEVKGGV | ATDLVRADS- | 120 |
| SEQ-ID-NO-977 | GESQAQIGYL | LEASDDDLGL | PPPT-----A | STTDAEGRSE | ETELVRVAS- | 105 |
| SEQ-ID-NO-979 | GESQAQIGYL | LEASDDDLGL | PPAG------ | NSSAPEEKNV | EAELVRVAS- | 105 |
| SEQ-ID-NO-999 | KTDQPDLGFL | LEASDDELGL | PPPV----LS | NSSAPQEKNV | ADDPAAEGVA | 117 |
| SEQ-ID-NO-985 | MPPQPELGFL | LEASDDELGL | PPAA----- | SSDDGGEAPA | GWEPE----- | 115 |
| SEQ-ID-NO-995 | AAPQPELGFL | LEASDDELGL | PPAA-----G | GASSSSDDAG | GWEPE----- | 116 |
| SEQ-ID-NO-1015 | PTTQPELGFL | LEASDDELGL | PPAA------ | AASSSSDDAG | AGEPE----- | 107 |
| SEQ-ID-NO-1009 | PAHQPELGFL | LEASDDELGL | PPAT------ | -ASSSEEEAG | AGAPD----- | 114 |
| SEQ-ID-NO-991 | PSQQPELGFL | LEASDDELGL | PPAG----SA | ASSSEEEAVA | AGPPE----- | 115 |
| SEQ-ID-NO-993 | PSQQPELGFL | LEASDDELGL | PPAG-----S | AAASSEEAGL | AGPPEPAAP- | 121 |
| SEQ-ID-NO-1005 | ESVCL-SE-L | WGLDDEFIK- | | VY--DGDNNI | NNGEYVALDG | 142 |
| SEQ-ID-NO-953 | DSSGI-DE-T | WGFEDHVSN- | -YDSFESGF | GV----GDGG | -DYVAVEG | 169 |
| SEQ-ID-NO-971 | DSSGI-DE-T | WGFEDHVPD- | -YGGLDFGS | GV----GDCG | -DYVTVEG | 159 |
| SEQ-ID-NO-963 | QSSGVGGE-L | WGFEDQIPT- | -YGSLDFGS | GD---SNYSS | -DYVGFDD | 162 |
| SEQ-ID-NO-955 | NSSGIHD-L | WGFEEQNPN- | -YDSFGLGV | VDNFNDGT- | -VAYDG | 158 |
| SEQ-ID-NO-977 | DSSGI-GE-T | MEFEEEQIPR- | -YDSFEFGF | GFGYECDTT- | -EYAAFGG | 146 |
| SEQ-ID-NO-979 | DSSGI-GE-T | MEFEDQIPR- | -YDSFDLGM | GFGYECDAT- | -EYAAFCE | 146 |
| SEQ-ID-NO-999 | VEGVFGQ-T | WGLDDD-IGY | -YDIGFDLGI | GPDDRVDTTH | -EYDGVFYDG | 164 |
| SEQ-ID-NO-985 | EAAGLFGEQI | WGFEDEIDGA | YAFGGVAYSP | EAAAAAAAAA | AEWGDDGFDA | 165 |
| SEQ-ID-NO-995 | EPAGVFGEQI | WGFEDEIDGA | YAFGGVASSP | EAAAAAAAAA | AEWGDDGFDA | 166 |
| SEQ-ID-NO-1015 | DAIGFGQQ-T | WGFEDEIGGG | G--YAGFALTS | PEAVAAAAAA | AEWDDDFDA | 155 |
| SEQ-ID-NO-1009 | VAAGLDGQ-T | WGFEDEIDGG | FGGYSPEA | AA------ | AAWDDDFDA | 158 |
| SEQ-ID-NO-991 | PAAALYGQ-T | WGFDDEIDGG | FGGYSPEA | AA------ | AAWDDDVFGA | 159 |
| SEQ-ID-NO-993 | AAAALYGQ-T | WAFDDEIDGG | FGGYSPEA | AA------ | AAWDDDVFGA | 165 |

Figure 11 (continued)

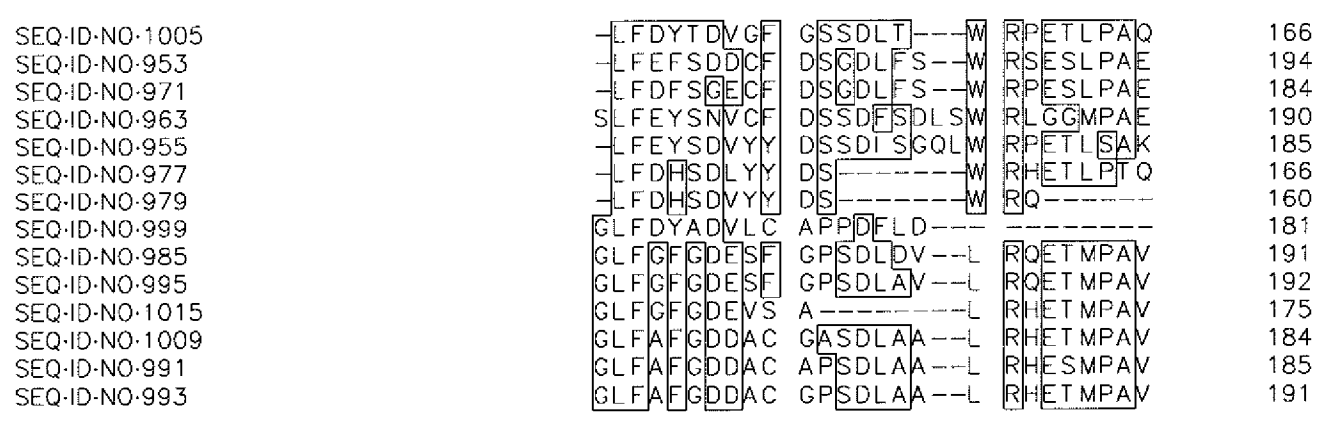

| | | | | |
|---|---|---|---|---|
| SEQ ID NO:1005 | LFDYTDVGF | GSSDLT--- | -W | RPETLPAQ | 166 |
| SEQ ID NO:953 | LFEFSDDCF | DSGDLFS-- | -W | RSESLPAE | 194 |
| SEQ ID NO:971 | LFDFSGECF | DSGDLFS-- | -W | RPESLPAE | 184 |
| SEQ ID NO:963 | SLFEYSNVCF | DSSDFSDLSW | | RLGGMPAE | 190 |
| SEQ ID NO:955 | LFEYSDVYY | DSSDISGQLW | | RPETLSAK | 185 |
| SEQ ID NO:977 | LFDHSDLYY | DS------- | -W | RHETLPT  | 166 |
| SEQ ID NO:979 | LFDHSDVYY | DS------- | -W | RQ------ | 160 |
| SEQ ID NO:999 | GLFDYADVLC | APPDFLD-- | -- | -------- | 181 |
| SEQ ID NO:985 | GLFGFGDESF | GPSDLDV-- | -L | RQETMPAV | 191 |
| SEQ ID NO:995 | GLFGFGDESF | GPSDLAV-- | -L | RQETMPAV | 192 |
| SEQ ID NO:1015 | GLFGFGDEVS | A-------- | -L | RHETMPAV | 175 |
| SEQ ID NO:1009 | GLFAFGDDAC | GASDLAA-- | -L | RHETMPAV | 184 |
| SEQ ID NO:991 | GLFAFGDDAC | APSDLAA-- | -L | RHESMPAV | 185 |
| SEQ ID NO:993 | GLFAFGDDAC | GPSDLAA-- | -L | RHETMPAV | 191 |

Figure 12

| | | | | | | |
|---|---|---|---|---|---|---|
| SEQ-ID-NO-1024 | MSRVLTCPPL | VFARNHVGVQ | NLVESTKLKR | | LEKKEKKEKR | 50 |
| SEQ-ID-NO-1039 | MSRYFTSPPPP | VYARNWANGQ | NLVESTKIER | TLDSKKAHR | KEKKERKKDK | 50 |
| SEQ-ID-NO-1042 | MSRCFPYPPP | VYLGNPV--- | AVAEAESTAK | QIVTSKKVHP | -KKDKRSDK | 45 |
| SEQ-ID-NO-1043 | MSRCFPFPPP | GYVRNPVAV | AAAEAQATTK | LQKERERAHK | -KKEKRSDR | 48 |
| SEQ-ID-NO-1040 | MSRCFPFPPP | GYMKLRFDL | DTPKKDRKKK | LQKEREKAEK | KEKREKRKRE | 49 |
| SEQ-ID-NO-1029 | MSRCFPYPPP | GYQIE---- | SIKRKEKEK | NRKEIDKNER | KEKKERRKHR | 45 |
| | | | | SITESHKDIK | | |

| | | | | | | |
|---|---|---|---|---|---|---|
| SEQ-ID-NO-1024 | KEKKETKREK | SHKHSIKAT- | -DNHHKLIFL | PSKKVS-DES | DSLEKSGLTD | 97 |
| SEQ-ID-NO-1039 | KQKNEKTIEH | --------- | -------VYL | PTKQVS-DES | EQLEKSCLTE | 82 |
| SEQ-ID-NO-1042 | KAPQLGETSK | HSKHNHKRK | LEDVSTGDQE | PKKVFK-ESA | ELLEKSGLSE | 94 |
| SEQ-ID-NO-1043 | KALPHGEISK | HSKRTHKKRK | HEDINNADQK | SRKVSSMEPG | EQLEKSGLSE | 98 |
| SEQ-ID-NO-1040 | KELKQKDSIT | SHASFGGAMK | LKDINGKLLM | GED---YEN | EQLERSGITE | 95 |
| SEQ-ID-NO-1029 | KENKDQCYT | VGKSHQKGK- | -------TFL | PR-----EKK | EEAEKSDLTE | 82 |

| | | | | | | |
|---|---|---|---|---|---|---|
| SEQ-ID-NO-1024 | ELEEP--QKH | LGYLSDGSQN | SKKRIRDDSP | PAVESLIKAA | PVAGKPLRIR | 145 |
| SEQ-ID-NO-1039 | EHEK------ | --YLSDGSQS | SKKR--REAS | PSVESNIKAT | PVTGNPLRIR | 123 |
| SEQ-ID-NO-1042 | EHGAPCFVQM | FRDSPESSQD | SSKKR--RKAVL | PSPSQA---- | -KNGNIIRIK | 138 |
| SEQ-ID-NO-1043 | EHGAPCFTQT | VHGSPESSQD | SSKKR--RKVVL | PSPSQA---- | -KNGNILRIK | 142 |
| SEQ-ID-NO-1040 | ELEQPVSSPQ | EPYSSDSTQS | SKRK-RCTLL | PNQDHE---- | -DAIKDR--- | 136 |
| SEQ-ID-NO-1029 | EHNEPVCLQN | CYLSDDGIR | SNKK-RKLEQ | ATNDDK---- | -PRNVFRIR | 125 |

| | | | | | | |
|---|---|---|---|---|---|---|
| SEQ-ID-NO-1024 | ----- | VFKKPKEEVP | TLPR-EAVVC | STTVAKSLS- | --------- | 174 |
| SEQ-ID-NO-1039 | F---- | VFKKPKEAEF | VVPQ-EDLVC | STS------- | --------- | 146 |
| SEQ-ID-NO-1042 | LKSNQDPQSV | LEKPRVLEQ | PLVQ-QMSSV | SSLSSKQNSI | -NRKVNVR | 184 |
| SEQ-ID-NO-1043 | RRDQDSSAS | LSEKSNVVQT | PI-VH-QMGSV | SSLPSKKNSM | QPHNTEMMWR | 190 |
| SEQ-ID-NO-1040 | L-------- | PLTKHSEPEK | SKQGFQFGSC | STSVGIGDSL | TQETRRIDRP | 177 |
| SEQ-ID-NO-1029 | L-------- | PLTRHKEPDV | PLN--SEGLC | STS-GRADSV | SGQNEGVHLS | 163 |

| | | | | | | |
|---|---|---|---|---|---|---|
| SEQ-ID-NO-1024 | ---------- | ---------- | ---------- | ---------- | ---------- | 174 |
| SEQ-ID-NO-1039 | ---------- | ---------- | ---------- | ---------- | ---------- | 146 |
| SEQ-ID-NO-1042 | S-TAGQQWVN | GDSQAVQKSL | VTETLSRAMQ | RTVPQPAVKV | TRRADPQLSV | 233 |
| SEQ-ID-NO-1043 | TASTQQQSIK | CDFQAV---- | ------LK | QGMPTPA-KV | MPRVDVPPSM | 227 |
| SEQ-ID-NO-1040 | L--------- | ---------- | ---------- | ---------- | ---------- | 178 |
| SEQ-ID-NO-1029 | ---------- | ---------- | ---------- | ---------- | ---------- | 163 |

Figure 12 (continued)

```
SEQ-ID-NO-1024  ----------  ----------  ----------  ----------  ----------  DVITSSISSS  186
SEQ-ID-NO-1039  ----------  ----------  ----------  ----------  ------HQGT  EISSSVSGHD  158
SEQ-ID-NO-1042  KAPVGRSDL-  PPKFSGSVGP  SPARVTCRFC  ----------  PAPVKTQQRI  EHPPSMVSQR  282
SEQ-ID-NO-1043  RASKERVGLR  PAEMLANVGP  SPSKAKQIVN  ----------  PAAAKVTQRV  DPPPAKASQR  277
SEQ-ID-NO-1040  ----------  ----------  ----------  ----------  -------TKV  ETPNQQLHRN  191
SEQ-ID-NO-1029  ----------  ----------  ----------  ----------  ------HQ--  ETVNSKAGTV  175

SEQ-ID-NO-1024  KTS-------  ----------  ----------  ----------  ---ELEKNL-  PSTSIAAIDE  205
SEQ-ID-NO-1039  ENL-------  ----------  ----------  ----------  -----LPASL  ESVETAILSE  176
SEQ-ID-NO-1042  VDP---QAKVS  QKEMGSAVCL  PQAP-----H  PPVLQKPKDL  PVPKQREPIN  325
SEQ-ID-NO-1043  LDPLLPSKVH  IDATRSFTKL  SQTEIKPEVQ  ----------  PPIPKVPVAM  PTINRQQIDT  327
SEQ-ID-NO-1040  SAS-------  ----------  ----------  ----------  -KVCKPLQNL  VPVDALEANK  213
SEQ-ID-NO-1029  VGE-------  ----------  ----------  ----------  ---LASPEKM  PCLSVSEKKS  195

SEQ-ID-NO-1024  TKKRK-----  ----------  ----------  ----------  --KHRSSKED  QYNALFDGWT  228
SEQ-ID-NO-1039  SKKKK-----  ----------  ----------  ----------  --KIHKTSKES  RYSSLFDFPV  199
SEQ-ID-NO-1042  SLPKEEPCFS  GRTVEADQGK  EAKLSRSDRK  KIHKTEKKNK  KFRDLFVTWN  375
SEQ-ID-NO-1043  SQPKEFPCSS  CRNAEAASVS  VEKQSKSDRK  KSRKAEKKEK  KFKDLFVTWD  377
SEQ-ID-NO-1040  TVDDE-----  ----------  ----------  ----------  ---SRCVES  LYKSLL---H  231
SEQ-ID-NO-1029  IVCHESGISR  FKLPN-----  ----------  ----------  --KKMRKADS  PYKVLIEDMV  228

SEQ-ID-NO-1024  PPSMCIADAS  SNDNGDYWLF  GNKTQEVLKP  KA----AVKV  DDDTMMRPGD  274
SEQ-ID-NO-1039  IPCLSIEEDD  GNS--DDWLL  SGRRQENSST  KS----TMDED  MVMNLQKSGE  244
SEQ-ID-NO-1042  PLLMENEGSD  LGG---QDWLF  SSTRSSDGSM  AQPTVPDGLG  PIHPMVQQQP  423
SEQ-ID-NO-1043  PPSMEMDDMD  LGD---QDWLL  GSTRKPDAGI  GN----CREIVD  PLTSQSAEQF  423
SEQ-ID-NO-1040  IQPIAYELFD  ALD---QDWLF  SSVKIEAKHV  SK-------K  QKTDAFRCSK  272
SEQ-ID-NO-1029  SPPPQFELND  SDD---QEWLS  EASKRERHGN  ------LN  ACRDVLCHES  270

SEQ-ID-NO-1024  SSWPRAQFLS  EVGLYSLPYT  VPF  297
SEQ-ID-NO-1039  SCFPSSQFLS  EVGTFSLPYT  VLF  267
SEQ-ID-NO-1042  YLQPRATELP  DLHIYQLPYV  VPF  446
SEQ-ID-NO-1043  SLQPRALHLP  DLHVYQLPYV  VPF  446
SEQ-ID-NO-1040  SLWPRAQFMP  EVNILALPYT  IPF  295
SEQ-ID-NO-1029  SLFPRGHYLP  EADVYALPYT  IPF  293
```

Figure 13

```
SEQ:ID:NO:1099  MAFLQDQFQR  H-YQQQQQPQ  P--------  ----------  ----------  28
SEQ:ID:NO:1139  MALPHHHLQL  H-IQQQPQQQ  S--------  ----------  ----------  27
SEQ:ID:NO:1100  MALPHHHLQL  H-IQQQPHQQ  Q--------  ----------  QTKSFRNL    30
SEQ:ID:NO:1101  MALPHHHLQL  HIQQQQPHQQ  Q--------  ----------  ---KSYRDIY  29
SEQ:ID:NO:1105  MAVQAQHLSH  A-FPHDLHAY  N--------  ----------  QQSKSYRDLY  22
SEQ:ID:NO:1134  MAVQAQYLSH  ASFPHDLYGL  R--------  ----------  ---SKSYRDLY 21
SEQ:ID:NO:1111  MAVEAHSLLL  A-GGHKQLTS  A--GWPWTT  ----------  -----SV     42
SEQ:ID:NO:1131  MAVEAHLLLH  A-GGQRPQLL  APHEGWAW-A ----------  ----------  48
SEQ:ID:NO:1047  MAVQAHHMN-  -FSQFISPN   R--------  GDEARC---   ATARPSHQQA  21
SEQ:ID:NO:1083  MPVQARHMN-  -FSPQLLSN   R--------  GDAACCEAPA  ATAAGQGQRR  19
SEQ:ID:NO:1085  MAVEASYMNL  -LPSQLLTN   R--------  ----------  ---DC       29
SEQ:ID:NO:1053  -MH-------  -EGSQLLPL   Y--------  ----------  ELIKSNQQLQ  11
SEQ:ID:NO:1057  MAVEAPHTNL  N-FPSHLLTN  R--------  ----------  DFAKVNQANM  30

SEQ:ID:NO:1099  QTEGQMSQQ   MAFYNPT--D  LQDQSQHPPY  PPF---GFA   PGPVIPA--D  71
SEQ:ID:NO:1139  NNMDGQISTP  VAYFNGS--N  LPEQSQHPPY  PPFQVVGLA   PG------L   68
SEQ:ID:NO:1100  NNMDGQITNP  VVYFNGS--N  LPEQSQHPPY  PPFQVVGLA   PG------T   71
SEQ:ID:NO:1101  NNMDGQITTP  VVYFNGS--N  LPEQSQHPPY  PPEQVVGLA   PG------T   70
SEQ:ID:NO:1105  GALEDEMTGG  SLFF-----  -PENLKRGPE  LEGAGNTVFG  DIPRVDP--T  63
SEQ:ID:NO:1134  -ALEGATAAG  SLFLDDH--G  CCAPATPAAA  AAGIGHTVLS  DLPRSELT-C  67
SEQ:ID:NO:1111  FQLQQASCVG  VGVGLPA--A  APVSSAAAAP  PAPMIAQQYA  AGCRLFVG-D  89
SEQ:ID:NO:1131  LAGKQQQQQH  YRFQQPC--A  A-TPAAAAGP  RLVAPTGRYA  PGPQLCAA-D  94
SEQ:ID:NO:1047  VKFQENMNHG  EFEFTGG--  -EVPLIT     GESFAVEPLA  AKANF---N   60
SEQ:ID:NO:1083  VNFKQDMNHG  EFITGET--L  AVDPLSNAAA  KPSF-----   CDP------N  52
SEQ:ID:NO:1085  HQLNSDYMYN  TTTQMDSSSA  LPQPATMPES  LSFYQSNF-   -QPL-----N  72
SEQ:ID:NO:1053  ----------  ---------  ----------  ----------  CHPNISA--N  23
SEQ:ID:NO:1057  SLYNTQMDSG  LVFNEP---   ----MPET    MPET        LSFYQSSLG   CDPVSAKASN 70
```

Figure 13 (continued)

| SEQ-ID | Seq1 | Seq2 | Seq3 | Seq4 | Seq5 | # |
|---|---|---|---|---|---|---|
| SEQ-ID-NO-1099 | GSDGGV-DLH | WNFGLE--- | ---PERKRLKE | QDFLENNSQ- | ISSVDFLQPR | 113 |
| SEQ-ID-NO-1139 | VDDGGL-DLQ | WNYGLE--- | -PKRKKRPKE | QDFLENNNSQ | ISSIDFLQPR | 111 |
| SEQ-ID-NO-1100 | ADDGGL-DLQ | WNYGLE--- | -PKKKRPKE | QDFMENNNSQ | ISSVDLLQRR | 114 |
| SEQ-ID-NO-1101 | ADDGGL-DLQ | WNYGLE--- | -PKKKRPKE | QDFMENNNSQ | ISSVDLFQRR | 113 |
| SEQ-ID-NO-1105 | WHDNTTRSHG | F--------- | -AQRKRARV | VPEAPSYLE- | ---------- | 91 |
| SEQ-ID-NO-1134 | NDNNGA-GYG | F--------- | -VPRKRARL | -DADESAGAL | MAAAAAQQQR | 104 |
| SEQ-ID-NO-1111 | AAESGV-TFG | GGGAV-QQE- | -APRKRKRA | ---------- | ---------- | 114 |
| SEQ-ID-NO-1131 | ASESCV-TFG | GGGGG-AQQQ | AMAPRKRKRA | ---------- | ---------- | 122 |
| SEQ-ID-NO-1047 | KAESGL-SYN | FTVPP----- | -LSTKRQRD | FQFSDSNAPV | ---------- | 92 |
| SEQ-ID-NO-1083 | KSESGL-TYN | FNSFNVVP-- | PPPRKRPRV | SQYLDSDARF | ASAV------ | 91 |
| SEQ-ID-NO-1085 | KADSGL-TYH | -P-------- | -LQRKRSRD | FTTELTSL-- | ---------- | 99 |
| SEQ-ID-NO-1053 | KADSGLTTYN | MSIPVS---- | -APRKRSRD | SFTNGFDS-- | ---------- | 55 |
| SEQ-ID-NO-1057 | KDDSGL-TYN | VPAVV----- | -APRKRSRD | SINDNFDAF- | ---------- | 101 |
| SEQ-ID-NO-1099 | SVSTGLGLSL | DNTRLASTGD | SALLSLIG-- | ----DDI--- | DRELQ-QQDL | 153 |
| SEQ-ID-NO-1139 | SVSTGLGLSL | DNGRLASSGD | SAFLGLVG-- | ----DDI--- | ERELQ-RQDA | 151 |
| SEQ-ID-NO-1100 | SVSTGLGLSL | DNGRLASSCD | SAFLGLVG-- | ----DDI--- | ERELQ-RQDA | 154 |
| SEQ-ID-NO-1101 | SVSTGLGLSL | DNGRLASSCD | SAFLGLVG-- | ----DDI--- | ERELQ-RQDA | 153 |
| SEQ-ID-NO-1105 | -NQRGQGLVP | VGDVLTRAVG | SGTASTSGRM | INAACPPQDL | LSQLY-RQGM | 139 |
| SEQ-ID-NO-1134 | MVLPPHGLVF | PGDVQSRAVG | CGAASTSGRA | GNAAGLSQGL | LSQLY-HQGV | 153 |
| SEQ-ID-NO-1111 | ---------- | ---EQGQTP | PPVLGTGA-- | ----ADV--- | AAQFQ-QQLV | 140 |
| SEQ-ID-NO-1131 | ---------- | ---GEGQ-P | APALRLAS-- | ----ADV--- | AARFQ-QQLV | 147 |
| SEQ-ID-NO-1047 | ---------- | ---KRRSVAFD | SSSPSLIN-- | ----VEL--- | VSQI-QNQQQS | 121 |
| SEQ-ID-NO-1083 | ---------- | ---KLGSGPFG | SPS-SLIN-- | ----AEL--- | VSHI-QNQQQL | 119 |
| SEQ-ID-NO-1085 | ---------- | ---PAHQKNKI | SSDPSFLN-- | ----QEI--- | LYQFQ-NQQS | 127 |
| SEQ-ID-NO-1053 | ---------- | ---YSLPQNNN | LSGASSDV-- | ----DDV--- | FSQIQ-QQH | 82 |
| SEQ-ID-NO-1057 | ---------- | ---HASQKTKV | CPFSSFID-- | ----QDI--- | FQIQ-QQQS | 129 |

Figure 13 (continued)

| SEQ-ID-NO-1099 | EMDRFLKLQG | EQLRQTILEK | VQATQLQSVS | IEDKVLQKL | REKETEVEN | 203 |
|---|---|---|---|---|---|---|
| SEQ-ID-NO-1139 | EIDRYIKVQG | DRLRQAJLEK | VQANQLQTVT | YVEEKVLQKL | REKETEVEDI | 201 |
| SEQ-ID-NO-1100 | EIDRYIKVQG | DRLRQAVLEK | VQANQIQAIT | YVEEKVLQKL | RERDTEVDDI | 204 |
| SEQ-ID-NO-1101 | EIDRYIKVQG | DRLRQAVLEK | VQANQIQAIT | YVEEKVLQKL | RERDTEVDDI | 203 |
| SEQ-ID-NO-1105 | EIDAVLRLET | DRMRAGLEEA | RQQHVRALVS | AAERAAARRL | RAAEAALELA | 189 |
| SEQ-ID-NO-1134 | EIDALVRLES | ERMRAGLEEA | RRRHVRAVVS | TVERAAAGRL | RAAEAELERA | 203 |
| SEQ-ID-NO-1111 | DVDRLVLQHT | AKMWAGLTEQ | RRRHARQVVA | TVEAAAAPRL | RAKEEEIQRM | 190 |
| SEQ-ID-NO-1131 | DVDRLVLQHT | SKMWADLREQ | RRRHAGQVVA | AVEAAAAKRL | RAKDEEIEHI | 197 |
| SEQ-ID-NO-1047 | EIDRFVAQQT | EKLRIEIEAR | QQTQTRMLAS | AVQNMLAKKL | KEKDDEIVRI | 171 |
| SEQ-ID-NO-1083 | EIDRFVAQQT | EKLRIEIEAR | QQTQTQMLAS | AVQNALAMKL | KEKDDEILRM | 169 |
| SEQ-ID-NO-1085 | EIDRVLAHHT | EKVRMELEEQ | KMRQSRMFVS | AIQEAMAKKL | KEKDQEIQRM | 177 |
| SEQ-ID-NO-1053 | DIDRFISDHT | EKLRLEVEER | RKRQSRMFTT | AIQERVMKKL | KEKDEEIQRI | 132 |
| SEQ-ID-NO-1057 | EIDRFIAEHN | QKVRMELEDR | RKRQSRMLVS | AIQGGMVRKL | TEKDEEIQRM | 179 |

| SEQ-ID-NO-1099 | NKRNMELEDQ | MEQLSVEAGA | WQQRARYNEN | MIAALKFNLQ | QAYLQGRDSK | 253 |
|---|---|---|---|---|---|---|
| SEQ-ID-NO-1139 | NKKNMELELR | TEQLALEANA | WQQRAKYNEN | LINTLKVNLQ | HVYAQSRDSK | 251 |
| SEQ-ID-NO-1100 | NKKNMELELR | MEQLALEANA | WQQRAKYNEN | LINTLKVNLQ | HVYAQSRDSK | 254 |
| SEQ-ID-NO-1101 | NKKNMELELR | MEQLDLEANA | WQQRAKYNEN | LINTLKVNLQ | HVYAQSRDSK | 253 |
| SEQ-ID-NO-1105 | RCRNAKLSER | TQICAEGQA | MTRVAKSHEA | VAAGLQATLD | QLLQSPCAAV | 239 |
| SEQ-ID-NO-1134 | RCRNMELEER | LRQMTAEGQA | WLSVAKSHEA | VAAGLRAITLD | QLLQSPCAAL | 253 |
| SEQ-ID-NO-1111 | RRVNWALEER | VKSMYVEAHM | WRDLAQSNDA | AVTIALRGELQ | QALDAQQTRR | 240 |
| SEQ-ID-NO-1131 | GRLNWALEER | VRSLYVEAQV | WRDLAQSNEA | AANALRGELQ | QALDAQQAR— | 246 |
| SEQ-ID-NO-1047 | RNLNWVLQER | VKSLYVENQI | WRDIAQTNEA | NANTLRTNLD | QVLAQIEFFP | 221 |
| SEQ-ID-NO-1083 | RNLNCVLQER | VKSLCMENQI | WRELAQTNES | QANNLRTNLD | QVLAQIELLP | 219 |
| SEQ-ID-NO-1085 | GKLNWALQER | VKSLYVENQL | WRDIAQTNEA | TANYLRSNLE | QVLAHVGEER | 227 |
| SEQ-ID-NO-1053 | GKLNWVLQER | VKSLYVETQI | WRDLAQTNEA | TANSLRNNLE | QVLAHAGDS— | 181 |
| SEQ-ID-NO-1057 | GKLNWVLQEK | VKSLYVETQI | WRDLAQANEA | TANSLRSNLE | QVLAHVSEDR | 229 |

Figure 13 (continued)

| SEQ-ID-NO | | | | | | |
|---|---|---|---|---|---|---|
| SEQ-ID-NO-1099 | EGCG---- | -------- | DSEVDDTAS | -CCNGRSLD- | -------- | -NSNMKDLMK-- | 290 |
| SEQ-ID-NO-1139 | EGCG---- | -------- | DSEVDDTAS | -CCNGRATD- | -FHLLSNE- | -SNEMKELMT-- | 288 |
| SEQ-ID-NO-1100 | EGCG---- | -------- | DSEVDDTAS | -CCNGRATD- | -LHLLCRD- | -SKEMKELMT-- | 291 |
| SEQ-ID-NO-1101 | EGCG---- | -------- | DSEVDDTAS | -CCNGRATD- | -LHLLCRD- | -SKEMKELMT-- | 290 |
| SEQ-ID-NO-1105 | AATGADG- | -------- | DGDAEDARS | -CCFETPAG- | -LHLLCRD- | -DAAASKASA-- | 273 |
| SEQ-ID-NO-1134 | AVAGAAGAGG | -------- | AEGDAEDAQS | -CCYETPCG- | -------D | -DAAASKTPAA-- | 297 |
| SEQ-ID-NO-1111 | -------- | -------- | -RADDADS | CCCGENDVFI | -GDNAGAD | -EAGTSSSSG-- | 276 |
| SEQ-ID-NO-1131 | ---CG-- | -GGVL | ADGGAGDAES | CCCGENDVA- | TEAGAAENEE | -DEGEDEAGT-- | 287 |
| SEQ-ID-NO-1047 | TAS----- | -------- | -AVVEDDAES | -SCGSC--- | -AGGTGAG | -EAVTAVGGG-- | 253 |
| SEQ-ID-NO-1083 | -------- | -------- | -TAVENDVES | -SCGSCVEG- | -CGDGCC | -EAITAVSGG-- | 246 |
| SEQ-ID-NO-1085 | ---GG-- | -------- | -ATVADDAQS | -SCGSNDAA- | ------G | -ASAAAATGRG-- | 260 |
| SEQ-ID-NO-1053 | -------- | -------- | -AALADDAES | -SCGSSDQGW | -EAGNDTA | -SCGAQDNNKA | 223 |
| SEQ-ID-NO-1057 | YING--- | -------- | -ATVADDAES | -SCGSSDHG- | REVVTPQAQG | -EEGAVKDKLV | 269 |

| SEQ-ID-NO | | | | | | |
|---|---|---|---|---|---|---|
| SEQ-ID-NO-1099 | -------- | -------- | -CKAC | RVNEVTMVLL | PCKHLCLCKD | C-ESK-LSFC | 322 |
| SEQ-ID-NO-1139 | -------- | -------- | -CKVC | RVNEVSMLLL | PCKHLCLCKE | C-ESK-LSLC | 320 |
| SEQ-ID-NO-1100 | -------- | -------- | -CRVC | RTNEVCMLLL | PCKHLCLCKE | C-ESK-LSLC | 323 |
| SEQ-ID-NO-1101 | -------- | -------- | -CRVC | RTNEVCMLLL | PCKHLCLCKE | C-ESK-LSLC | 322 |
| SEQ-ID-NO-1105 | -------- | -AACRAC | GEGESCVLLL | PCRHLCLCSA | C-DAA-VDTC | 307 |
| SEQ-ID-NO-1134 | -------- | -ALCKAC | GAGEASMLLL | PCRHLCLCRC | C-EAA-VDAC | 331 |
| SEQ-ID-NO-1111 | -------- | -HVI RACAVC | GDNAADVLLL | PCRHLCACAP | C-AAA-ARAC | 313 |
| SEQ-ID-NO-1131 | -PGT--- | -RRMCTVG | CEGAAEVLML | PCRHLCACAP | C-AGA-ARAC | 325 |
| SEQ-ID-NO-1047 | -------- | -CKRC | GEREASVLVL | PCRHLCLCTV | CGGSALL-RTC | 287 |
| SEQ-ID-NO-1083 | -------- | -RLCKNC | GEREASVLVL | PCRHLCLCTV | C-GSALL-RTC | 279 |
| SEQ-ID-NO-1085 | -------- | -CKRC | GLRESVLLL | PCRHLCLCTM | C-GST-VRNC | 294 |
| SEQ-ID-NO-1053 | VVVGNN-- | -NRKCRKC | GEKESSVLLL | PCRHLCLCTM | C-GST-MVGTC | 265 |
| SEQ-ID-NO-1057 | VVKDNNSSKN | I NHNRMCKKC | GERESSVLLL | PCRHLCLCTL | C-GSNL-GTC | 318 |

Figure 13 (continued)

| SEQ-ID-NO | Sequence | # |
|---|---|---|
| SEQ-ID-NO-1099 | PLCQSSKFIG MEVYM- | 337 |
| SEQ-ID-NO-1139 | PLCQSTKYIG MEIYM- | 335 |
| SEQ-ID-NO-1100 | PLCQSTKYIG MEVYM- | 338 |
| SEQ-ID-NO-1101 | PLCQSTKYIG MEVYM- | 337 |
| SEQ-ID-NO-1105 | PLCATTKNAS LHVLLS- | 323 |
| SEQ-ID-NO-1134 | PVCAATKNAS LHVLLS- | 347 |
| SEQ-ID-NO-1111 | PACGCAKNGS VCVNFS- | 329 |
| SEQ-ID-NO-1131 | PACGCAKNGS VCVNFS- | 341 |
| SEQ-ID-NO-1047 | PVCDMVMNAS VHVNMSS- | 304 |
| SEQ-ID-NO-1083 | PVCDSVMNAS VHVNMSS- | 296 |
| SEQ-ID-NO-1085 | PICDSDMDAS VHVNLS- | 310 |
| SEQ-ID-NO-1053 | PVCLSLTNAS VHVNML- | 281 |
| SEQ-ID-NO-1057 | PVCDSVMDAS VHVNMA- | 334 |

[Figure: Multiple sequence alignment showing protein sequences for SEQ-ID-NO-1258, 1263, 1211, 1215, 1264, 1209, 1223, 1246, 1151, 1155, and 1172.]

Figure 14 (continued)

| SEQ ID | Sequence | # |
|---|---|---|
| SEQ-ID-NO-1258 | R----WEQEM--------QQQQ YQQQ-MACYT QSQI PAG----TVWMVPSS | 255 |
| SEQ-ID-NO-1263 | R----RSEDKD LQHNNYHMSN MLQSSTYGSI PASHQIGHIP | 226 |
| SEQ-ID-NO-1211 | R----PEQEL---SQMGS YLIQSSTGSL PASHASN---- ATTLYMMTNN | 295 |
| SEQ-ID-NO-1215 | RTSSGGSEQD LSSLQHQMGS YLMQSSAGSI PASHTQI---- TAAFWMVAGH | 319 |
| SEQ-ID-NO-1264 | R----AEQELQ QHQ-HHQIGN YLVQSSTGPM AASHASI---- PANIWMVANS | 285 |
| SEQ-ID-NO-1209 | ----------DEMGS FATPACFWAV PARPDFG---- PANFMTLANS | 180 |
| SEQ-ID-NO-1223 | ----------VTAAM APAP-GFWAL PARGDFG---- QVWSFASH | 201 |
| SEQ-ID-NO-1246 | ----------EPTVA APAP-GFWAL PCRADLG---- QLWSFAPP | 165 |
| SEQ-ID-NO-1151 | S---------ETSGP TAAP-MWAVA PPSRSGA---- QLWSFAAA | 263 |
| SEQ-ID-NO-1155 | RTGMPEQEPG LF---QITNV MPAPAMWAVA PATTNGG---- GNTFWMLPVP | 246 |
| SEQ-ID-NO-1172 | RAGVQDQETA GSI-RPTTNM LPTPMWAVA PAATTNG---- NAFWMLPVG | 299 |
| | | |
| SEQ-ID-NO-1258 | ---NAQAAGG GAPPGGGG--- -----ESIWT FPQSC-SCGG GGAATVYRGV | 294 |
| SEQ-ID-NO-1263 | ---NNNTSHH DPNN------ ----CSMWA SPSNS---- --NIENS | 252 |
| SEQ-ID-NO-1211 | ---GNQAMSG GGSVGGCNNG SSDN-NPIWA LPSVG---- --NSGVYRGA | 334 |
| SEQ-ID-NO-1215 | ---NNQIMSG G--------- -----DPIWT FPSVN NNSA NSAAALYRGA | 347 |
| SEQ-ID-NO-1264 | ---SNNNNNN NNNNNNNGMG S---DPIWT QQAAM AAAAXLYRGT | 328 |
| SEQ-ID-NO-1209 | ---QEMFLQQ QQQQQQQPAA AALFVHQQQQ APAMA | 212 |
| SEQ-ID-NO-1223 | ---P------ ----------VAAAA EMMAA | 212 |
| SEQ-ID-NO-1246 | ---PEMM--- ---------- ---------- TPAMA | 179 |
| SEQ-ID-NO-1151 | TTAGNQMESS SNNNTAAGHR A-----PPMWP FVNSAGGGAG GGGGAATHFM | 309 |
| SEQ-ID-NO-1155 | ---GGATAAS ATVPE----- -----AQMWT FPAHY---- | 268 |
| SEQ-ID-NO-1172 | ---GGATPLS SVQE------ -----PQMWT FPAAA---- AGVPSMQRVN | 330 |
| | | |
| SEQ-ID-NO-1258 | ---PSGLHFM NFPATPM--- ------AL-- PGGQQLGLAG AGGG-GEGHP | 330 |
| SEQ-ID-NO-1263 | NIRGGLLNFM NFHQPTL--- ---------- -GTRGGGGGGG TA---AEGQW | 285 |
| SEQ-ID-NO-1211 | MSAPGCIHFM NF-ASPMNLM PGGQLGSGIV GGGGGGGNL- GAQLLSESNL | 383 |
| SEQ-ID-NO-1215 | VS-TSGLHFM NF-PQPMALL PGGQLG-NSS GGGGGGNL-- MNMMMNEGHL | 394 |
| SEQ-ID-NO-1264 | V---SSGLHFM NF-PAPV--- ------AL-- PSQQIGGNV- -LGEGQL | 360 |
| SEQ-ID-NO-1209 | ---------- ---------- ---------- GEASAARVG NYLP-GHL | 228 |
| SEQ-ID-NO-1223 | ---------- ---------- ---QLG-SFL GEASAARVG NYLPMAQANL | 231 |
| SEQ-ID-NO-1246 | ---------- ---------- ---QLG-SMI GEASAARVG NYLPMAQGNL | 198 |
| SEQ-ID-NO-1151 | AGTGFSFPMD QYRGSPL--- ---QLG-SMI AQPQPTQNLG LSMP--DSNL | 350 |
| SEQ-ID-NO-1155 | --SGGGR--- ---GNPV--- ---------- LQQQQAGQQ LGLGVTETNM | 303 |
| SEQ-ID-NO-1172 | FGGGGGRV-- ----SSPV--- ---------- VQQQVGANQQ LGLGISESNM | 368 |

Figure 14 (continued)

| | | | | | | | |
|---|---|---|---|---|---|---|---|
| SEQ-ID-NO-1258 | GIL-AALNAY | RAQAAQPDAG | AAAQNGAQGS | SQHRQHQHHG | GGGGGDERH | 379 |
| SEQ-ID-NO-1263 | GMLT-AAMNSY | RQ------- | ---SGG---- | ----HASGSS | NQHNGGDDHQ | 316 |
| SEQ-ID-NO-1211 | GML-AALNAY | RQIPAN---- | ---GVS---- | ----EPPGSA | GQHHGGDDGR | 417 |
| SEQ-ID-NO-1215 | SML-AGLSPY | RPVSDHHQQH | HQPSGS---- | ----QSHHHR | SGSHEHDDRH | 435 |
| SEQ-ID-NO-1264 | G---NFMNPY | RNIGG----- | ---------- | ----ASESQA | SGSHGGDDRH | 391 |
| SEQ-ID-NO-1209 | NLL-ASLS-- | ---------- | ---GGA---- | -------PG | SGRREDDQR- | 249 |
| SEQ-ID-NO-1223 | NLL-ASFS-- | ---------- | ---GGP---- | ----GCAGQA | TGRAEEETAH | 257 |
| SEQ-ID-NO-1246 | NLL-AYFS-- | ---------- | ---GGP---- | ----APTAT | AGRAEEESAR | 223 |
| SEQ-ID-NO-1151 | GML-AALNSA | YSRGGNAN-- | ---ANAEQAN | NAVEHQEKQQ | QSDHDDDSRE | 394 |
| SEQ-ID-NO-1155 | GLLGSGMNVY | SN-------- | ---NNRVGLK | MNLEQQHHHE | NQTQGSDSGD | 342 |
| SEQ-ID-NO-1172 | GMLGGVNPY | SSSRVGLG-- | ---MNL---- | ----EHHNQD | NQPQGSDSGD | 405 |

| | | |
|---|---|---|
| SEQ-ID-NO-1258 | ESMSASDS | 387 |
| SEQ-ID-NO-1263 | HHS----- | 319 |
| SEQ-ID-NO-1211 | DSTSQHS- | 424 |
| SEQ-ID-NO-1215 | DN------ | 437 |
| SEQ-ID-NO-1264 | DSTSHHS- | 398 |
| SEQ-ID-NO-1209 | -------- | 249 |
| SEQ-ID-NO-1223 | -------- | 257 |
| SEQ-ID-NO-1246 | -------- | 223 |
| SEQ-ID-NO-1151 | ENSNSSE- | 401 |
| SEQ-ID-NO-1155 | ENPATDSQ | 350 |
| SEQ-ID-NO-1172 | ENPNDSQ- | 412 |

| | | | | | | |
|---|---|---|---|---|---|---|
| SEQ-ID-NO-1301 | SGDVGT | LLKWRAR | YGS | TLQSCVI | LGG | TL V DR | 180 |
| SEQ-ID-NO-1317 | SGDVGT | LLKWRAE | YGS | TLQSCVI | LGG | TR V DR | 178 |
| SEQ-ID-NO-1303 | AGEL D | MLKWKA | DFGS | TLGSCVI | LGA | SSASASPSPS | 233 |
| SEQ-ID-NO-1326 | AGEL S | LLKWKA | DFGS | TLGSCVI | LGA | SSA GK | 236 |
| SEQ-ID-NO-1279 | G GEL GI | LLKWRA | DFGS | TLDSCVI | LGA | ASVF NNVHFQ | 219 |
| SEQ-ID-NO-1285 | SGEL GI | LLKWRA | DFGS | TLDNCVI | LGA | ASVI TNN--K | 228 |
| SEQ-ID-NO-1294 | SGEL GI | LLKWRA | EFGS | TLENCVI | LGA | SSVI P-- | 213 |
| SEQ-ID-NO-1277 | SGEL GI | LLKWRA | EFGS | TLDNCVI | LGA | SSVI | 228 |

| | | | | | | |
|---|---|---|---|---|---|---|
| SEQ-ID-NO-1301 | ---- | EPSAAED | GGS | MPESFYTNGG | S | KLRVVWTI S | 226 |
| SEQ-ID-NO-1317 | ---- | HEPSLED | NGS | MPESFYTNGG | S | KLRVVWTI S | 224 |
| SEQ-ID-NO-1303 | PS--- | EPDECV | DSGS | IPESFYTNGG | S | F KLRVVWTI S | 281 |
| SEQ-ID-NO-1326 | PA--- | D | -- E T GS | IPESFYTSGG | S | KLRVVWTI S | 279 |
| SEQ-ID-NO-1279 | INGS | NVGNG D | --- | IPESFYTNGG | S | KLRVVWTI S | 264 |
| SEQ-ID-NO-1285 | AA-- | AAAADD | --- | IPESFYTNGG | S | KLRVVWTI S | 271 |
| SEQ-ID-NO-1294 | SS-- | AP VAAV | E-- | IPESFYTNGG | S | KLRVVWTI S | 256 |
| SEQ-ID-NO-1277 | VE--- | APGSGS | D-- | IPESFYTNGG | S | KLRVVWTI S | 271 |

| | | | | | | |
|---|---|---|---|---|---|---|
| SEQ-ID-NO-1301 | LLRSI | KEHP | TL RSLVLA DA | DGQGT L CMGA | EQLA E FRESR | LSASAC SNRT | 276 |
| SEQ-ID-NO-1317 | LLRSI | KDHP | TL TSLVLTDA | DGQGT L CMGA | EQLKEFRENQ | SASACSNRT | 274 |
| SEQ-ID-NO-1303 | LLQPI | ADHK | TLER DL TDA | DGQGVLT MDK | CQLQELRVRP | VS T SRGSHRT | 331 |
| SEQ-ID-NO-1326 | LLQPI | ADHT | TLESLDL TDA | DGQGVLT MDK | WQLQELRVKP | VSASGGSHRT | 329 |
| SEQ-ID-NO-1279 | LLQSI | AEHK | TLDSLVLTDA | DGQGVLCMNG | EQLEELRVKP | LSASSASKRT | 314 |
| SEQ-ID-NO-1285 | LLQPI | AEHK | TLDSLVLA DA | DGQGVLCMNR | EQLEELRVKP | LSASSASKRT | 321 |
| SEQ-ID-NO-1294 | LLQPI | AEHK | TLDSLVLTD V | DGQGVLCMNR | DQLEELRVKP | LSASSASKRT | 306 |
| SEQ-ID-NO-1277 | LLQPI | AEHK | TLDSLVLTDS | DGQGVLCMNR | DQLEELRVKP | LAASSASKRT | 321 |

| | | | | | | |
|---|---|---|---|---|---|---|
| SEQ-ID-NO-1301 | QVPA C SMKLK | YAPYLELPGG | L GL QGATLVA | IKPSG D GA CG | CH V GRKETE A | 326 |
| SEQ-ID-NO-1317 | QVPA C NMKLK | YAPYLELPGG | A L QGATLVA | KPST EGSNG | GHTSRKETDA | 324 |
| SEQ-ID-NO-1303 | L MPE L SM W L W | YAPC ELPGG | LVL NGATLVA | KPSEEGTGD | TVWNGA AGAA | 381 |
| SEQ-ID-NO-1326 | L MPALSMRLW | YAPHI ELPCG | LVL NGATLVA | KPTEEATRD | TVGS G I AGSA | 379 |
| SEQ-ID-NO-1279 | L VPALNMRLW | YAPH L DLPDG | VVL QGATLVA | RPSEQS ASK | KEVSD A S | 361 |
| SEQ-ID-NO-1285 | L VPALNMRLW | YAPH L ELPDG | VVLKGATLVA | RPSEQ AATK | KDVSDVS | 368 |
| SEQ-ID-NO-1294 | L VPALNMRLW | YAPS L ELPDG | T VLKGATLVA | RPSE -- SK | KEV C DVS | 350 |
| SEQ-ID-NO-1277 | L VPALNMRLW | YAPT L ELPDG | TVLKGATLVA | RPSE --- SK | KEVSDIS | 365 |

Figure 15 (continued)

| | | | | | |
|---|---|---|---|---|---|
| ---FVSGAFD | GPFRFAAKAL | MKRRTYLLEM | NGF | 356 | SEQ-ID-NO-1301 |
| ---FISGAFD | GPFKVAVKAL | TKRRTYLLEM | NGF | 354 | SEQ-ID-NO-1317 |
| ---WVLDAFE | EPYRTAVRML | LKQRTYSLEM | NSF | 411 | SEQ-ID-NO-1303 |
| GGCWVSDAFE | EPYRTAVGML | LKRRTYSLEM | NSF | 412 | SEQ-ID-NO-1326 |
| ---WLSSAFE | EPYGTAAKML | VKRRTYCLEM | NSF | 391 | SEQ-ID-NO-1279 |
| ---WVSTIFE | EPYGTAAKML | VKRRTYCLEM | NSF | 398 | SEQ-ID-NO-1285 |
| ---WVSSAFD | EPYGVAAKML | VKRRTYCLEM | NSF | 380 | SEQ-ID-NO-1294 |
| ---WVSSAFE | EPYETAAKML | VKRRTYCLEM | NSF | 395 | SEQ-ID-NO-1277 |

| SEQ-ID-NO-1427 | -GG|FVKVSM|DGAPYLRKID|LRVYGGYSEL|LKALETMFK-|LT|GEYSERE| | 138 |
|---|---|---|---|---|---|---|---|
| SEQ-ID-NO-1430 | -GG|FVKVSM|DGAPYLRKID|LRVYGGYSEL|LKALETMFK-|LT|GEYSERE| | 138 |
| SEQ-ID-NO-1419 | QGF|LYVKVSM|DGAPYLRKID|LKT|YKNYKDL|STALE|KMFSG|FIST|GKDGLSE| | 185 |
| SEQ-ID-NO-1422 | QGF|LYVKVSM|DGAPYLRKID|LKT|YKNYKDL|STALE|KMFSG|FIST|GKDGSXE| | 187 |
| SEQ-ID-NO-1347 | RSSMYVKV|KM|DGVA|ARKVD|KLFNSYES|L|TNSL|TMFT-|----|EY|EDC| | 200 |
| SEQ-ID-NO-1431 | SKPLYVKVNM|EGVGMGRQIN|LRLYNSYQTL|KDSL|SMFV-|----|KC|QNF| | 166 |
| SEQ-ID-NO-1429 | SNSMY|KVKM|EGVGI ARKID|VS|VYRC|PTL|KHTL|DMFG-|----|CQ--| | 191 |

| SEQ-ID-NO-1427 | GYK|GSEYAPT|YEDKDCGDWML|VGDVPWDMFV|TSCKRLRI MK|GTEAKGLGCG | 188 |
|---|---|---|---|---|---|---|
| SEQ-ID-NO-1430 | GYK|GSEYAPT|YEDKDGGDWML|VGDVPWD--V|TSCKRLRI MK|GTEAKGLGCG | 186 |
| SEQ-ID-NO-1419 | YRKDGEYVLT|YEDKDGDWML|VGDVPWEMFA|DSCRRLRI MK|GSDA|GLAPR | 235 |
| SEQ-ID-NO-1422 | YRKDGEYVLT|YEDKDGDWML|VGDVPWEMFA|GSCRRLRI MK|GSDA|GLAPR | 237 |
| SEQ-ID-NO-1347 | DRED|TNY|FT|FQ|KEGDWLL|RGDVT|WKI FA|ESVHRI|S|IR|DRPCAYTRCL | 250 |
| SEQ-ID-NO-1431 | EETGANY|LT|FQNK|QGEWK|TSH|TWQ|SF|GT|VRRLA|LR|NGE|CETI-- | 213 |
| SEQ-ID-NO-1429 | -ENS|SNY|RLT|YQDREGDWLL|AE|DVPWRNFL|GS|VQRL KLMR|S|SN------ | 233 |

| SEQ-ID-NO-1427 | V-------- | 189 |
|---|---|---|
| SEQ-ID-NO-1430 | V-------- | 187 |
| SEQ-ID-NO-1419 | AADKSKNRN | 244 |
| SEQ-ID-NO-1422 | AADKSKNRN | 246 |
| SEQ-ID-NO-1347 | F-------- | 251 |
| SEQ-ID-NO-1431 | --------- | 213 |
| SEQ-ID-NO-1429 | --------- | 233 |

| SEQ-ID-NO | | | | | | |
|---|---|---|---|---|---|---|
| SEQ-ID-NO-1480 | VAVRGS--VYS | PGQSVTSPSQ | HTYPGAV--TN | WPLSRSASFI | ASPRWPGHSS | 227 |
| SEQ-ID-NO-1475 | VAVRGS--VYS | PGQSATSPGH | HAYQGAV--TS | WPLSRSASFI | ASPRWPGHSS | 225 |
| SEQ-ID-NO-1477 | VAVRGS--GYS | PGQSATSPGQ | HAYQGAV--TS | WPLSRSTSFI | ASPRWPGHSN | 232 |
| SEQ-ID-NO-1471 | ASSRGSPLYP | PVHNSGSTGP | HSYTGTM--AS | WTYPR--GSFI | PSPRWQSPSN | 244 |
| SEQ-ID-NO-1457 | VP-------- | ---------- | QSYPL------ | WS----R-ASFI | ASPRWQDPSS | 192 |
| SEQ-ID-NO-1467 | VP-------- | ---------- | QSYPL------ | WS----R-ASFI | ASPRWQDPSS | 192 |
| SEQ-ID-NO-1460 | VSLRGSPIYQ | TVPSPATPGQ | QSHPGGI--TN | WS----R-ASFI | PSPRWQGPSS | 224 |
| SEQ-ID-NO-1462 | VPLRGSPIYP | TVSSPTTPGQ | QSYPGGLAIT | WS----R-ASFI | TSPRWQAPSS | 223 |
| SEQ-ID-NO-1480 | YAQVIVPPGL | VQVPGWNPYA | AQIGSISSSDD | QQ-RTACGAQ | YYTGSRHSET | 276 |
| SEQ-ID-NO-1475 | YAQVIVPPGL | VQVPGWSPYA | AQIGSISSSDD | QQ-RTPGAAQ | YYTGSRQSCT | 274 |
| SEQ-ID-NO-1477 | YAQVLVPPGL | VQVPGWNPYT | AQIGSISSSED | QQ-QTPGAAQ | YYTGSRQSGT | 281 |
| SEQ-ID-NO-1471 | YTPMIVPQGL | VQVPNWNSYP | CQMVPVSSPE | SRLQSPGAQQ | YYGTSROGEA | 294 |
| SEQ-ID-NO-1457 | YASLIMPRGV | VPVQGWNPYS | CQLGSVSPSG | -------TGNDQ | NYRNLQQNET | 237 |
| SEQ-ID-NO-1467 | YASLIMPQGV | VPVQCWNPYS | CQLGSVSPSG | -------TGNDQ | NYRNLQQNET | 237 |
| SEQ-ID-NO-1460 | YASLILPQGM | VSVPGWNAYS | CQLASVSSSE | NLQQTNVNHQ | IHGTSRQNES | 274 |
| SEQ-ID-NO-1462 | YTPLILPQGV | VSVPGWNAYS | CQLGSVSSPE | SQ-QQTGNSQ | IYGTSRHSES | 272 |
| SEQ-ID-NO-1480 | -DQGM | FSSYQAG--SV | PL--GLYTVQR | ESIFPERPDQ | PECQFYMKTG | 322 |
| SEQ-ID-NO-1475 | -DRCM | FSSYQAG--SV | PV--GLYAVQT | ENVFPERPDQ | PECQFYMKTG | 320 |
| SEQ-ID-NO-1477 | -DQGM | FSSYQAG--SV | PV--GLYAVQR | ENVFPERPDQ | PECQFYMKTG | 327 |
| SEQ-ID-NO-1471 | -NQGM | QSPYRSS--SF | PA-PQYALQR | ENVFPERPDQ | PECIYYIKTG | 339 |
| SEQ-ID-NO-1457 | ESGSQSQGS | FSGYNPGSSV | PLGGYYALPR | ENVFPERPGQ | PECQFYMKTG | 287 |
| SEQ-ID-NO-1467 | ESGSQSQGS | FSGYNPGCSV | PLGGYYALPR | ENVFPERPGE | PECQFYMKTG | 287 |
| SEQ-ID-NO-1460 | ATAG--SQAS | FSELRSG--SV | PV--GVYALQR | ENVFPERPCE | PECQFYMKTG | 320 |
| SEQ-ID-NO-1462 | VNAG--SQGT | FSPYRSG--SA | PL--GFYALQR | ESVFPERPGQ | PECQFYMKTG | 318 |
| SEQ-ID-NO-1480 | DCKFGAVCKF | HHPKERIIPT | PNCALSSLGL | PLRPGEPICT | FYSRYGICKF | 372 |
| SEQ-ID-NO-1475 | DCKFGSVCKF | HHPRERIIPT | PNCALSPLGL | PLRPGEPICS | FYNRYGMCKF | 370 |
| SEQ-ID-NO-1477 | DCKFGVMCKF | HHPRERIPA | PNCALSSLGL | PLRPGEPICS | FYSRYGMCKF | 377 |
| SEQ-ID-NO-1471 | DCKFGAVCKF | HHPRVRSQPP | PDCILSPMGL | PLRPGEELCK | FYTRYGICKF | 389 |
| SEQ-ID-NO-1457 | DCKFGTVCKF | HHPRDRQAPP | PDCLLSSIGL | SLRPGEPLCV | FYTRYGICKF | 337 |
| SEQ-ID-NO-1467 | DCKFGTVCKF | HHPRDRQAPP | PDCLLSSIGL | PLRPGEPLCI | FYSRYGICKF | 337 |
| SEQ-ID-NO-1460 | DCKFGAVCKF | HHPRERVLPA | PDCVLSPIGL | PLRPGEPLCI | FYSRYGICKF | 370 |
| SEQ-ID-NO-1462 | DCKFGAVCRF | HHPRERLIPA | PDCVLSPIGL | PLRPGEPLCI | FYSRYGICKF | 368 |

Figure 17 (continued)

| | | | | | |
|---|---|---|---|---|---|
| SEQ·ID·NO·1480 | GPNCKFDH------ | --PMGTVMYG | LATSPTGDVS | ARRM------ | -APVPAHSEV | 412 |
| SEQ·ID·NO·1475 | GPNCKFHH------ | --PMGNPMYG | HASSPTSEAQ | TSRRM------ | LAHVPSHPEV | 411 |
| SEQ·ID·NO·1477 | GPNCKFDH------ | --PIGTVMYG | HVSSPTSEVP | TSRRM------ | LAYVPSHPEV | 418 |
| SEQ·ID·NO·1471 | GVNCKFDHPM | AAPMGVYAYG | YSASASPNAP | M--------- | ---------- | 420 |
| SEQ·ID·NO·1457 | GPSCKFDH------ | --PMRVFTYD | NTASETDEV- | ---------- | ---------- | 362 |
| SEQ·ID·NO·1467 | GPSCKFNH------ | --PMRVFTYD | NTASETDEV- | ---------- | ---------- | 362 |
| SEQ·ID·NO·1460 | GPSCKFDH------ | --PMGIFTYS | YSPSSPSDAP | VHCFLGSSSG | TAGLNLSSEG | 416 |
| SEQ·ID·NO·1462 | GPSCKFDH------ | --PMGVFTYN | LTASSADAP | VRRLLGSSSG | SPGLTLSSEG | 414 |

| | | | | | |
|---|---|---|---|---|---|
| SEQ·ID·NO·1480 | SPDNVSGRSR | RITHSDSQQI | PSGERGTERE | AS-------- | 444 |
| SEQ·ID·NO·1475 | SPDSGSGRSR | RIVHSDSQQI | PSVERITERE | AS-------- | 443 |
| SEQ·ID·NO·1477 | LPDNGSGRSR | RITHSDSQQI | PSGERSTERE | AS-------- | 450 |
| SEQ·ID·NO·1471 | -------GR | RLLESPSGSA | YAS------- | ---------- | 435 |
| SEQ·ID·NO·1457 | -VETSTGKSR | RLSVSETRQA | ATTSSGKDTT | IDNTQQ | 397 |
| SEQ·ID·NO·1467 | -VETSTGKSR | RLSVSETRQA | ATTSSGKDTT | IDNTQQ | 397 |
| SEQ·ID·NO·1460 | LVEAVPTKPR | RLSLSENRQL | SPSDD-IDAE | G--------- | 446 |
| SEQ·ID·NO·1462 | LVEAGPTKPR | RLSLSEPRQM | PPGDDNIDTG | G--------- | 445 |

Figure 18

| SEQ-ID-NO | | | | | | |
|---|---|---|---|---|---|---|
| SEQ-ID-NO:1512 | MSVSSSMGG | GGGDAGGRT | VWFRRDLRV | EDNPALAAAA | RAGGEVVPAY | 50 |
| SEQ-ID-NO:1499 | ---MSG | ------ | VWFRRDLRV | EDNPALAACV | RA-GAVAVF | 36 |
| SEQ-ID-NO:1506 | ---MSNCSC | G------ | VWFRRDLRV | EDNPALAAAV | RA-GPVIAVF | 41 |
| SEQ-ID-NO:1497 | MSGSVSGCGS | GGCS | VWFRRDLRV | EDNPALAAAV | RA-GPVIALF | 43 |
| SEQ-ID-NO:1502 | MSGSVSGCGS | GGCS | VWFRRDLRV | EDNPALAAAV | RA-GPVNALF | 43 |

| SEQ-ID-NO:1512 | VWAPEEDGPY | YPGRVSRWWL | SQSLKHLDAS | LRRGACKLV | TRRSADAVVA | 100 |
|---|---|---|---|---|---|---|
| SEQ-ID-NO:1499 | VWAPEEEGHY | YPGRVSRWWL | KQSLAHLDSS | LRSLCTS--LV | TKRSTDSVST | 85 |
| SEQ-ID-NO:1506 | VWAPEEEGHY | QPGRVSRWWL | KNSLAQLDSS | LRSLGTC--LI | TKRSTDSVAS | 90 |
| SEQ-ID-NO:1497 | VWAPEEEGHY | HPGRVSRWWL | KNSLAQLDSS | LRSLGTC--LI | TKRSTDSVAS | 92 |
| SEQ-ID-NO:1502 | VWAPEEEGHY | HPGRVSRWWL | KNSLAQLDSS | LRSLGTC--LI | TKRSTDSVAS | 92 |

| SEQ-ID-NO:1512 | LLQLVRDTGA | TRLFFNHLYD | PISLVRDHRL | KEMMAEGIL | VQSFNADLLY | 150 |
|---|---|---|---|---|---|---|
| SEQ-ID-NO:1499 | LLEVIKSTGA | TQLFFNHLYD | PLSLVRDHRA | KEVLTAQGIA | VRSFNADLLY | 135 |
| SEQ-ID-NO:1506 | LEVVKSTGA | SQIFFNHLYD | PLSLVRDHRA | KDALTAEGIA | VKSFNADLLY | 140 |
| SEQ-ID-NO:1497 | LDVVKSTGA | SQIFFNHLYD | PLSLVRDHRA | KDVLTAQGIA | VRSFNADLLY | 142 |
| SEQ-ID-NO:1502 | LDVVKSTGA | SQIFFNHLYD | PLSLVRDHRA | KDVLTAQGIA | VRSFNADLLY | 142 |

| SEQ-ID-NO:1512 | EPWEVVDDEG | QSFTMFAPFW | NRCLSMPYDP | AAPLLPPKR | NSGDLSMCPS | 200 |
|---|---|---|---|---|---|---|
| SEQ-ID-NO:1499 | EPWDVNDAQG | RPFTTFATFW | DRCLSMPFDP | EAPLLPPKKI | SGDASRCPS | 185 |
| SEQ-ID-NO:1506 | EPWEVTDELG | RPFSMFAAFW | ERCLSMPYDP | ESPLLPPKKI | SGDVSKCVA | 190 |
| SEQ-ID-NO:1497 | EPWEVTDELG | RPFSMFAAFW | ERCLSMPYDP | ESPLLPPKKI | SGDVSKCVA | 192 |
| SEQ-ID-NO:1502 | EPWEVTDELG | RPFSMFAAFW | ERCLSMPYDP | ESPLLPPKKI | SGDVSKCVA | 192 |

| SEQ-ID-NO:1512 | DDLIFEDDSE | RGSNALLARA | WSPGWQNADK | ALTAFLNGPL | HYSMNRKKA | 250 |
|---|---|---|---|---|---|---|
| SEQ-ID-NO:1499 | EMLVFEDELE | KGSNALLARA | WSPGWSNADR | ALTFINGPL | EYSKNRRKA | 235 |
| SEQ-ID-NO:1506 | DTLIFEDESE | KGSNALLARA | WSPGWSNADK | ALTFINGPL | EYSKNRRKA | 240 |
| SEQ-ID-NO:1497 | DPLVFEDDSE | KGSNALLARA | WSPGWSNGDK | ALTFINGPL | EYSKNRRKA | 242 |
| SEQ-ID-NO:1502 | DPLVFEDDSE | KGSNALLARA | WSPGWSNGDK | ALTTFINGPL | EYSKNRRKA | 242 |

| SEQ-ID-NO:1512 | DSASTSLLSP | YLHFGELSVR | KVFHLVRMKQ | LVWSNEGNRA | AEESCTLFLR | 300 |
|---|---|---|---|---|---|---|
| SEQ-ID-NO:1499 | DSATTSFLSP | HLHFGEVSVR | KVFHLVRIKQ | VLWANEGNKA | GEESVNLFLK | 285 |
| SEQ-ID-NO:1506 | DSATTSFLSP | HLHFGEVSVR | KVFHLLRIKQ | VAWANEGNQA | GEESVNLFLK | 290 |
| SEQ-ID-NO:1497 | DSATTSFLSP | HLHFGEVSVR | KVFHLVRIKQ | VAWANEGNEA | GEESVNLFLK | 292 |
| SEQ-ID-NO:1502 | DSATTSFLSP | HLHFGEVSVR | KVFHLVRIKQ | VAWANEGNEA | GEESVNLFLK | 292 |

Figure 18 (continued)

| SEQ ID NO | Sequence | Position |
|---|---|---|
| SEQ-ID-NO-1512 | SIGLREYSRY LSFNHPCSHE KPLLAHLRFF PWMNECYFK IWRQGRTGYP | 350 |
| SEQ-ID-NO-1499 | SIGLREYSRY LSFNHPYSHE RPLLGHLKFF PWMVDGGYFK AWRQGRTGYP | 335 |
| SEQ-ID-NO-1506 | SIGLREYSRY ISFNHPYSHE RPLLGHLKFF PWAVDENYFK AWRQGRTGYP | 340 |
| SEQ-ID-NO-1497 | SIGLREYSRY ISFNHPYSHE RPLLGHLKFF PWAVDENYFK AWRQGRTGYP | 342 |
| SEQ-ID-NO-1502 | SIGLREYSRY SFNHPYSHE RPLLGHLKFF PWAVDENYFK AWRQGRTGYP | 342 |
| | | |
| SEQ-ID-NO-1512 | LVDAGMRELW ATGWLHDRIR VVVSSFFVKV LQLPWRWGMK YFWDTLLDAD | 400 |
| SEQ-ID-NO-1499 | LVDAGMRELW ATGWLHDRIR VVVASFFVKV LQLPWRWGMK YFWDTLLDAD | 385 |
| SEQ-ID-NO-1506 | LVDAGMRELW ATGWLHDRIR VVVSSFFVKV LQLPWRWGMK YFWDTLLDAD | 390 |
| SEQ-ID-NO-1497 | LVDAGMRELW ATGWLHDRIR VVVSSFFVKV LQLPWRWGMK YFWDTLLDAD | 392 |
| SEQ-ID-NO-1502 | LVDAGMRELW ATGWLHDRIR VVVSSFFVKV LQLPWRWGMK YFWDTLLDAD | 392 |
| | | |
| SEQ-ID-NO-1512 | LESDALGWQY SGSLPDGRE LDRIDNPQLE GYKFDPHGEY VRRWLPELAR | 450 |
| SEQ-ID-NO-1499 | LESDALGWQY ITGTLPDGRE FDRIDNPQFE GYKFDPNGEY VRRWLPELAR | 435 |
| SEQ-ID-NO-1506 | LESDALGWQY ITGTLPDSRE FDRIDNPQFE GYKFDPNGEY VRRWLPELSR | 440 |
| SEQ-ID-NO-1497 | LESDALGWQY ITGTLPDSRE FDRIDNPQFE GYKFDPNGEY VRRWLPELSR | 442 |
| SEQ-ID-NO-1502 | LESDALGWQY ITGTLPDSRE FDRIDNPQFE GYKFDPNGEY VRRWLPELSR | 442 |
| | | |
| SEQ-ID-NO-1512 | LPTEWIHHPW DAPASVLQAA GVELGSNYPL PIVGLDAANA RLQEALSEMW | 500 |
| SEQ-ID-NO-1499 | LPTEWIHHPW NAPESVLQAA GIELGSNYPL PIVGIDAAKV RLEEALSEMW | 485 |
| SEQ-ID-NO-1506 | LPTEWIHHPW NAPESVLQAA GIELGSNYPL PIVGLDEAKA RLHEALSQMW | 490 |
| SEQ-ID-NO-1497 | LPTDWIHHPW NAPESVLQAA GIELGSNYPL PIVGLDEAKA RLHEALSQMW | 492 |
| SEQ-ID-NO-1502 | LPTDWIHHPW NAPESVLQAA GIELGSNYPL PIVGLDEAKA RLHEALSQMW | 492 |
| | | |
| SEQ-ID-NO-1512 | QLEAASRAAM DNGMEEGLGD SSE--VPPIE FPRELQMEVD REPARVTANV | 548 |
| SEQ-ID-NO-1499 | QQEAASRAAI ENGTEEGLGD SSE--SAPIA FPQDINMEEN HEPVRN---NP | 531 |
| SEQ-ID-NO-1506 | QLEAASRAAI ENGSEEGLGD STEFVEAPIE FPRDITMEET -EPTRL---NP | 537 |
| SEQ-ID-NO-1497 | QLEAASRAAI ENGSEEGLGD SAEVEAPIE FPRDITMEET -EPTRL---NP | 539 |
| SEQ-ID-NO-1502 | QLEAASRAAI ENGSEEGLGD SAEVEAPIE FPRDITMEET -EPTRL---NP | 539 |
| | | |
| SEQ-ID-NO-1512 | LTTARRREDQ MVPTMTSSLN RA--ETELSA DFMNSVLDSR AEVPITR-VNF | 594 |
| SEQ-ID-NO-1499 | PATNRRYEDQ MVPSMTSSFL RI--EDEETSS DVRNSTGDGR AEVPRDL-VNV | 579 |
| SEQ-ID-NO-1506 | ---VRRYEDQ MVPSITTSSLI RPEEDQESSL SLRNSCGDSR AEVPRNMVNT | 584 |
| SEQ-ID-NO-1497 | ---NRRYEDQ MVPSITSSLI RPEEDEESSL NLRNSVGDSR AEVPRNMVNT | 586 |
| SEQ-ID-NO-1502 | ---NRRYEDQ MVPSITSSLI RPEEDEESSL NLRNSVGDSR AEVPRNMVNT | 586 |

Figure 18 (continued)

| | | | | | | | | |
|---|---|---|---|---|---|---|---|---|
| SEQ-ID-NO-1512 | EPA | EREE | NF | RTT | AGN | ART | NG | HEH | NNFQ | QPQ | HRMRN | VL | APS | VSE | ASSG | 644 |
| SEQ-ID-NO-1499 | NQQPRRDT | LN | QGF | VQS | HND | NSL | PPFN | --- | V | RGLAN | VE | DSTAESSSSG | 625 |
| SEQ-ID-NO-1506 | NQARQQE | ARA | DPV | SNQV | --- | T | AMI | PEFN | --- | RI | VAENTE | ESTAESSSSG | 628 |
| SEQ-ID-NO-1497 | NQAQQR | --- | RA | EPA | SNQV | --- | T | AMI | PEFN | --- | RI | VAESTE | DSTAESSSSG | 628 |
| SEQ-ID-NO-1502 | NQAQQR | --- | RA | EPA | SNQV | --- | T | AMI | PEFN | --- | RI | VAESTE | DSTAESSSSG | 628 |

| | | | | | | |
|---|---|---|---|---|---|---|
| SEQ-ID-NO-1512 | WTG | REGGVVP | VWSPPAASDH | SE | LFA | SDEAD | --- | SSRSY | LDR | HPQS | HRL | 690 |
| SEQ-ID-NO-1499 | RRERDGGI | VP | VWSPPASS | --- | Y | SEQFV | GDENG | G | --- | A | SSY | LPR | HPQS | HQI | 671 |
| SEQ-ID-NO-1506 | RRERDGGI | VP | EWSG | --- | --- | SEQFA | SEENG | GGGSTTSSY | --- | LQNH | --- | HEI | 670 |
| SEQ-ID-NO-1497 | RRERSGGI | VP | EWSPG | --- | Y | SEQFP | SEENG | GGGSTTSSY | --- | LQNH | --- | HEI | 671 |
| SEQ-ID-NO-1502 | RRERSGGI | VP | EWSPG | --- | Y | SEQFP | SEENG | GGGSTTSSY | --- | LQNH | --- | HEI | 671 |

| | | |
|---|---|---|
| SEQ-ID-NO-1512 | MNWS | QL | SQSL | 700 |
| SEQ-ID-NO-1499 | LNWRRL | P | QTG | 681 |
| SEQ-ID-NO-1506 | VNWRRLSQTG | 680 |
| SEQ-ID-NO-1497 | LNWRRLSQTG | 681 |
| SEQ-ID-NO-1502 | LNWRRLSQTG | 681 |

Figure 19

| SEQ ID | Seq | # |
|---|---|---|
| SEQ-ID-NO-1612 | MDEAL--------------------- | 5 |
| SEQ-ID-NO-1597 | MDGASGGSGG-----GEGST------ | 19 |
| SEQ-ID-NO-1609 | MAAEHATAAV-----GEPPP------ | 23 |
| SEQ-ID-NO-1614 | MGEPSPPPPA----------ATSQPAEG | 17 |
| SEQ-ID-NO-1589 | -MAPPPVEQN-----PAAEA---AG | 14 |
| SEQ-ID-NO-1587 | ------MPGEQT---GDATT------ | 46 |
| SEQ-ID-NO-1596 | -MAPLPAEQT----GET-PTVAGVG | 14 |
| SEQ-ID-NO-1591 | -MPPLPVEQT-----GESAP------ | 26 |
| SEQ-ID-NO-1603 | ---------------GE-SPA------ | 1 |
| SEQ-ID-NO-1605 | --------------------------- | 0 |
| SEQ-ID-NO-1606 | --------------------------- | 0 |

| SEQ ID | Seq | # |
|---|---|---|
| SEQ-ID-NO-1612 | ----GSSCSL P-PFLAKTYE MVDDLSTNSI VSWSVSSKSF VWNPPEFAR | 50 |
| SEQ-ID-NO-1597 | APTPMLNANA PPPFLSKTYD MVDDPSTDAI VSWSATNNSF VVWDPPEFAR | 69 |
| SEQ-ID-NO-1609 | VTAAAGQRSV PTPFLSKTYQ LVDDPAVDDI SWNDDGSAF VVWRPAEFAR | 73 |
| SEQ-ID-NO-1614 | VGVGQQQRTV PTPFLTKTYQ LVDDPAVDDV SWNDDGSTFF VVWRPAEFAR | 67 |
| SEQ-ID-NO-1589 | -GTAESQRSI PTPFLTKTYQ LVDDHTI DDV VWNPTVFAR VWRPAEFAR | 63 |
| SEQ-ID-NO-1587 | GGGGDSQRSI PTPFLTKTYQ LVEDPVYDEL SWNEDGTFF VWRPAEFAR | 96 |
| SEQ-ID-NO-1596 | ---TELQRSI PTPFLTKTYQ LVDDPSADDL SWNEDGTSF VWRPAEFAR | 61 |
| SEQ-ID-NO-1591 | SGSGDSQRSL PTPFLTKTYQ LVDDPSVDDL SWNDDGSTFF VWRPAEFAR | 76 |
| SEQ-ID-NO-1603 | VFTMESQKSV PAPFLTKTYQ LVDDPLTDH VSWSDDETTF VVWRPPEFAR | 51 |
| SEQ-ID-NO-1605 | ------MSQRTA PAPFLLKTYQ LVDDAATDDV I SWNEL GTIF VVWKTAEFAK | 46 |
| SEQ-ID-NO-1606 | ------MSQRTV PAPFLTKTYQ LVDDATTDDV VSWNESGTTF VVWKTAEFAK | 46 |

| SEQ ID | Seq | # |
|---|---|---|
| SEQ-ID-NO-1612 | DLLPRFFKHN NFSSFIRQLN TYGFKKIDPE QWEFANDDFV RGQPHLMKNI | 100 |
| SEQ-ID-NO-1597 | DLLPKFFKHN NFSSFVRQLN TYGFRKVDPD RWEFANEGFL RGQKQLLKS | 119 |
| SEQ-ID-NO-1609 | DLLPKYFKHN NFSSFVRQLN TYGFRKIVPD RWEFANDCFR RGEKRLLCDI | 123 |
| SEQ-ID-NO-1614 | DLLPKYFKHN NFSSFVRQLN TYGFRKIVPD RWEFANDCFR RGERRLLCEI | 117 |
| SEQ-ID-NO-1589 | DLLPKYFKHN NFSSFVRQLN TYGFRKVVPD RWEFSNDYFR RGEKRLLCEI | 113 |
| SEQ-ID-NO-1587 | DLLPKYFKHN NFSSFVRQLN TYGFRKVVPD RWEFSNDCFR RGEALLRDI | 146 |
| SEQ-ID-NO-1596 | DLLPKYFKHN NFSSFVRQLN TYGFRKVVPD RWEFANDCFR RGEKALLRDI | 111 |
| SEQ-ID-NO-1591 | DLLPKYFKHN NFSSFVRQLN TYGFRKVVPD RWEFANDYFK RGERALLRDI | 126 |
| SEQ-ID-NO-1603 | DLLPNFFKHN NFSSFVRQLN TYGFKKVVVA RWEFANENFK KGAKHLLCEI | 101 |
| SEQ-ID-NO-1605 | DLLPKYFKHN NFSSFVRQLN TYGFRKIVPD KWEFANENFK RCQKELLTAI | 96 |
| SEQ-ID-NO-1606 | DLVPTYFKHN NFSSFVRQLN TYGFRKIVPD KWEFANENFK RGQKELLTAL | 96 |

Figure 19 (continued)

```
SEQ-ID-NO-1612  HRRKPVHSHS  LQNLQAQGPL  GDSERQGFTD  GIEKLKRDKE  RLLVELQ-KF  149
SEQ-ID-NO-1597  SRRKPAHGHT  QQQAQQPHGQ  SSSVGACVEV  GKFGLEEEVE  RLKRDKNVLM  169
SEQ-ID-NO-1609  HRRKV-----  -------SPATGA  VTTAAAVA-AA  ----LP----  ------MA    148
SEQ-ID-NO-1614  HRRKV-----  -------TPPAPA  ATTAAVA-AA  ----LP----  ------MA    141
SEQ-ID-NO-1589  QRRKL-----  ---SSPTAAA   VTVAPVTVAA  ----LP----  ------MA    139
SEQ-ID-NO-1587  QRRKISQPAM  AAAAAAAAA    VAASAVTVAA  ----VP----  ------VV    180
SEQ-ID-NO-1596  QRRKL-----  --LPVPPAAAA  PAAVTANTVT  ----VA----  ------VA    139
SEQ-ID-NO-1591  QRRKI-----  ---STMAASA   VTSASVTVAA  ----LP----  ------TV    152
SEQ-ID-NO-1603  HRRKT-----  ----------   SVAACAS--   ---------   -------PQ   108
SEQ-ID-NO-1605  RRRKT-----  -VTSTPAGGK   --------    ---------   ---------   117
SEQ-ID-NO-1606  RRRKT-----  -VTPTPAGGK   SVVPGTS--   ---------   ---------   117

SEQ-ID-NO-1612  QHEWQTYEIQ  IHCSNDRLEK  L-----EQK   QHKMVSSISH  VLQKPVLAVN  193
SEQ-ID-NO-1597  QELVRLRQQQ  QTTDGQLQTM  VQRLQGMEQR  QQQMMSFLAK  AVQSPGFFAQ  219
SEQ-ID-NO-1609  LPV-------  GSPVYSGEEQ  V-------   ----LSS    SSPEPPSLQQ  175
SEQ-ID-NO-1614  LPVTTTRDGS  PVLSGEEQ    V-------   ------S    SSSSPEPPLV  172
SEQ-ID-NO-1589  KPI-------  ISPSNSGDEQSP  V-------   ------S    SASSP-----  162
SEQ-ID-NO-1587  AHI-------  VSPSNSGEEQ  V-------   ------S    SNSSPAAAA-  206
SEQ-ID-NO-1596  APAVRT----  VSPTTSGDEQ  V-------   ------LS   SNSSP-----  163
SEQ-ID-NO-1591  ARA-------  VSPANSGDDQ  G-------   ------S    STSSP-----  173
SEQ-ID-NO-1603  HYQQQYYEQS  PQIFQPDE    S-------   ------LC   WIDSP-----  134
SEQ-ID-NO-1605  AS--------  PDNSGDD     G-------   ------SS   STSSP-----  135
SEQ-ID-NO-1606  AS--------  PDNSGEDL    G-------   ------SS   STSSP-----  135

SEQ-ID-NO-1612  ILPLTETMDR  KRRLPRSGHY  YDESSIEDAI  ETSQMLPREN  AENTTVLTLN   243
SEQ-ID-NO-1597  FVQQONDSNR  RITEVNKKRR  ---LKQDGTA  ETIEQATPPD  GQIVKYQPMM   266
SEQ-ID-NO-1609  HPPAPSGSG-  ---SGG      VVSGDVG     EENERLRREN  ARLARELCQM   214
SEQ-ID-NO-1614  LPQAPSGSG-  ---SGG      VASGDVG     DENERLRREN  AQLARELSQM   211
SEQ-ID-NO-1589  --SRLNQAG-  ---------   TVMAELM     KENEKLRKEN  VQLNKQLSEM   196
SEQ-ID-NO-1587  AIGGVVGGG-  ---------   TTAPELV     ERLRKEMTKL  ERLRKEMTKL   250
SEQ-ID-NO-1596  --GGAGTAGG  ---------   TTAPELL     EENERLRKEN  IQLSNELSQL   206
SEQ-ID-NO-1591  --GGAGTAGG  ---------   TTPEIL      EENERLRKEN  SALSHELTQL   218
SEQ-ID-NO-1603  -LPSPKSNT-  ---------   DILTALS     EDNQRLRRKN  FMLLSELSHM   169
SEQ-ID-NO-1605  ---DSKNPG-  --SVDTPGKL  SQFTDLS     DENEKLKKDN  QMLSSELVQA   176
SEQ-ID-NO-1606  ---DSKNPG-  --SVDTPGK-  SQFADLS     DENEKLKKDN  QMLSSELAQA   175
```

| SEQ ID | Sequence | # |
|---|---|---|
| SEQ-ID-NO-1612 | --ASETQEVQ --- --- --- --KDCDGRKN EGKPNDHSKF WWNIRNANNL | 389 |
| SEQ-ID-NO-1597 | YMAPETDDGF MDPSSLGSLP IDLDCLSPGA DIDDLLSNSI WDDLLQTPIP | 455 |
| SEQ-ID-NO-1609 | --GVCAAEVK AEP------- VDARPDQQ RQRNATEPQS WPIYRPRPVY | 348 |
| SEQ-ID-NO-1614 | --DDHAATVK AEP------- MDGRPHGK DEQSA-ETQA WPIYRPRPVY | 349 |
| SEQ-ID-NO-1589 | --PGGSEIK LEP------- LDCQNRGR DDDRGIQDAP WLRQFHRANQ | 322 |
| SEQ-ID-NO-1587 | --GEQSSDVK AEP------- ME------ ENNSGNHNGS WLELGK---- | 377 |
| SEQ-ID-NO-1596 | --PDHGSDVK SEP------- LD-----GD DSDYQDHDPH WLEL------ | 355 |
| SEQ-ID-NO-1591 | --KEHESDVK AEP------- LD-----GS SGNSDHQDQR ---------- | 337 |
| SEQ-ID-NO-1603 | --PSN----- --------- --------- ---------- ---------- | 243 |
| SEQ-ID-NO-1605 | --PDENLETC GGR------- LD-----GK MMKTVDYNGP WMKMSSPAGE | 295 |
| SEQ-ID-NO-1606 | --PDENADIS GSR------- -------GK MMKTMDYNLP WMKMSSAPGE | 285 |

| SEQ ID | Sequence | # |
|---|---|---|
| SEQ-ID-NO-1612 | SEPMGHVGQA EKT------- NGWDNNTQPL DQLTEQMGLL ---------- | 402 |
| SEQ-ID-NO-1597 | EDFEANIDEI SRGNEVQPTE DSR------- ---------- SSDAKRI--- | 502 |
| SEQ-ID-NO-1609 | HPLRACNGSG SAGSDHDGSN SNST------ ---------- ---------- | 371 |
| SEQ-ID-NO-1614 | QPIRACNGYE YDRAGSDQDG --------- ---------- ---------- | 373 |
| SEQ-ID-NO-1589 | RVCN------ ---------- --------- ---------- ---------- | 326 |
| SEQ-ID-NO-1587 | ---------- ---------- --------- ---------- ---------- | 377 |
| SEQ-ID-NO-1596 | ---------- ---------- --------- ---------- ---------- | 355 |
| SEQ-ID-NO-1591 | ---------- ---------- --------- ---------- ---------- | 337 |
| SEQ-ID-NO-1603 | ---------- ---------- --------- ---------- ---------- | 243 |
| SEQ-ID-NO-1605 | SSKVCN---- ---------- --------- ---------- ---------- | 301 |
| SEQ-ID-NO-1606 | SNKVCN---- ---------- --------- ---------- ---------- | 292 |

Figure 20

| SEQ ID | Sequence | # |
|---|---|---|
| SEQ-ID-NO-1646 | MPANPKLAAK | 15 |
| SEQ-ID-NO-1648 | MPANPKLAAK | 10 |
| SEQ-ID-NO-1650 | MSSKFN- | 12 |
| SEQ-ID-NO-1642 | | 15 |
| SEQ-ID-NO-1644 | | 28 |
| SEQ-ID-NO-1651 | PSPSPPTAAA --MSFPTAAS ----MVAA[A] AG[D]AET[D]LTL | 49 |
| SEQ-ID-NO-1653 | PSPSTAEPPP -AASRPKATA KPPLGAGYRD ----MA MAT VDC PLPS | 50 |
| SEQ-ID-NO-1637 | QTASRPKATA KPPLGAGYRD --MA TA[D]GD PPQF | 22 |
| SEQ-ID-NO-1635 | --SSQF[SS] -MDF[SD] EDDDENC[FGS] | 14 |
|  |  |  |
| SEQ-ID-NO-1646 | | 16 |
| SEQ-ID-NO-1648 | | 11 |
| SEQ-ID-NO-1650 | | 13 |
| SEQ-ID-NO-1642 | | 16 |
| SEQ-ID-NO-1644 | | 29 |
| SEQ-ID-NO-1651 | [P]---PRASS RAARALKPSG NGAASRRPSK RLKPSSSCCS GKENLPAAAG | 95 |
| SEQ-ID-NO-1653 | [P]---PRASS RAARALKPSG NGAASRRPSK RLKPSSSCCS GKENRPAAAG | 96 |
| SEQ-ID-NO-1637 | [P]LSQTPKQTL SIRN--KPAD --NPRRPS K-KPKKPPNP GKENI--- | 60 |
| SEQ-ID-NO-1635 | [P]---PSSQL SIRKPLHPTN ANNISHRPPN K-KPRLCRYP GKENV--- | 54 |
|  |  |  |
| SEQ-ID-NO-1646 | | 16 |
| SEQ-ID-NO-1648 | | 11 |
| SEQ-ID-NO-1650 | | 13 |
| SEQ-ID-NO-1642 | | 16 |
| SEQ-ID-NO-1644 | | 29 |
| SEQ-ID-NO-1651 | SKGAGVGETL GVVSRVSSGV PGGDKARGGG ICGLLRCGSD | 145 |
| SEQ-ID-NO-1653 | SKGAGVGETL GVVSRVSSGV PGGDKARGGG ICGLLRCGSD | 146 |
| SEQ-ID-NO-1637 | | 60 |
| SEQ-ID-NO-1635 | | 54 |
|  |  |  |
| SEQ-ID-NO-1646 | | 16 |
| SEQ-ID-NO-1648 | | 11 |
| SEQ-ID-NO-1650 | | 13 |
| SEQ-ID-NO-1642 | | 16 |
| SEQ-ID-NO-1644 | | 29 |
| SEQ-ID-NO-1651 | DFSSVSNGKK GLDRYWRRDG GLHSRPNPMD STVSMPDATC DLENGGSQVA | 195 |
| SEQ-ID-NO-1653 | DFSSVSNGKK GLDRYWRRDG GLHSRPNPMD STVSMPDATC DLENGGSQVA | 196 |
| SEQ-ID-NO-1637 | | 60 |
| SEQ-ID-NO-1635 | | 54 |

Figure 20 (continued)

```
SEQ-ID-NO-1646                                                                          16
SEQ-ID-NO-1648                                                                          11
SEQ-ID-NO-1650                                                                          13
SEQ-ID-NO-1642                                                                          16
SEQ-ID-NO-1644                                                                          29
SEQ-ID-NO-1651  QMLSSNDRIS         VQLEGNAKVE  LGKSESDPTT  MRKERNGSGA  CESDHPARLI      245
SEQ-ID-NO-1653  QMLSSNDRIS         VQLEGNAKVE  LGKSESDPTT  MRKERNGSGA  CESDHPARLI      246
SEQ-ID-NO-1637                                 ---DPNSLL   LYQKTESGAN  DFNLDE---       82
SEQ-ID-NO-1635                                 ----TPPP-   ---SPDPDLF  CSSSTP---       71

SEQ-ID-NO-1646                                                                          16
SEQ-ID-NO-1648                                                                          11
SEQ-ID-NO-1650                                                                          13
SEQ-ID-NO-1642                                                                          16
SEQ-ID-NO-1644                                                                          29
SEQ-ID-NO-1651  EPRLLTLVTN         CDFGGADSMD  SKELGSAI HP  SVSKDRNVEN  ESGGASVCTF     295
SEQ-ID-NO-1653  EPRLLTLVTN         CDFGGADSMD  SKELGSAI HP  SVSKDRNVEN  ESGGASVCTF     296
SEQ-ID-NO-1637                                                                          82
SEQ-ID-NO-1635                                                                          71

SEQ-ID-NO-1646                                                                          16
SEQ-ID-NO-1648                                                                          11
SEQ-ID-NO-1650                                                                          13
SEQ-ID-NO-1642                                                                          16
SEQ-ID-NO-1644                                                                          29
SEQ-ID-NO-1651  ALHNRNCHSS         CVESELELLN  AKYDLGPRDC  KESQEGPGLC  SLI SEERTVA     345
SEQ-ID-NO-1653  ALHNRNCHSS         CVESELEMLN  AKYDLGPRDC  KESQEGPGLC  SLI SEERTVA     346
SEQ-ID-NO-1637  ----NCSLD          FIESSID---                ---C     TVS----S        99
SEQ-ID-NO-1635  ----HCI LD         CI PSSVD---                ---C     SLGDFNGPI S    94

SEQ-ID-NO-1646                                                                          16
SEQ-ID-NO-1648                                                                          11
SEQ-ID-NO-1650                                                                          13
SEQ-ID-NO-1642              -F[N]   DGVNE---                           EE---           25
SEQ-ID-NO-1644                                                                          29
SEQ-ID-NO-1651  AEGDATFTFE         ERGNTSSGLE  ACKGSHCLDP  VEPKLMDSCA  TH----ALEG     391
SEQ-ID-NO-1653  AEGDATFTFE         ERGNTSSGLE  ACKGSHCLDP  VEPKLMDSCA  TH----ALEG     392
SEQ-ID-NO-1637  KVGNEKF---         SGSGKKEKLE  VS-GGYLCNS  I EARLMKSRV  DY--SGVNV     143
SEQ-ID-NO-1635  SLGEEDK---[E]     D---KDDCI K  VNREGYLCNS  MEARLLKSRI  CLGFDSGI HE    139
```

| | | | | | |
|---|---|---|---|---|---|
| SEQ-ID-NO-1646 | GIEKP---AS | GMTEKVC--- | -------GPPVQ | KNLFQAWGIQ | KPPREEAAQG | 123 |
| SEQ-ID-NO-1648 | GIEKPRR-DG | RGAGDSS--- | ---------LVQ | RSLFQAWGIE | RPQRE----- | 113 |
| SEQ-ID-NO-1650 | GIERPRREEG | AGAGDSS--- | ---------LVQ | RSLFQAWGIE | RPKRE----- | 121 |
| SEQ-ID-NO-1642 | CLQENSPDTT | KKKMK----- | ---------- | TDLFQSWGLQ | KP-------- | 110 |
| SEQ-ID-NO-1644 | GFKRNVEFES | PNQGGYCDVV | GEGSVSSEKK | SVKRGNWGSI | LRD------- | 145 |
| SEQ-ID-NO-1651 | NLENTKKAKI | PMNG------ | -------N | KLITEYFRCP | SSDQ------ | 594 |
| SEQ-ID-NO-1653 | NLENTKKAKI | PMNG------ | -------N | KLITEYFRCP | SSDQ------ | 595 |
| SEQ-ID-NO-1637 | EVGSRRSHGA | EMQVEASKII | GDDTSKPTAN | KLITDYFPGS | VPIK------ | 376 |
| SEQ-ID-NO-1635 | GHVTERQRDK | STTRKAS--- | --EPKKPTAN | KLITEFFPGQ | AT-------- | 354 |

| | | | | | |
|---|---|---|---|---|---|
| SEQ-ID-NO-1646 | VPVGAGASSS | SPSPSVAGS | --GRKRRWGGS | DEN--CASRK | PVACPFYKQI | 169 |
| SEQ-ID-NO-1648 | ---GLGAGDS | SPSSLSGSL | LARKRRRGST | EEERVAAK-K | PLACPFYKKI | 159 |
| SEQ-ID-NO-1650 | ---GGGAGDA | SPSPSRSGSW | SGRKRRRGGP | EEEVAAAAMN | PRTCPFYKKI | 168 |
| SEQ-ID-NO-1642 | ---SPFTSPA | SNSAKKTTSA | LGKRRRDSSF | SND------S | PRPCPFYKKL | 151 |
| SEQ-ID-NO-1644 | ---TGKVVEN | SKSTGKRKSF | HGEKRI---- | ------V | TRSCPFYKKM | 178 |
| SEQ-ID-NO-1651 | ---RQKKACK | VNTPSNLNSQ | KNSNAKATGG | RRTVKG---K | VKDTPIWCCI | 638 |
| SEQ-ID-NO-1653 | ---RQKKACK | VNTPSNLNSQ | KKSNAKATGG | RRTVKG---K | VKDTPIWCCI | 639 |
| SEQ-ID-NO-1637 | ---KKTSVIS | KEQRCAEKSQ | PGYVRKQGVK | NYTKKC---K | FKDIPLWCSI | 420 |
| SEQ-ID-NO-1635 | ---EGTKIRT | APKFVAEKSP | SDSSSRRAVR | RNGNG----K | SKVIPHWNCL | 398 |

| | | | | | |
|---|---|---|---|---|---|
| SEQ-ID-NO-1646 | PGTPFTVDAF | RYGAVEMCSA | YFLSHFHYDH | YGGLTKKWCH | GPIYCTALTA | 219 |
| SEQ-ID-NO-1648 | PGTPFTVDAF | RYGQVEGCSA | YFLSHFHHDH | YGGLTKKWCH | GPIYCSALTA | 209 |
| SEQ-ID-NO-1650 | PGTPFTVDAF | RYGEVEGCSA | YFLSHFHHDH | YGGLTKKWCH | GPIYCSALTA | 218 |
| SEQ-ID-NO-1642 | PGTPFTVDAF | RYGCVQGCSA | YFLTHFHADH | YIGLTKAWSH | GPIYCSSLTS | 201 |
| SEQ-ID-NO-1644 | PGTPFTVDAF | RYGCVEECSA | YFLSHFHADH | YGGLSKKMSH | GPIYCSPLTG | 228 |
| SEQ-ID-NO-1651 | PGTPFRVDAF | RY-LRGDCCH | WFLTHFHVDH | YQGLTKSFCH | GKIYCSSVTA | 687 |
| SEQ-ID-NO-1653 | PGTPFRVDAF | RY-LRGDCCH | WFLTHFHVDH | YQGLTKSFCH | GKIYCSSVTA | 688 |
| SEQ-ID-NO-1637 | PGTPFRVDAF | KY-LRGDCSH | WFLTHFHMQH | YQGLTRSFCH | GKIYCSLTA | 469 |
| SEQ-ID-NO-1635 | PGTPFRVDAF | KY-LTRDCCH | WFLTHFHLDH | YQGLTKSFSH | GKIYCSLVIA | 447 |

| | | | | | |
|---|---|---|---|---|---|
| SEQ-ID-NO-1646 | RLVKMLSTD | SAYVCPLELD | TEYVDGVKV | TFLEANHCPG | AALIHFRPSD | 269 |
| SEQ-ID-NO-1648 | RLVKMCLSVN | SEYICPLELD | TEYVEGVTV | TLLEANHCPG | AALIHFRLSD | 259 |
| SEQ-ID-NO-1650 | RLVKMCLSVN | SDYICPLELD | TEYVEGVTV | TLLEANHCPG | AALIHFRLSD | 268 |
| SEQ-ID-NO-1642 | RLLRLSLSVN | PSSIHPLELD | VEYTNGIKV | TLIEANHCPG | AALIHFRLLD | 251 |
| SEQ-ID-NO-1644 | RLVQMCLYVN | PSYICPLEFD | TEYVDGIKV | TLLDANHCPG | AALIHFELPN | 278 |
| SEQ-ID-NO-1651 | NLVHYKIGIP | WDRLHVLPLN | EKITAGVNL | TCFDANHCPG | AVIILFEPSN | 737 |
| SEQ-ID-NO-1653 | NLVHYKIGIP | WDRLHVLPLN | EKITAGVNL | TCFDANHCPG | AVIILFEPSN | 738 |
| SEQ-ID-NO-1637 | KLVNLKIGIP | WDSLHVLPLN | QKIVCIAGVDV | TCLDANHCPG | AVIILFEPPN | 519 |
| SEQ-ID-NO-1635 | KLVNMKIGIP | WERLQVLDLG | QKIVNSGIDV | TCFDANHCPG | SIMILFEPAN | 497 |

| SEQ-ID-NO | Sequence | Pos |
|---|---|---|
| SEQ-ID-NO-544 | MSNSCSGGGG CSIVWFRRDL RVEDNPALAA AVRAGPVIAV FVWAPEEEGH | 50 |
| SEQ-ID-NO-539 | ----------MAA CIIVWFRRDL RLEDNPALAA AARAGTVVPV FVWSPAEDGQ | 43 |
| SEQ-ID-NO-549 | -------MAGSE RTVVWFRRDL RIDDNPALAS AARDGAVLPV FIWCPADEGQ | 45 |
| SEQ-ID-NO-543 | -------MSTNK KTIVWFRRDL RIEDNPALAA AAHEGSVFPV FIWCPEEEGQ | 45 |
| SEQ-ID-NO-538 | -------MKMDK KTIVWFRRDL RIEDNPALAA AAHEGSVFPV FIWCPEEEGQ | 45 |
| SEQ-ID-NO-542 | -------MTTNK KTIVWFRRDL RIEDNPALAA AAHQGSVFPV FIWCPEEEGQ | 45 |
| SEQ-ID-NO-547 | -------MESNY KTIVWFRRDL RIEDNPALAA AARNGSVFPV FIWCPKEEGQ | 45 |
| SEQ-ID-NO-548 | -------MESNS KTIVWFRRDL RIEDNPALAA AARNGSVFPV FIWSPKEEGQ | 45 |
| SEQ-ID-NO-541 | -------MDRS- KTIVWFRRDL RIEDNPALAA AARDGCVFPV FI GA | 44 |
| SEQ-ID-NO-545 | ---------MN- RTIVWFRRDL RIEDNPALAA AARDGSVFPV FICPKEEGQ | 42 |
| SEQ-ID-NO-546 | -------MGSN- RTIVWFRRDL RIEDNPALAA AARDGSVFPV FIWCPKEEGQ | 44 |

| SEQ-ID-NO | Sequence | Pos |
|---|---|---|
| SEQ-ID-NO-544 | YQPGRVSRWW LKNSLAQLDS SLRSLGTCLI TKRSTDSVAS LLEVVKSTGA | 100 |
| SEQ-ID-NO-539 | FHPGRVSRWW LKQSLTHLEL SLKKLGSPLI LRKSPDTLSV LLEIAEALGA | 93 |
| SEQ-ID-NO-549 | FYPGRCSRWW LKQSLPHLSQ SLESLGCPLV LIRAESTLEA LDCVRATGA | 95 |
| SEQ-ID-NO-543 | FYPGRASRWW MKQSLAHLTQ SLKALGSEPT LIKTHNTVSA LDCIRVTGA | 95 |
| SEQ-ID-NO-538 | FYPGRASRWW MKQSLAHLSQ SLKALGSDLT LIKTHNTISA LDCIRVTGA | 95 |
| SEQ-ID-NO-542 | FYPGRASRWW MKQSLAHLSQ SLKSLGAELV LMKAQSTLSA LTECVDAVGA | 95 |
| SEQ-ID-NO-547 | FYPGRVSRWW LKQSLHLEQ SLKSLGAELV LIKAQSTLSA LDCIEAVGA | 95 |
| SEQ-ID-NO-548 | FYPGRVSRWW LKQSLAHLSQ SLKSLGAELV LIKTHSTVAA LDCIED GA | 94 |
| SEQ-ID-NO-541 | FYPGRVSRWW LKQSLYHLDQ SLKSLGAGLV LIKTDSTLKA LLECVNAVQA | 92 |
| SEQ-ID-NO-545 | FYPGRVSRWW LKQSLAHLDQ SLKSLGAKLV LIKTDSTLNA LLECVNAIQA | 94 |
| SEQ-ID-NO-546 | FYPGRVSRWW LKQSLAHLDQ SLKSLGAKLV LIKTDSTLNA LLECVNAIQA | 94 |

| SEQ-ID-NO | Sequence | Pos |
|---|---|---|
| SEQ-ID-NO-544 | SQIFNHLYD PLSLVRDHRA KDALTAEGI VKSFNADLLY EPWEVIDELG | 150 |
| SEQ-ID-NO-539 | TQVEYNHLYD PVSLVRDHRV KQGLSQRGI VHITFNGDLLY EPWEVYDEEG | 143 |
| SEQ-ID-NO-549 | TRLVYNHLYD PVSLVRDHDKI KKELSALGIS QSFNGDLLY EPWEIYDDSG | 145 |
| SEQ-ID-NO-543 | TKVVFNHLYD PVSLVRDHTV KEKLVERGIS VQSYNGDLLY EPWEIYCEKG | 145 |
| SEQ-ID-NO-538 | TKVVFNHLYD PVSLVRDHTV KEKLVERGIS VQSYNGDLLY EPWEIYCEKG | 145 |
| SEQ-ID-NO-542 | TKVVYNHLYD PVSLVRDHNI KQKLVELGIS VQSYNGDLLN EPWEVYDDDG | 145 |
| SEQ-ID-NO-547 | TKVVYNHLYD PVSLVRDHNI KQKLGELGIS VQSYNGDLLN EPWEVYDDDG | 145 |
| SEQ-ID-NO-548 | TKVVYNHLYD PVSLVRDHNI KEKLVELGIS VQSYNGDLLY EPWDIYDERG | 145 |
| SEQ-ID-NO-541 | TRVVFNHLYD PVSLVRDHNI KEKLVELGIS VQSYNGDLLY EPWDIYDESG | 144 |
| SEQ-ID-NO-545 | KKVVFNHLYD PVSLVRDHNI KEKLVELGIS VKSYNGDLLH EPWELYDEKG | 142 |
| SEQ-ID-NO-546 | TKVVFNHLYD PVSLVRDHNI KEKLVELGIS VKSYNGDLLY EPWELYDEKG | 144 |

| | | | | | | |
|---|---|---|---|---|---|---|
| SEQ-ID-NO-544 | MANEGNQAGE | ESVNLFLKSI | GLREYSRYIS | FNHPYSHERP | LLGHLKFFPW | 346 |
| SEQ-ID-NO-539 | WAREGNAGGE | ABVNMFLRAL | GFREYSRYLS | FHFPFTHERS | LLANLKSFPW | 320 |
| SEQ-ID-NO-549 | MENEGTSEAE | ESIHFFMRSI | GLREYSRYLS | FNFPFTHEKS | LLGNLKHYPW | 321 |
| SEQ-ID-NO-543 | WARDKNCOGV | ESAVFLRG | GLRDYSRYI C | FNFPFTHEQS | LLSHLRFFPW | 320 |
| SEQ-ID-NO-538 | WARDKNSEGE | ESADLFLRG | GLREYSRYI C | FNFPFTHEQS | LLSHLRFFPW | 321 |
| SEQ-ID-NO-542 | WARDKNSEGE | ESTDLFLKG | GLREYSRYI C | FNFPFTHEQS | LLNNLRFFPW | 321 |
| SEQ-ID-NO-547 | WTKEGNSVGK | DSAT I YLRAI | GLREYSRYI C | FNFPFTHERS | LLNNLKFFPW | 318 |
| SEQ-ID-NO-548 | WTKEGNSVGD | ESASLYLRAI | GLREYSRYLC | FNFPFTHERS | LLRNLKYFPW | 318 |
| SEQ-ID-NO-541 | WAKEENLMGK | ESVTLFLRSI | GLREYSRYLC | FNFPFTHERS | LLGNLKFFPW | 316 |
| SEQ-ID-NO-545 | WKNEGNLVGE | ESATFLRAI | GLREYSRYLC | FSFPFTVERP | LLGNLKFFPW | 315 |
| SEQ-ID-NO-546 | WGNEGNSVGK | ESVTLFLRAI | GLREYSRYLC | FNFPFTHERA | LLGHLSFFPW | 317 |

| | | | | | | |
|---|---|---|---|---|---|---|
| SEQ-ID-NO-544 | AVDENYFKAW | RQGRTGYPLV | DAGMRELWAT | GWLHDRI RVV | VSSFFVKVQ | 396 |
| SEQ-ID-NO-539 | RADEGYFKAW | RQGRTGYPLV | DAGMRELWAT | GWAHNRI RVV | VASFSVKFLQ | 370 |
| SEQ-ID-NO-549 | KVDEERFKSW | RQGMTGYPLV | DAGMRELWAT | GWTHNRI RVI | I SSFAVKFLL | 371 |
| SEQ-ID-NO-543 | DADVEKFKAW | RQGRTGYPLV | DAGMRELWAT | GWMHNRI RVI | VSSFAVKFLL | 370 |
| SEQ-ID-NO-538 | DADVDKFKAW | RQGRTGYPLV | DAGMRELWAT | GWMHNRI RVI | VSSFAVKFLL | 371 |
| SEQ-ID-NO-542 | DADVDKFKAW | RQGRTGYPLV | DAGMRELWAT | GWMHNRI RVI | VSSFAVKFLL | 371 |
| SEQ-ID-NO-547 | NADQAHFKAW | RQGRTGYPLV | DAGMRELWAT | GWVHNKI RVI | VSSFFVKFLL | 368 |
| SEQ-ID-NO-548 | NADQARFKAW | RQGRTGYPLV | DAGMRELWAT | GWI HNKI RVI | VASFEVKFLL | 368 |
| SEQ-ID-NO-541 | NDNQVHFKAW | RQGRTGYPLV | DAGMRELWAT | GWI HNKI RVI | VASFAVKVL | 366 |
| SEQ-ID-NO-545 | NTDPSKFKAW | RLGRTGYPLV | DAGMRELWAT | GWI HNKMRVI | VSSFAVKML | 365 |
| SEQ-ID-NO-546 | NADPSNFKTW | RQGRTGYPLV | DAGMRELWAT | GWMHNRI RVI | VSSFAVKML | 367 |

| | | | | | | |
|---|---|---|---|---|---|---|
| SEQ-ID-NO-544 | LPWRWGMKYF | WDTLLDADLE | SDALGWQYI T | GTLPDSREED | RI DNPQEGY | 446 |
| SEQ-ID-NO-539 | LPWRWGMKYF | WDVLLDADLE | CDVLGWQYI S | GSLPDGHELD | RI ENPEVEGY | 420 |
| SEQ-ID-NO-549 | LPWIWGMKYF | WDVLLDADLE | SDI LGWQYI S | GSLPDGHELS | RLDNPEVQGQ | 421 |
| SEQ-ID-NO-543 | LPWKWGMKYF | WDTLLDADLE | CDI LGWQYI S | GSLPDGHELD | RLDNPAI QGA | 420 |
| SEQ-ID-NO-538 | LPWKWGMKYF | WDTLLDADLE | CDI LGWQYI S | GSI PDGHELD | RLDNPAI QGA | 421 |
| SEQ-ID-NO-542 | LPWKWGMKYF | WDTLLDADLE | CDI LGWQYI S | GSLPDGHELD | RLDNPALQGA | 421 |
| SEQ-ID-NO-547 | LPWQWGMKYF | WDTLLDADLE | SDI LGWQYI S | GSLPDGHELE | RLDNPEVQGF | 418 |
| SEQ-ID-NO-548 | LPWQWGMKYF | WDTLLDADLE | SDI LGWQYI S | GSLPDGHELE | RLDNPEVQGF | 418 |
| SEQ-ID-NO-541 | LPWRWGMKYF | WDTLLDADLE | SDI LGWQYI S | GSLPDAHELE | RLDNPEI QGS | 416 |
| SEQ-ID-NO-545 | LPWKWGMKYF | WDTLLDADLE | SDI LGWQYI S | GSLPDGHELE | RLDDPEI QGT | 415 |
| SEQ-ID-NO-546 | LPWKWGMKYF | WDTLLDADLE | CDI LGWQYI S | GCLPDGHELE | RLDDPEI LGA | 417 |

Figure 22 (continued)

| SEQ ID | Sequence | # |
|---|---|---|
| SEQ-ID-NO-544 | KFDPN GEYVR RWLPELSRLP TEWI HHPWNA PESVLQAAGI ELGSNYPRPI | 496 |
| SEQ-ID-NO-539 | RFDPDGDYVR RWIPELARLP NEWVHHPWDA PPSAL RAAGV ELGTNYPRPI | 470 |
| SEQ-ID-NO-549 | KYDPDGMYVR TWIPELARMP TEWIHHPWDA PSCILEVAGV ELGFNYPKPI | 471 |
| SEQ-ID-NO-543 | KYDPEGEYIR QWLPELARLP TEWIHHPWDA PLTVLKASGV ELGTNYAKPI | 470 |
| SEQ-ID-NO-538 | KYDPEGEYIR QWLPELARLP TEWIHHPWDA PLTVLKASGV ELGTNYVKPI | 471 |
| SEQ-ID-NO-542 | KFDPEGEYVR QWLPELARLP AEWIHHPWDA PLNVLKAAGV ELGMNYPNPI | 471 |
| SEQ-ID-NO-547 | NYDPEGEYVR HWLPELARMP AEWIHHPWDA PLTVLKAAGV ELGMNYPKPI | 468 |
| SEQ-ID-NO-548 | NYDPEGEYVR HWLPELARMP AEWIHHPWDA SIAVLKAAGV ELGINYPKPI | 468 |
| SEQ-ID-NO-541 | KFDPEGEYVR RWLPELARIP TEWIHHPWDA PLTVLKASGI ELGQNYPKPI | 466 |
| SEQ-ID-NO-545 | KYDPEGEYIR QWLPELARIP TEWIHHPWNA PLSVLRASGV ELGQNYPKPI | 465 |
| SEQ-ID-NO-546 | KFDPEGEYVR QWLPELARMP TEWIHHPWNA PLSVLRASGV ELGQNYPNPI | 467 |

| SEQ ID | Sequence | # |
|---|---|---|
| SEQ-ID-NO-544 | VGIDEAKARL HEALSQMWQL EAASRAAIEN GSEEEGLGDST EFVE------ | 540 |
| SEQ-ID-NO-539 | VEIGAARERL QASLAEMWER DAAMKAALAN GLEEGLGETV EVAGTGGPEH | 520 |
| SEQ-ID-NO-549 | VDLHIAREQL DDSISTMWQL QTAEKLAELD G--TEVVEDN SNI------- | 512 |
| SEQ-ID-NO-543 | VDIDTARELL TKAISRTREA QIMIGAA--- --PDEIVADSF ---------- | 505 |
| SEQ-ID-NO-538 | VDIDTARELL AKAISRTREA QIMIGAA--- --PDEIVADSF ---------- | 507 |
| SEQ-ID-NO-542 | VDIDTARELL TKAISRTREA EAAVNTSHAN GTVEVVFDNS ENVG------ | 507 |
| SEQ-ID-NO-547 | DVDVARDRL MQAIFIMREK EAAANAADAN GTNEVVFDNS ENVG------ | 512 |
| SEQ-ID-NO-548 | DVDVARDRL MEAIFKMWEM EAAARASNTN GTNEVVVDNT DDT------- | 512 |
| SEQ-ID-NO-541 | DIDLAREQL TQAIFKMWED EAAASKASTSE NKHEVVDDS ---------- | 509 |
| SEQ-ID-NO-545 | DIDLAREKL TQAIFKMWEI QAAASKASGSE ARDEVVVDN ---------- | 504 |
| SEQ-ID-NO-546 | | 506 |

| SEQ ID | Sequence | # |
|---|---|---|
| SEQ-ID-NO-544 | APIEEPRDIT MEETEPTRL- NPVRRYEDQM VPSITTSLIR PEEDQESSLS | 589 |
| SEQ-ID-NO-539 | ERMDVPR-VM VHMQRDADM- SCNSSRRDQL VPELVPN--- ---------- | 555 |
| SEQ-ID-NO-549 | KTFDIPK-VV LREITSP--- CA--LPIDQR VPHA------ ---------- | 539 |
| SEQ-ID-NO-543 | EALEAAN--T V-KEHGY--- CPL-SSNDQQ VPSDV----- ---------- | 532 |
| SEQ-ID-NO-538 | EALGANT--- L-KEPGL--- CPSVSSNDQQ VPSAV----- ---------- | 535 |
| SEQ-ID-NO-542 | GALEGNT--- V-KETGL--- CPSVSSNDQQ VPSAV----- ---------- | 535 |
| SEQ-ID-NO-547 | DSASIPKDDV V-KGKEP--- CPSSSYDQR VPSMQ----- ---------- | 543 |
| SEQ-ID-NO-548 | DSVN-PK-V V-KGKVP--- CPSSSYDQR VPSMQ----- ---------- | 540 |
| SEQ-ID-NO-541 | ENLAPK-VV L-KDKVT--- CPTNSSNDQR VPTNQN---- ---------- | 540 |
| SEQ-ID-NO-545 | ENLSIPK-VF L-KDKAPR-- GATSSSNDQK VPLQNP---- ---------- | 537 |
| SEQ-ID-NO-546 | ENQDIPK-VI L-KDKGP--- CMTSANDQK VPALPDP---- ---------- | 538 |

| | | | | |
|---|---|---|---|---|
| SEQ-ID-NO-544 | VNWRRLSQTG | ---------- | ---------- | 704 |
| SEQ-ID-NO-539 | SNKQAEEEDF | YVPKLVKWTQ | PRKRRVKQDG | 727 |
| SEQ-ID-NO-549 | SSTADSGSSL | SRQRKAA--- | ---------- | 651 |
| SEQ-ID-NO-543 | ---TSLGKNG | CK-------- | ---------- | 618 |
| SEQ-ID-NO-538 | ---TSLGKNG | ---------- | ---------- | 612 |
| SEQ-ID-NO-542 | ---TKLGKNG | ---------- | ---------- | 617 |
| SEQ-ID-NO-547 | DT-------- | ---------- | ---------- | 635 |
| SEQ-ID-NO-548 | DMEINSCKNE | KQLHFIV--- | ---------- | 641 |
| SEQ-ID-NO-541 | EMEQSSSKDG | ---------- | ---------- | 646 |
| SEQ-ID-NO-545 | ---------- | ---------- | ---------- | 600 |
| SEQ-ID-NO-546 | DMEQSSGKDG | PT-------- | ---------- | 629 |

Figure 23

```
SEQ-ID-NO-606   ---MDYSSMHQ  -NVMGVSSCS  ----------  ----------  LSATRPAPPE  QSLRCPRCDS   47
SEQ-ID-NO-609   MNPSSGQP--  QQMSSQSVE-  ----------  TQDYQNQKKP  KKPKPKP-HPE  QALKCPRCDS   35
SEQ-ID-NO-607   MGMDSSSGQQ  QQMSNQSLE-  ----------  SMLTCSKGEQ  DKKPKPQPE-  -ALKCPRCDS   48
SEQ-ID-NO-608   ---MDSSSEQQ  HQQMSNQSLE  ----------  SMLTCSKGEQ  DKKAKP-QPE  -ALKCPRCDS   46

SEQ-ID-NO-606   TNTKFCYYNN  YSLSQPRYFC  ----------  KSCRRYWTKG  GL-RNIPIGG  AYRKHKRS-S   96
SEQ-ID-NO-609   TNTKFCYYNN  YSLSQPRYFC  ----------  KSCRRYWTKG  GTLRNVPVGG  GCRKKR---S   82
SEQ-ID-NO-607   NNTKFCYYNN  YSLSQPRYFC  ----------  KSCRRYWTKG  GTLRNVPVGG  GCRKNKRSSS   98
SEQ-ID-NO-608   SNTKFCYYNN  YSLSQPRYFC  ----------  KSCRRYWTKG  GTLRNVPVGG  GCRKNKRSSS   96

SEQ-ID-NO-606   SATKSLRTTP  EPTMTHDGKS  ----------  FPTASFGYNN  NNISNEQME-  ---GLA----  139
SEQ-ID-NO-609   SSLKRAQGQT  LTPNLNPLTT  ----------  LPHLSYDSND  FTLAVARFQK  QSSGOLGYN-  131
SEQ-ID-NO-607   ASSKRSQDQP  FQLNPNPLTC  ----------  FPSLSYDSND  LTLALARLQK  GH-GFDH---  145
SEQ-ID-NO-608   SVSRRIQDQA  FVNNPNPVTC  ----------  FPSLSYDSND  LTLALARLQK  GQLGFDH---  143

SEQ-ID-NO-606   ---YALLNKQ  P---------  ---------  -LGVSSHLG  FG-SSQSPMA  MDGV----YG  170
SEQ-ID-NO-609   DRDLSILGNP  T---------  ---------TG  SFCDILGNSG  MNPSSANPSF  LDAIRTGFL-  174
SEQ-ID-NO-607   EHDFSILGNQ  N---------  ---------N  TSCGILNNHG  MNHSSNNGF  FEAL------MG  183
SEQ-ID-NO-608   EHDFSILGNH  ANSNININN  ----------  TSCAVLNNHG  MNHSSNHGF  FEAL------MG  189

SEQ-ID-NO-606   TISHQMENTG  YAFGNGGGG-  ----------  VDNGNSGVVG  VSGEMMLPYD  QVIMSNATTQ  189
SEQ-ID-NO-609   TQNH-LQNLY  CMYGNGDLGE  ----------  VDNGNANCNG  NGEMMLPYD  HE---ADMSIATTQ  223
SEQ-ID-NO-607   SQNN-VQNLY  V-------MGE  ----------  VDNGNV----  SGEMMLPYD  HE---MSIATTQ  224
SEQ-ID-NO-608   SQNN-VQNLY  YGYGNRDMGE  ----------  VDNGNV----  SGEMMLPYD  HE---MSIATTQ  232

SEQ-ID-NO-606   ----------  MEQMATSDPN  ----------  RVLMGFPWQM  NMGGGSGHGH  GHVDQID-SG  228
SEQ-ID-NO-609   SVSV--MKQE  MCSRREQSER  ----------  RVLGFPWQI  N---------  TNIGELD-SG  263
SEQ-ID-NO-607   AVTVTMKQE  MCNVREQNEN  ----------  RVLGFPWQF  N-------NGD  TNMAEMDHLG  268
SEQ-ID-NO-608   AVTVTMKQE  MCNVREQNES  ----------  RVLLGFPWQF  N-------NGD  SNMDEIDHSG  276

245
SEQ-ID-NO-606   RE---WSSTV  NYINTG----  ALL                                            245
SEQ-ID-NO-609   RT-ASWNSFT  NSW-HGFQS  PLM                                            285
SEQ-ID-NO-607   RAG--WNGLT  SSWGHGLLNS  PLM                                            289
SEQ-ID-NO-608   RAG--WNGLT  SPW-HGLLNS  PLM                                            296
```

Figure 24

MODULATING LIGHT RESPONSE PATHWAYS IN PLANTS, INCREASING LIGHT-RELATED TOLERANCES IN PLANTS, AND INCREASING BIOMASS IN PLANTS

CROSS-REFERENCE TO RELATED APPLICATIONS

This application is a divisional of U.S. patent application Ser. No. 13/630,902 filed Sep. 28, 2012 which application is a continuation-in-part application of and claims priority to U.S. patent application Ser. No. 13/630,902 filed Sep. 28, 2012 which application is a continuation-in-part application of and claims priority to U.S. patent application Ser. No. 12/863,102, filed Apr. 11, 2011, which is a National Stage application under 35 U.S.C. § 371 of International Application No. PCT/US2009/031292, filed Jan. 16, 2009, which claims the benefit of priority under 35 U.S.C. § 119(e) to U.S. Provisional Patent Application Ser. No. 61/021,943, filed Jan. 18, 2008, U.S. patent application Ser. No. 13/630,902 filed Sep. 28, 2012, is also a continuation-in-part application of and claims priority to U.S. patent application Ser. No. 12/373,134, filed Apr. 6, 2010, which is a National Stage application under 35 U.S.C. § 371 of International Application No. PCT/US2007/073154, filed Jul. 10, 2007, which claims the benefit of priority under 35 U.S.C. § 119(e) to U.S. Provisional Patent Application Ser. No. 60/819,763, filed Jul. 10, 2006. U.S. patent application Ser. No. 13/630,902 filed Sep. 28, 2012, is also a continuation-in-part application of and claims priority to U.S. patent application Ser. No. 12/513,086, filed Apr. 23, 2010, which is a National Stage application under 35 U.S.C. § 371 of International Application No. PCT/US2007/083495, filed Nov. 2, 2007, which claims the benefit of priority under 35 U.S.C. § 119(e) to U.S. Provisional Patent Application Ser. No. 60/856,613, filed Nov. 3, 2006, U.S. patent application Ser. No. 13/630,902 filed Sep. 28, 2012, is also a continuation-in-part application of and claims priority to U.S. patent application Ser. No. 12/515,687, filed Apr. 6, 2010, which is a National Stage application under 35 U.S.C. § 371 of International Application No. PCT/US2007/085237, filed Nov. 20, 2007, which claims the benefit of priority under 35 U.S.C. § 119(e) to U.S. Provisional Patent Application Ser. No. 60/860,145, filed Nov. 20, 2006. U.S. patent application Ser. No. 13/630, 902 filed Sep. 28, 2012, is also a continuation-in-part application of and claims priority to U.S. patent application Ser. No. 12/307,561, filed Nov. 23, 2009, which is a National Stage application under 35 U.S.C. § 371 of International Application No. PCT/US2007/072877, filed Jul. 5, 2007, which claims priority under 35 U.S.C. § 119(e) to U.S. Provisional Patent Application Ser. No. 60/818,569, filed Jul. 5, 2006. U.S. patent application Ser. No. 13/630,902 filed Sep. 28, 2012, is also a continuation-in-part application of and claims priority to U.S. patent application Ser. No. 13/119,572, filed Mar. 17, 2011, which is a National Stage application under 35 U.S.C. § 371 of International Application No. PCT/US2009/057116, filed Sep. 16, 2009, which claims the benefit of priority under 35 U.S.C. § 119(e) to U.S. Provisional Patent Application Ser. No. 61/097,789, filed Sep. 17, 2008. The disclosures of these prior applications are considered part of (and are incorporated by reference in their entirety in) the disclosure of this application.

TECHNICAL FIELD

This document relates to methods and materials involved in plant shade and/or low light tolerance, and red light specific responses. For example, this document provides plants having increased shade and/or low light tolerance as well as materials and methods for making plants having increased shade and/or low light tolerance. This document also relates to methods and materials involved in increasing UV-B tolerance in plants and methods and materials involved in modulating biomass levels in plants.

BACKGROUND

Light is the source of energy that fuels plant growth through photosynthesis. Light is also a developmental signal that modulates morphogenesis, such as de-etiolation and the transition to reproductive development. Since plants cannot choose their surroundings, they are forced to adapt their growth to ambient light conditions and have evolved complex mechanisms for monitoring the quantity and quality of the surrounding light. For example, many kinds of plants respond to growth under dense canopies or at high densities by growing faster and taller (Cerdan and Chory (2003) Nature, 423:881). Densely planted crops tend to place energy into stem and petiole elongation to lift the leaves into the sunlight rather than putting energy into storage or reproductive structures. The response to low light conditions and/or shade conditions negatively affects crop yields by reducing the amount of harvestable products such as seeds, fruits and tubers. In addition, tall spindly plants tend to be less wind resistant and lodge more easily, further reducing crop yield.

There is a continuing need for plants that can thrive under less than optimal environmental conditions. One strategy to improve a plant's ability to withstand suboptimal environmental conditions relies upon traditional plant breeding methods. Another approach involves genetic manipulation of plant characteristics through the introduction of exogenous nucleic acids conferring a desirable trait.

SUMMARY

The spectral energy distribution of daylight is dramatically altered by vegetation. Light reflected from neighboring vegetation is depleted in red (R) wavelengths, but remains rich in far-red (FR) wavelengths. It is desirable to have plants that exhibit increased shade tolerance. Plants having increased shade tolerance described herein exhibit an increased tolerance to shade conditions, in particular, Short Day plus End-of-Day Far-Red (SD+EODFR) conditions. Wild-type plants typically exhibit shade avoidance responses to SD+EODFR conditions, whereas the SD+EODFR-tolerant plants described herein display a reduction in the level of shade avoidance responses relative to the level of shade avoidance responses displayed by non-SD+EODFR-tolerant plants.

The quantity of light can dictate the eventual biomass and yield of plants. Wild-type plants typically exhibit low light responses, whereas the low light-tolerant plants described herein display a reduction in the level of low light responses relative to the level of low light responses displayed by non-low light-tolerant plants.

Increasing the SD+EODFR and/or low light tolerance of plants can increase the crop yields of such plants, which can benefit both food consumers and producers. This document provides methods and materials related to plants having increased shade and/or low light tolerance. For example, this document provides transgenic plants having increased SD+EODFR and/or low light tolerance, nucleic acids used to generate transgenic plants having increased SD+EODFR and/or low light tolerance, and methods for making plants having increased SD+EODFR and/or low light tolerance. Such plants may be useful to produce biomass which may be converted to a liquid fuel or other chemicals and/or to produce crops with increased yield and/or quality.

Methods of producing a plant are provided herein. In one aspect, a method comprises growing a plant cell comprising an exogenous nucleic acid. The exogenous nucleic acid comprises a regulatory region operably linked to a nucleotide sequence encoding a polypeptide. The Hidden Markov Model (HMM) bit score of the amino acid sequence of the polypeptide is greater than about 20, using an HMM generated from the amino acid sequences depicted in one of FIGS. 1-24. A plant produced from the cell has a difference in low light or SD+EODFR tolerance as compared to a control plant that does not comprise the exogenous nucleic acid.

In another aspect, the exogenous nucleic acid comprises a regulatory region operably linked to a nucleotide sequence encoding a polypeptide having 80 percent or greater sequence identity to an amino acid sequence set forth in SEQ ID NOs:3, 5, 7, 9, 10, 12, 14, 16, 18, 20, 22, 24, 25, 26, 28, 30, 32, 34, 36, 38, 40, 42, 44, 46, 48, 49, 51, 53, 55, 57, 59, 60, 61, 62, 63, 65, 67, 70, 72, 74, 76, 78, 80, 82, 84, 86, 88, 89, 90, 91, 93, 95, 96, 97, 98, 99, 100, 101, 102, 103, 105, 107, 109, 111, 113, 115, 116, 117, 118, 119, 120, 121, 122, 124, 126, 129, 130, 131, 132, 133, 135, 137, 139, 141, 143, 145, 147, 149, 151, 153, 155, 157, 159, 161, 163, 165, 167, 169, 171, 173, 175, 177, 179, 181, 183, 185, 187, 188, 189, 191, 193, 195, 197, 199, 201, 203, 205, 207, 209, 211, 213, 215, 217, 219, 221, 223, 225, 227, 229, 230, 231, 232, 233, 234, 235, 236, 237, 238, 239, 241, 243, 245, 247, 249, 251, 253, 255, 257, 259, 261, 262, 264, 266, 268, 270, 271, 273, 275, 277, 279, 281, 283, 285, 287, 289, 291, 292, 293, 294, 295, 296, 297, 298, 299, 300, 301, 302, 303, 304, 306, 308, 310, 312, 314, 317, 319, 321, 323, 325, 327, 329, 330, 331, 332, 334, 337, 339, 341, 343, 344, 346, 347, 348, 349, 350, 351, 352, 353, 354, 355, 357, 359, 361, 362, 364, 365, 366, 367, 368, 370, 372, 374, 376, 378, 379, 381, 383, 385, 387, 389, 391, 393, 395, 397, 399, 401, 403, 405, 407, 409, 411, 413, 415, 417, 419, 421, 423, 425, 427, 429, 431, 433, 435, 437, 439, 441, 443, 445, 447, 449, 451, 453, 456, 457, 458, 459, 460, 462, 464, 466, 468, 470, 472, 474, 475, 477, 478, 479, 480, 481, 482, 483, 484, 485, 486, 487, 488, 489, 491, 493, 494, 495, 496, 497, 498, 499, 501, 503, 505, 507, 508, 509, 510, 511, 512, 514, 515, 516, 518, 520, 521, 522, 523, 524, 525, 526, 527, 528, 529, 530, 531, 532, 533, 534, 535, 536, 538, 539, 541, 542, 543, 544, 545, 546, 547, 548, 549, 550, 552, 554, 555, 556, 557, 558, 559, 560, 561, 562, 563, 564, 565, 567, 570, 572, 574, 576, 578, 579, 580, 582, 584, 586, 588, 590, 592, 594, 596, 598, 600, 601, 603, 606, 607, 608, 609, 611, 613, 615, 616, 617, 618, 620, 621, 622, 624, 625, 626, 628, 629, 631, 634, 636, 637, 638, 639, 641, 644, 645, 647, 649, 651, 653, 655, 657, 659, 661, 663, 665, 667, 669, 671, 673, 675, 676, 678, 680, 682, 684, 686, 688, 690, 692, 694, 695, 697, 699, 701, 702, 704, 706, 708, 709, 711, 712, 713, 714, 716, 718, 720, 721, 723, 725, 726, 728, 730, 732, 734, 736, 738, 740, 741, 742, 743, 744, 745, 747, 749, 750, 751, 753, 755, 757, 759, 761, 762, 763, 764, 765, 767, 769, 771, 773, 774, 776, 778, 779, 780, 782, 783, 784, 786, 788, 790, 792, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 826, 827, 829, 830, 831, 832, 833, 834, 835, 837, 838, 839, 840, 841, 843, 845, 847, 850, 851, 853, 855, 857, 859, 861, 862, 863, 864, 865, 866, 868, 870, 872, 874, 876, 877, 879, 881, 883, 885, 887, 889, 891, 893, 895, 897, 898, 900, 902, 904, 907, 909, 911, 913, 915, 917, 919, 920, 922, 923, 924, 926, 928, 929, 930, 931, 932, 934, 936, 937, 938, 939, 940, 941, 943, 945, 947, 948, 949, 950, 953, 955, 957, 959, 961, 963, 965, 966, 967, 969, 971, 973, 975, 977, 979, 981, 983, 985, 987, 989, 991, 993, 995, 997, 999, 1001, 1003, 1005, 1007, 1009, 1011, 1013, 1014, 1015, 1016, 1018, 1024, 1025, 1027, 1029, 1030, 1032, 1033, 1035, 1037, 1039, 1040, 1042, 1043, 1044, 1047, 1049, 1051, 1053, 1055, 1057, 1059, 1061, 1063, 1065, 1067, 1068, 1069, 1071, 1072, 1073, 1074, 1075, 1077, 1078, 1080, 1081, 1083, 1085, 1087, 1089, 1091, 1093, 1095, 1097, 1098, 1099, 1100, 1101, 1103, 1105, 1107, 1109, 1111, 1113, 1115, 1117, 1119, 1121, 1123, 1125, 1127, 1129, 1131, 1133, 1134, 1135, 1136, 1137, 1138, 1139, 1141, 1143, 1145, 1147, 1149, 1151, 1153, 1155, 1157, 1159, 1160, 1161, 1162, 1164, 1166, 1168, 1170, 1172, 1174, 1176, 1178, 1180, 1182, 1184, 1186, 1188, 1190, 1192, 1194, 1196, 1198, 1199, 1200, 1201, 1202, 1203, 1204, 1206, 1208, 1209, 1211, 1213, 1214, 1215, 1216, 1217, 1219, 1221, 1223, 1225, 1227, 1229, 1230, 1232, 1234, 1236, 1238, 1240, 1242, 1244, 1246, 1248, 1250, 1252, 1254, 1255, 1256, 1257, 1258, 1259, 1260, 1261, 1262, 1263, 1264, 1266, 1268, 1270, 1272, 1274, 1277, 1279, 1281, 1283, 1285, 1287, 1289, 1291, 1293, 1294, 1295, 1297, 1298, 1299, 1301, 1303, 1305, 1307, 1309, 1311, 1313, 1315, 1317, 1319, 1321, 1322, 1323, 1324, 1325, 1326, 1327, 1328, 1329, 1330, 1331, 1332, 1334, 1336, 1338, 1340, 1342, 1344, 1347, 1349, 1351, 1352, 1353, 1355, 1357, 1358, 1360, 1362, 1364, 1366, 1367, 1368, 1370, 1372, 1374, 1375, 1377, 1379, 1381, 1383, 1385, 1387, 1389, 1391, 1393, 1395, 1397, 1399, 1401, 1402, 1404, 1406, 1408, 1410, 1411, 1412, 1413, 1414, 1415, 1417, 1419, 1421, 1422, 1423, 1424, 1425, 1426, 1427, 1429, 1430, 1431, 1433, 1434, 1435, 1436, 1438, 1439, 1440, 1442, 1444, 1446, 1448, 1450, 1452, 1457, 1458, 1460, 1462, 1464, 1466, 1467, 1468, 1469, 1471, 1473, 1475, 1477, 1478, 1479, 1480, 1481, 1482, 1483, 1484, 1485, 1486, 1488, 1490, 1492, 1494, 1497, 1499, 1501, 1502, 1503, 1504, 1505, 1506, 1508, 1510, 1511, 1512, 1513, 1514, 1515, 1516, 1518, 1519, 1520, 1521, 1522, 1523, 1524, 1525, 1527, 1528, 1529, 1531, 1532, 1533, 1534, 1535, 1536, 1540, 1541, 1543, 1545, 1547, 1549, 1551, 1553, 1554, 1555, 1556, 1557, 1558, 1559, 1561, 1563, 1564, 1565, 1566, 1567, 1568, 1570, 1572, 1574, 1576, 1578, 1580, 1582, 1584, 1587, 1589, 1591, 1593, 1594, 1596, 1597, 1598, 1599, 1600, 1601, 1602, 1603, 1604, 1605, 1606, 1607, 1609, 1611, 1612, 1613, 1614, 1615, 1616, 1617, 1618, 1619, 1620, 1621, 1623, 1625, 1630, 1631, 1632, 1635, 1637, 1639, 1641, 1642, 1643, 1644, 1646, 1648, 1650, 1651, 1652, 1653, 1654, 1655, 1657, 1659, 1661, 1663, 1665, 1667, 1669, 1671, 1673, 1675, 1677, 1679, 1681, 1682, 1684, 1686, 1688, 1690, 1692, 1694, 1696, 1698, 1699, 1700, 1701, 1702, 1703, 1704, 1705, 1707, 1709, 1711, 1713, 1715, 1717, 1719, 1720, 1721, 1722, 1723, 1725, 1727, 1729, 1730, 1732, 1734, 1736, 1738, 1739, 1740, 1741, 1742, 1743, 1744, 1745, 1746, 1748, 1750, 1751, 1752, 1754, 1756, 1758, 1760, 1762, 1764, 1766, 1767, 1768, 1769, 1770, 1771, 1772, 1773, 1774, 1775, 1776, 1777, 1778, 1780, 1782, 1784, 1786, 1788, 1790, 1792, 1794, 1796, 1798, 1800, 1802, 1804, 1805, 1806, 1807, 1808, 1809, 1810, 1811, 1812, 1813, 1814, 1815, 1816, 1817, 1818, 1819, 1820, 1821, 1822, 1823, 1824, 1825, 1826, 1827, 1828, 1829, 1830, 1831, 1832, 1833, 1834, 1835, 1836, 1837, 1838, 1839, 1840, 1842, 1843, 1844, 1845, 1846, 1847, 1848, 1850, 1852, 1854, 1856, 1858, 1859, 1860, 1861, 1862, 1863, 1864, 1865, 1866, 1867, 1869, 1870, 1871, 1873, 1875, 1877, 1879, 1881, 1883, 1885, 1887, 1889, 1891, 1893, 1895, 1897, 1899, 1901, 1903, 1905, 1907, 1909, 1911, 1913, 1915, 1917, 1919, 1921, 1923, 1925, 1927, 1929, 1931, 1933, 1935, 1937, 1939, 1941, 1943, 1945, 1947, 1949, 1951, 1953, 1955, 1957, 1959, 1961, 1963, 1965, 1967, 1969, 1971, 1973, 1975, 1977, 1979, 1981, 1983, 1985, 1987, 1989, 1991, 1993, 1995, 1997, 1999, 2001, 2003, 2005, 2007, 2009, 2011, 2013, 2015, 2017, 2019, 2021, 2023, 2025, 2027, 2029, 2030, 2031, 2032, 2033, 2034, 2035, 2036, 2037, 2038, 2039, 2040, 2041, 2042, 2043, 2044, 2045, 2046, 2047, 2048, 2049, 2050, 2051, 2052, 2053, 2054, 2055, 2056, 2057, 2058, 2059, 2060, 2061, 2062, 2063, 2064, 2065, 2066, 2067, 2069, 2070, 2072, 2074, 2076, 2078, 2080, 2081, 2083, 2084, 2085, 2087, 2089, 2091, 2093, 2095, 2097, 2099, 2101, 2103, 2105, 2107, 2109, 2111, 2113, 2114, 2115, 2116, 2117, 2118, 2119, 2120, 2121, 2123, 2125, 2127, 2129, 2131, 2133, 2135, 2136, 2137, 2138, 2139, 2140, 2141, 2142, 2143, 2144, 2146, 2148, 2150, 2152, 2154, 2156, 2158, 2160, 2162, 2164, 2166, 2168, 2170, 2172, 2174, 2176, 2178, 2180, 2182, 2183, 2184, 2185, 2186, 2187, 2188, 2189, 2190, 2191, 2192, 2193, 2194, 2195, 2196, 2197, 2198, 2199, 2200, 2201, 2202, 2203, 2204, 2205, 2206, 2207, 2208, 2209, 2210, 2211, 2212, 2213, 2214, 2215, 2216, 2217, 2218, 2219, 2220, 2221, 2222, 2223, 2224, 2225, 2226, 2227, 2228, 2229, 2230, 2231, 2232, 2233, 2234, 2235, 2236, 2237, 2238, 2239, 2240, 2241, 2242, 2243, 2244, 2245, 2246, 2247, 2248, 2249, 2250, 2251, 2252, 2253, 2254, 2255, 2256, 2257, 2258, 2259, 2260, 2261, 2262, 2263, 2264, 2266, 2268, 2269, 2270, 2271, 2272, 2273, 2274, 2275, 2276, 2277, 2278, 2280, 2282, 2284, 2286, 2288, 2290, 2292, 2294, 2296, 2298, 2300, 2302, 2304, 2306, 2308, 2310, 2312, 2314, 2316, 2318, 2320, 2322, 2323, 2324, 2325, 2326, 2327, 2328, 2329, 2330, 2331, 2332, 2333, 2334, 2335, 2336, 2337, 2338, 2339, 2340, 2341, 2342, 2343, 2344, 2345, 2346, 2347, 2348, 2350, 2352, 2354, 2356, 2358, 2360, 2362, 2364, 2366, 2368, 2370, 2372, 2374, 2375, 2376, 2377, 2378, 2379, 2380, or 2381. A plant produced from the plant cell has a difference in low light or SD+EODFR tolerance as compared to a control plant that does not comprise the exogenous nucleic acid.

In one aspect, the polypeptide further comprises a CDI domain having 70 percent or greater sequence identity to the CDI domain of SEQ ID NO:70. In another aspect, the polypeptide further comprises an AUX/IAA domain having 70 percent or greater sequence identity to the AUX/IAA domain of SEQ ID NO:129 or SEQ ID NO:1347. In another aspect, the polypeptide further comprises a homeobox domain having 70 percent or greater sequence identity to the homeobox domain of SEQ ID NO:317. In another aspect, the polypeptide further comprises a zf_C3HC4 domain having 70 percent or greater sequence identity to the zf_C3HC4 domain of SEQ ID NO:337. In another aspect, the polypeptide further comprises a B-box zinc finger domain having 70 percent or greater sequence identity to the B-box zinc finger domain of SEQ ID NO:456 and a CCT motif having 70 percent or greater sequence identity to the CCT motif of SEQ ID NO:456. In another aspect, the polypeptide further comprises a FAD_binding_7 domain having 70 percent or greater sequence identity to the FAD_binding_7 domain of SEQ ID NO:538 or SEQ ID NO:1497 and a DNA photolyase domain having 70 percent or greater sequence identity to the DNA photolyase domain of SEQ ID NO:538 or SEQ ID NO:1497. In another aspect, the polypeptide further comprises a zf_Dof domain having 70 percent or greater sequence identity to the zf_Dof domain of SEQ ID NO:606. In another aspect, the polypeptide further comprises an AP2 domain having 70 percent or greater sequence identity to the AP2 domain of SEQ ID NO:645. In another aspect, the polypeptide further comprises a VQ motif having 70 percent or greater sequence identity to the VQ motif of SEQ ID NO:850. In another aspect, the polypeptide further comprises a zf_C2H2 domain having 70 percent or greater sequence identity to the zf_C2H2 domain of SEQ ID NO:907. In another aspect, the polypeptide further comprises a TCP domain having 70 percent or greater sequence identity to the TCP domain of SEQ ID NO:1151. In another aspect, the polypeptide further comprises an F-box domain having 70 percent or greater sequence identity to the F-box domain of SEQ ID NO:1277. In another aspect, the polypeptide further comprises a zf_CCCH domain having 70 percent or greater sequence identity to the zf_CCCH domain of SEQ ID NO:1457. In another aspect, the polypeptide further comprises a PDX domain having 70 percent or greater sequence identity to the PDX domain of SEQ ID NO:1540 and a homeobox domain having 70 percent or greater sequence identity to the homeobox domain of SEQ ID NO:1540. In another aspect, the polypeptide further comprises an HSF-type DNA-binding domain having 70 percent or greater sequence identity to the HSF-type DNA-binding domain of SEQ ID NO:1587. In another aspect, the polypeptide further comprises a SAM_1 domain having 70 percent or greater sequence identity to the SAM_1 domain of SEQ ID NO:1635 and a DRMBL domain having 70 percent or greater sequence identity to the DRMBL domain of SEQ ID NO:1635.

In another aspect, a method of producing a plant comprises growing a plant cell comprising an exogenous nucleic acid, where the exogenous nucleic acid comprises a regulatory region operably linked to a nucleotide sequence having 80 percent or greater sequence identity to a nucleotide sequence, or a fragment thereof, set forth in SEQ ID NOs:1, 2, 4, 6, 8, 11, 13, 15, 17, 19, 21, 23, 27, 29, 31, 33, 35, 37, 39, 41, 43, 45, 47, 50, 52, 54, 56, 58, 64, 66, 68, 69, 71, 73, 75, 77, 79, 81, 83, 85, 87, 92, 94, 104, 106, 108, 110, 112, 114, 123, 125, 127, 128, 134, 136, 138, 140, 142, 144, 146, 148, 150, 152, 154, 156, 158, 160, 162, 164, 166, 168, 170, 172, 174, 176, 178, 180, 182, 184, 186, 190, 192, 194, 196, 198, 200, 202, 204, 206, 208, 210, 212, 214, 216, 218, 220, 222, 224, 226, 228, 240, 242, 244, 246, 248, 250, 252, 254, 256, 258, 260, 263, 265, 267, 269, 272, 274, 276, 278, 280, 282, 284, 286, 288, 290, 305, 307, 309, 311, 313, 315, 316, 318, 320, 322, 324, 326, 328, 333, 335, 336, 338, 340, 342, 345, 356, 358, 360, 363, 369, 371, 373, 375, 377, 380, 382, 384, 386, 388, 390, 392, 394, 396, 398, 400, 402, 404, 406, 408, 410, 412, 414, 416, 418, 420, 422, 424, 426, 428, 430, 432, 434, 436, 438, 440, 442, 444, 446, 448, 450, 452, 454, 455, 461, 463, 465, 467, 469, 471, 473, 476, 490, 492, 500, 502, 504, 506, 513, 517, 519, 537, 540, 551, 553, 566, 568, 569, 571, 573, 575, 577, 581, 583, 585, 587, 589, 591, 593, 595, 597, 599, 602, 604, 605, 610, 612, 614, 619, 623, 627, 630, 632, 633, 635, 640, 642, 643, 646, 648, 650, 652, 654, 656, 658, 660, 662, 664, 666, 668, 670, 672, 674, 677, 679, 681, 683, 685, 687, 689, 691, 693, 696, 698, 700, 703, 705, 707, 710, 715, 717, 719, 722, 724, 727, 729, 731, 733, 735, 737, 739, 746, 748, 752, 754, 756, 758, 760, 766, 768, 770, 772, 775, 777, 781, 785, 787, 789, 791, 793, 825, 828, 836, 842, 844, 846, 848, 849, 852, 854, 856, 858, 860, 867, 869, 871, 873, 875, 878, 880, 882, 884, 886, 888, 890, 892, 894, 896, 899, 901, 903, 905, 906, 908, 910, 912, 914, 916, 918, 921, 925, 927, 933, 935, 942, 944, 946, 951, 952, 954, 956, 958, 960, 962, 964, 968, 970, 972, 974, 976, 978, 980, 982, 984, 986, 988, 990, 992, 994, 996, 998, 1000, 1002, 1004, 1006, 1008, 1010, 1012, 1017, 1019, 1020, 1021, 1022, 1023, 1026, 1028, 1031, 1034, 1036, 1038, 1041, 1045, 1046, 1048, 1050, 1052, 1054, 1056, 1058, 1060, 1062, 1064, 1066, 1070, 1076, 1079, 1082, 1084, 1086, 1088, 1090, 1092, 1094, 1096, 1102, 1104, 1106, 1108, 1110, 1112, 1114, 1116, 1118, 1120, 1122, 1124, 1126, 1128, 1130, 1132, 1140, 1142, 1144, 1146, 1148, 1150, 1152, 1154, 1156, 1158, 1163, 1165, 1167, 1169, 1171, 1173, 1175, 1177, 1179, 1181, 1183, 1185, 1187, 1189, 1191, 1193, 1195, 1197, 1205, 1207, 1210, 1212, 1218, 1220, 1222, 1224, 1226, 1228, 1231, 1233, 1235, 1237, 1239, 1241, 1243, 1245, 1247, 1249, 1251, 1253, 1265, 1267, 1269, 1271, 1273, 1275, 1276, 1278, 1280, 1282, 1284, 1286, 1288, 1290, 1292, 1296, 1300, 1302, 1304, 1306, 1308, 1310, 1312, 1314, 1316, 1318, 1320, 1333, 1335, 1337, 1339, 1341, 1343, 1345, 1346, 1348, 1350, 1354, 1356, 1359, 1361, 1363, 1365, 1369, 1371, 1373, 1376, 1378, 1380, 1382, 1384, 1386, 1388, 1390, 1392, 1394, 1396, 1398, 1400, 1403, 1405, 1407, 1409, 1416, 1418, 1420, 1428, 1432, 1437, 1441, 1443, 1445, 1447, 1449, 1451, 1453, 1454, 1455, 1456, 1459, 1461, 1463, 1465, 1470, 1472, 1474, 1476, 1487, 1489, 1491, 1493, 1495, 1496, 1498, 1500, 1507, 1509, 1517, 1526, 1530, 1537, 1538, 1539, 1542, 1544, 1546, 1548, 1550, 1552, 1560, 1562, 1569, 1571, 1573, 1575, 1577, 1579, 1581, 1583, 1585, 1586, 1588, 1590, 1592, 1595, 1608, 1610, 1622, 1624, 1626, 1627, 1628, 1629, 1633, 1634, 1636, 1638, 1640, 1645, 1647, 1649, 1656, 1658, 1660, 1662, 1664, 1666, 1668, 1670, 1672, 1674, 1676, 1678, 1680, 1683, 1685, 1687, 1689, 1691, 1693, 1695, 1697, 1706, 1708, 1710, 1712, 1714, 1716, 1718, 1724, 1726, 1728, 1731, 1733, 1735, 1737, 1747, 1749, 1753, 1755, 1757, 1759, 1761, 1763, 1765, 1779, 1781, 1783, 1785, 1787, 1789, 1791, 1793, 1795, 1797, 1799, 1801, 1803, 1841, 1849, 1851, 1853, 1855, 1857, 1868, 1872, 1874, 1876, 1878, 1880, 1882, 1884, 1886, 1888, 1890, 1892, 1894, 1896, 1898, 1900, 1902, 1904, 1906, 1908, 1910, 1912, 1914, 1916, 1918, 1920, 1922, 1924, 1926, 1928, 1930, 1932, 1934, 1936, 1938, 1940, 1942, 1944, 1946, 1948, 1950, 1952, 1954, 1956, 1958, 1960, 1962, 1964, 1966, 1968, 1970, 1972, 1974, 1976, 1978, 1980, 1982, 1984, 1986, 1988, 1990, 1992, 1994, 1996, 1998, 2000, 2002, 2004, 2006, 2008, 2010, 2012, 2014, 2016, 2018, 2020, 2022, 2024, 2026, 2028, 2068, 2071, 2073, 2075, 2077, 2079, 2082, 2086, 2088, 2090, 2092, 2094, 2096, 2098, 2100, 2102, 2104, 2106, 2108, 2110, 2112, 2122, 2124, 2126, 2128, 2130, 2132, 2134, 2145, 2147, 2149, 2151, 2153, 2155, 2157, 2159, 2161, 2163, 2165, 2167, 2169, 2171, 2173, 2175, 2177, 2179, 2181, 2265, 2267, 2279, 2281, 2283, 2285, 2287, 2289, 2291, 2293, 2295, 2297, 2299, 2301, 2303, 2305, 2307, 2309, 2311, 2313, 2315, 2317, 2319, 2321, 2349, 2351, 2353, 2355, 2357, 2359, 2361, 2363, 2365, 2367, 2369, 2371, or 2373. A plant produced from the plant cell has a difference in low light or SD+EODFR tolerance as compared to a control plant that does not comprise the exogenous nucleic acid.

Methods of modulating low light tolerance in a plant are provided herein. In one aspect, a method comprises introducing into a plant cell an exogenous nucleic acid, that comprises a regulatory region operably linked to a nucleotide sequence encoding a polypeptide. The HMM bit score of the amino acid sequence of the polypeptide is greater than about 20, using an HMM generated from the amino acid sequences depicted in one of FIGS. 1-24. A plant produced from the plant cell has a difference in low light tolerance as compared to a control plant that does not comprise the exogenous nucleic acid.

In another aspect, a method comprises introducing into a plant cell an exogenous nucleic acid that comprises a regulatory region operably linked to a nucleotide sequence encoding a polypeptide having 80 percent or greater sequence identity to an amino acid sequence set forth in SEQ ID NOs:3, 5, 7, 9, 10, 12, 14, 16, 18, 20, 22, 24, 25, 26, 28, 30, 32, 34, 36, 38, 40, 42, 44, 46, 48, 49, 51, 53, 55, 57, 59, 60, 61, 62, 63, 65, 67, 70, 72, 74, 76, 78, 80, 82, 84, 86, 88, 89, 90, 91, 93, 95, 96, 97, 98, 99, 100, 101, 102, 103, 105, 107, 109, 111, 113, 115, 116, 117, 118, 119, 120, 121, 122, 124, 126, 129, 130, 131, 132, 133, 135, 137, 139, 141, 143, 145, 147, 149, 151, 153, 155, 157, 159, 161, 163, 165, 167, 169, 171, 173, 175, 177, 179, 181, 183, 185, 187, 188, 189, 191, 193, 195, 197, 199, 201, 203, 205, 207, 209, 211, 213, 215, 217, 219, 221, 223, 225, 227, 229, 230, 231, 232, 233, 234, 235, 236, 237, 238, 239, 241, 243, 245, 247, 249, 251, 253, 255, 257, 259, 261, 262, 264, 266, 268, 270, 271, 273, 275, 277, 279, 281, 283, 285, 287, 289, 291, 292, 293, 294, 295, 296, 297, 298, 299, 300, 301, 302, 303, 304, 306, 308, 310, 312, 314, 317, 319, 321, 323, 325, 327, 329, 330, 331, 332, 334, 337, 339, 341, 343, 344, 346, 347, 348, 349, 350, 351, 352, 353, 354, 355, 357, 359, 361, 362, 364, 365, 366, 367, 368, 370, 372, 374, 376, 378, 379, 381, 383, 385, 387, 389, 391, 393, 395, 397, 399, 401, 403, 405, 407, 409, 411, 413, 415, 417, 419, 421, 423, 425, 427, 429, 431, 433, 435, 437, 439, 441, 443, 445, 447, 449, 451, 453, 456, 457, 458, 459, 460, 462, 464, 466, 468, 470, 472, 474, 475, 477, 478, 479, 480, 481, 482, 483, 484, 485, 486, 487, 488, 489, 491, 493, 494, 495, 496, 497, 498, 499, 501, 503, 505, 507, 508, 509, 510, 511, 512, 514, 515, 516, 518, 520, 521, 522, 523, 524, 525, 526, 527, 528, 529, 530, 531, 532, 533, 534, 535, 536, 538, 539, 541, 542, 543, 544, 545, 546, 547, 548, 549, 550, 552, 554, 555, 556, 557, 558, 559, 560, 561, 562, 563, 564, 565, 567, 570, 572, 574, 576, 578, 579, 580, 582, 584, 586, 588, 590, 592, 594, 596, 598, 600, 601, 603, 606, 607, 608, 609, 611, 613, 615, 616, 617, 618, 620, 621, 622, 624, 625, 626, 628, 629, 631, 634, 636, 637, 638, 639, 641, 644, 645, 647, 649, 651, 653, 655, 657, 659, 661, 663, 665, 667, 669, 671, 673, 675, 676, 678, 680, 682, 684, 686, 688, 690, 692, 694, 695, 697, 699, 701, 702, 704, 706, 708, 709, 711, 712, 713, 714, 716, 718, 720, 721, 723, 725, 726, 728, 730, 732, 734, 736, 738, 740, 741, 742, 743, 744, 745, 747, 749, 750, 751, 753, 755, 757, 759, 761, 762, 763, 764, 765, 767, 769, 771, 773, 774, 776, 778, 779, 780, 782, 783, 784, 786, 788, 790, 792, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 826, 827, 829, 830, 831, 832, 833, 834, 835, 837, 838, 839, 840, 841, 843, 845, 847, 850, 851, 853, 855, 857, 859, 861, 862, 863, 864, 865, 866, 868, 870, 872, 874, 876, 877, 879, 881, 883, 885, 887, 889, 891, 893, 895, 897, 898, 900, 902, 904, 907, 909, 911, 913, 915, 917, 919, 920, 922, 923, 924, 926, 928, 929, 930, 931, 932, 934, 936, 937, 938, 939, 940, 941, 943, 945, 947, 948, 949, 950, 953, 955, 957, 959, 961, 963, 965, 966, 967, 969, 971, 973, 975, 977, 979, 981, 983, 985, 987, 989, 991, 993, 995, 997, 999, 1001, 1003, 1005, 1007, 1009, 1011, 1013, 1014, 1015, 1016, 1018, 1024, 1025, 1027, 1029, 1030, 1032, 1033, 1035, 1037, 1039, 1040, 1042, 1043, 1044, 1047, 1049, 1051, 1053, 1055, 1057, 1059, 1061, 1063, 1065, 1067, 1068, 1069, 1071, 1072, 1073, 1074, 1075, 1077, 1078, 1080, 1081, 1083, 1085, 1087, 1089, 1091, 1093, 1095, 1097, 1098, 1099, 1100, 1101, 1103, 1105, 1107, 1109, 1111, 1113, 1115, 1117, 1119, 1121, 1123, 1125, 1127, 1129, 1131, 1133, 1134, 1135, 1136, 1137, 1138, 1139, 1141, 1143, 1145, 1147, 1149, 1151, 1153, 1155, 1157, 1159, 1160, 1161, 1162, 1164, 1166, 1168, 1170, 1172, 1174, 1176, 1178, 1180, 1182, 1184, 1186, 1188, 1190, 1192, 1194, 1196, 1198, 1199, 1200, 1201, 1202, 1203, 1204, 1206, 1208, 1209, 1211, 1213, 1214, 1215, 1216, 1217, 1219, 1221, 1223, 1225, 1227, 1229, 1230, 1232, 1234, 1236, 1238, 1240, 1242, 1244, 1246, 1248, 1250, 1252, 1254, 1255, 1256, 1257, 1258, 1259, 1260, 1261, 1262, 1263, 1264, 1266, 1268, 1270, 1272, 1274, 1277, 1279, 1281, 1283, 1285, 1287, 1289, 1291, 1293, 1294, 1295, 1297, 1298, 1299, 1301, 1303, 1305, 1307, 1309, 1311, 1313, 1315, 1317, 1319, 1321, 1322, 1323, 1324, 1325, 1326, 1327, 1328, 1329, 1330, 1331, 1332, 1334, 1336, 1338, 1340, 1342, 1344, 1347, 1349, 1351, 1352, 1353, 1355, 1357, 1358, 1360, 1362, 1364, 1366, 1367, 1368, 1370, 1372, 1374, 1375, 1377, 1379, 1381, 1383, 1385, 1387, 1389, 1391, 1393, 1395, 1397, 1399, 1401, 1402, 1404, 1406, 1408, 1410, 1411, 1412, 1413, 1414, 1415, 1417, 1419, 1421, 1422, 1423, 1424, 1425, 1426, 1427, 1429, 1430, 1431, 1433, 1434, 1435, 1436, 1438, 1439, 1440, 1442, 1444, 1446, 1448, 1450, 1452, 1457, 1458, 1460, 1462, 1464, 1466, 1467, 1468, 1469, 1471, 1473, 1475, 1477, 1478, 1479, 1480, 1481, 1482, 1483, 1484, 1485, 1486, 1488, 1490, 1492, 1494, 1497, 1499, 1501, 1502, 1503, 1504, 1505, 1506, 1508, 1510, 1511, 1512, 1513, 1514, 1515, 1516, 1518, 1519, 1520, 1521, 1522, 1523, 1524, 1525, 1527, 1528, 1529, 1531, 1532, 1533, 1534, 1535, 1536, 1540, 1541, 1543, 1545, 1547, 1549, 1551, 1553, 1554, 1555, 1556, 1557, 1558, 1559, 1561, 1563, 1564, 1565, 1566, 1567, 1568, 1570, 1572, 1574, 1576, 1578, 1580, 1582, 1584, 1587, 1589, 1591, 1593, 1594, 1596, 1597, 1598, 1599, 1600, 1601, 1602, 1603, 1604, 1605, 1606, 1607, 1609, 1611, 1612, 1613, 1614, 1615, 1616, 1617, 1618, 1619, 1620, 1621, 1623, 1625, 1630, 1631, 1632, 1635, 1637, 1639, 1641, 1642, 1643, 1644, 1646, 1648, 1650, 1651, 1652, 1653, 1654, 1655, 1657, 1659, 1661, 1663, 1665, 1667, 1669, 1671, 1673, 1675, 1677, 1679, 1681, 1682, 1684, 1686, 1688, 1690, 1692, 1694, 1696, 1698, 1699, 1700, 1701, 1702, 1703, 1704, 1705, 1707, 1709, 1711, 1713, 1715, 1717, 1719, 1720, 1721, 1722, 1723, 1725, 1727, 1729, 1730, 1732, 1734, 1736, 1738, 1739, 1740, 1741, 1742, 1743, 1744, 1745, 1746, 1748, 1750, 1751, 1752, 1754, 1756, 1758, 1760, 1762, 1764, 1766, 1767, 1768, 1769, 1770, 1771, 1772, 1773, 1774, 1775, 1776, 1777, 1778, 1780, 1782, 1784, 1786, 1788, 1790, 1792, 1794, 1796, 1798, 1800, 1802, 1804, 1805, 1806, 1807, 1808, 1809, 1810, 1811, 1812, 1813, 1814, 1815, 1816, 1817, 1818, 1819, 1820, 1821, 1822, 1823, 1824, 1825, 1826, 1827, 1828, 1829, 1830, 1831, 1832, 1833, 1834, 1835, 1836, 1837, 1838, 1839, 1840, 1842, 1843, 1844, 1845, 1846, 1847, 1848, 1850, 1852, 1854, 1856, 1858, 1859, 1860, 1861, 1862, 1863, 1864, 1865, 1866, 1867, 1869, 1870, 1871, 1873, 1875, 1877, 1879, 1881, 1883, 1885, 1887, 1889, 1891, 1893, 1895, 1897, 1899, 1901, 1903, 1905, 1907, 1909, 1911, 1913, 1915, 1917, 1919, 1921, 1923, 1925, 1927, 1929, 1931, 1933, 1935, 1937, 1939, 1941, 1943, 1945, 1947, 1949, 1951, 1953, 1955, 1957, 1959, 1961, 1963, 1965, 1967, 1969, 1971, 1973, 1975, 1977, 1979, 1981, 1983, 1985, 1987, 1989, 1991, 1993, 1995, 1997, 1999, 2001, 2003, 2005, 2007, 2009, 2011, 2013, 2015, 2017, 2019, 2021, 2023, 2025, 2027, 2029, 2030, 2031, 2032, 2033, 2034, 2035, 2036, 2037, 2038, 2039, 2040, 2041, 2042, 2043, 2044, 2045, 2046, 2047, 2048, 2049, 2050, 2051, 2052, 2053, 2054, 2055, 2056, 2057, 2058, 2059, 2060, 2061, 2062, 2063, 2064, 2065, 2066, 2067, 2069, 2070, 2072, 2074, 2076, 2078, 2080, 2081, 2083, 2084, 2085, 2087, 2089, 2091, 2093, 2095, 2097, 2099, 2101, 2103, 2105, 2107, 2109, 2111, 2113, 2114, 2115, 2116, 2117, 2118, 2119, 2120, 2121, 2123, 2125, 2127, 2129, 2131, 2133, 2135, 2136, 2137, 2138, 2139, 2140, 2141, 2142, 2143, 2144, 2146, 2148, 2150, 2152, 2154, 2156, 2158, 2160, 2162, 2164, 2166, 2168, 2170, 2172, 2174, 2176, 2178, 2180, 2182, 2183, 2184, 2185, 2186, 2187, 2188, 2189, 2190, 2191, 2192, 2193, 2194, 2195, 2196, 2197, 2198, 2199, 2200, 2201, 2202, 2203, 2204, 2205, 2206, 2207, 2208, 2209, 2210, 2211, 2212, 2213, 2214, 2215, 2216, 2217, 2218, 2219, 2220, 2221, 2222, 2223, 2224, 2225, 2226, 2227, 2228, 2229, 2230, 2231, 2232, 2233, 2234, 2235, 2236, 2237, 2238, 2239, 2240, 2241, 2242, 2243, 2244, 2245, 2246, 2247, 2248, 2249, 2250, 2251, 2252, 2253, 2254, 2255, 2256, 2257, 2258, 2259, 2260, 2261, 2262, 2263, 2264, 2266, 2268, 2269, 2270, 2271, 2272, 2273, 2274, 2275, 2276, 2277, 2278, 2280, 2282, 2284, 2286, 2288, 2290, 2292, 2294, 2296, 2298, 2300, 2302, 2304, 2306, 2308, 2310, 2312, 2314, 2316, 2318, 2320, 2322, 2323, 2324, 2325, 2326, 2327, 2328, 2329, 2330, 2331, 2332, 2333, 2334, 2335, 2336, 2337, 2338, 2339, 2340, 2341, 2342, 2343, 2344, 2345, 2346, 2347, 2348, 2350, 2352, 2354, 2356, 2358, 2360, 2362, 2364, 2366, 2368, 2370, 2372, 2374, 2375, 2376, 2377, 2378, 2379, 2380, or 2381. A plant produced from the plant cell has a difference in low light tolerance as compared to a control plant that does not comprise the exogenous nucleic acid.

In another aspect, a method comprises introducing into a plant cell an exogenous nucleic acid, that comprises a regulatory region operably linked to a nucleotide sequence having 80 percent or greater sequence identity to a nucleotide sequence set forth in SEQ ID NOs:1, 2, 4, 6, 8, 11, 13, 15, 17, 19, 21, 23, 27, 29, 31, 33, 35, 37, 39, 41, 43, 45, 47, 50, 52, 54, 56, 58, 64, 66, 68, 69, 71, 73, 75, 77, 79, 81, 83, 85, 87, 92, 94, 104, 106, 108, 110, 112, 114, 123, 125, 127, 128, 134, 136, 138, 140, 142, 144, 146, 148, 150, 152, 154, 156, 158, 160, 162, 164, 166, 168, 170, 172, 174, 176, 178, 180, 182, 184, 186, 190, 192, 194, 196, 198, 200, 202, 204, 206, 208, 210, 212, 214, 216, 218, 220, 222, 224, 226, 228, 240, 242, 244, 246, 248, 250, 252, 254, 256, 258, 260, 263, 265, 267, 269, 272, 274, 276, 278, 280, 282, 284, 286, 288, 290, 305, 307, 309, 311, 313, 315, 316, 318, 320, 322, 324, 326, 328, 333, 335, 336, 338, 340, 342, 345, 356, 358, 360, 363, 369, 371, 373, 375, 377, 380, 382, 384, 386, 388, 390, 392, 394, 396, 398, 400, 402, 404, 406, 408, 410, 412, 414, 416, 418, 420, 422, 424, 426, 428, 430, 432, 434, 436, 438, 440, 442, 444, 446, 448, 450, 452, 454, 455, 461, 463, 465, 467, 469, 471, 473, 476, 490, 492, 500, 502, 504, 506, 513, 517, 519, 537, 540, 551, 553, 566, 568, 569, 571, 573, 575, 577, 581, 583, 585, 587, 589, 591, 593, 595, 597, 599, 602, 604, 605, 610, 612, 614, 619, 623, 627, 630, 632, 633, 635, 640, 642, 643, 646, 648, 650, 652, 654, 656, 658, 660, 662, 664, 666, 668, 670, 672, 674, 677, 679, 681, 683, 685, 687, 689, 691, 693, 696, 698, 700, 703, 705, 707, 710, 715, 717, 719, 722, 724, 727, 729, 731, 733, 735, 737, 739, 746, 748, 752, 754, 756, 758, 760, 766, 768, 770, 772, 775, 777, 781, 785, 787, 789, 791, 793, 825, 828, 836, 842, 844, 846, 848, 849, 852, 854, 856, 858, 860, 867, 869, 871, 873, 875, 878, 880, 882, 884, 886, 888, 890, 892, 894, 896, 899, 901, 903, 905, 906, 908, 910, 912, 914, 916, 918, 921, 925, 927, 933, 935, 942, 944, 946, 951, 952, 954, 956, 958, 960, 962, 964, 968, 970, 972, 974, 976, 978, 980, 982, 984, 986, 988, 990, 992, 994, 996, 998, 1000, 1002, 1004, 1006, 1008, 1010, 1012, 1017, 1019, 1020, 1021, 1022, 1023, 1026, 1028, 1031, 1034, 1036, 1038, 1041, 1045, 1046, 1048, 1050, 1052, 1054, 1056, 1058, 1060, 1062, 1064, 1066, 1070, 1076, 1079, 1082, 1084, 1086, 1088, 1090, 1092, 1094, 1096, 1102, 1104, 1106, 1108, 1110, 1112, 1114, 1116, 1118, 1120, 1122, 1124, 1126, 1128, 1130, 1132, 1140, 1142, 1144, 1146, 1148, 1150, 1152, 1154, 1156, 1158, 1163, 1165, 1167, 1169, 1171, 1173, 1175, 1177, 1179, 1181, 1183, 1185, 1187, 1189, 1191, 1193, 1195, 1197, 1205, 1207, 1210, 1212, 1218, 1220, 1222, 1224, 1226, 1228, 1231, 1233, 1235, 1237, 1239, 1241, 1243, 1245, 1247, 1249, 1251, 1253, 1265, 1267, 1269, 1271, 1273, 1275, 1276, 1278, 1280, 1282, 1284, 1286, 1288, 1290, 1292, 1296, 1300, 1302, 1304, 1306, 1308, 1310, 1312, 1314, 1316, 1318, 1320, 1333, 1335, 1337, 1339, 1341, 1343, 1345, 1346, 1348, 1350, 1354, 1356, 1359, 1361, 1363, 1365, 1369, 1371, 1373, 1376, 1378, 1380, 1382, 1384, 1386, 1388, 1390, 1392, 1394, 1396, 1398, 1400, 1403, 1405, 1407, 1409, 1416, 1418, 1420, 1428, 1432, 1437, 1441, 1443, 1445, 1447, 1449, 1451, 1453, 1454, 1455, 1456, 1459, 1461, 1463, 1465, 1470, 1472, 1474, 1476, 1487, 1489, 1491, 1493, 1495, 1496, 1498, 1500, 1507, 1509, 1517, 1526, 1530, 1537, 1538, 1539, 1542, 1544, 1546, 1548, 1550, 1552, 1560, 1562, 1569, 1571, 1573, 1575, 1577, 1579, 1581, 1583, 1585, 1586, 1588, 1590, 1592, 1595, 1608, 1610, 1622, 1624, 1626, 1627, 1628, 1629, 1633, 1634, 1636, 1638, 1640, 1645, 1647, 1649, 1656, 1658, 1660, 1662, 1664, 1666, 1668, 1670, 1672, 1674, 1676, 1678, 1680, 1683, 1685, 1687, 1689, 1691, 1693, 1695, 1697, 1706, 1708, 1710, 1712, 1714, 1716, 1718, 1724, 1726, 1728, 1731, 1733, 1735, 1737, 1747, 1749, 1753, 1755, 1757, 1759, 1761, 1763, 1765, 1779, 1781, 1783, 1785, 1787, 1789, 1791, 1793, 1795, 1797, 1799, 1801, 1803, 1841, 1849, 1851, 1853, 1855, 1857, 1868, 1872, 1874, 1876, 1878, 1880, 1882, 1884, 1886, 1888, 1890, 1892, 1894, 1896, 1898, 1900, 1902, 1904, 1906, 1908, 1910, 1912, 1914, 1916, 1918, 1920, 1922, 1924, 1926, 1928, 1930, 1932, 1934, 1936, 1938, 1940, 1942, 1944, 1946, 1948, 1950, 1952, 1954, 1956, 1958, 1960, 1962, 1964, 1966, 1968, 1970, 1972, 1974, 1976, 1978, 1980, 1982, 1984, 1986, 1988, 1990, 1992, 1994, 1996, 1998, 2000, 2002, 2004, 2006, 2008, 2010, 2012, 2014, 2016, 2018, 2020, 2022, 2024, 2026, 2028, 2068, 2071, 2073, 2075, 2077, 2079, 2082, 2086, 2088, 2090, 2092, 2094, 2096, 2098, 2100, 2102, 2104, 2106, 2108, 2110, 2112, 2122, 2124, 2126, 2128, 2130, 2132, 2134, 2145, 2147, 2149, 2151, 2153, 2155, 2157, 2159, 2161, 2163, 2165, 2167, 2169, 2171, 2173, 2175, 2177, 2179, 2181, 2265, 2267, 2279, 2281, 2283, 2285, 2287, 2289, 2291, 2293, 2295, 2297, 2299, 2301, 2303, 2305, 2307, 2309, 2311, 2313, 2315, 2317, 2319, 2321, 2349, 2351, 2353, 2355, 2357, 2359, 2361, 2363, 2365, 2367, 2369, 2371, or 2373, or a fragment thereof. A plant produced from the plant cell has a difference in low light tolerance as compared to a control plant that does not comprise the exogenous nucleic acid.

Methods of modulating SD+EODFR tolerance in a plant are provided herein. In one aspect, a method comprises introducing into a plant cell an exogenous nucleic acid, that comprises a regulatory region operably linked to a nucleotide sequence encoding a polypeptide. The HMM bit score of the amino acid sequence of the polypeptide is greater than about 20, using an HMM generated from the amino acid sequences depicted in one of FIG. 16 or 24-27. A plant produced from the plant cell has a difference in SD+EODFR tolerance as compared to a control plant that does not comprise the exogenous nucleic acid.

In another aspect, a method comprises introducing into a plant cell an exogenous nucleic acid that comprises a regulatory region operably linked to a nucleotide sequence encoding a polypeptide having 80 percent or greater sequence identity to an amino acid sequence set forth in SEQ ID NOs:538, 539, 541, 542, 543, 544, 545, 546, 547, 548, 549, 550, 552, 554, 555, 556, 557, 558, 559, 560, 561, 562, 563, 564, 565, 567, 570, 572, 574, 576, 578, 579, 580, 582, 584, 586, 588, 590, 592, 594, 596, 598, 600, 601, 603, 606, 607, 608, 609, 611, 613, 615, 616, 617, 618, 620, 621, 622, 624, 625, 626, 628, 629, 631, 1347, 1349, 1351, 1352, 1353, 1355, 1357, 1358, 1360, 1362, 1364, 1366, 1367, 1368, 1370, 1372, 1374, 1375, 1377, 1379, 1381, 1383, 1385, 1387, 1389, 1391, 1393, 1395, 1397, 1399, 1401, 1402, 1404, 1406, 1408, 1410, 1411, 1412, 1413, 1414, 1415, 1417, 1419, 1421, 1422, 1423, 1424, 1425, 1426, 1427, 1429, 1430, 1431, 1433, 1434, 1435, 1436, 1438, 1439, 1440, 1442, 1444, 1446, 1448, 1450, 1452, 1540, 1541, 1543, 1545, 1547, 1549, 1551, 1553, 1554, 1555, 1556, 1557, 1558, 1559, 1561, 1563, 1564, 1565, 1566, 1567, 1568, 1570, 1572, 1574, 1576, 1578, 1580, 1582, 1584, 1679, 1681, 1682, 1748, 1750, 1751, 1752, 1850, 1852, 1854, 1856, 1858, 1859, 1860, 1861, 1862, 1863, 1864, 1865, 1866, 1867, 1869, 1870, 1871, 1873, 1875, 1877, 1879, 1881, 1883, 1885, 1887, 1889, 1891, 1893, 1895, 1897, 1899, 1901, 1903, 1905, 1907, 2268, 2269, 2270, 2271, 2272, 2273, 2274, 2275, 2276, 2277, or 2278. A plant produced from the plant cell has a difference in SD+EODFR tolerance as compared to a control plant that does not comprise the exogenous nucleic acid.

In another aspect, a method comprises introducing into a plant cell an exogenous nucleic acid, that comprises a regulatory region operably linked to a nucleotide sequence having 80 percent or greater sequence identity to a nucleotide sequence set forth in SEQ ID NOs:537, 540, 551, 553, 566, 568, 569, 571, 573, 575, 577, 581, 583, 585, 587, 589, 591, 593, 595, 597, 599, 602, 604, 605, 610, 612, 614, 619, 623, 627, 630, 1345, 1346, 1348, 1350, 1354, 1356, 1359, 1361, 1363, 1365, 1369, 1371, 1373, 1376, 1378, 1380, 1382, 1384, 1386, 1388, 1390, 1392, 1394, 1396, 1398, 1400, 1403, 1405, 1407, 1409, 1416, 1418, 1420, 1428, 1432, 1437, 1441, 1443, 1445, 1447, 1449, 1451, 1537, 1538, 1539, 1542, 1544, 1546, 1548, 1550, 1552, 1560, 1562, 1569, 1571, 1573, 1575, 1577, 1579, 1581, 1583, 1678, 1680, 1747, 1749, 1849, 1851, 1853, 1855, 1857, 1868, 1872, 1874, 1876, 1878, 1880, 1882, 1884, 1886, 1888, 1890, 1892, 1894, 1896, 1898, 1900, 1902, 1904, 1906, and 2267, or a fragment thereof. A plant produced from the plant cell has a difference in SD+EODFR tolerance as compared to a control plant that does not comprise the exogenous nucleic acid.

Plant cells comprising an exogenous nucleic acid are provided herein. In one aspect, the exogenous nucleic acid comprises a regulatory region operably linked to a nucleotide sequence encoding a polypeptide. The HMM bit score of the amino acid sequence of the polypeptide is greater than about 20, using an HMM based on the amino acid sequences depicted in one of FIGS. 1-24. A plant produced from the cells has a difference in low light or SD+EODFR tolerance as compared to a control plant that does not comprise the exogenous nucleic acid. In another aspect, the exogenous nucleic acid comprises a regulatory region operably linked to a nucleotide sequence encoding a polypeptide having 80 percent or greater sequence identity to an amino acid sequence selected from the group consisting of SEQ ID NOs:3, 5, 7, 9, 10, 12, 14, 16, 18, 20, 22, 24, 25, 26, 28, 30, 32, 34, 36, 38, 40, 42, 44, 46, 48, 49, 51, 53, 55, 57, 59, 60, 61, 62, 63, 65, 67, 70, 72, 74, 76, 78, 80, 82, 84, 86, 88, 89, 90, 91, 93, 95, 96, 97, 98, 99, 100, 101, 102, 103, 105, 107, 109, 111, 113, 115, 116, 117, 118, 119, 120, 121, 122, 124, 126, 129, 130, 131, 132, 133, 135, 137, 139, 141, 143, 145, 147, 149, 151, 153, 155, 157, 159, 161, 163, 165, 167, 169, 171, 173, 175, 177, 179, 181, 183, 185, 187, 188, 189, 191, 193, 195, 197, 199, 201, 203, 205, 207, 209, 211, 213, 215, 217, 219, 221, 223, 225, 227, 229, 230, 231, 232, 233, 234, 235, 236, 237, 238, 239, 241, 243, 245, 247, 249, 251, 253, 255, 257, 259, 261, 262, 264, 266, 268, 270, 271, 273, 275, 277, 279, 281, 283, 285, 287, 289, 291, 292, 293, 294, 295, 296, 297, 298, 299, 300, 301, 302, 303, 304, 306, 308, 310, 312, 314, 317, 319, 321, 323, 325, 327, 329, 330, 331, 332, 334, 337, 339, 341, 343, 344, 346, 347, 348, 349, 350, 351, 352, 353, 354, 355, 357, 359, 361, 362, 364, 365, 366, 367, 368, 370, 372, 374, 376, 378, 379, 381, 383, 385, 387, 389, 391, 393, 395, 397, 399, 401, 403, 405, 407, 409, 411, 413, 415, 417, 419, 421, 423, 425, 427, 429, 431, 433, 435, 437, 439, 441, 443, 445, 447, 449, 451, 453, 456, 457, 458, 459, 460, 462, 464, 466, 468, 470, 472, 474, 475, 477, 478, 479, 480, 481, 482, 483, 484, 485, 486, 487, 488, 489, 491, 493, 494, 495, 496, 497, 498, 499, 501, 503, 505, 507, 508, 509, 510, 511, 512, 514, 515, 516, 518, 520, 521, 522, 523, 524, 525, 526, 527, 528, 529, 530, 531, 532, 533, 534, 535, 536, 538, 539, 541, 542, 543, 544, 545, 546, 547, 548, 549, 550, 552, 554, 555, 556, 557, 558, 559, 560, 561, 562, 563, 564, 565, 567, 570, 572, 574, 576, 578, 579, 580, 582, 584, 586, 588, 590, 592, 594, 596, 598, 600, 601, 603, 606, 607, 608, 609, 611, 613, 615, 616, 617, 618, 620, 621, 622, 624, 625, 626, 628, 629, 631, 634, 636, 637, 638, 639, 641, 644, 645, 647, 649, 651, 653, 655, 657, 659, 661, 663, 665, 667, 669, 671, 673, 675, 676, 678, 680, 682, 684, 686, 688, 690, 692, 694, 695, 697, 699, 701, 702, 704, 706, 708, 709, 711, 712, 713, 714, 716, 718, 720, 721, 723, 725, 726, 728, 730, 732, 734, 736, 738, 740, 741, 742, 743, 744, 745, 747, 749, 750, 751, 753, 755, 757, 759, 761, 762, 763, 764, 765, 767, 769, 771, 773, 774, 776, 778, 779, 780, 782, 783, 784, 786, 788, 790, 792, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 826, 827, 829, 830, 831, 832, 833, 834, 835, 837, 838, 839, 840, 841, 843, 845, 847, 850, 851, 853, 855, 857, 859, 861, 862, 863, 864, 865, 866, 868, 870, 872, 874, 876, 877, 879, 881, 883, 885, 887, 889, 891, 893, 895, 897, 898, 900, 902, 904, 907, 909, 911, 913, 915, 917, 919, 920, 922, 923, 924, 926, 928, 929, 930, 931, 932, 934, 936, 937, 938, 939, 940, 941, 943, 945, 947, 948, 949, 950, 953, 955, 957, 959, 961, 963, 965, 966, 967, 969, 971, 973, 975, 977, 979, 981, 983, 985, 987, 989, 991, 993, 995, 997, 999, 1001, 1003, 1005, 1007, 1009, 1011, 1013, 1014, 1015, 1016, 1018, 1024, 1025, 1027, 1029, 1030, 1032, 1033, 1035, 1037, 1039, 1040, 1042, 1043, 1044, 1047, 1049, 1051, 1053, 1055, 1057, 1059, 1061, 1063, 1065, 1067, 1068, 1069, 1071, 1072, 1073, 1074, 1075, 1077, 1078, 1080, 1081, 1083, 1085, 1087, 1089, 1091, 1093, 1095, 1097, 1098, 1099, 1100, 1101, 1103, 1105, 1107, 1109, 1111, 1113, 1115, 1117, 1119, 1121, 1123, 1125, 1127, 1129, 1131, 1133, 1134, 1135, 1136, 1137, 1138, 1139, 1141, 1143, 1145, 1147, 1149, 1151, 1153, 1155, 1157, 1159, 1160, 1161, 1162, 1164, 1166, 1168, 1170, 1172, 1174, 1176, 1178, 1180, 1182, 1184, 1186, 1188, 1190, 1192, 1194, 1196, 1198, 1199, 1200, 1201, 1202, 1203, 1204, 1206, 1208, 1209, 1211, 1213, 1214, 1215, 1216, 1217, 1219, 1221, 1223, 1225, 1227, 1229, 1230, 1232, 1234, 1236, 1238, 1240, 1242, 1244, 1246, 1248, 1250, 1252, 1254, 1255, 1256, 1257, 1258, 1259, 1260, 1261, 1262, 1263, 1264, 1266, 1268, 1270, 1272, 1274, 1277, 1279, 1281, 1283, 1285, 1287, 1289, 1291, 1293, 1294, 1295, 1297, 1298, 1299, 1301, 1303, 1305, 1307, 1309, 1311, 1313, 1315, 1317, 1319, 1321, 1322, 1323, 1324, 1325, 1326, 1327, 1328, 1329, 1330, 1331, 1332, 1334, 1336, 1338, 1340, 1342, 1344, 1347, 1349, 1351, 1352, 1353, 1355, 1357, 1358, 1360, 1362, 1364, 1366, 1367, 1368, 1370, 1372, 1374, 1375, 1377, 1379, 1381, 1383, 1385, 1387, 1389, 1391, 1393, 1395, 1397, 1399, 1401, 1402, 1404, 1406, 1408, 1410, 1411, 1412, 1413, 1414, 1415, 1417, 1419, 1421, 1422, 1423, 1424, 1425, 1426, 1427, 1429, 1430, 1431, 1433, 1434, 1435, 1436, 1438, 1439, 1440, 1442, 1444, 1446, 1448, 1450, 1452, 1457, 1458, 1460, 1462, 1464, 1466, 1467, 1468, 1469, 1471, 1473, 1475, 1477, 1478, 1479, 1480, 1481, 1482, 1483, 1484, 1485, 1486, 1488, 1490, 1492, 1494, 1497, 1499, 1501, 1502, 1503, 1504, 1505, 1506, 1508, 1510, 1511, 1512, 1513, 1514, 1515, 1516, 1518, 1519, 1520, 1521, 1522, 1523, 1524, 1525, 1527, 1528, 1529, 1531, 1532, 1533, 1534, 1535, 1536, 1540, 1541, 1543, 1545, 1547, 1549, 1551, 1553, 1554, 1555, 1556, 1557, 1558, 1559, 1561, 1563, 1564, 1565, 1566, 1567, 1568, 1570, 1572, 1574, 1576, 1578, 1580, 1582, 1584, 1587, 1589, 1591, 1593, 1594, 1596, 1597, 1598, 1599, 1600, 1601, 1602, 1603, 1604, 1605, 1606, 1607, 1609, 1611, 1612, 1613, 1614, 1615, 1616, 1617, 1618, 1619, 1620, 1621, 1623, 1625, 1630, 1631, 1632, 1635, 1637, 1639, 1641, 1642, 1643, 1644, 1646, 1648, 1650, 1651, 1652, 1653, 1654, 1655, 1657, 1659, 1661, 1663, 1665, 1667, 1669, 1671, 1673, 1675, 1677, 1679, 1681, 1682, 1684, 1686, 1688, 1690, 1692, 1694, 1696, 1698, 1699, 1700, 1701, 1702, 1703, 1704, 1705, 1707, 1709, 1711, 1713, 1715, 1717, 1719, 1720, 1721, 1722, 1723, 1725, 1727, 1729, 1730, 1732, 1734, 1736, 1738, 1739, 1740, 1741, 1742, 1743, 1744, 1745, 1746, 1748, 1750, 1751, 1752, 1754, 1756, 1758, 1760, 1762, 1764, 1766, 1767, 1768, 1769, 1770, 1771, 1772, 1773, 1774, 1775, 1776, 1777, 1778, 1780, 1782, 1784, 1786, 1788, 1790, 1792, 1794, 1796, 1798, 1800, 1802, 1804, 1805, 1806, 1807, 1808, 1809, 1810, 1811, 1812, 1813, 1814, 1815, 1816, 1817, 1818, 1819, 1820, 1821, 1822, 1823, 1824, 1825, 1826, 1827, 1828, 1829, 1830, 1831, 1832, 1833, 1834, 1835, 1836, 1837, 1838, 1839, 1840, 1842, 1843, 1844, 1845, 1846, 1847, 1848, 1850, 1852, 1854, 1856, 1858, 1859, 1860, 1861, 1862, 1863, 1864, 1865, 1866, 1867, 1869, 1870, 1871, 1873, 1875, 1877, 1879, 1881, 1883, 1885, 1887, 1889, 1891, 1893, 1895, 1897, 1899, 1901, 1903, 1905, 1907, 1909, 1911, 1913, 1915, 1917, 1919, 1921, 1923, 1925, 1927, 1929, 1931, 1933, 1935, 1937, 1939, 1941, 1943, 1945, 1947, 1949, 1951, 1953, 1955, 1957, 1959, 1961, 1963, 1965, 1967, 1969, 1971, 1973, 1975, 1977, 1979, 1981, 1983, 1985, 1987, 1989, 1991, 1993, 1995, 1997, 1999, 2001, 2003, 2005, 2007, 2009, 2011, 2013, 2015, 2017, 2019, 2021, 2023, 2025, 2027, 2029, 2030, 2031, 2032, 2033, 2034, 2035, 2036, 2037, 2038, 2039, 2040, 2041, 2042, 2043, 2044, 2045, 2046, 2047, 2048, 2049, 2050, 2051, 2052, 2053, 2054, 2055, 2056, 2057, 2058, 2059, 2060, 2061, 2062, 2063, 2064, 2065, 2066, 2067, 2069, 2070, 2072, 2074, 2076, 2078, 2080, 2081, 2083, 2084, 2085, 2087, 2089, 2091, 2093, 2095, 2097, 2099, 2101, 2103, 2105, 2107, 2109, 2111, 2113, 2114, 2115, 2116, 2117, 2118, 2119, 2120, 2121, 2123, 2125, 2127, 2129, 2131, 2133, 2135, 2136, 2137, 2138, 2139, 2140, 2141, 2142, 2143, 2144, 2146, 2148, 2150, 2152, 2154, 2156, 2158, 2160, 2162, 2164, 2166, 2168, 2170, 2172, 2174, 2176, 2178, 2180, 2182, 2183, 2184, 2185, 2186, 2187, 2188, 2189, 2190, 2191, 2192, 2193, 2194, 2195, 2196, 2197, 2198, 2199, 2200, 2201, 2202, 2203, 2204, 2205, 2206, 2207, 2208, 2209, 2210, 2211, 2212, 2213, 2214, 2215, 2216, 2217, 2218, 2219, 2220, 2221, 2222, 2223, 2224, 2225, 2226, 2227, 2228, 2229, 2230, 2231, 2232, 2233, 2234, 2235, 2236, 2237, 2238, 2239, 2240, 2241, 2242, 2243, 2244, 2245, 2246, 2247, 2248, 2249, 2250, 2251, 2252, 2253, 2254, 2255, 2256, 2257, 2258, 2259, 2260, 2261, 2262, 2263, 2264, 2266, 2268, 2269, 2270, 2271, 2272, 2273, 2274, 2275, 2276, 2277, 2278, 2280, 2282, 2284, 2286, 2288, 2290, 2292, 2294, 2296, 2298, 2300, 2302, 2304, 2306, 2308, 2310, 2312, 2314, 2316, 2318, 2320, 2322, 2323, 2324, 2325, 2326, 2327, 2328, 2329, 2330, 2331, 2332, 2333, 2334, 2335, 2336, 2337, 2338, 2339, 2340, 2341, 2342, 2343, 2344, 2345, 2346, 2347, 2348, 2350, 2352, 2354, 2356, 2358, 2360, 2362, 2364, 2366, 2368, 2370, 2372, 2374, 2375, 2376, 2377, 2378, 2379, 2380, and 2381.

Also provided herein is a method of identifying whether a polymorphism is associated with variation in low light or SD+EODFR tolerance. The method includes the steps of: determining whether one or more genetic polymorphisms in a population of plants is associated with the locus for a polypeptide selected from the group consisting of the polypeptides depicted in FIGS. 1-24 and functional homologs thereof; and measuring the correlation between variation in the low light or SD+EODFR tolerance in plants of the population and the presence of the genetic polymorphisms in plants of the population, thereby identifying whether or not one or more genetic polymorphisms are associated with variation in low light or SD+EODFR tolerance. The population of plants can be a population of switchgrass, sorghum, sugar cane, or miscanthus plants.

A method of making a plant line is also provided herein. The method includes the steps of: determining whether one or more genetic polymorphisms in a population of plants is associated with the locus for a polypeptide selected from the group consisting of the polypeptides depicted in FIGS. 1-24 and functional homologs thereof; identifying one or more plants in the population in which the presence of at least one allele at the one or more genetic polymorphisms is associated with variation in low light or SD+EODFR tolerance; crossing each of the identified plants with itself or a different plant to produce seed; crossing at least one progeny plant grown from the seed with itself or a different plant; and repeating the crossing steps for an additional 0-5 generations to make the plant line, wherein the allele is present in the plant line. The population of plants can be a population of switchgrass plants.

In another aspect, this document provides a method of producing a plant. The method comprises growing a plant cell comprising an exogenous nucleic acid, wherein the exogenous nucleic acid is effective for down-regulating an endogenous nucleic acid in the plant cell. The endogenous nucleic acid can encode a polypeptide. The HMM bit score of the amino acid sequence of the polypeptide can be greater than about 210. The HMM can be based on the amino acid sequences depicted in one of FIGS. 6, 11, and 21. The plant produced from the cell can have an increase in hypocotyl length as compared to a control plant that does not comprise the exogenous nucleic acid.

In another aspect, a transgenic plant cell is provided. The plant cell comprises an exogenous nucleic acid. The exogenous nucleic acid is effective for down-regulating an endogenous nucleic acid in the plant cell. The endogenous nucleic acid can encode a polypeptide. The HMM bit score of the amino acid sequence of the polypeptide is greater than about 210. The HMM is based on the amino acid sequences depicted in one of FIGS. 6, 11, and 21.

A transgenic plant is also provided. The transgenic plant comprises a plant cell comprising an exogenous nucleic acid. The exogenous nucleic acid is effective for down-regulating an endogenous nucleic acid in the plant cell. The endogenous nucleic acid can encode a polypeptide. The HMM bit score of the amino acid sequence of the polypeptide is greater than about 210. The HMM is based on the amino acid sequences depicted in one of FIGS. 6, 11, and 21. The plant has an increase in hypocotyl length as compared to a control plant that does not comprise the plant cell.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

Figure 1:
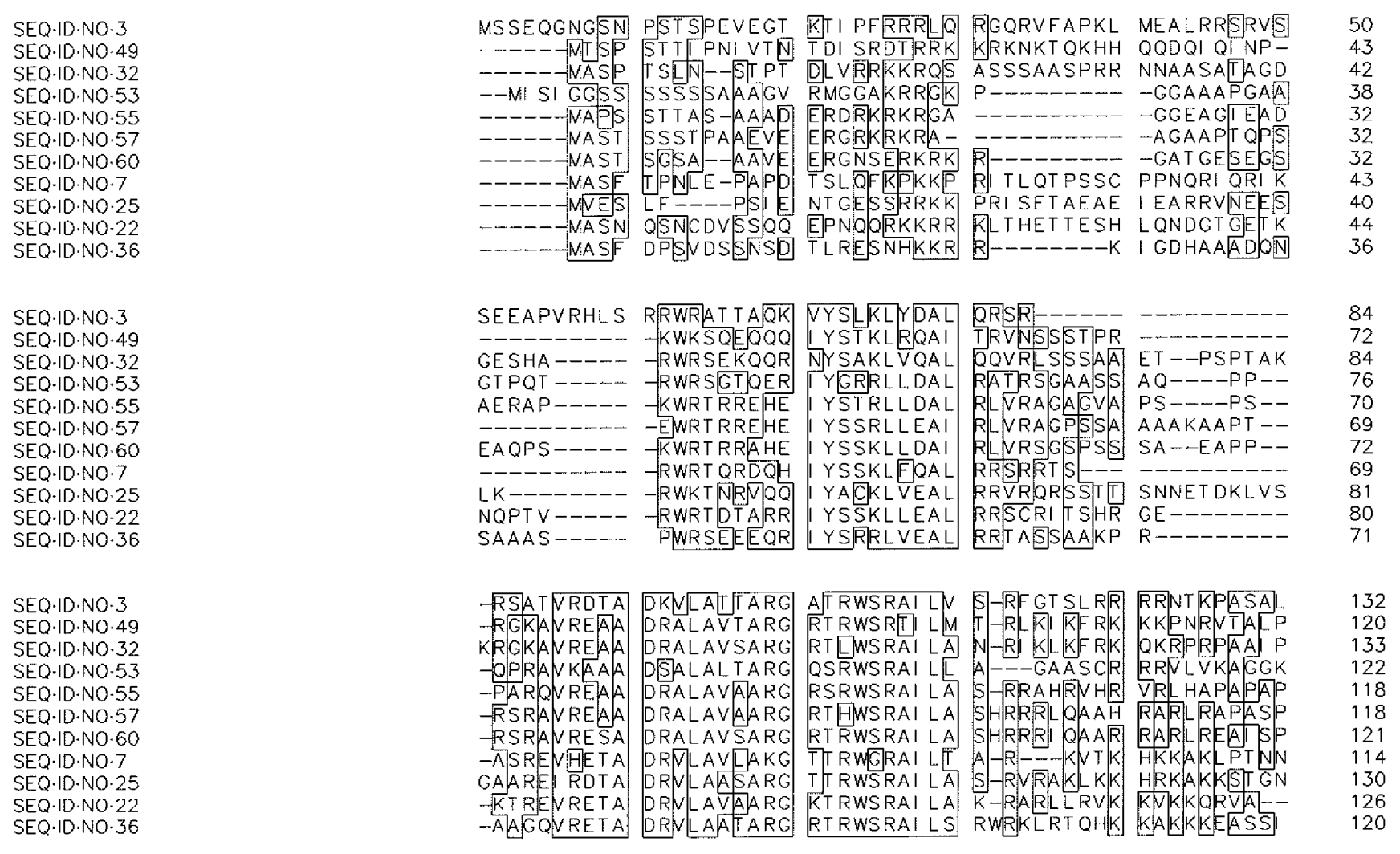
Figure 1:
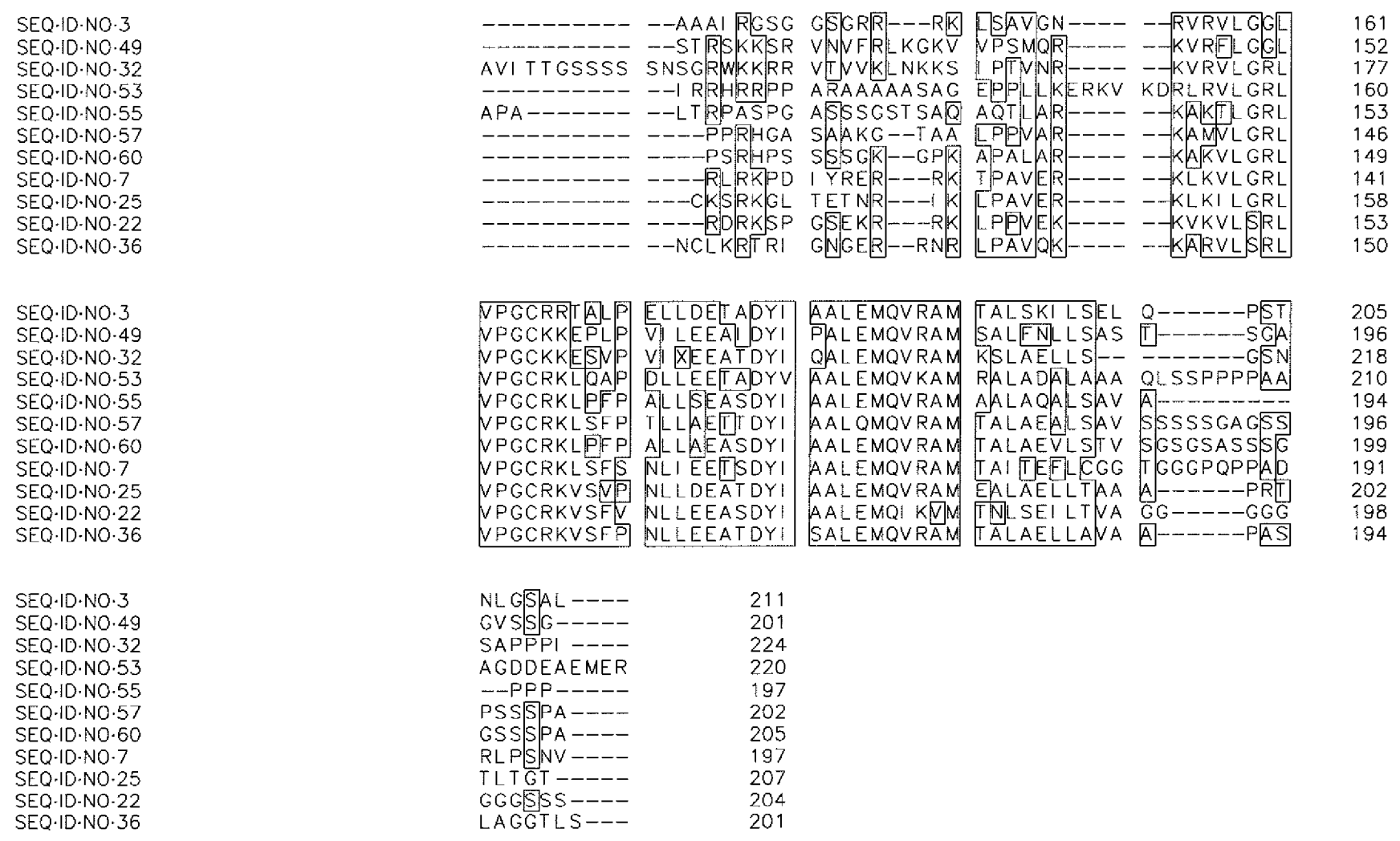

FIG. 1 is an alignment of At4g37295 (Ceres Seedline ME05268; SEQ ID NO:3) with homologous and/or orthologous amino acid sequences including Ceres CLONE ID no. 1844057 (SEQ ID NO:7), Ceres ANNOT ID no. 1469148 (SEQ ID NO:22), Public GI ID no. 18390998 (SEQ ID NO:25), Ceres CLONE ID no. 1065656 (SEQ ID NO:32), Ceres CLONE ID no. 1652677 (SEQ ID NO:36), Public GI ID no. 92874556 (SEQ ID NO:49), Ceres CLONE ID no. 1329161 (SEQ ID NO:53), Ceres CLONE ID no. 1030378 (SEQ ID NO:55), Ceres CLONE ID no. 1413787 (SEQ ID NO:57), and Public GI ID no. 125543598 (SEQ ID NO:60). In all the alignment figures shown herein, a dash in an aligned sequence represents a gap, i.e., a lack of an amino acid at that position. Identical amino acids or conserved amino acid substitutions among aligned sequences are identified by boxes. FIG. 1 and the other alignment figures provided herein were generated using the program MUSCLE version 3.52.

FIG. 2 is an alignment of At2g32710 (Ceres Seedline ME06120; SEQ ID NO:70) with homologous and/or orthologous amino acid sequences including Ceres CLONE ID no. 1975934 (SEQ ID NO:72), Ceres ANNOT ID no. 1529913 (SEQ ID NO:80), Ceres CLONE ID no. 977794 (SEQ ID NO:93), Public GI ID no. 42362378 (SEQ ID NO:96), Public GI ID no. 23899378 (SEQ ID NO:99), Public GI ID no. 15963346 (SEQ ID NO:101), Public GI ID no. 15963344+B816 (SEQ ID NO:102), Public GI ID no. 92429657 (SEQ ID NO:103), Ceres CLONE ID no. 746644 (SEQ ID NO:105), Ceres CLONE ID no. 623089 (SEQ ID NO:109), Ceres CLONE ID no. 1913678 (SEQ ID NO:115), and Public GI ID no. 115450609 (SEQ ID NO:119).

FIG. 3 is an alignment of At2g46990 (Ceres Seedline ME09503; SEQ ID NO:129) with homologous and/or orthologous amino acid sequences including Public GI ID no. 34550779 (SEQ ID NO:133), Ceres CLONE ID no. 1932235 (SEQ ID NO:137), Ceres CLONE ID no. 981738 (SEQ ID NO:201), Ceres CLONE ID no. 565974 (SEQ ID NO:209), Public GI ID no. 1352058 (SEQ ID NO:231), Public GI ID no. 11131101 (SEQ ID NO:234), Public GI ID no. 4887018 (SEQ ID NO:236), Public GI ID no. 4887018 (SEQ ID NO:236), Ceres CLONE ID no. 644455 (SEQ ID NO:247), Ceres CLONE ID no. 1731500 (SEQ ID NO:270), Public GI ID no. 20269063 (SEQ ID NO:300), Public GI ID no. 50404477 (SEQ ID NO:302), and Public GI ID no. 62125392 (SEQ ID NO:303).

FIG. 4 is an alignment of At4g03250 (Ceres Seedline ME10007; SEQ ID NO:317) with homologous and/or orthologous amino acid sequences including Ceres CLONE ID no. 1842125 (SEQ ID NO:319), Ceres ANNOT ID no. 1461360 (SEQ ID NO:321), Ceres CLONE ID no. 480906 (SEQ ID NO:327), Public GI ID no. 92889352 (SEQ ID NO:330), and Public GI ID no. 56201850 (SEQ ID NO:331).

FIG. 5 is an alignment of At2g04240 (Ceres Seedline ME10852; SEQ ID NO:337), Ceres CLONE ID no. 952050 (SEQ ID NO:339) with homologous and/or orthologous amino acid sequences including Public GI ID no. 115477050 (SEQ ID NO:349), Public GI ID no. 87162911 (SEQ ID NO:355), Ceres CLONE ID no. 1790901 (SEQ ID NO:357), Ceres CLONE ID no. 1460088 (SEQ ID NO:370), Ceres CLONE ID no. 1734065 (SEQ ID NO:393), Ceres CLONE ID no. 473509 (SEQ ID NO:395), Ceres CLONE ID no. 849918 (SEQ ID NO:401), Ceres CLONE ID no. 633470 (SEQ ID NO:409), Ceres CLONE ID no. 1808334 (SEQ ID NO:417), and Ceres ANNOT ID no. 1525600 (SEQ ID NO:437).

FIG. 6 is an alignment of At5g14370 (Ceres Seedline ME11939; SEQ ID NO:456) with homologous and/or orthologous amino acid sequences including Public GI ID no. 58430585 (SEQ ID NO:457), Ceres CLONE ID no. 1842825 (SEQ ID NO:466), Ceres ANNOT ID no. 1449721 (SEQ ID NO:474), Public GI ID no. 41323978 (SEQ ID NO:475), Public GI ID no. 2895186 (SEQ ID NO:478), Public GI ID no. 22854950 (SEQ ID NO:481), Public GI ID no. 116010474 (SEQ ID NO:485), Public GI ID no. 4091804 (SEQ ID NO:488), Public GI ID no. 60459257 (SEQ ID NO:494), Public GI ID no. 45544881 (SEQ ID NO:496), Public GI ID no. 36789802 (SEQ ID NO:498), Public GI ID no. 92875402 (SEQ ID NO:508), Public GI ID no. 118406898 (SEQ ID NO:510), Public GI ID no. 107770485 (SEQ ID NO:511), Public GI ID no. 21655154 (SEQ ID NO:532), Public GI ID no. 90657642 (SEQ ID NO:536), and Ceres CLONE ID no. 1569555 (SEQ ID NO:1842).

FIG. 7 is an alignment of At1g70270 (Ceres Seedline ME13456; SEQ ID NO:634) with homologous and/or orthologous amino acid sequences including Public GI ID no. 98961985 (SEQ ID NO:637).

FIG. 8 is an alignment of At4g25480 (Ceres Seedline ME15935; SEQ ID NO:644) with homologous and/or orthologous amino acid sequences including SEQ ID NO:645, Ceres CLONE ID no. 1849479 (SEQ ID NO:767), Public GI ID no. 89275008 (SEQ ID NO:796), Public GI ID no. 120400525 (SEQ ID NO:797), Public GI ID no. 98980426 (SEQ ID NO:804), Public GI ID no. 71983373 (SEQ ID NO:808), Public GI ID no. 41351817 (SEQ ID NO:809), Public GI ID no. 76446191 (SEQ ID NO:811), Public GI ID no. 5616086 (SEQ ID NO:813), Ceres CLONE ID no. 1052602 (SEQ ID NO:826), Public GI ID no. 72068957 (SEQ ID NO:830), Public GI ID no. 71534113 (SEQ ID NO:831), Public GI ID no. 37147896 (SEQ ID NO:832), Public GI ID no. 92918850 (SEQ ID NO:834), Public GI ID no. 40647095 (SEQ ID NO:835), Ceres ANNOT ID no. 1527711 (SEQ ID NO:837), Public GI ID no. 71041116 (SEQ ID NO:838), Public GI ID no. 12003384 (SEQ ID NO:839), Public GI ID no. 18535580 (SEQ ID NO:840), and Public GI ID no. 115353971 (SEQ ID NO:1843).

FIG. 9 is an alignment of At2g33780 (Ceres SEEDLINE ID no.ME16594, SEQ ID NO:850) with homologous and/or orthologous amino acid sequences including Ceres CLONE ID no.1833093 (SEQ ID NO:853), Ceres ANNOT ID no.1502190 (SEQ ID NO:857), Ceres CLONE ID no.565641 (SEQ ID NO:876), Public GI ID no.87240507 (SEQ ID NO:877), Ceres CLONE ID no.1325382 (SEQ ID NO:881), Ceres CLONE ID no.1558265 (SEQ ID NO:885), Ceres CLONE ID no.1823669 (SEQ ID NO:895), and Public GI ID no.115464921 (SEQ ID NO:898).

FIG. 10 is an alignment of At4g17810 (Ceres SEEDLINE ID no.ME16597, SEQ ID NO:907) with homologous and/or orthologous amino acid sequences including Ceres CLONE ID no.1940797 (SEQ ID NO:909), Ceres ANNOT ID no.1538900 (SEQ ID NO:911), Ceres CLONE ID no.1126868 (SEQ ID NO:922), Public GI ID no.89257684 (SEQ ID NO:923), Public GI ID no.124360460 (SEQ ID NO:929), Public GI ID no.62865694 (SEQ ID NO:931), Public GI ID no.62865692 (SEQ ID NO:932), Ceres CLONE ID no.260368 (SEQ ID NO:936), Ceres CLONE ID no.1873510 (SEQ ID NO:947), Public GI ID no.125541662 (SEQ ID NO:948), Public GI ID no.48716268 (SEQ ID NO:950), and Public GI ID no. 62865696 (SEQ ID NO:1844).

FIG. 11 is an alignment of At1g13360 (Ceres SEEDLINE ID no.ME16630, SEQ ID NO:953) with homologous and/or orthologous amino acid sequences including Ceres CLONE ID no.1798705 (SEQ ID NO:955), Ceres ANNOT ID no.1458907 (SEQ ID NO:963), Ceres CLONE ID no.1090409 (SEQ ID NO:971), Ceres CLONE ID no.479817 (SEQ ID NO:977), Ceres CLONE ID no.1041793 (SEQ ID NO:979), Ceres CLONE ID no.684633 (SEQ ID NO:985), Ceres CLONE ID no.371815 (SEQ ID NO:991), Ceres CLONE ID no.1686460 (SEQ ID NO:993), Ceres CLONE ID no.1448595 (SEQ ID NO:995), Ceres CLONE ID no.1734477 (SEQ ID NO:999), Ceres CLONE ID no.1605693 (SEQ ID NO:1005), Ceres CLONE ID no.1757400 (SEQ ID NO:1009), and Public GI ID no.115434334 (SEQ ID NO:1015).

FIG. 12 is an alignment of At1g75860 (Ceres SEEDLINE ID no.ME17128, SEQ ID NO:1024) with homologous and/or orthologous amino acid sequences including Ceres ANNOT ID no.1452905 (SEQ ID NO:1029), Ceres CLONE ID no.956176 (SEQ ID NO:1039), Public GI ID no.92870366 (SEQ ID NO:1040), Ceres CLONE ID no.294166 (SEQ ID NO:1042), and Public GI ID no.125543067 (SEQ ID NO:1043).

FIG. 13 is an alignment of At4g19700 (Ceres SEEDLINE ID no.ME17578, SEQ ID NO:1047) with homologous and/or orthologous amino acid sequences including Ceres CLONE ID no.1837694 (SEQ ID NO:1053), Ceres ANNOT ID no.1483367 (SEQ ID NO:1057), Ceres CLONE ID no.1077781 (SEQ ID NO:1083), Ceres CLONE ID no.471026 (SEQ ID NO:1085), Public GI ID no.92888885 (SEQ ID NO:1099), Public GI ID no.45544873 (SEQ ID NO:1100), Public GI ID no.45758663 (SEQ ID NO:1101), Ceres CLONE ID no.772927 (SEQ ID NO:1105), Ceres CLONE ID no.895080 (SEQ ID NO:1111), Ceres CLONE ID no.1806128 (SEQ ID NO:1131), Public GI ID no.115458192 (SEQ ID NO:1134), and Public GI ID no.82470795 (SEQ ID NO:1139).

FIG. 14 is an alignment of At1g58100 (Ceres SEEDLINE ID no.ME18158, SEQ ID NO:1151) with homologous and/or orthologous amino acid sequences including Ceres CLONE ID no.1851526 (SEQ ID NO:1155), Ceres ANNOT ID no.1486769 (SEQ ID NO:1172), Public GI ID no.83032232 (SEQ ID NO:1209), Ceres CLONE ID no.1620420 (SEQ ID NO:1211), Public GI ID no.92892428 (SEQ ID NO:1215), Ceres CLONE ID no.884742 (SEQ ID NO:1223), Ceres CLONE ID no.1821559 (SEQ ID NO:1246), Public GI ID no.51535021 (SEQ ID NO:1258), Public GI ID no.113205304 (SEQ ID NO:1263), and Public GI ID no.37719051 (SEQ ID NO:1264).

FIG. 15 is an alignment of At5g46170 (Ceres SEEDLINE ID no.ME18314, SEQ ID NO:1277) with homologous and/or orthologous amino acid sequences including Ceres CLONE ID no.1926352 (SEQ ID NO:1279), Ceres ANNOT ID no.1448905 (SEQ ID NO:1285), Public GI ID no.15236865 (SEQ ID NO:1294), Ceres CLONE ID no.934771 (SEQ ID NO:1301), Ceres CLONE ID no.338386 (SEQ ID NO:1303), Ceres CLONE ID no.1780691 (SEQ ID NO:1317), and Public GI ID no.115464819 (SEQ ID NO:1326).

FIG. 16 is an alignment of At4g32280 (Ceres SEEDLINE ID no.ME18408, SEQ ID NO:1347) with homologous and/or orthologous amino acid sequences including Ceres CLONE ID no.285028 (SEQ ID NO:1419), Ceres CLONE ID no.100969565 (SEQ ID NO:1422), Public GI ID no.1352057 (SEQ ID NO:1427), Ceres ANNOT ID no.1453784 (SEQ ID NO:1429), Public GI ID no.452777 (SEQ ID NO:1430), and Public GI ID no.92873297 (SEQ ID NO:1431).

FIG. 17 is an alignment of At3g02830 (Ceres SEEDLINE ID no.ME19304, SEQ ID NO:1457) with homologous and/or orthologous amino acid sequences including Ceres CLONE ID no.1924904 (SEQ ID NO:1460), Ceres ANNOT ID no.1543346 (SEQ ID NO:1462), Public GI ID no.18396338 (SEQ ID NO:1467), Ceres CLONE ID no.833872 (SEQ ID NO:1471), Ceres CLONE ID no.1579587 (SEQ ID NO:1475), Ceres CLONE ID no.1786411 (SEQ ID NO:1477), and Public GI ID no.108864370 (SEQ ID NO:1480).

FIG. 18 is an alignment of At4g08920 (Ceres SEEDLINE ID no.ME19738, SEQ ID NO:1497) with homologous and/or orthologous amino acid sequences including Ceres ANNOT ID no.1443463 (SEQ ID NO:1499), Public GI ID no.13605525 (SEQ ID NO:1502), Public GI ID no.94965681 (SEQ ID NO:1506), and Public GI ID no.28201254 (SEQ ID NO:1512).

FIG. 19 is an alignment of At4g11660 (Ceres SEEDLINE ID no.ME20871, SEQ ID NO:1587) with homologous and/or orthologous amino acid sequences including Ceres CLONE ID no.1839577 (SEQ ID NO:1589), Ceres ANNOT ID no.1491567 (SEQ ID NO:1591), Ceres CLONE ID no.574505 (SEQ ID NO:1596), Public GI ID no.56117815 (SEQ ID NO:1597), Public GI ID no.92874021 (SEQ ID NO:1603), Public GI ID no.123684 (SEQ ID NO:1605), Public GI ID no.5821136 (SEQ ID NO:1606), Ceres CLONE ID no.283366 (SEQ ID NO:1609), Public GI ID no.16118447 (SEQ ID NO:1612), and Public GI ID no.125562434 (SEQ ID NO:1614).

FIG. 20 is an alignment of At2g45700 (Ceres SEEDLINE ID no.ME21508, SEQ ID NO:1635) with homologous and/or orthologous amino acid sequences including Ceres ANNOT ID no.1508307 (SEQ ID NO:1637), Public GI ID no.1495267 (SEQ ID NO:1642), Public GI ID no.87241310 (SEQ ID NO:1644), Ceres CLONE ID no.938390 (SEQ ID NO:1646), Ceres CLONE ID no.272338 (SEQ ID NO:1648), Ceres CLONE ID no.1993510 (SEQ ID NO:1650), Public GI ID no.125563862 (SEQ ID NO:1651), and Public GI ID no.125605833 (SEQ ID NO:1653).

FIG. 22 is an alignment of At1g04400 (Ceres SEEDLINE ID no.ME12006, SEQ ID NO:538) with homologous and/or orthologous amino acid sequences including Public GI ID no.5731739 (SEQ ID NO:539), Ceres ANNOT ID no.1538045 (SEQ ID NO:541), Public GI ID no.29467479 (SEQ ID NO:542), Public GI ID no.133921974 (SEQ ID NO:543), Public GI ID no.113197027 (SEQ ID NO:544), Public GI ID no.92879277 (SEQ ID NO:545), Public GI ID no.45935260 (SEQ ID NO:546), Public GI ID no.8101444 (SEQ ID NO:547), Public GI ID no.78217443 (SEQ ID NO:548), and Public GI ID no.28372347 (SEQ ID NO:549).

FIG. 23 is an alignment of At3g45610 (Ceres SEEDLINE ID no.ME12899, SEQ ID NO:606) with homologous and/or orthologous amino acid sequences including Public GI ID no.92873064 (SEQ ID NO:607), Public GI ID no.37051125 (SEQ ID NO:608), and Public GI ID no.112363376 (SEQ ID NO:609).

FIG. 24 is an alignment of At4g08330 (Ceres SEEDLINE ID no.ME12596, SEQ ID NO:570) with homologous and/or orthologous amino acid sequences including Ceres CLONE ID no.1919714 (SEQ ID NO:572), Ceres ANNOT ID no.1443290 (SEQ ID NO:574), Ceres CLONE ID no.1042157 (SEQ ID NO:576), Ceres CLONE ID no.1384304 (SEQ ID NO:578), and Public GI ID no.115464375 (SEQ ID NO:579).

DETAILED DESCRIPTION

Figure 21:
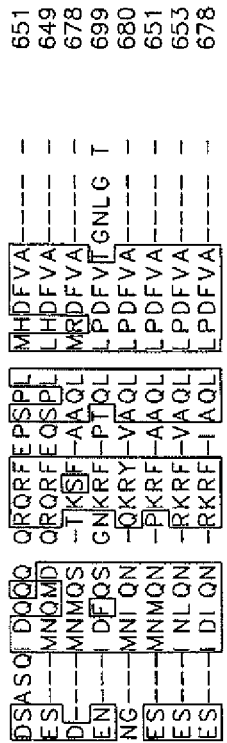
FIG. 21 is an alignment of At2g35940 (Ceres SEEDLINE ID no.ME19971, SEQ ID NO:1540) with homologous and/or orthologous amino acid sequences including Ceres CLONE ID no.1943265 (SEQ ID NO:1543), Ceres ANNOT ID no.1454522 (SEQ ID NO:1547), Public GI ID no.31323447 (SEQ ID NO:1556), Ceres CLONE ID no.1583941 (SEQ ID NO:1561), Ceres CLONE ID no.1792942 (SEQ ID NO:1563), Public GI ID no.77548772 (SEQ ID NO:1565), and Public GI ID no.84453182 (SEQ ID NO:1567).

This document provides methods and materials related to modulating tolerance of plants to Short Day plus End-of-Day Far-Red (SD+EODFR) conditions or low light irradiation. In some embodiments, the plants may have increased SD+EODFR tolerance and increased low light tolerance. The methods can include transforming a plant cell with a nucleic acid encoding an SD+EODFR and/or low light-tolerance polypeptide, wherein expression of the polypeptide results in increased SD+EODFR and/or low light tolerance. Plant cells produced using such methods can be grown to produce plants having an increased SD+EODFR and/or low light tolerance. Such plants can also be used to produce crops, plant products, biomass, and/or nitrogen fixating plants in shady or low light areas, such as under the canopy of another crop. For example, the methods and materials provided herein can be used to produce a legume (a member of Fabaceae, e.g., peas, beans, lupins, lentils, chick peas, vethes, soybeans, clovers, alfalfas, and peanuts) having an increased SD+EODFR and/or low light tolerance and which can be grown under the canopy of a taller crop (e.g., corn, switchgrass, sorghum, sugar cane, or miscanthus). In other embodiments, the taller plant is a nitrogen fixating plant (e.g., a member of Fabaceae, such as tamarind, mimosa, acacia, and carob) and the SD+EODFR and/or low light tolerant plant is a shorter plant, such as corn, switchgrass, sorghum, sugar cane, or miscanthus.

I. Definitions

"Amino acid" refers to one of the twenty biologically occurring amino acids and to synthetic amino acids, including D/L optical isomers.

"Cell type-preferential promoter" or "tissue-preferential promoter" refers to a promoter that drives expression preferentially in a target cell type or tissue, respectively, but may also lead to some transcription in other cell types or tissues as well.

"Control plant" refers to a plant that does not contain the exogenous nucleic acid present in a transgenic plant of interest, but otherwise has the same or similar genetic background as such a transgenic plant. A suitable control plant can be a non-transgenic wild type plant, a non-transgenic segregant from a transformation experiment, or a transgenic plant that contains an exogenous nucleic acid other than the exogenous nucleic acid of interest.

"Domains" are groups of substantially contiguous amino acids in a polypeptide that can be used to characterize protein families and/or parts of proteins. Such domains have a "fingerprint" or "signature" that can comprise conserved primary sequence, secondary structure, and/or three-dimensional conformation. Generally, domains are correlated with specific in vitro and/or in vivo activities. A domain can have a length of from 10 amino acids to 400 amino acids, e.g., 10 to 50 amino acids, or 25 to 100 amino acids, or 35 to 65 amino acids, or 35 to 55 amino acids, or 45 to 60 amino acids, or 200 to 300 amino acids, or 300 to 400 amino acids.

"Down-regulation" refers to regulation that decreases the level of an expression product (mRNA, polypeptide, or both) relative to basal or native states.

"Exogenous" with respect to a nucleic acid indicates that the nucleic acid is part of a recombinant nucleic acid construct, or is not in its natural environment. For example, an exogenous nucleic acid can be a sequence from one species introduced into another species, i.e., a heterologous nucleic acid. Typically, such an exogenous nucleic acid is introduced into the other species via a recombinant nucleic acid construct. An exogenous nucleic acid can also be a sequence that is native to an organism and that has been reintroduced into cells of that organism. An exogenous nucleic acid that includes a native sequence can often be distinguished from the naturally occurring sequence by the presence of non-natural sequences linked to the exogenous nucleic acid, e.g., non-native regulatory sequences flanking a native sequence in a recombinant nucleic acid construct. In addition, stably transformed exogenous nucleic acids typically are integrated at positions other than the position where the native sequence is found. It will be appreciated that an exogenous nucleic acid may have been introduced into a progenitor and not into the cell under consideration. For example, a transgenic plant containing an exogenous nucleic acid can be the progeny of a cross between a stably transformed plant and a non-transgenic plant. Such progeny are considered to contain the exogenous nucleic acid.

"Expression" refers to the process of converting genetic information of a polynucleotide into RNA through transcription, which is catalyzed by an enzyme, RNA polymerase, and into protein, through translation of mRNA on ribosomes.

"Heterologous polypeptide" as used herein refers to a polypeptide that is not a naturally occurring polypeptide in a plant cell, e.g., a transgenic *Panicum virgatum* plant transformed with and expressing the coding sequence for a nitrogen transporter polypeptide from a *Zea mays* plant.

"Isolated nucleic acid" as used herein includes a naturally-occurring nucleic acid, provided one or both of the sequences immediately flanking that nucleic acid in its naturally-occurring genome is removed or absent. Thus, an isolated nucleic acid includes, without limitation, a nucleic acid that exists as a purified molecule or a nucleic acid molecule that is incorporated into a vector or a virus. A nucleic acid existing among hundreds to millions of other nucleic acids within, for example, cDNA libraries, genomic libraries, or gel slices containing a genomic DNA restriction digest, is not to be considered an isolated nucleic acid.

"Modulation" of the level of tolerance to a stimulus (e.g., low light conditions or SD+EODFR conditions) refers to the change in the level of tolerance of the indicated stimulus that is observed as a result of expression of, or transcription from, an exogenous nucleic acid in a plant cell. The change in level is measured relative to the corresponding level in control plants.

"Nucleic acid" and "polynucleotide" are used interchangeably herein, and refer to both RNA and DNA, including cDNA, genomic DNA, synthetic DNA, and DNA or RNA containing nucleic acid analogs. Polynucleotides can have any three-dimensional structure. A nucleic acid can be double-stranded or single-stranded (i.e., a sense strand or an antisense strand). Non-limiting examples of polynucleotides include genes, gene fragments, exons, introns, messenger RNA (mRNA), transfer RNA, ribosomal RNA, siRNA, micro-RNA, ribozymes, cDNA, recombinant polynucleotides, branched polynucleotides, nucleic acid probes and nucleic acid primers. A polynucleotide may contain unconventional or modified nucleotides.

"Operably linked" refers to the positioning of a regulatory region and a sequence to be transcribed in a nucleic acid so that the regulatory region is effective for regulating transcription or translation of the sequence. For example, to operably link a coding sequence and a regulatory region, the translation initiation site of the translational reading frame of the coding sequence is typically positioned between one and about fifty nucleotides downstream of the regulatory region. A regulatory region can, however, be positioned as much as about 5,000 nucleotides upstream of the translation initiation site, or about 2,000 nucleotides upstream of the transcription start site.

"Polypeptide" as used herein refers to a compound of two or more subunit amino acids, amino acid analogs, or other peptidomimetics, regardless of post-translational modification, e.g., phosphorylation or glycosylation. The subunits may be linked by peptide bonds or other bonds such as, for example, ester or ether bonds. Full-length polypeptides, truncated polypeptides, point mutants, insertion mutants, splice variants, chimeric proteins, and fragments thereof are encompassed by this definition.

"Progeny" includes descendants of a particular plant or plant line. Progeny of an instant plant include seeds formed on $F_1$, $F_2$, $F_3$, $F_4$, $F_5$, $F_6$ and subsequent generation plants, or seeds formed on $BC_1$, $BC_2$, $BC_3$, and subsequent generation plants, or seeds formed on $F_1BC_1$, $F_1BC_2$, $F_1BC_3$, and subsequent generation plants. The designation $F_1$ refers to the progeny of a cross between two parents that are genetically distinct. The designations $F_2$, $F_3$, $F_4$, $F_5$ and $F_6$ refer to subsequent generations of self- or sib-pollinated progeny of an $F_1$ plant.

"Regulatory region" refers to a nucleic acid having nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, introns, and combinations thereof. A regulatory region typically comprises at least a core (basal) promoter. A regulatory region also may include at least one control element, such as an enhancer sequence, an upstream element or an upstream activation region (UAR). For example, a suitable enhancer is a cis-regulatory element (−212 to −154) from the upstream region of the octopine synthase (ocs) gene. Fromm et al., *The Plant Cell,* 1:977-984 (1989).

"Up-regulation" refers to regulation that increases the level of an expression product (mRNA, polypeptide, or both) relative to basal or native states.

"Vector" refers to a replicon, such as a plasmid, phage, or cosmid, into which another DNA segment may be inserted so as to bring about the replication of the inserted segment. Generally, a vector is capable of replication when associated with the proper control elements. The term "vector" includes cloning and expression vectors, as well as viral vectors and integrating vectors. An "expression vector" is a vector that includes a regulatory region.

II. Polypeptides

Polypeptides described herein include SD+EODFR and/or low light tolerancepolypeptides. SD+EODFR and/or low light tolerance polypeptides can be effective to increase SD+EODFR and/or low light tolerance when expressed in a plant or plant cell. Such polypeptides typically contain at least one domain indicative of SD+EODFR and/or low light tolerance polypeptides, as described in more detail herein. SD+EODFR and/or low light tolerance polypeptides typically have an HMM bit score that is greater than 20 for an HMM model based on one of the alignments set forth in FIGS. 1-24, as described in more detail herein. In some embodiments, SD+EODFR and/or low light tolerance polypeptides have greater than 40% identity to SEQ ID NO:3, SEQ ID NO:70, SEQ ID NO:129, SEQ ID NO:317, SEQ ID NO:337, SEQ ID NO:456, SEQ ID NO:538, SEQ ID NO:570, SEQ ID NO:606, SEQ ID NO:634, SEQ ID NO:644, SEQ ID NO:850, SEQ ID NO:907, SEQ ID NO:953, SEQ ID NO:1024, SEQ ID NO:1047, SEQ ID NO:1151, SEQ ID NO:1277, SEQ ID NO:1347, SEQ ID NO:1457, SEQ ID NO:1497, SEQ ID NO:1540, SEQ ID NO:1587, SEQ ID NO:1630, or SEQ ID NO:1635 as described in more detail herein.

Polypeptides described herein include red light specific response pathway polypeptides. Red light specific response pathway polypeptides can be effective to decrease hypocotyl length when over-expressed in a plant or plant cell. Such polypeptides typically contain at least one domain indicative of red light specific response pathway polypeptides, as described in more detail herein. Red light specific response pathway polypeptides typically have an HMM bit score that is greater than 20 for an HMM model based on one of the alignments set forth in FIGS. 6, 11, and 24, as described in more detail herein. In some embodiments, red light specific response pathway polypeptides have greater than 40% identity to SEQ ID NO:456, SEQ ID NO:953, or SEQ ID NO:1540 as described in more detail herein.

A. Domains Indicative of SD+EODFR and/or Low Light Tolerance Polypeptides

A low light tolerance polypeptide can contain a cyclin dependent kinase inhibitor (CDI) domain. Cell cycle progression is negatively controlled by cyclin-dependent kinases inhibitors (CDIs). CDIs are involved in cell cycle arrest at the G1 phase. The motif is also present in SEQ ID NO:70, which sets forth the amino acid sequence of an *Arabidopsis* clone, identified herein as At2g32710 (SEQ ID NO:69), that is predicted to encode a cyclin-dependent kinase inhibitor 4 (KIP4) polypeptide.

A low light tolerance polypeptide can contain an AUX/IAA domain, which is predicted to be characteristic of an Aux/IAA transcriptional repressor. AUX/IAA proteins act as repressors of auxin-induced gene expression, possibly through modulating the activity of DNA-binding auxin response factors (ARFs). SEQ ID NO:129 sets forth the amino acid sequence of an *Arabidopsis* clone, identified herein as At2g46990 (SEQ ID NO:127), that is predicted to encode an auxin-induced IAA21 polypeptide. An SD+EODFR tolerance and low light tolerance polypeptide can also contain an AUX/IAA domain. SEQ ID NO:1347 sets forth the amino acid sequence of an *Arabidopsis* clone, identified herein as At1g32280 (SEQ ID NO:1345), that is predicted to encode an auxin-responsive IAA29 polypeptide containing an AUX/IAA domain.

A low light tolerance polypeptide can contain a homeobox domain. Homeobox domains bind DNA through a helix-turn-helix (HTH) structure. The HTH motif is characterised by two alpha-helices, which make intimate contacts with the DNA and are joined by a short turn. The second helix binds to DNA via a number of hydrogen bonds and hydrophobic interactions, which occur between specific side chains and the exposed bases and thymine methyl groups within the major groove of the DNA. The first helix helps to stabilise the structure. SEQ ID NO:317 sets forth the amino acid sequence of an *Arabidopsis* clone, identified herein as At4g03250 (SEQ ID NO:315), that is predicted to encode a polypeptide containing a homeobox domain.

A low light tolerance polypeptide can contain a C3HC4 type zinc-finger (zf_C3HC4) domain. The C3HC4 type zinc-finger (RING finger) is a cysteine-rich domain of 40 to 60 residues that coordinates two zinc ions, and has the consensus sequence: C-X2-C-X(9-39)-C-X(1-3)-H-X(2-3)-C-X2-C-X(4-48)-C-X2-C where X is any amino acid. Many proteins containing a RING finger play a role in the ubiquitination pathway. SEQ ID NO:337 sets forth the amino acid sequence of an *Arabidopsis* clone, identified herein as At2g04240 (SEQ ID NO:335), that is predicted to encode a polypeptide containing zf_C3HC4 domain.

A low light tolerance polypeptide can contain a B-box zinc finger (zf-B_box) domain and a CCT motif A B-box zinc finger domain is about 40 amino acids in length. One or two copies of this domain are generally associated with a ring finger and a coiled coil motif B-box zinc finger domains are found in transcription factors, ribonucleoproteins and protooncoproteins, but no function is clearly assigned. The CCT (CONSTANS, CO-like, and TOC1) motif is a highly conserved basic domain of about 43 amino acids, and is found near the C-terminus of plant proteins often involved in light signal transduction. The CCT motif is found in association with other domains, such as B-box zinc finger domains, GATA-type zinc finger domains, ZIM motifs, or response regulatory domains. The CCT motif contains a putative nuclear localization signal within the second half of the CCT motif, has been shown to be involved in nuclear localization, and likely has a role in protein-protein interaction. SEQ ID NO:456 sets forth the amino acid sequence of an *Arabidopsis* clone, identified herein as At5g14370 (SEQ ID NO:454), that is predicted to encode a polypeptide containing a B-box zinc finger domain and a CCT motif.

An SD+EODFR tolerance polypeptide can contain a DNA photolyase domain and a FAD_binding_7 domain (FAD binding domain of DNA photolyase). DNA photolyases are enzymes that repair mismatched pyrimidine dimers in DNA that are induced by exposure to ultra-violet light. Proteins containing a FAD_binding_7 domain include *Arabidopsis* cryptochromes 1 (CRY1) and 2 (CRY2), which are blue light photoreceptors that mediate blue light-induced gene expression. SEQ ID NO:538 sets forth the amino acid sequence of an *Arabidopsis* clone, identified herein as At1g04400 (SEQ ID NO:537), that is predicted to encode a cryptochrome 2 apoprotein polypeptide containing a FAD_binding_7 domain and a DNA photolyase domain. A low light-tolerance polypeptide can also FAD_binding_7 domain and a DNA photolyase domain. SEQ ID NO:1497 sets forth the amino acid sequence of an *Arabidopsis* clone, identified herein as At4g08920 (SEQ ID NO:1496), that is predicted to encode a cryptochrome 1 (CRY1), flavin-type blue-light photoreceptor apoprotein polypeptide containing a FAD_binding_7 domain and a DNA photolyase domain.

An SD+EODFR tolerance polypeptide can contain a zf_Dof domain, which is predicted to be characteristic of a Dof domain zinc finger polypeptide. SEQ ID NO:606 sets forth the amino acid sequence of an *Arabidopsis* clone, identified herein as At3g45610 (SEQ ID NO:605), that is predicted to encode a polypeptide containing a zf_Dof domain.

A low light tolerance polypeptide can contain an AP2 domain, which is predicted to be characteristic of an ERF/AP2 transcription factor. AP2 domains are typically about 60 amino acid residues in length. SEQ ID NO:645 sets forth the amino acid sequence of an *Arabidopsis* clone, identified herein as At4g25480 (SEQ ID NO:642), that is predicted to encode a DREB subfamily A-1 polypeptide of the ERF/AP2 transcription factor family containing an AP2 domain.

A low light tolerance polypeptide can contain a VQ motif. VQ motifs are short conserved motifs of FXhVQChTG, where X is any amino acid and h is a hydrophobic amino acid, that is found in a variety of plant proteins. SEQ ID NO:850 sets forth the amino acid sequence of an *Arabidopsis* clone, identified herein as At2g33780 (SEQ ID NO:848), that is predicted to encode a polypeptide containing a VQ motif.

A low light tolerance polypeptide can contain a zf_C2H2 domain, which is predicted to be characteristic of a C2H2-type zinc finger. C2H2 zinc fingers are composed of two short beta strands followed by an alpha helix. The amino terminal part of the helix binds the major groove of DNA. The two conserved cysteines and histidines of a C2H2 zinc finger domain coordinate a zinc ion. SEQ ID NO:907 sets forth the amino acid sequence of an *Arabidopsis* clone, identified herein as At4g17810 (SEQ ID NO:905), that is predicted to encode a polypeptide containing a zf_C2H2 domain.

A low light tolerance polypeptide can contain a TCP domain, which is predicted to be characteristic of a TCP family transcription factor. The TCP family of transcription factors is named after its first characterized members, TB1, CYC and PCF1 and PCF2. TCP domains are predicted to form non-canonical basic-Helix-Loop-Helix (bHLP) structures. The TCP domains found in two rice DNA-binding proteins, PCF1 and PCF2, have been shown to be involved in DNA-binding and dimerization. SEQ ID NO:1151 sets forth the amino acid sequence of an *Arabidopsis* clone, identified herein as At1g58100 (SEQ ID NO:1150), that is predicted to encode a polypeptide containing a TCP domain.

A low light tolerance polypeptide can contain an F-box domain. F-box domains have a role in mediating protein-protein interactions in a variety of contexts, such as polyubiquitination, transcription elongation, centromere binding and translational repression. Two motifs that are commonly found associated with F-box domains are leucine rich repeats and WD repeats. SEQ ID NO:1277 sets forth the amino acid sequence of an *Arabidopsis* clone, identified herein as At5g46170 (SEQ ID NO:1276), that is predicted to encode a polypeptide containing an F-box domain.

A low light tolerance polypeptide can contain a zf_CCCH domain, which is predicted to be characteristic of a C-x8-C-x5-C-x3-H type zinc finger polypeptide. The zf-CCCH domain is often found associated with proteins that interact with the 3' untranslated region of various mRNAs. SEQ ID NO:1457 sets forth the amino acid sequence of an *Arabidopsis* clone, identified herein as At3g02830 (SEQ ID NO:1456), that is predicted to encode a polypeptide containing a zf_CCCH domain.

An SD+EODFR tolerance and low light tolerance polypeptide can contain a PDX domain and a homeobox domain. PDX domains are often found in plant proteins with a homeobox domain, indicating that such proteins are likely transcription factors. SEQ ID NO:1540 sets forth the amino acid sequence of an *Arabidopsis* clone, identified herein as At2g35940 (SEQ ID NO:1537), that is predicted to encode a BEL1-like homeodomain 1 polypeptide containing a PDX domain and a homeobox domain.

A low light tolerance polypeptide can contain an HSF-type DNA-binding domain, which is predicted to be characteristic of heat shock factor transcription activator. Heat shock factor transcription activators are often found associated with heat shock protein promoters during heat shock. SEQ ID NO:1587 sets forth the amino acid sequence of an *Arabidopsis* clone, identified herein as At4g11660 (SEQ ID NO:1586), that is predicted to encode a polypeptide containing an HSF-type DNA-binding domain.

A low light tolerance polypeptide can contain a sterile alpha motif (SAM_1) domain and a DNA repair metallo-beta-lactamase (DRMBL) domain, which is predicted to be characteristic of a DNA repair metallo-beta-lactamase. SEQ ID NO:1635 sets forth the amino acid sequence of an *Arabidopsis* clone, identified herein as Ceres At2g45700 (SEQ ID NO:1634), that is predicted to encode a polypeptide containing a SAM domain and a DRMBL domain.

B. Domains Indicative of Red Light Specific Response Pathway Polypeptides

A red light specific response pathway polypeptide can contain a B-box zinc finger (zf-B_box) domain and a CCT motif A B-box zinc finger domain is about 40 amino acids in length. One or two copies of this domain are generally associated with a ring finger and a coiled coil motif B-box zinc finger domains are found in transcription factors, ribonucleoproteins and protooncoproteins, but no function is clearly assigned. The CCT (CONSTANS, CO-like, and TOC1) motif is a highly conserved basic domain of about 43 amino acids, and is found near the C-terminus of plant proteins often involved in light signal transduction. The CCT motif is found in association with other domains, such as B-box zinc finger domains, GATA-type zinc finger domains, ZIM motifs, or response regulatory domains. The CCT motif contains a putative nuclear localization signal within the second half of the CCT motif, has been shown to be involved in nuclear localization, and likely has a role in protein-protein interaction. SEQ ID NO:456 sets forth the amino acid sequence of an *Arabidopsis* clone, identified herein as At5g14370 (SEQ ID NO:454), that is predicted to encode a polypeptide containing a B-box zinc finger domain and a CCT motif.

A red light specific response pathway polypeptide can contain a PDX domain and a homeobox domain. PDX domains are often found in plant proteins with a homeobox domain, indicating that such proteins are likely transcription factors. SEQ ID NO:1540 sets forth the amino acid sequence of an *Arabidopsis* clone, identified herein as At2g35940

(SEQ ID NO:1537), that is predicted to encode a BELL-like homeodomain 1 polypeptide containing a PDX domain and a homeobox domain.

C. Functional Homologs Identified by Reciprocal BLAST

In some embodiments, one or more functional homologs of a reference SD+EODFR and/or low light tolerance polypeptide defined by one or more of the pfam descriptions indicated above are suitable for use as SD+EODFR and/or low light tolerance polypeptides. A functional homolog is a polypeptide that has sequence similarity to a reference polypeptide, and that carries out one or more of the biochemical or physiological function(s) of the reference polypeptide. A functional homolog and the reference polypeptide may be natural occurring polypeptides, and the sequence similarity may be due to convergent or divergent evolutionary events. As such, functional homologs are sometimes designated in the literature as homologs, or orthologs, or paralogs. Variants of a naturally occurring functional homolog, such as polypeptides encoded by mutants of a wild type coding sequence, may themselves be functional homologs. Functional homologs can also be created via site-directed mutagenesis of the coding sequence for an SD+EODFR and/or low light tolerance polypeptide, or by combining domains from the coding sequences for different naturally-occurring SD+EODFR and/or low light tolerance polypeptides ("domain swapping"). The term "functional homolog" is sometimes applied to the nucleic acid that encodes a functionally homologous polypeptide.

Functional homologs can be identified by analysis of nucleotide and polypeptide sequence alignments. For example, performing a query on a database of nucleotide or polypeptide sequences can identify homologs of SD+EODFR and/or low light tolerance polypeptides. Sequence analysis can involve BLAST, Reciprocal BLAST, or PSI-BLAST analysis of nonredundant databases using an SD+EODFR and/or low light tolerance polypeptide amino acid sequence as the reference sequence. Amino acid sequence is, in some instances, deduced from the nucleotide sequence. Those polypeptides in the database that have greater than 40% sequence identity are candidates for further evaluation for suitability as an SD+EODFR and/or low light tolerance polypeptide Amino acid sequence similarity allows for conservative amino acid substitutions, such as substitution of one hydrophobic residue for another or substitution of one polar residue for another. If desired, manual inspection of such candidates can be carried out in order to narrow the number of candidates to be further evaluated. Manual inspection can be performed by selecting those candidates that appear to have domains present in SD+EODFR and/or low light tolerance polypeptides, e.g., conserved functional domains.

Conserved regions can be identified by locating a region within the primary amino acid sequence of an SD+EODFR and/or low light tolerance polypeptide that is a repeated sequence, forms some secondary structure (e.g., helices and beta sheets), establishes positively or negatively charged domains, or represents a protein motif or domain. See, e.g., the Pfam web site describing consensus sequences for a variety of protein motifs and domains on the World Wide Web at sanger.ac.uk/Software/Pfam/and pfam.janelia.org/. A description of the information included at the Pfam database is described in Sonnhammer et al., *Nucl. Acids Res.*, 26:320-322 (1998); Sonnhammer et al., *Proteins*, 28:405-420 (1997); and Bateman et al., *Nucl. Acids Res.*, 27:260-262 (1999). Conserved regions also can be determined by aligning sequences of the same or related polypeptides from closely related species. Closely related species preferably are from the same family. In some embodiments, alignment of sequences from two different species is adequate.

Typically, polypeptides that exhibit at least about 40% amino acid sequence identity are useful to identify conserved regions. Conserved regions of related polypeptides exhibit at least 45% amino acid sequence identity (e.g., at least 50%, at least 60%, at least 70%, at least 80%, or at least 90% amino acid sequence identity). In some embodiments, a conserved region exhibits at least 92%, 94%, 96%, 98%, or 99% amino acid sequence identity.

Amino acid sequences of functional homologs of the polypeptide set forth in SEQ ID NO:3 are provided in FIG. 1. Such functional homologs include Ceres CLONE ID no. 1844057 (SEQ ID NO:7), Ceres ANNOT ID no. 1469148 (SEQ ID NO:22), Public GI ID no. 18390998 (SEQ ID NO:25), Ceres CLONE ID no. 1065656 (SEQ ID NO:32), Ceres CLONE ID no. 1652677 (SEQ ID NO:36), Public GI ID no. 92874556 (SEQ ID NO:49), Ceres CLONE ID no. 1329161 (SEQ ID NO:53), Ceres CLONE ID no. 1030378 (SEQ ID NO:55), Ceres CLONE ID no. 1413787 (SEQ ID NO:57), and Public GI ID no. 125543598 (SEQ ID NO:60). Other functional homologs of SEQ ID NO:3 include Ceres CLONE ID no. 1793691 (SEQ ID NO:5), Ceres CLONE ID no. 1933784 (SEQ ID NO:9), Ceres CLONE ID no. 100030408 (SEQ ID NO:10), Ceres CLONE ID no. 1837059 (SEQ ID NO:12), Ceres CLONE ID no. 1793801 (SEQ ID NO:14), Ceres CLONE ID no. 1855480 (SEQ ID NO:16), Ceres CLONE ID no. 1915644 (SEQ ID NO:18), Ceres CLONE ID no. 1898104 (SEQ ID NO:20), Ceres ANNOT ID no. 1464241 (SEQ ID NO:24), Public GI ID no. 18697627 (SEQ ID NO:26), Ceres CLONE ID no. 9391 (SEQ ID NO:28), Ceres CLONE ID no. 111154 (SEQ ID NO:30), Ceres CLONE ID no. 973975 (SEQ ID NO:34), Ceres CLONE ID no. 676695 (SEQ ID NO:38), Ceres CLONE ID no. 680331 (SEQ ID NO:40), Ceres CLONE ID no. 654515 (SEQ ID NO:42), Ceres CLONE ID no. 626154 (SEQ ID NO:44), Ceres CLONE ID no. 710603 (SEQ ID NO:46), Ceres CLONE ID no. 648076 (SEQ ID NO:48), Ceres CLONE ID no. 749439 (SEQ ID NO:51), Ceres CLONE ID no. 295936 (SEQ ID NO:59), Public GI ID no. 125525139 (SEQ ID NO:61), Public GI ID no. 115452643 (SEQ ID NO:62), Public GI ID no. 24059889 (SEQ ID NO:63), Ceres ANNOT ID no. 6012747 (SEQ ID NO:65), Ceres ANNOT ID no. 6027628 (SEQ ID NO:67), and sequences identified as functional homologs of the sequences of FIG. 1, as set forth in the sequence listing. In some cases, a functional homolog of SEQ ID NO:3 has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:3.

Figure 2:
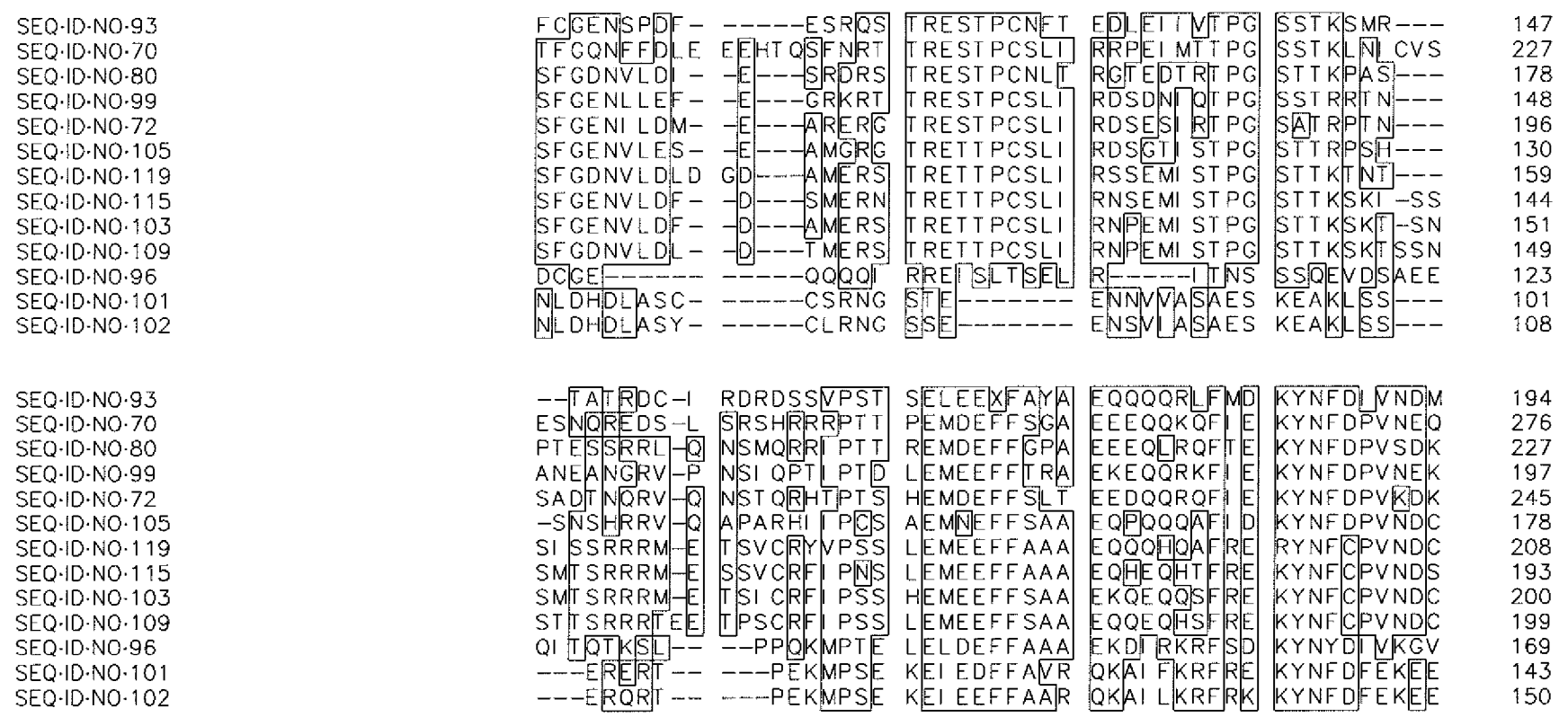

Amino acid sequences of functional homologs of the polypeptide set forth in SEQ ID NO:70 are provided in FIG. 2. Such functional homologs include Ceres CLONE ID no. 1975934 (SEQ ID NO:72), Ceres ANNOT ID no. 1529913 (SEQ ID NO:80), Ceres CLONE ID no. 977794 (SEQ ID NO:93), Public GI ID no. 42362378 (SEQ ID NO:96), Public GI ID no. 23899378 (SEQ ID NO:99), Public GI ID no. 15963346 (SEQ ID NO:101), Public GI ID no. 15963344+B816 (SEQ ID NO:102), Public GI ID no. 92429657 (SEQ ID NO:103), Ceres CLONE ID no. 746644 (SEQ ID NO:105), Ceres CLONE ID no. 623089 (SEQ ID NO:109), Ceres CLONE ID no. 1913678 (SEQ ID NO:115), and Public GI ID no. 115450609 (SEQ ID NO:119). Other functional homologs of SEQ ID NO:70 include Ceres CLONE ID no. 1835084 (SEQ ID NO:74), Ceres CLONE ID no. 1846153 (SEQ ID NO:76), Ceres CLONE ID no.

1930884 (SEQ ID NO:78), Ceres ANNOT ID no. 1493858 (SEQ ID NO:82), Ceres ANNOT ID no. 1498646 (SEQ ID NO:84), Ceres ANNOT ID no. 1440974 (SEQ ID NO:86), Ceres CLONE ID no. 1189183 (SEQ ID NO:88), Public GI ID no. 26450253 (SEQ ID NO:89), Public GI ID no. 15239719 (SEQ ID NO:90), Public GI ID no. 15230194 (SEQ ID NO:91), Ceres CLONE ID no. 630905 (SEQ ID NO:95), Public GI ID no. 42362389 (SEQ ID NO:97), Public GI ID no. 70906129 (SEQ ID NO:98), Public GI ID no. 23899381 (SEQ ID NO:100), Ceres CLONE ID no. 298166 (SEQ ID NO:107), Ceres CLONE ID no. 1448390 (SEQ ID NO:111), Ceres CLONE ID no. 1734216 (SEQ ID NO:113), Public GI ID no. 125542322 (SEQ ID NO:116), Public GI ID no. 125532331 (SEQ ID NO:117), Public GI ID no. 125541233 (SEQ ID NO:118), Public GI ID no. 125584844 (SEQ ID NO:120), Public GI ID no. 115482472 (SEQ ID NO:121), Public GI ID no. 125575112 (SEQ ID NO:122), Ceres ANNOT ID no.6003994 (SEQ ID NO:124), Ceres ANNOT ID no. 6068427 (SEQ ID NO:126), and sequences identified as functional homologs of the sequences of FIG. 2, as set forth in the sequence listing. In some cases, a functional homolog of SEQ ID NO:70 has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:70.

Figure 3:
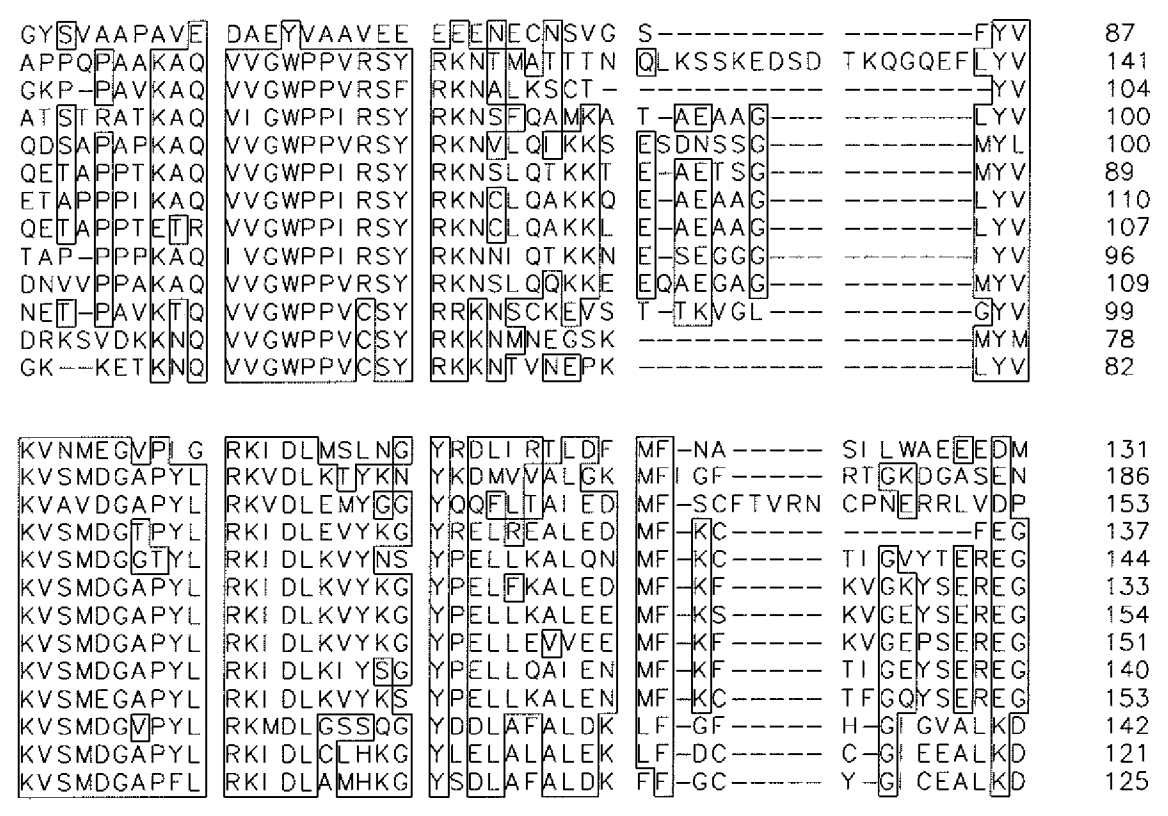

Amino acid sequences of functional homologs of the polypeptide set forth in SEQ ID NO:129 are provided in FIG. 3. Such functional homologs include Public GI ID no. 34550779 (SEQ ID NO:133), Ceres CLONE ID no. 1932235 (SEQ ID NO:137), Ceres CLONE ID no. 981738 (SEQ ID NO:201), Ceres CLONE ID no. 565974 (SEQ ID NO:209), Public GI ID no. 1352058 (SEQ ID NO:231), Public GI ID no. 11131101 (SEQ ID NO:234), Public GI ID no. 4887018 (SEQ ID NO:236), Public GI ID no. 4887018 (SEQ ID NO:236), Ceres CLONE ID no. 644455 (SEQ ID NO:247), Ceres CLONE ID no. 1731500 (SEQ ID NO:270), Public GI ID no. 20269063 (SEQ ID NO:300), Public GI ID no. 50404477 (SEQ ID NO:302), and Public GI ID no. 62125392 (SEQ ID NO:303). Other functional homologs of SEQ ID NO:129 include Public GI ID no. 32396293 (SEQ ID NO:130), Public GI ID no. 32396299 (SEQ ID NO:131), Public GI ID no. 32396295 (SEQ ID NO:132), Ceres CLONE ID no. 1855369 (SEQ ID NO:135), Ceres CLONE ID no. 1948456 (SEQ ID NO:139), Ceres CLONE ID no. 1920182 (SEQ ID NO:141), Ceres CLONE ID no. 1835797 (SEQ ID NO:143), Ceres CLONE ID no. 1794204 (SEQ ID NO:145), Ceres CLONE ID no. 1853542 (SEQ ID NO:147), Ceres CLONE ID no. 1838776 (SEQ ID NO:149), Ceres CLONE ID no. 1854675 (SEQ ID NO:151), Ceres CLONE ID no. 1833078 (SEQ ID NO:153), Ceres CLONE ID no. 1850667 (SEQ ID NO:155), Ceres CLONE ID no. 1918745 (SEQ ID NO:157), Ceres CLONE ID no. 1929487 (SEQ ID NO:159), Ceres ANNOT ID no. 1497918 (SEQ ID NO:161), Ceres ANNOT ID no. 1459563 (SEQ ID NO:163), Ceres ANNOT ID no. 1452610 (SEQ ID NO:165), Ceres ANNOT ID no. 1496539 (SEQ ID NO:167), Ceres ANNOT ID no. 1498819 (SEQ ID NO:169), Ceres ANNOT ID no. 1446583 (SEQ ID NO:171), Ceres ANNOT ID no. 1535123 (SEQ ID NO:173), Ceres ANNOT ID no. 1463397 (SEQ ID NO:175), Ceres ANNOT ID no. 1499563 (SEQ ID NO:177), Ceres ANNOT ID no. 1495753 (SEQ ID NO:179), Ceres ANNOT ID no. 1488767 (SEQ ID NO:181), Ceres ANNOT ID no. 1522920 (SEQ ID NO:185), Ceres ANNOT ID no. 1469532 (SEQ ID NO:187), Public GI ID no. 15219692 (SEQ ID NO:188), Public GI ID no. 18420964 (SEQ ID NO:189), Ceres CLONE ID no. 1342080 (SEQ ID NO:191), Ceres CLONE ID no. 123105 (SEQ ID NO:193), Ceres CLONE ID no. 32727 (SEQ ID NO:195), Ceres CLONE ID no. 41161 (SEQ ID NO:197), Ceres CLONE ID no. 37274 (SEQ ID NO:199), Ceres CLONE ID no. 538020 (SEQ ID NO:203), Ceres CLONE ID no. 476244 (SEQ ID NO:205), Ceres CLONE ID no. 1623662 (SEQ ID NO:207), Ceres CLONE ID no. 626817 (SEQ ID NO:211), Ceres CLONE ID no. 537469 (SEQ ID NO:213), Ceres CLONE ID no. 582463 (SEQ ID NO:215), Ceres CLONE ID no.1069818 (SEQ ID NO:217), Ceres CLONE ID no. 511737 (SEQ ID NO:219), Ceres CLONE ID no. 565422 (SEQ ID NO:221), Ceres CLONE ID no. 514595 (SEQ ID NO:223), Ceres CLONE ID no. 566396 (SEQ ID NO:225), Ceres CLONE ID no. 612705 (SEQ ID NO:227), Ceres CLONE ID no. 564134 (SEQ ID NO:229), Public GI ID no. 92872146 (SEQ ID NO:230), Public GI ID no. 11131103 (SEQ ID NO:232), Public GI ID no. 416641 (SEQ ID NO:233), Public GI ID no. 11131105 (SEQ ID NO:235), Public GI ID no. 4887016 (SEQ ID NO:237), Public GI ID no. 4887022 (SEQ ID NO:238), Public GI ID no. 81074526 (SEQ ID NO:239), Ceres CLONE ID no. 742023 (SEQ ID NO:241), Ceres CLONE ID no. 576268 (SEQ ID NO:243), Ceres CLONE ID no. 615386 (SEQ ID NO:245), Ceres CLONE ID no. 756966 (SEQ ID NO:249), Ceres CLONE ID no. 1052710 (SEQ ID NO:251), Ceres CLONE ID no. 697018 (SEQ ID NO:253), Ceres CLONE ID no. 618577 (SEQ ID NO:255), Ceres CLONE ID no. 935194 (SEQ ID NO:257), Ceres CLONE ID no. 1557429 (SEQ ID NO:259), Ceres CLONE ID no. 305337 (SEQ ID NO:261), Ceres CLONE ID no. 100872943 (SEQ ID NO:262), Ceres CLONE ID no. 305454 (SEQ ID NO:264), Ceres CLONE ID no. 1534670 (SEQ ID NO:266), Ceres CLONE ID no. 207963 (SEQ ID NO:268), Public GI ID no. 20257219 (SEQ ID NO:271), Ceres CLONE ID no. 1876818 (SEQ ID NO:273), Ceres CLONE ID no. 1817533 (SEQ ID NO:275), Ceres CLONE ID no. 1958631 (SEQ ID NO:277), Ceres CLONE ID no. 1963215 (SEQ ID NO:279), Ceres CLONE ID no. 1770022 (SEQ ID NO:281), Ceres CLONE ID no. 1796223 (SEQ ID NO:283), Ceres CLONE ID no. 2016695 (SEQ ID NO:285), Ceres CLONE ID no. 1757085 (SEQ ID NO:287), Ceres CLONE ID no. 1769256 (SEQ ID NO:289), Ceres CLONE ID no. 1994871 (SEQ ID NO:291), Public GI ID no. 17154533 (SEQ ID NO:292), Public GI ID no. 125557426 (SEQ ID NO:293), Public GI ID no. 125524736 (SEQ ID NO:294), Public GI ID no. 125527656 (SEQ ID NO:295), Public GI ID no. 125599342 (SEQ ID NO:296), Public GI ID no. 125569626 (SEQ ID NO:297), Public GI ID no. 115465401 (SEQ ID NO:298), Public GI ID no. 40539038 (SEQ ID NO:299), Public GI ID no. 20269059 (SEQ ID NO:301), Public GI ID no. 110826446 (SEQ ID NO:304), Ceres ANNOT ID no. 6029073 (SEQ ID NO:306), Ceres ANNOT ID no. 6011329 (SEQ ID NO:308), Ceres ANNOT ID no. 6034498 (SEQ ID NO:310), Ceres ANNOT ID no. 6095057 (SEQ ID NO:312), Ceres ANNOT ID no. 6095058 (SEQ ID NO:314), and sequences identified as functional homologs of the sequences of FIG. 3, as set forth in the sequence listing. In some cases, a functional homolog of SEQ ID NO:129 has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:129.

Amino acid sequences of functional homologs of the polypeptide set forth in SEQ ID NO:317 are provided in FIG. 4. Such functional homologs include Ceres CLONE ID no. 1842125 (SEQ ID NO:319), Ceres ANNOT ID no. 1461360 (SEQ ID NO:321), Ceres CLONE ID no. 480906

(SEQ ID NO:327), Public GI ID no. 92889352 (SEQ ID NO:330), and Public GI ID no. 56201850 (SEQ ID NO:330). Other functional homologs of SEQ ID NO:317 include Ceres ANNOT ID no. 1440334 (SEQ ID NO:323), Ceres ANNOT ID no. 1493205 (SEQ ID NO:325), Ceres CLONE ID no. 482270 (SEQ ID NO:329), Public GI ID no. 125571531 (SEQ ID NO:332), Ceres ANNOT ID no. 6042411 (SEQ ID NO:334), and sequences identified as functional homologs of the sequences of FIG. 4, as set forth in the sequence listing. In some cases, a functional homolog of SEQ ID NO:317 has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:317.

Figure 5:
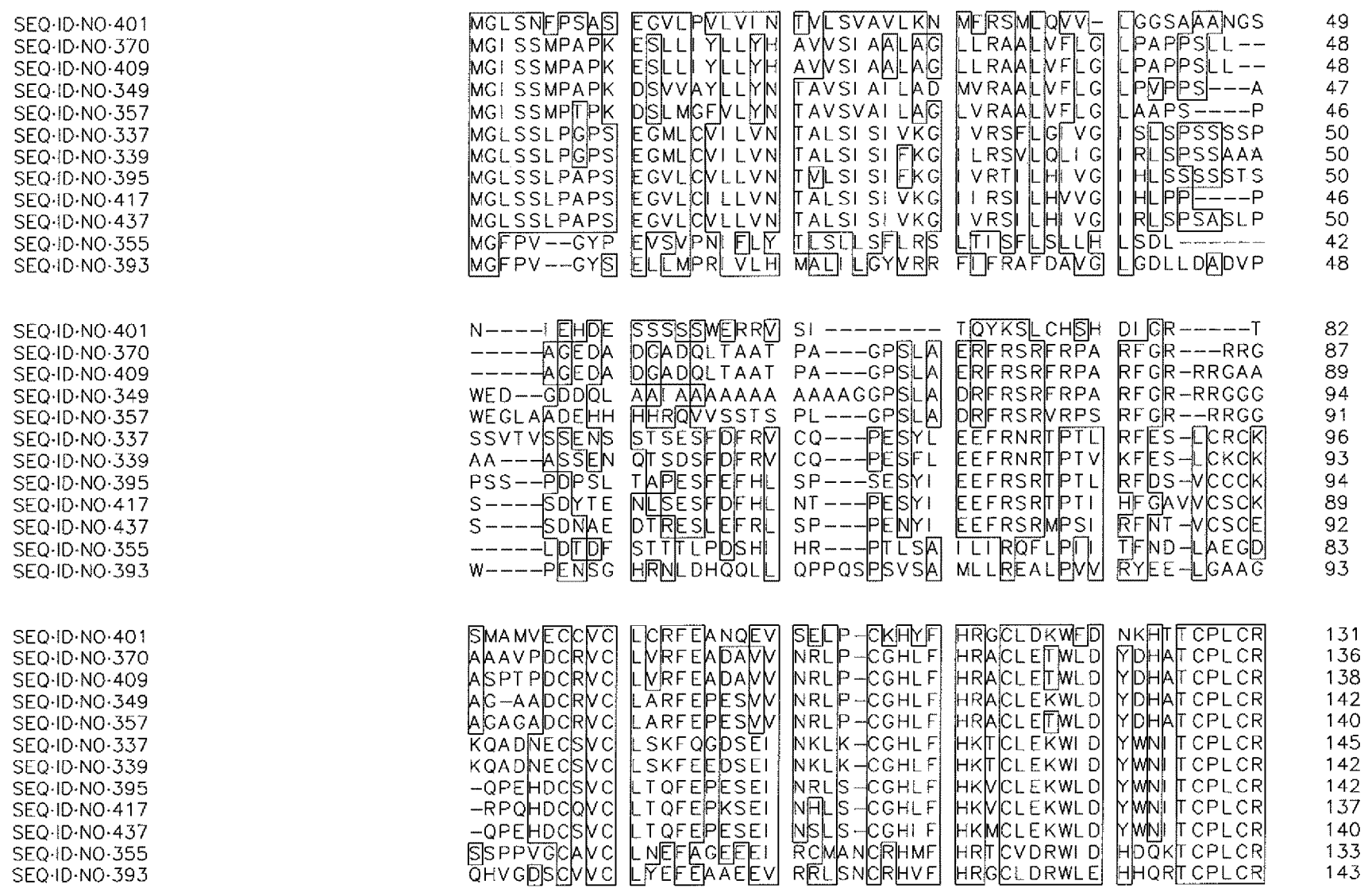

Amino acid sequences of functional homologs of the polypeptide set forth in SEQ ID NO:337 are provided in FIG. 5. Such functional homologs include Ceres CLONE ID no. 952050 (SEQ ID NO:339), Public GI ID no. 115477050 (SEQ ID NO:349), Public GI ID no. 87162911 (SEQ ID NO:355), Ceres CLONE ID no. 1790901 (SEQ ID NO:357), Ceres CLONE ID no. 1460088 (SEQ ID NO:370), Ceres CLONE ID no. 1734065 (SEQ ID NO:393), Ceres CLONE ID no. 473509 (SEQ ID NO:395), Ceres CLONE ID no. 849918 (SEQ ID NO:401), Ceres CLONE ID no. 633470 (SEQ ID NO:409), Ceres CLONE ID no. 1808334 (SEQ ID NO:417), and Ceres ANNOT ID no. 1525600 (SEQ ID NO:437). Other functional homologs of SEQ ID NO:337 include Ceres CLONE ID no. 1265097 (SEQ ID NO:341), Ceres CLONE ID no. 942980 (SEQ ID NO:343), Public GI ID no. 37901055 (SEQ ID NO:344), Ceres CLONE ID no. 1609912 (SEQ ID NO:346), Public GI ID no. 76446335 (SEQ ID NO:347), Public GI ID no. 125560204 (SEQ ID NO:348), Public GI ID no. 125303087 (SEQ ID NO:350), Public GI ID no. 115460088 (SEQ ID NO:351), Public GI ID no. 125591385 (SEQ ID NO:352), Public GI ID no. 115447931 (SEQ ID NO:353), Public GI ID no. 92893514 (SEQ ID NO:354), Ceres CLONE ID no. 2019320 (SEQ ID NO:359), Ceres CLONE ID no. 1890013 (SEQ ID NO:361), Public GI ID no. 20340241 (SEQ ID NO:362), Ceres CLONE ID no. 25801 (SEQ ID NO:364), Public GI ID no. 9743343 (SEQ ID NO:365), Public GI ID no. 15238072 (SEQ ID NO:366), Public GI ID no. 15222553 (SEQ ID NO:367), Public GI ID no. 21554155 (SEQ ID NO:368), Ceres CLONE ID no. 374439 (SEQ ID NO:372), Ceres CLONE ID no. 1465572 (SEQ ID NO:374), Ceres CLONE ID no. 1565524 (SEQ ID NO:376), Ceres CLONE ID no. 322302 (SEQ ID NO:378), Ceres CLONE ID no. 101136485 (SEQ ID NO:379), Ceres CLONE ID no. 1376133 (SEQ ID NO:381), Ceres CLONE ID no. 1374381 (SEQ ID NO:383), Ceres CLONE ID no. 1566473 (SEQ ID NO:385), Ceres CLONE ID no. 318088 (SEQ ID NO:387), Ceres CLONE ID no. 1452604 (SEQ ID NO:389), Ceres CLONE ID no. 337906 (SEQ ID NO:391), Ceres CLONE ID no. 1662513 (SEQ ID NO:397), Ceres CLONE ID no. 1662527 (SEQ ID NO:399), Ceres CLONE ID no. 571184 (SEQ ID NO:403), Ceres CLONE ID no. 665689 (SEQ ID NO:405), Ceres CLONE ID no. 1365853 (SEQ ID NO:407), Ceres CLONE ID no. 1052457 (SEQ ID NO:411), Ceres CLONE ID no. 579918 (SEQ ID NO:413), Ceres CLONE ID no. 863299 (SEQ ID NO:415), Ceres CLONE ID no. 1855611 (SEQ ID NO:419), Ceres CLONE ID no. 1845975 (SEQ ID NO:421), Ceres CLONE ID no. 1808298 (SEQ ID NO:423), Ceres CLONE ID no. 1841236 (SEQ ID NO:425), Ceres CLONE ID no. 1808269 (SEQ ID NO:427), Ceres CLONE ID no. 1850628 (SEQ ID NO:429), Ceres CLONE ID no. 1846911 (SEQ ID NO:431), Ceres CLONE ID no. 1916014 (SEQ ID NO:433), Ceres CLONE ID no. 1842594 (SEQ ID NO:435), Ceres ANNOT ID no. 1472192 (SEQ ID NO:439), Ceres ANNOT ID no. 1447489 (SEQ ID NO:441), Ceres ANNOT ID no. 1513000 (SEQ ID NO:443), Ceres ANNOT ID no. 1438658 (SEQ ID NO:445), Ceres ANNOT ID no. 1497255 (SEQ ID NO:447), Ceres ANNOT ID no. 6092104 (SEQ ID NO:449), Ceres ANNOT ID no. 6041700 (SEQ ID NO:451), Ceres ANNOT ID no. 6007297 (SEQ ID NO:453), and sequences identified as functional homologs of the sequences of FIG. 5, as set forth in the sequence listing. In some cases, a functional homolog of SEQ ID NO:337 has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:337.

Figure 6:
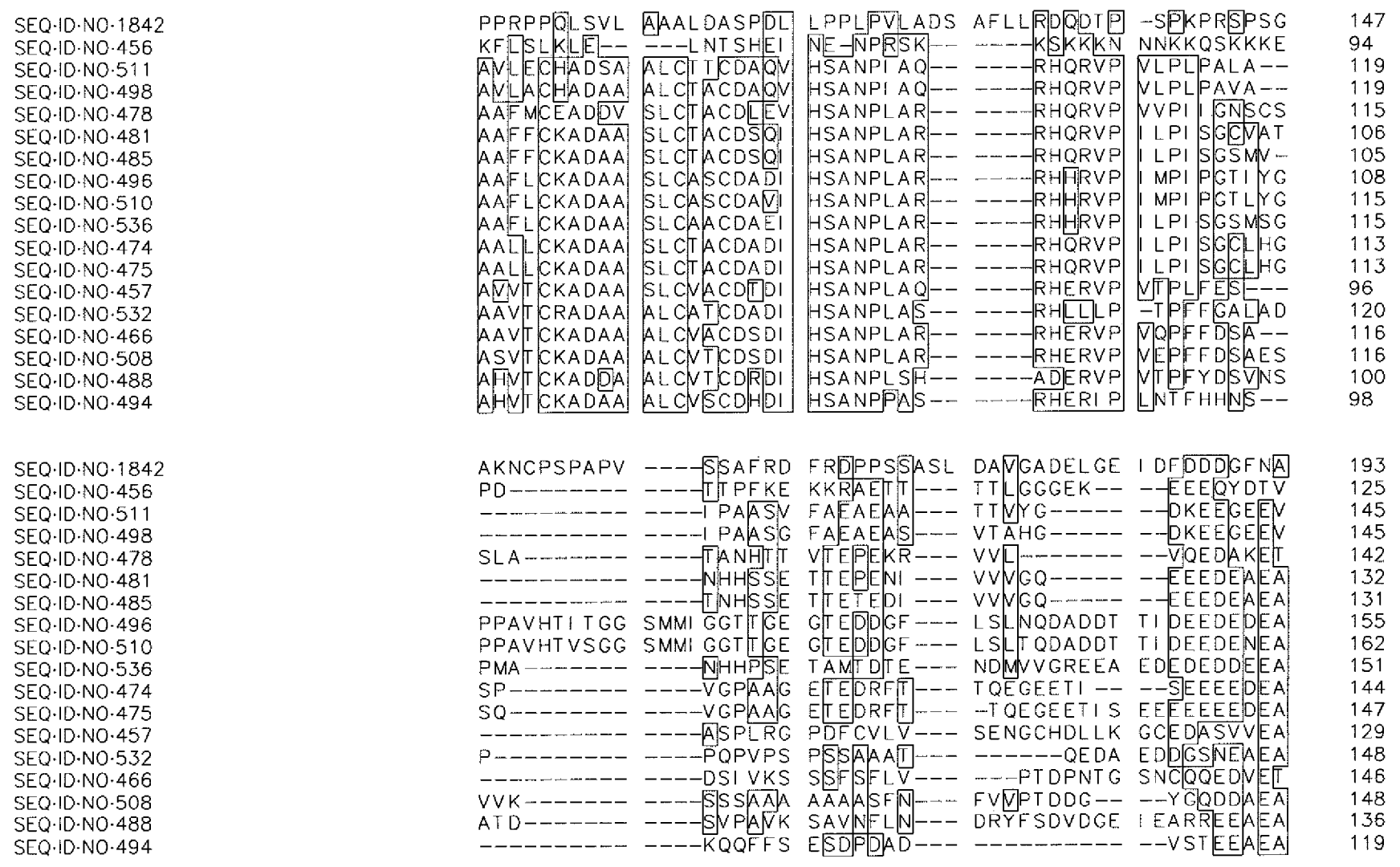
Figure 6:
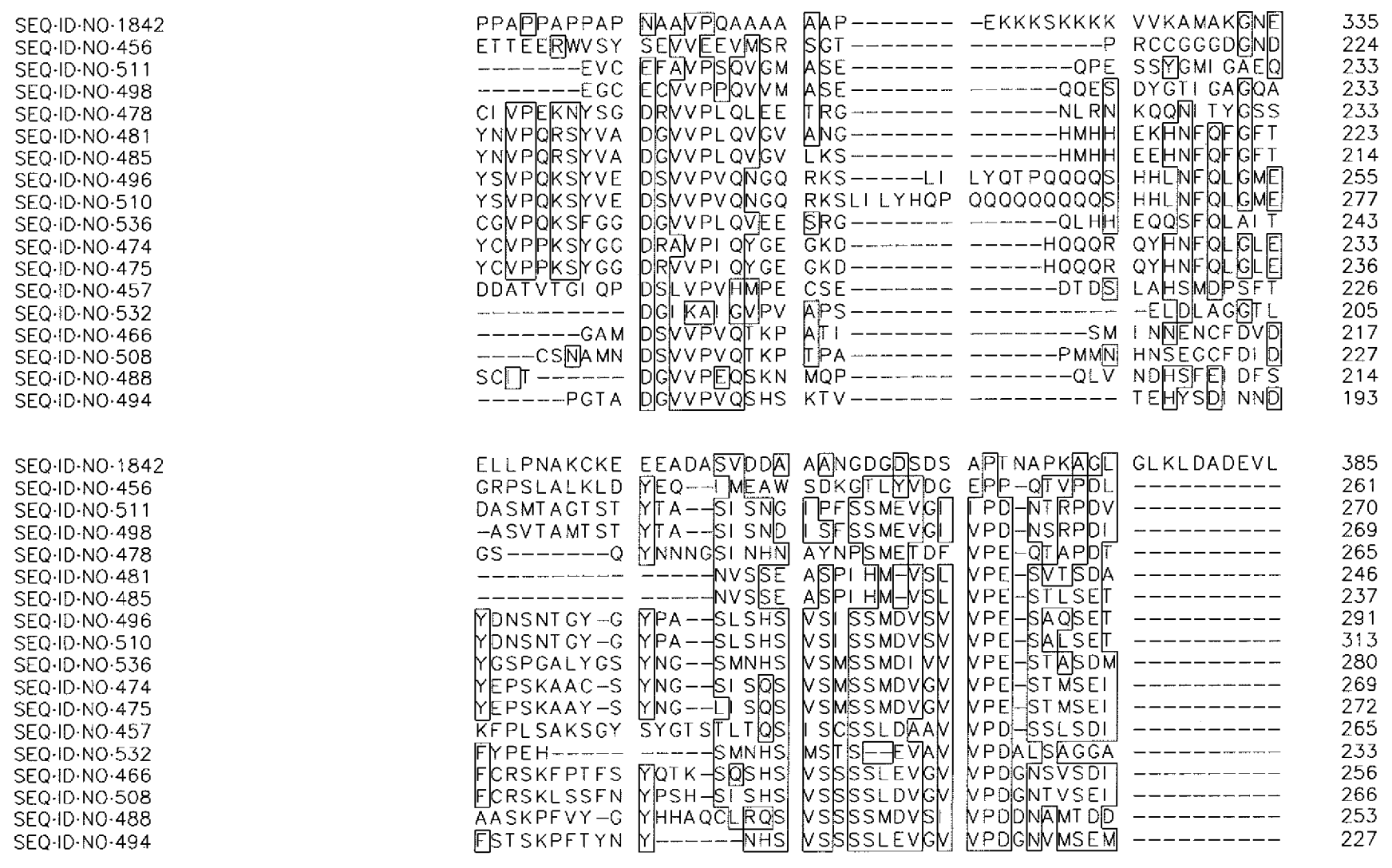

Amino acid sequences of functional homologs of the polypeptide set forth in SEQ ID NO:456 are provided in FIG. 6. Such functional homologs include Public GI ID no. 58430585 (SEQ ID NO:457), Ceres CLONE ID no. 1842825 (SEQ ID NO:466), Ceres ANNOT ID no. 1449721 (SEQ ID NO:474), Public GI ID no. 41323978 (SEQ ID NO:475), Public GI ID no. 2895186 (SEQ ID NO:478), Public GI ID no. 22854950 (SEQ ID NO:481), Public GI ID no. 116010474 (SEQ ID NO:485), Public GI ID no. 4091804 (SEQ ID NO:488), Public GI ID no. 60459257 (SEQ ID NO:494), Public GI ID no. 45544881 (SEQ ID NO:496), Public GI ID no. 36789802 (SEQ ID NO:498), Public GI ID no. 92875402 (SEQ ID NO:508), Public GI ID no. 118406898 (SEQ ID NO:510), Public GI ID no. 107770485 (SEQ ID NO:511), Public GI ID no. 21655154 (SEQ ID NO:532), Public GI ID no. 90657642 (SEQ ID NO:536), and Ceres CLONE ID no. 1569555 (SEQ ID NO:1842). Other homologs of SEQ ID NO:456 include Public GI ID no. 66841018 (SEQ ID NO:458), Public GI ID no. 66841020 (SEQ ID NO:459), Public GI ID no. 108859343 (SEQ ID NO:460), Ceres CLONE ID no. 1937613 (SEQ ID NO:462), Ceres CLONE ID no. 1834027 (SEQ ID NO:464), Ceres ANNOT ID no. 1477832 (SEQ ID NO:468), Ceres ANNOT ID no. 1482536 (SEQ ID NO:470), Ceres ANNOT ID no. 1478227 (SEQ ID NO:472), Ceres CLONE ID no. 19906 (SEQ ID NO:478), Public GI ID no. 2895184 (SEQ ID NO:479), Public GI ID no. 2895188 (SEQ ID NO:480), Public GI ID no. 11037313 (SEQ ID NO:482), Public GI ID no. 22854908 (SEQ ID NO:483), Public GI ID no. 40787165 (SEQ ID NO:484), Public GI ID no. 116010475 (SEQ ID NO:486), Public GI ID no. 3341723 (SEQ ID NO:487), Public GI ID no. 4091806 (SEQ ID NO:489), Ceres CLONE ID no. 523203 (SEQ ID NO:491), Ceres CLONE ID no. 463157 (SEQ ID NO:493), Public GI ID no. 61611678 (SEQ ID NO:495), Public GI ID no. 45544887 (SEQ ID NO:497), Public GI ID no. 36789793 (SEQ ID NO:481), Ceres CLONE ID no. 907473 (SEQ ID NO:501), Ceres CLONE ID no. 1674443 (SEQ ID NO:503), Ceres CLONE ID no. 1559496 (SEQ ID NO:505), Ceres CLONE ID no. 530984 (SEQ ID NO:507), Public GI ID no. 61611682 (SEQ ID NO:509), Public GI ID no. 36789785 (SEQ ID NO:512), Ceres CLONE ID no. 702632 (SEQ ID NO:514), Public GI ID no. 61657299 (SEQ ID NO:515), Public GI ID no. 10946337 (SEQ ID NO:516), Ceres CLONE ID no. 1996408 (SEQ ID NO:518), Ceres CLONE ID no. 1725313 (SEQ ID NO:520), Public GI ID no. 78058606 (SEQ ID NO:521), Public GI ID no. 125538317 (SEQ ID NO:522), Public GI ID no. 125556324 (SEQ ID NO:523), Public GI ID no. 125548890 (SEQ ID NO:524), Public GI ID no. 93211100 (SEQ ID NO:525), Public GI ID no. 115444217 (SEQ ID NO:526), Public GI ID no. 115467558 (SEQ ID NO:527), Public GI ID no. 11094209 (SEQ ID NO:528), Public GI ID no. 125596830 (SEQ ID NO:529), Public GI ID no. 115469296 (SEQ ID NO:530), Public GI ID no. 115447239 (SEQ ID NO:531), Public GI ID no. 21667485 (SEQ ID NO:533), Public GI ID no. 21667475 (SEQ ID NO:534), Public GI ID no. 21655158 (SEQ ID NO:535), and sequences identified as functional homologs of the sequences of FIG. 6, as set forth in the sequence listing. In some cases, a functional homolog of SEQ ID NO:456 has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:456.

Amino acid sequences of functional homologs of the polypeptide set forth in SEQ ID NO:634 are provided in FIG. 7. Such functional homologs include Public GI ID no. 98961985 (SEQ ID NO:637). Other functional homologs of SEQ ID NO:634 include Ceres CLONE ID no. 1916112 (SEQ ID NO:636), Public GI ID no. 9369405 (SEQ ID NO:638), Public GI ID no. 9369406 (SEQ ID NO:639), Ceres CLONE ID no. 1238706 (SEQ ID NO:641), and sequences identified as functional homologs of the sequences of FIG. 7, as set forth in the sequence listing. In some cases, a functional homolog of SEQ ID NO:634 has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:634.

Figure 8:
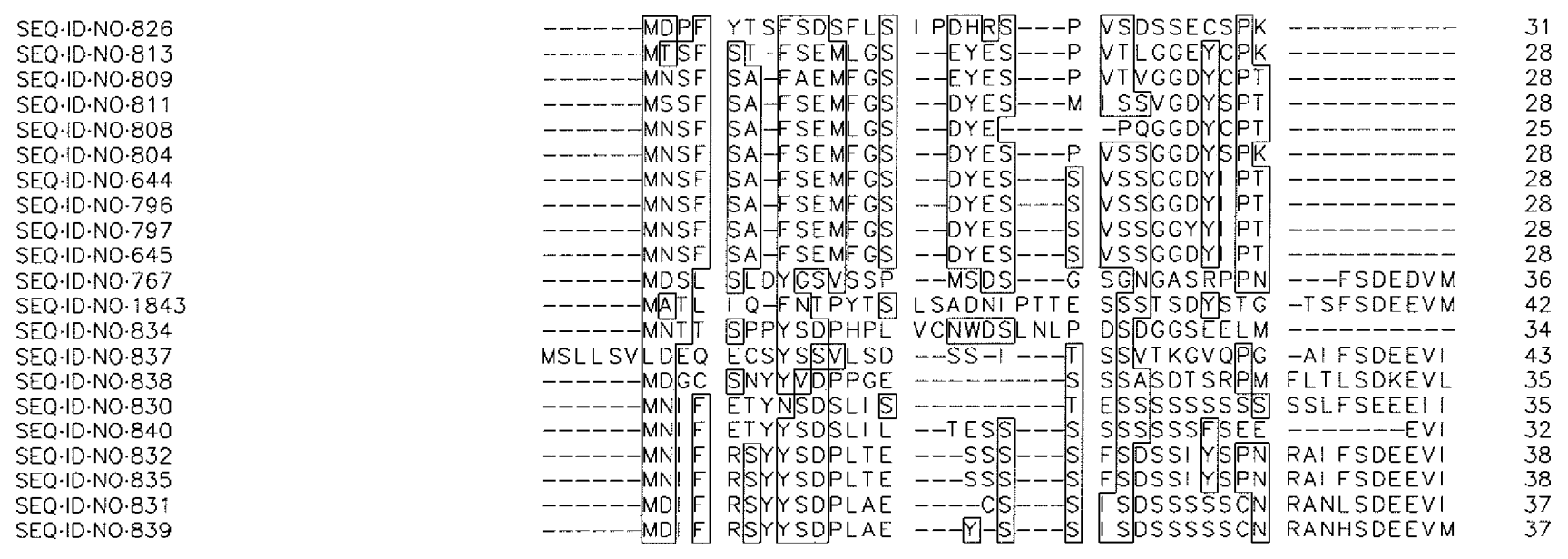
Figure 8:
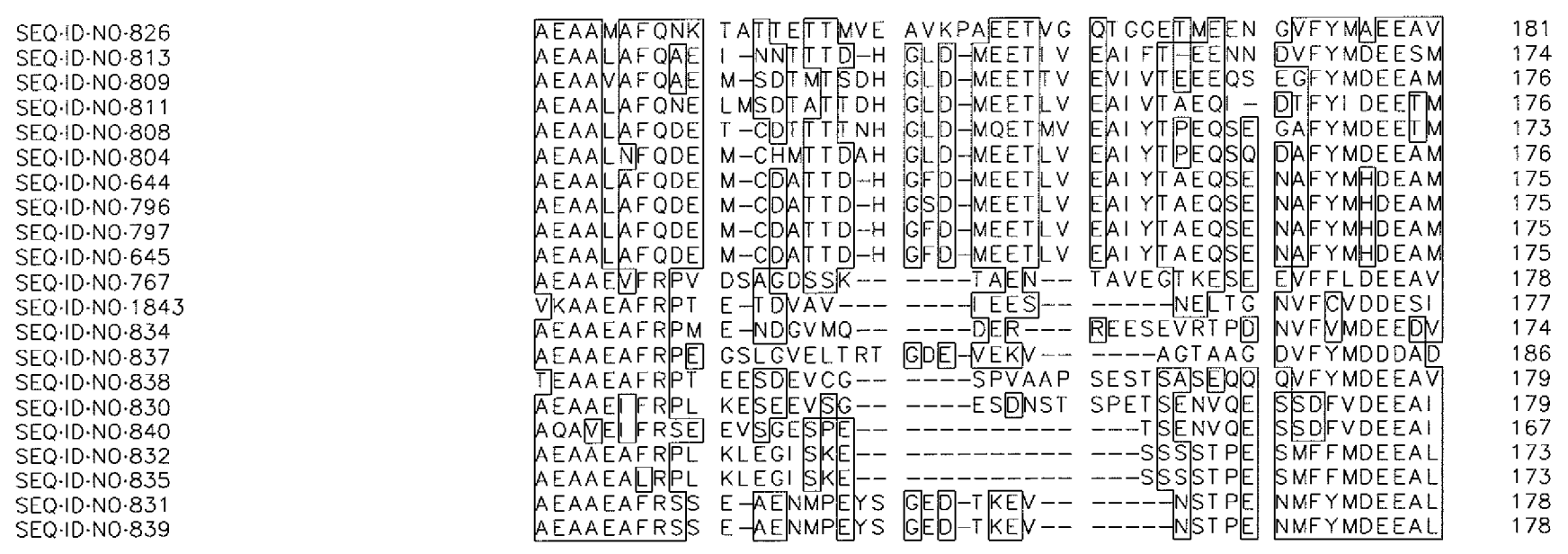

Amino acid sequences of functional homologs of the polypeptide set forth in SEQ ID NO:644 are provided in FIG. 8. Such functional homologs include SEQ ID NO:645, Ceres CLONE ID no. 1849479 (SEQ ID NO:767), Public GI ID no. 89275008 (SEQ ID NO:796), Public GI ID no. 120400525 (SEQ ID NO:797), Public GI ID no. 98980426 (SEQ ID NO:804), Public GI ID no. 71983373 (SEQ ID NO:808), Public GI ID no. 41351817 (SEQ ID NO:809), Public GI ID no. 76446191 (SEQ ID NO:811), Public GI ID no. 5616086 (SEQ ID NO:813), Ceres CLONE ID no. 1052602 (SEQ ID NO:826), Public GI ID no. 72068957 (SEQ ID NO:830), Public GI ID no. 71534113 (SEQ ID NO:831), Public GI ID no. 37147896 (SEQ ID NO:832), Public GI ID no. 92918850 (SEQ ID NO:834), Public GI ID no. 40647095 (SEQ ID NO:835), Ceres ANNOT ID no. 1527711 (SEQ ID NO:837), Public GI ID no. 71041116 (SEQ ID NO:838), Public GI ID no. 12003384 (SEQ ID NO:839), Public GI ID no. 18535580 (SEQ ID NO:840), and Public GI ID no. 115353971 (SEQ ID NO:1843). Other functional homologs of SEQ ID NO:644 include Ceres CLONE ID no. 991178 (SEQ ID NO:647), Ceres CLONE ID no. 1626038 (SEQ ID NO:649), Ceres CLONE ID no. 341615 (SEQ ID NO:651), Ceres CLONE ID no. 1832518 (SEQ ID NO:653), Ceres CLONE ID no. 1832588 (SEQ ID NO:655), Ceres CLONE ID no. 1936806 (SEQ ID NO:657), Ceres CLONE ID no. 973892 (SEQ ID NO:659), Ceres CLONE ID no. 565251 (SEQ ID NO:661), Ceres CLONE ID no. 681088 (SEQ ID NO:663), Ceres CLONE ID no. 707775 (SEQ ID NO:665), Ceres CLONE ID no. 453357 (SEQ ID NO:667), Ceres CLONE ID no. 1916958 (SEQ ID NO:669), Ceres CLONE ID no. 1940632 (SEQ ID NO:671), Ceres CLONE ID no. 476784 (SEQ ID NO:673), Ceres CLONE ID no. 1869284 (SEQ ID NO:675), Public GI ID no. 125540662 (SEQ ID NO:676), Ceres CLONE ID no. 1648272 (SEQ ID NO:678), Ceres CLONE ID no. 1987804 (SEQ ID NO:680), Ceres CLONE ID no. 1675695 (SEQ ID NO:682), Ceres CLONE ID no. 1169111 (SEQ ID NO:684), Ceres CLONE ID no. 572121 (SEQ ID NO:686), Ceres CLONE ID no. 1674836 (SEQ ID NO:688), Ceres ANNOT ID no. 1486207 (SEQ ID NO:690), Ceres CLONE ID no. 2023610 (SEQ ID NO:692), Ceres ANNOT ID no. 1496976 (SEQ ID NO:694), Public GI ID no. 116310031 (SEQ ID NO:695), Ceres CLONE ID no. 1626363 (SEQ ID NO:697), Ceres ANNOT ID no. 1483747 (SEQ ID NO:699), Ceres ANNOT ID no. 1471330 (SEQ ID NO:701), Ceres CLONE ID no. 101144964 (SEQ ID NO:702), Ceres ANNOT ID no. 1439439 (SEQ ID NO:704), Ceres CLONE ID no. 1446565 (SEQ ID NO:706), Ceres CLONE ID no. 1951962 (SEQ ID NO:708), Ceres CLONE ID no. 100960656 (SEQ ID NO:709), Ceres CLONE ID no. 285154 (SEQ ID NO:711), Public GI ID no. 61968916 (SEQ ID NO:712), Public GI ID no. 118026854 (SEQ ID NO:713), Public GI ID no. 63098612 (SEQ ID NO:714), Ceres ANNOT ID no. 1522310 (SEQ ID NO:716), Ceres CLONE ID no. 1854375 (SEQ ID NO:718), Ceres CLONE ID no. 709819 (SEQ ID NO:720), Public GI ID no. 115447695 (SEQ ID NO:721), Ceres CLONE ID no. 1726356 (SEQ ID NO:723), Ceres CLONE ID no. 1762419 (SEQ ID NO:725), Public GI ID no. 63098606 (SEQ ID NO:726), Ceres CLONE ID no. 1766572 (SEQ ID NO:728), Ceres CLONE ID no. 281871 (SEQ ID NO:730), Ceres CLONE ID no. 1560970 (SEQ ID NO:732), Ceres CLONE ID no. 1760747 (SEQ ID NO:734), Ceres ANNOT ID no. 1438772 (SEQ ID NO:736), Ceres ANNOT ID no. 1447378 (SEQ ID NO:738), Ceres ANNOT ID no. 1453360 (SEQ ID NO:740), Public GI ID no. 33637698 (SEQ ID NO:741), Public GI ID no. 118026860 (SEQ ID NO:742), Public GI ID no. 60116232 (SEQ ID NO:743), Public GI ID no.115477639 (SEQ ID NO:744), Public GI ID no.126567023 (SEQ ID NO:745), Ceres CLONE ID no.988971 (SEQ ID NO:747), Ceres CLONE ID no.1464521 (SEQ ID NO:749), Public GI ID no.63098610 (SEQ ID NO:750), Public GI ID no.126566972 (SEQ ID NO:751), Ceres CLONE ID no.1556129 (SEQ ID NO:753), Ceres CLONE ID no.1761385 (SEQ ID NO:755), Ceres ANNOT ID no.1488325 (SEQ ID NO:757), Ceres ANNOT ID no.1460483 (SEQ ID NO:759), Ceres CLONE ID no.1837825 (SEQ ID NO:761), Public GI ID no.27228310 (SEQ ID NO:762), Public GI ID no.117653881 (SEQ ID NO:763), Public GI ID no.115480233 (SEQ ID NO:764), Public GI ID no.37694048 (SEQ ID NO:765), Ceres CLONE ID no.1934653 (SEQ ID NO:769), Ceres CLONE ID no.1608106 (SEQ ID NO:771), Ceres CLONE ID no.1604576 (SEQ ID NO:773), Public GI ID no.55824656 (SEQ ID NO:774), Ceres CLONE ID no.1620272 (SEQ ID NO:776), Ceres CLONE ID no.1853170 (SEQ ID NO:778), Public GI ID no.79013962 (SEQ ID NO:779), Public GI ID no.98975385 (SEQ ID NO:780), Ceres ANNOT ID no.1438775 (SEQ ID NO:782), Public GI ID no.23495460 (SEQ ID NO:783), Public GI ID no.98975377 (SEQ ID NO:784), Ceres ANNOT ID no.1438776 (SEQ ID NO:786), Ceres CLONE ID no.1853601 (SEQ ID NO:788), Ceres CLONE ID no.1609048 (SEQ ID NO:790), Ceres CLONE ID no.322305 (SEQ ID NO:792), Ceres CLONE ID no.1823713 (SEQ ID NO:794), Public GI ID no.3660548 (SEQ ID NO:795), Public GI ID no.56154991 (SEQ ID NO:798), Public GI ID no.2980802 (SEQ ID NO:799), Public GI ID no.7269398 (SEQ ID NO:800), Public GI ID no.18416557 (SEQ ID NO:801), Public GI ID no.56154992 (SEQ ID NO:802), Public GI ID no.4091984 (SEQ ID NO:803), Public GI ID no.1899058 (SEQ ID NO:805), Public GI ID no.56154990 (SEQ ID NO:806), Public GI ID no.18416562 (SEQ ID NO:807), Public GI ID no.38683266 (SEQ ID NO:810), Public GI ID no.39983638 (SEQ ID NO:812), Public GI ID no.38426954 (SEQ ID NO:814), Public GI ID no.38426948 (SEQ ID NO:815), Public GI ID no.38146944 (SEQ ID NO:816), Public GI ID no.38426952 (SEQ ID NO:817), Public GI ID no.20303011 (SEQ ID NO:818), Public GI ID no.66269982 (SEQ ID NO:819), Public GI ID no.89212816 (SEQ ID NO:820), Public GI ID no.20303015 (SEQ ID NO:821), Public GI ID no.38426950 (SEQ ID NO:822), Public GI ID no.15242244 (SEQ ID NO:823), Public GI ID no.116831599 (SEQ ID NO:824), Public GI ID no.66269671 (SEQ ID NO:827), Ceres ANNOT ID no.1468919 (SEQ ID NO:829), Public GI ID no.57903606 (SEQ ID NO:833), Public GI ID no.45826358 (SEQ ID NO:841), Ceres ANNOT ID no.6085912 (SEQ ID NO:843), Ceres ANNOT ID no.6026171 (SEQ ID NO:845), Ceres ANNOT ID no.6031706 (SEQ ID NO:847), and sequences listing identified as functional homologs of the sequences of FIG. 8, as set forth in the sequence. In some cases, a functional homolog of SEQ ID NO:644 has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:644.

Amino acid sequences of functional homologs of the polypeptide set forth in SEQ ID NO:850 are provided in FIG. 9. Such functional homologs include Ceres CLONE ID no.1833093 (SEQ ID NO:853), Ceres ANNOT ID no.1502190 (SEQ ID NO:857), Ceres CLONE ID no.565641 (SEQ ID NO:876), Public GI ID no.87240507 (SEQ ID NO:877), Ceres CLONE ID no.1325382 (SEQ ID NO:881), Ceres CLONE ID no.1558265 (SEQ ID NO:885), Ceres CLONE ID no.1823669 (SEQ ID NO:895), and Public GI ID no.115464921 (SEQ ID NO:898). Other functional homologs of SEQ ID NO:850 include Ceres CLONE ID no.100040598 (SEQ ID NO:851), Ceres CLONE ID no.1847967 (SEQ ID NO:855), Ceres ANNOT ID no.1449186 (SEQ ID NO:859), Ceres ANNOT ID no.1466723 (SEQ ID NO:861), Public GI ID no.21805688 (SEQ ID NO:862), Public GI ID no.9795609 (SEQ ID NO:863), Public GI ID no.13877535 (SEQ ID NO:864), Public GI ID no.15232547 (SEQ ID NO:865), Public GI ID no.15238851 (SEQ ID NO:866), Ceres CLONE ID no.123863 (SEQ ID NO:868), Ceres CLONE ID no.652496 (SEQ ID NO:870), Ceres CLONE ID no.1656707 (SEQ ID NO:872), Ceres CLONE ID no.1660346 (SEQ ID NO:874), Ceres CLONE ID no.678878 (SEQ ID NO:879), Ceres CLONE ID no.340102 (SEQ ID NO:883), Ceres CLONE ID no.330491 (SEQ ID NO:887), Ceres CLONE ID no.992304 (SEQ ID NO:889), Ceres CLONE ID no.1509925 (SEQ ID NO:891), Ceres CLONE ID no.1543852 (SEQ ID NO:893), Ceres CLONE ID no.1785736 (SEQ ID NO:897), Ceres ANNOT ID no.6079909 (SEQ ID NO:900), Ceres ANNOT ID no.6040353 (SEQ ID NO:902), Ceres ANNOT ID no.6100173 (SEQ ID NO:904), and sequences listing identified as functional homologs of the sequences of FIG. 9, as set forth in the sequence. In some cases, a functional homolog of SEQ ID NO:850 has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:850.

Figure 10:
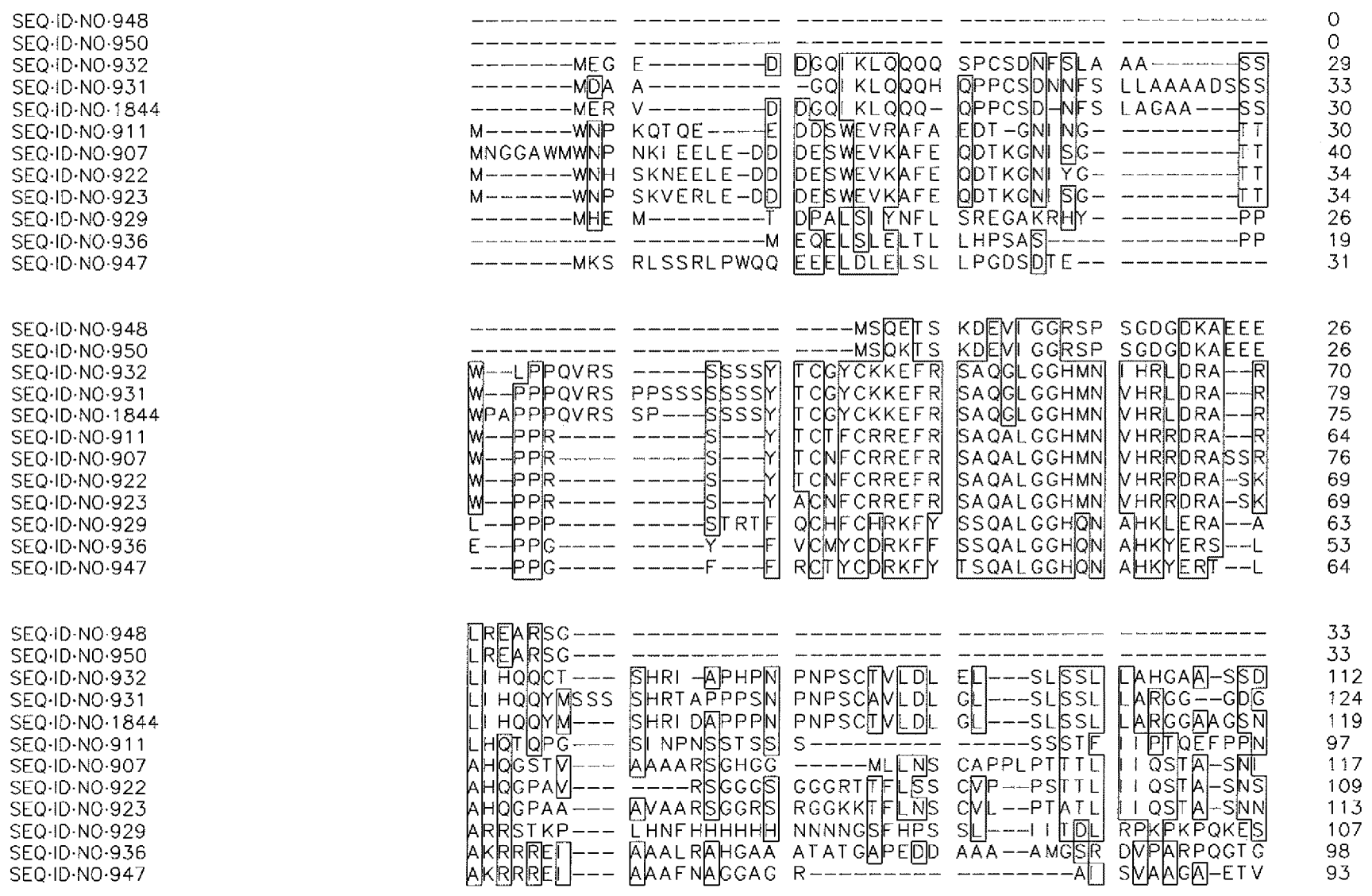

Amino acid sequences of functional homologs of the polypeptide set forth in SEQ ID NO:907 are provided in FIG. 10. Such functional homologs include Ceres CLONE ID no.1940797 (SEQ ID NO:909), Ceres ANNOT ID no.1538900 (SEQ ID NO:911), Ceres CLONE ID no.1126868 (SEQ ID NO:922), Public GI ID no.89257684 (SEQ ID NO:923), Public GI ID no.124360460 (SEQ ID NO:929), Public GI ID no.62865694 (SEQ ID NO:931), Public GI ID no.62865692 (SEQ ID NO:932), Ceres CLONE ID no.260368 (SEQ ID NO:936), Ceres CLONE ID no.1873510 (SEQ ID NO:947), Public GI ID no.125541662 (SEQ ID NO:948), Public GI ID no.48716268 (SEQ ID NO:950), and Public GI ID no. 62865696 (SEQ ID NO:1844). Other functional homologs of SEQ ID NO:907 include Ceres ANNOT ID no.1529131 (SEQ ID NO:913), Ceres ANNOT ID no.1454060 (SEQ ID NO:915), Ceres ANNOT ID no.1442787 (SEQ ID NO:917), Ceres ANNOT ID no.1452648 (SEQ ID NO:919), Public GI ID no.2245140 (SEQ ID NO:920), Public GI ID no.89274212 (SEQ ID NO:924), Ceres CLONE ID no.1104523 (SEQ ID NO:926), Ceres CLONE ID no.654265 (SEQ ID NO:928), Public GI ID no.42627704 (SEQ ID NO:930), Ceres CLONE ID no.887222 (SEQ ID NO:934), Public GI ID no.62865690 (SEQ ID NO:937), Public GI ID no.64175600 (SEQ ID NO:938), Public GI ID no.64175634 (SEQ ID NO:939), Public GI ID no.64175606 (SEQ ID NO:940), Public GI ID no.64175648 (SEQ ID NO:941), Ceres CLONE ID no.312184 (SEQ ID NO:943), Ceres CLONE ID no.380740 (SEQ ID NO:945), Public GI ID no.125531536 (SEQ ID NO:949), and sequences identified as functional homologs of the sequences of FIG. 10, as set forth in the sequence listing. In some cases, a functional homolog of SEQ ID NO:907 has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:907.

Amino acid sequences of functional homologs of the polypeptide set forth in SEQ ID NO:953 are provided in FIG. 11. Such functional homologs include Ceres CLONE ID no.1798705 (SEQ ID NO:955), Ceres ANNOT ID no.1458907 (SEQ ID NO:963), Ceres CLONE ID no.1090409 (SEQ ID NO:971), Ceres CLONE ID no.479817 (SEQ ID NO:977), Ceres CLONE ID no.1041793 (SEQ ID NO:979), Ceres CLONE ID no.684633 (SEQ ID NO:985), Ceres CLONE ID no.371815 (SEQ ID NO:991), Ceres CLONE ID no.1686460 (SEQ ID NO:993), Ceres CLONE ID no.1448595 (SEQ ID NO:995), Ceres CLONE ID no.1734477 (SEQ ID NO:999), Ceres CLONE ID no.1605693 (SEQ ID NO:1005), Ceres CLONE ID no.1757400 (SEQ ID NO:1009), and Public GI ID no.115434334 (SEQ ID NO:1015). Other functional homologs of SEQ ID NO:953 include Ceres CLONE ID no.1793754 (SEQ ID NO:957), Ceres CLONE ID no.1938045 (SEQ ID NO:959), Ceres CLONE ID no.1850004 (SEQ ID NO:961), Ceres ANNOT ID no.1489548 (SEQ ID NO:965), Public GI ID no.22329538 (SEQ ID NO:966), Public GI ID no.18404714 (SEQ ID NO:967), Ceres CLONE ID no.1110032 (SEQ ID NO:969), Ceres CLONE ID no.1095353 (SEQ ID NO:973), Ceres CLONE ID no.872121 (SEQ ID NO:975), Ceres CLONE ID no.562208 (SEQ ID NO:981), Ceres CLONE ID no.1042364 (SEQ ID NO:983), Ceres CLONE ID no.1031873 (SEQ ID NO:987), Ceres CLONE ID no.1377698 (SEQ ID NO:989), Ceres CLONE ID no.1742945 (SEQ ID NO:997), Ceres CLONE ID no.1742053 (SEQ ID NO:1001), Ceres CLONE ID no.1728365 (SEQ ID NO:1003), Ceres CLONE ID no.1609807 (SEQ ID NO:1007), Ceres CLONE ID no.1778566 (SEQ ID NO:1011), Ceres CLONE ID no.2020580 (SEQ ID NO:1013), Public GI ID no.125524285 (SEQ ID NO:1014), Public GI ID no.125568898 (SEQ ID NO:1016), Ceres ANNOT ID no.6055303 (SEQ ID NO:1018), and sequences identified as functional homologs of the sequences of FIG. 11, as set forth in the sequence listing. In some cases, a functional homolog of SEQ ID NO:953 has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:953.

Amino acid sequences of functional homologs of the polypeptide set forth in SEQ ID NO:1024 are provided in FIG. 12. Such functional homologs include Ceres ANNOT ID no.1452905 (SEQ ID NO:1029), Ceres CLONE ID no.956176 (SEQ ID NO:1039), Public GI ID no.92870366 (SEQ ID NO:1040), Ceres CLONE ID no.294166 (SEQ ID NO:1042), and Public GI ID no.125543067 (SEQ ID NO:1043). Other functional homologs of SEQ ID NO:1024 include SEQ ID NO:1025, Ceres ANNOT ID no.1442522 (SEQ ID NO:1027), Public GI ID no.8778818 (SEQ ID NO:1030), Ceres CLONE ID no.108095 (SEQ ID NO:1032), Public GI ID no.18394821 (SEQ ID NO:1033), Ceres CLONE ID no.6332 (SEQ ID NO:1035), Ceres CLONE ID no.1069047 (SEQ ID NO:1037), Public GI ID no.115480956 (SEQ ID NO:1044), and sequences identified as functional homologs of the sequences of FIG. 12, as set forth in the sequence listing. In some cases, a functional homolog of SEQ ID NO:1024 has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1024.

Amino acid sequences of functional homologs of the polypeptide set forth in SEQ ID NO:1047 are provided in FIG. 13. Such functional homologs include Ceres CLONE ID no.1837694 (SEQ ID NO:1053), Ceres ANNOT ID no.1483367 (SEQ ID NO:1057), Ceres CLONE ID no.1077781 (SEQ ID NO:1083), Ceres CLONE ID no.471026 (SEQ ID NO:1085), Public GI ID no.92888885 (SEQ ID NO:1099), Public GI ID no.45544873 (SEQ ID NO:1100), Public GI ID no.45758663 (SEQ ID NO:1101), Ceres CLONE ID no.772927 (SEQ ID NO:1105), Ceres CLONE ID no.895080 (SEQ ID NO:1111), Ceres CLONE ID no.1806128 (SEQ ID NO:1131), Public GI ID no.115458192 (SEQ ID NO:1134), and Public GI ID no.82470795 (SEQ ID NO:1139). Other functional homologs of SEQ ID NO:1047 include Ceres CLONE ID no.1837746 (SEQ ID NO:1049), Ceres CLONE ID no.1834764 (SEQ ID NO:1051), Ceres CLONE ID no.1853547 (SEQ ID NO:1055), Ceres ANNOT ID no.1474088 (SEQ ID NO:1059), Ceres ANNOT ID no.1536919 (SEQ ID NO:1061), Ceres ANNOT ID no.1467033 (SEQ ID NO:1063), Ceres ANNOT ID no.1485401 (SEQ ID NO:1065), Ceres ANNOT ID no.1486505 (SEQ ID NO:1067), Public GI ID no.17065054 (SEQ ID NO:1068), Public GI ID no.30694690 (SEQ ID NO:1069), Ceres CLONE ID no.12997 (SEQ ID NO:1071), Public GI ID no.30694694 (SEQ ID NO:1072), Public GI ID no.42572167 (SEQ ID NO:1073), Public GI ID no.110739742 (SEQ ID NO:1074), Public GI ID no.18412263 (SEQ ID NO:1075), Ceres CLONE ID no.36412 (SEQ ID NO:1077), Public GI ID no.18399792 (SEQ ID NO:1078), Ceres CLONE ID no.924 (SEQ ID NO:1080), Public GI ID no.15238000 (SEQ ID NO:1081), Ceres CLONE ID no.1626330 (SEQ ID NO:1087), Ceres CLONE ID no.1650419 (SEQ ID NO:1089), Ceres CLONE ID no.1641329 (SEQ ID NO:1091), Ceres CLONE ID no.1620406 (SEQ ID NO:1093), Ceres CLONE ID no.546832 (SEQ ID NO:1095), Ceres CLONE ID no.1243138 (SEQ ID NO:1097), Public GI ID no.92887260 (SEQ ID NO:1098), Ceres CLONE ID no.885628 (SEQ ID NO:1103), Ceres CLONE ID no.1376391 (SEQ ID NO:1107), Ceres CLONE ID no.465893 (SEQ ID NO:1109), Ceres CLONE ID no.218243 (SEQ ID NO:1113), Ceres CLONE ID no.1558456 (SEQ ID NO:1115), Ceres CLONE ID no.343008 (SEQ ID NO:1117), Ceres CLONE ID no.218463 (SEQ ID NO:1119), Ceres CLONE ID no.1565409 (SEQ ID NO:1121), Ceres CLONE ID no.1060968 (SEQ ID NO:1123), Ceres CLONE ID no.236111 (SEQ ID NO:1125), Ceres CLONE ID no.285598 (SEQ ID NO:1127), Ceres CLONE ID no.225881 (SEQ ID NO:1129), Ceres CLONE ID no.1811383 (SEQ ID NO:1133), Public GI ID no.49388268 (SEQ ID NO:1135), Public GI ID no.125590268 (SEQ ID NO:1136), Public GI ID no.115444009 (SEQ ID NO:1137), Public GI ID no.115447993 (SEQ ID NO:1138), Ceres ANNOT ID no.6033842 (SEQ ID NO:1141), Ceres ANNOT ID no.6029952 (SEQ ID NO:1143), Ceres ANNOT ID no.6035837 (SEQ ID NO:1145), Ceres ANNOT ID no.6035830 (SEQ ID NO:1147), Ceres ANNOT ID no.6029981 (SEQ ID NO:1149), and sequences identified as functional homologs of the sequences of FIG. 13, as set forth in the sequence listing. In some cases, a functional homolog of SEQ ID NO:1047 has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1047.

Figure 14:
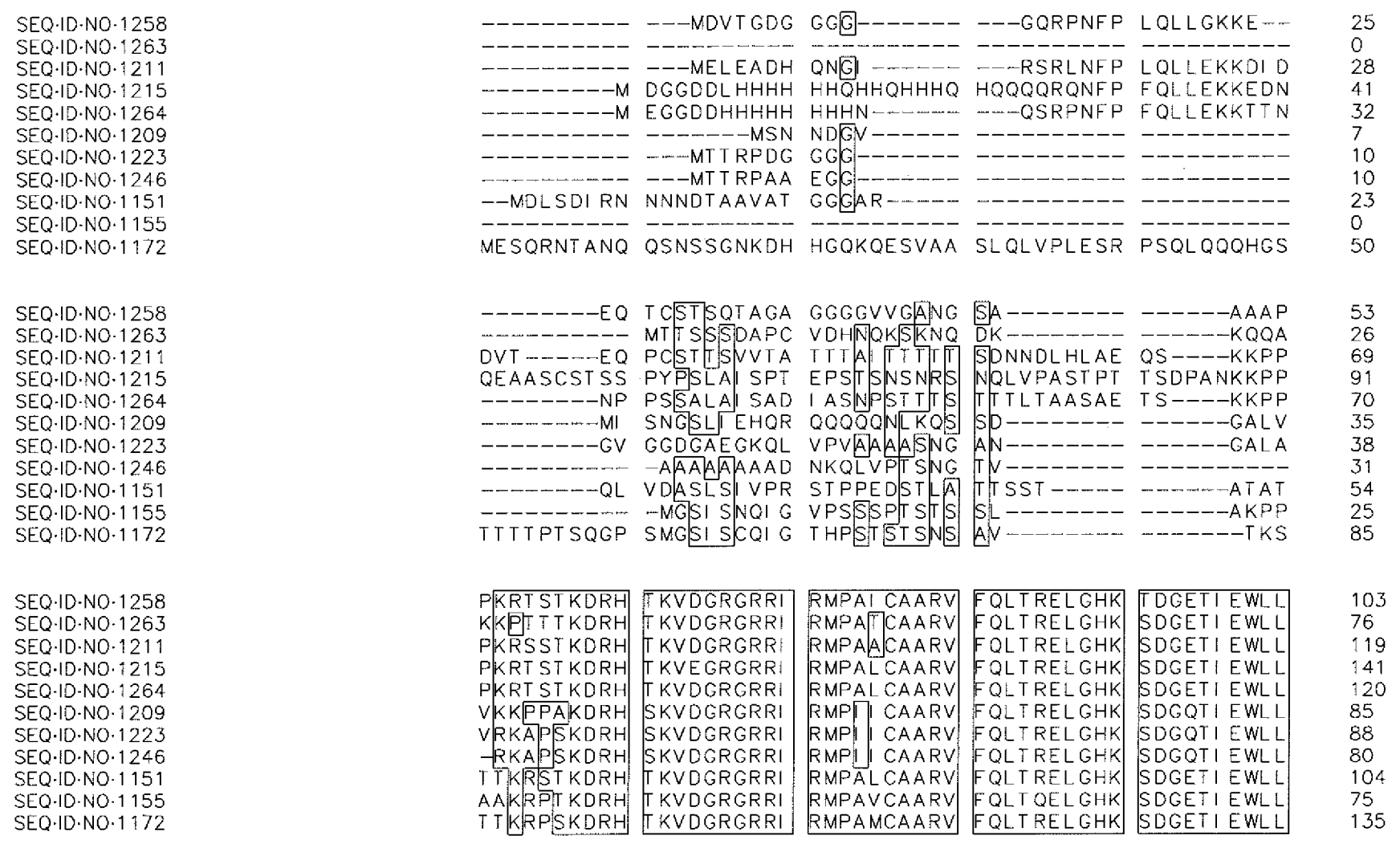

Amino acid sequences of functional homologs of the polypeptide set forth in SEQ ID NO:1151 are provided in FIG. 14. Such functional homologs include Ceres CLONE ID no.1851526 (SEQ ID NO:1155), Ceres ANNOT ID no.1486769 (SEQ ID NO:1172), Public GI ID no.83032232 (SEQ ID NO:1209), Ceres CLONE ID no.1620420 (SEQ ID NO:1211), Public GI ID no.92892428 (SEQ ID NO:1215), Ceres CLONE ID no.884742 (SEQ ID NO:1223), Ceres CLONE ID no.1821559 (SEQ ID NO:1246), Public GI ID no.51535021 (SEQ ID NO:1258), Public GI ID no.113205304 (SEQ ID NO:1263), and Public GI ID no.37719051 (SEQ ID NO:1264). Other functional homologs of SEQ ID NO:1151 include Ceres CLONE ID no.1918070 (SEQ ID NO:1153), Ceres CLONE ID no.1948426 (SEQ ID NO:1157), Ceres CLONE ID no.1937875 (SEQ ID NO:1159), Ceres CLONE ID no.100056542 (SEQ ID NO:1160), Public GI ID no.5731257 (SEQ ID NO:1161), Ceres CLONE ID no.100058043 (SEQ ID NO:1162), Ceres CLONE ID no.1838288 (SEQ ID NO:1164), Ceres CLONE ID no.1793597 (SEQ ID NO:1166), Ceres ANNOT ID no.1543031 (SEQ ID NO:1168), Ceres ANNOT ID no.1489643 (SEQ ID NO:1170), Ceres ANNOT ID no.1479721 (SEQ ID NO:1174), Ceres ANNOT ID no.1449170 (SEQ ID NO:1176), Ceres ANNOT ID no.1493696 (SEQ ID NO:1178), Ceres ANNOT ID no.1543534 (SEQ ID NO:1180), Ceres ANNOT ID no.1440815 (SEQ ID NO:1182), Ceres ANNOT ID no.1490137 (SEQ ID NO:1184), Ceres ANNOT ID no.1451054 (SEQ ID NO:1186), Ceres ANNOT ID no.1456669 (SEQ ID NO:1188), Ceres ANNOT ID no.1509865 (SEQ ID NO:1190), Ceres ANNOT ID no.1447910 (SEQ ID NO:1192), Ceres ANNOT ID no.1471068 (SEQ ID NO:1194), Ceres ANNOT ID no.1504118 (SEQ ID NO:1196), Ceres CLONE ID no.1343621 (SEQ ID NO:1198), Public GI ID no.15218305 (SEQ ID NO:1199), Public GI ID no.15219640 (SEQ ID NO:1200), Public GI ID no.18409345 (SEQ ID NO:1201), Public GI ID no.6522545 (SEQ ID NO:1202), Public GI ID no.15237274 (SEQ ID NO:1203), Public GI ID no.26452377 (SEQ ID NO:1204), Ceres CLONE ID no.33629 (SEQ ID NO:1206), Ceres CLONE ID no.1064407 (SEQ ID NO:1208), Ceres CLONE ID no.1656310 (SEQ ID NO:1213), Public GI ID no.92885257 (SEQ ID NO:1214), Public GI ID no.92868571 (SEQ ID NO:1216), Public GI ID no.53689778 (SEQ ID NO:1217), Ceres CLONE ID no.835598 (SEQ ID NO:1219), Ceres CLONE ID no.575649 (SEQ ID NO:1221), Ceres CLONE ID no.376567 (SEQ ID NO:1225), Ceres CLONE ID no.1284191 (SEQ ID NO:1227), Ceres CLONE ID no.367175 (SEQ ID NO:1229), Ceres CLONE ID no.100748296 (SEQ ID NO:1230), Ceres CLONE ID no.1597176 (SEQ ID NO:1232), Ceres CLONE ID no.375636 (SEQ ID NO:1234), Ceres CLONE ID no.288123 (SEQ ID NO:1236), Ceres CLONE ID no.303582 (SEQ ID NO:1238), Ceres CLONE ID no.1604759 (SEQ ID NO:1240), Ceres CLONE ID no.1955192 (SEQ ID NO:1242), Ceres CLONE ID no.2008687 (SEQ ID NO:1244), Ceres CLONE ID no.1995843 (SEQ ID NO:1248), Ceres CLONE ID no.2008591 (SEQ ID NO:1250), Ceres CLONE ID no.2046826 (SEQ ID NO:1252), Ceres CLONE ID no.1985573 (SEQ ID NO:1254), Public GI ID no.125541129 (SEQ ID NO:1255), Public GI ID no.125528922 (SEQ ID NO:1256), Public GI ID no.115487590 (SEQ ID NO:1257), Public GI ID no.115448671 (SEQ ID NO:1259), Public GI ID no.125596564 (SEQ ID NO:1260), Public GI ID no.125573161 (SEQ ID NO:1261), Public GI ID no.48716463 (SEQ ID NO:1262), Ceres ANNOT ID no.6054246 (SEQ ID NO:1266), Ceres ANNOT ID no.6086570 (SEQ ID NO:1268), Ceres ANNOT ID no.6024957 (SEQ ID NO:1270), Ceres ANNOT ID no.6016867 (SEQ ID NO:1272), Ceres ANNOT ID no.6091369 (SEQ ID NO:1274), and sequences identified as functional homologs of the sequences of FIG. 14, as set forth in the sequence listing. In some cases, a functional homolog of SEQ ID NO:1151 has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1151.

Figure 15:
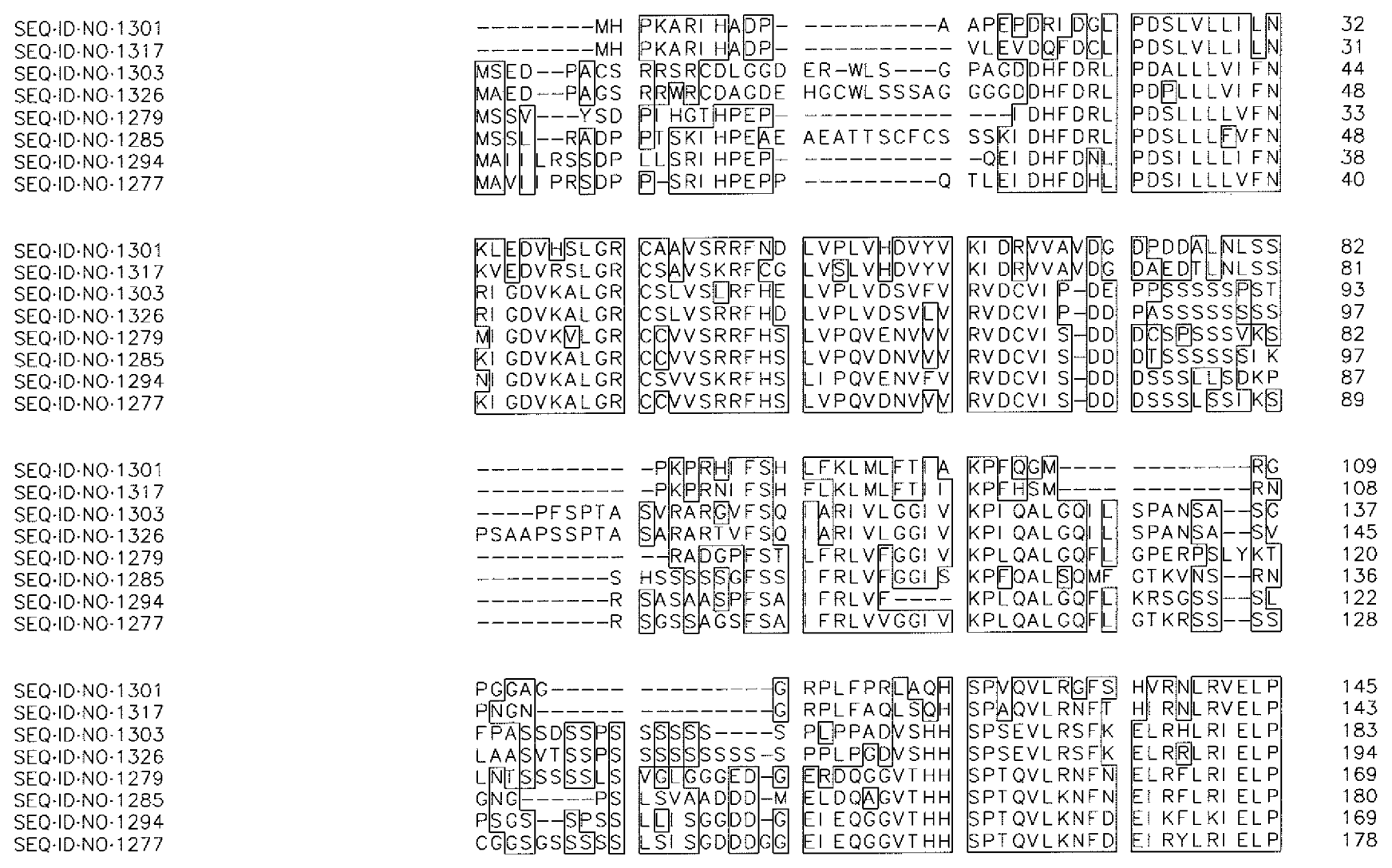

Amino acid sequences of functional homologs of the polypeptide set forth in SEQ ID NO:1277 are provided in FIG. 15. Such functional homologs include Ceres CLONE ID no.1926352 (SEQ ID NO:1279), Ceres ANNOT ID no.1448905 (SEQ ID NO:1285), Public GI ID no.15236865 (SEQ ID NO:1294), Ceres CLONE ID no.934771 (SEQ ID NO:1301), Ceres CLONE ID no.338386 (SEQ ID NO:1303), Ceres CLONE ID no.1780691 (SEQ ID NO:1317), and Public GI ID no.115464819 (SEQ ID NO:1326). Other functional homologs of SEQ ID NO:1277 include Ceres CLONE ID no.1848576 (SEQ ID NO:1281), Ceres CLONE ID no.1981528 (SEQ ID NO:1283), Ceres ANNOT ID no.1465978 (SEQ ID NO:1287), Ceres ANNOT ID no.1504997 (SEQ ID NO:1289), Ceres ANNOT ID no.1451909 (SEQ ID NO:1291), Ceres ANNOT ID no.1461635 (SEQ ID NO:1293), Public GI ID no.18397400 (SEQ ID NO:1295), Ceres CLONE ID no.16226 (SEQ ID NO:1297), Public GI ID no.18411823 (SEQ ID NO:1298), Public GI ID no.15219845 (SEQ ID NO:1299), Ceres CLONE ID no.1276710 (SEQ ID NO:1305), Ceres CLONE ID no.1479310 (SEQ ID NO:1307), Ceres CLONE ID no.376230 (SEQ ID NO:1309), Ceres CLONE ID no.1290713 (SEQ ID NO:1311), Ceres CLONE ID no.321681 (SEQ ID NO:1313), Ceres CLONE ID no.1869072 (SEQ ID NO:1315), Ceres CLONE ID no.1818502 (SEQ ID NO:1319), Ceres CLONE ID no.1750477 (SEQ ID NO:1321), Public GI ID no.125552947 (SEQ ID NO:1322), Public GI ID no.125527862 (SEQ ID NO:1323), Public GI ID no.125543660 (SEQ ID NO:1324), Public GI ID no.125528123 (SEQ ID NO:1325), Public GI ID no.115440195 (SEQ ID NO:1327), Public GI ID no.115452717 (SEQ ID NO:1328), Public GI ID no.115440629 (SEQ ID NO:1329), Public GI ID no.115464599 (SEQ ID NO:1330), Public GI ID no.20161462 (SEQ ID NO:1331), Public GI ID no.125586076 (SEQ ID NO:1332), Ceres CLONE ID no.1823216 (SEQ ID NO:1334), Ceres ANNOT ID no.6040230 (SEQ ID NO:1336), Ceres ANNOT ID no.6015489 (SEQ ID NO:1338), Ceres ANNOT ID no.6042890 (SEQ ID NO:1340), Ceres ANNOT ID no.6040033 (SEQ ID NO:1342), Ceres ANNOT ID no.6018414 (SEQ ID NO:1344), and sequences identified as functional homologs of the sequences of FIG. 15, as set forth in the sequence listing. In some cases, a functional homolog of SEQ ID NO:1277 has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1277.

Figure 16:
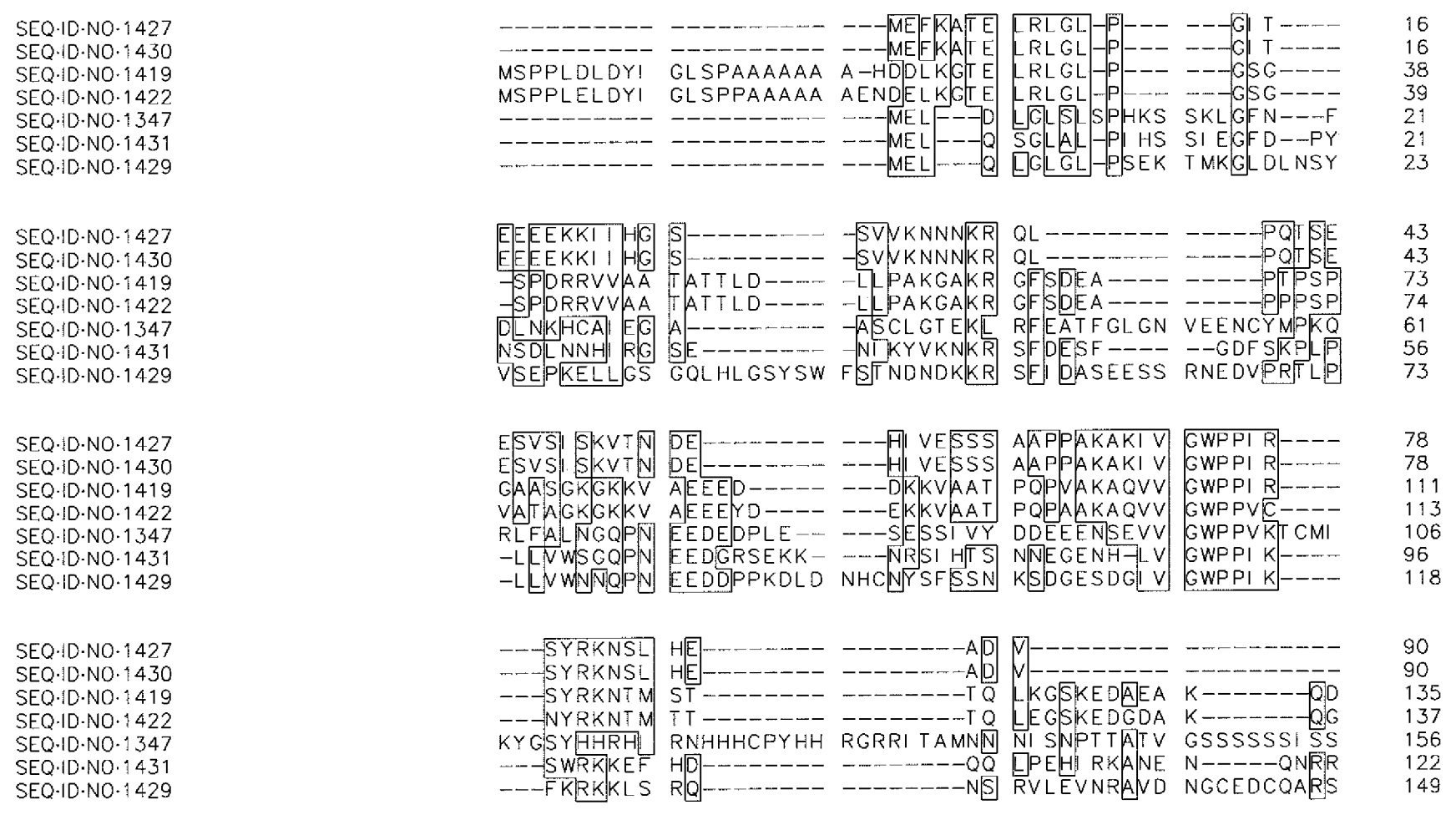

Amino acid sequences of functional homologs of the polypeptide set forth in SEQ ID NO:1347 are provided in FIG. 16. Such functional homologs include Ceres CLONE ID no.285028 (SEQ ID NO:1419), Ceres CLONE ID no.100969565 (SEQ ID NO:1422), Public GI ID no.1352057 (SEQ ID NO:1427), Ceres ANNOT ID no.1453784 (SEQ ID NO:1429), Public GI ID no.452777 (SEQ ID NO:1430), and Public GI ID no.92873297 (SEQ ID NO:1431). Other functional homologs of SEQ ID NO:1347 include Ceres ANNOT ID no.1452612 (SEQ ID NO:1349), Ceres CLONE ID no.520455 (SEQ ID NO:1351), Public GI ID no.75271810 (SEQ ID NO:1352), Public GI ID no.115489446 (SEQ ID NO:1353), Ceres CLONE ID no.499878 (SEQ ID NO:1355), Ceres ANNOT ID no.1491840 (SEQ ID NO:1357), Public GI ID no.125587204 (SEQ ID NO:1358), Ceres CLONE ID no.320997 (SEQ ID NO:1360), Ceres ANNOT ID no.1455585 (SEQ ID NO:1362), Ceres ANNOT ID no.1499460 (SEQ ID NO:1364), Ceres CLONE ID no.334484 (SEQ ID NO:1366), Ceres CLONE ID no.100819481 (SEQ ID NO:1367), Public GI ID no.115462401 (SEQ ID NO:1368), Ceres CLONE ID no.1448136 (SEQ ID NO:1370), Ceres CLONE ID no.277751 (SEQ ID NO:1372), Ceres ANNOT ID no.1491839 (SEQ ID NO:1374), Ceres CLONE ID no.100913241 (SEQ ID NO:1375), Ceres CLONE ID no.1053224 (SEQ ID NO:1377), Ceres CLONE ID no.425766 (SEQ ID NO:1379), Ceres CLONE ID no.485480 (SEQ ID NO:1381), Ceres CLONE ID no.474845 (SEQ ID NO:1383), Ceres CLONE ID no.354561 (SEQ ID NO:1385), Ceres CLONE ID no.540858 (SEQ ID NO:1387), Ceres CLONE ID no.2032994 (SEQ ID NO:1389), Ceres CLONE ID no.2015315 (SEQ ID NO:1391), Ceres CLONE ID no.2016149 (SEQ ID NO:1393), Ceres CLONE ID no.1922843 (SEQ ID NO:1395), Ceres CLONE ID no.2000263 (SEQ ID NO:1397), Ceres CLONE ID no.1943510 (SEQ ID NO:1399), Ceres CLONE ID no.1835498 (SEQ ID NO:1401), Ceres CLONE ID no.101116694 (SEQ ID NO:1402), Ceres CLONE ID no.1930596 (SEQ ID NO:1404), Ceres CLONE ID no.846036 (SEQ ID NO:1406), Ceres CLONE ID no.941614 (SEQ ID NO:1408), Ceres CLONE ID no.238788 (SEQ ID NO:1410), Public GI ID no.125554220 (SEQ ID NO:1411), Public GI ID no.125559895 (SEQ ID NO:1412), Public GI ID no.75252070 (SEQ ID NO:1413), Public GI ID no.115466632 (SEQ ID NO:1414), Public GI ID no.125541525 (SEQ ID NO:1415), Ceres CLONE ID no.1805110 (SEQ ID NO:1417), Ceres CLONE ID no.1725309 (SEQ ID NO:1421), Ceres CLONE ID no.100861679 (SEQ ID NO:1423), Public GI ID no.75226278 (SEQ ID NO:1424), Public GI ID no.125525030 (SEQ ID NO:1425), Public GI ID no.115435474 (SEQ ID NO:1426), Ceres CLONE ID no.1728516 (SEQ ID NO:1433), Public GI ID no.115467910 (SEQ ID NO:1434), Public GI ID no.15239950 (SEQ ID NO:1435), Public GI ID no.4887012 (SEQ ID NO:1436), Ceres ANNOT ID no.1478544 (SEQ ID NO:1438), Public GI ID no.90811713 (SEQ ID NO:1439), Public GI ID no.25989504 (SEQ ID NO:1440), Ceres CLONE ID no.1113354 (SEQ ID NO:1442), Ceres CLONE ID no.1113630 (SEQ ID NO:1444), Ceres ANNOT ID no.6072030 (SEQ ID NO:1446), Ceres ANNOT ID no.6025654 (SEQ ID NO:1448), Ceres ANNOT ID no.6091150 (SEQ ID NO:1450), Ceres ANNOT ID no.6100390 (SEQ ID NO:1452), and sequences identified as functional homologs of the sequences of FIG. 16, as set forth in the sequence listing. In some cases, a functional homolog of SEQ ID NO:1347 has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1347.

Figure 17:
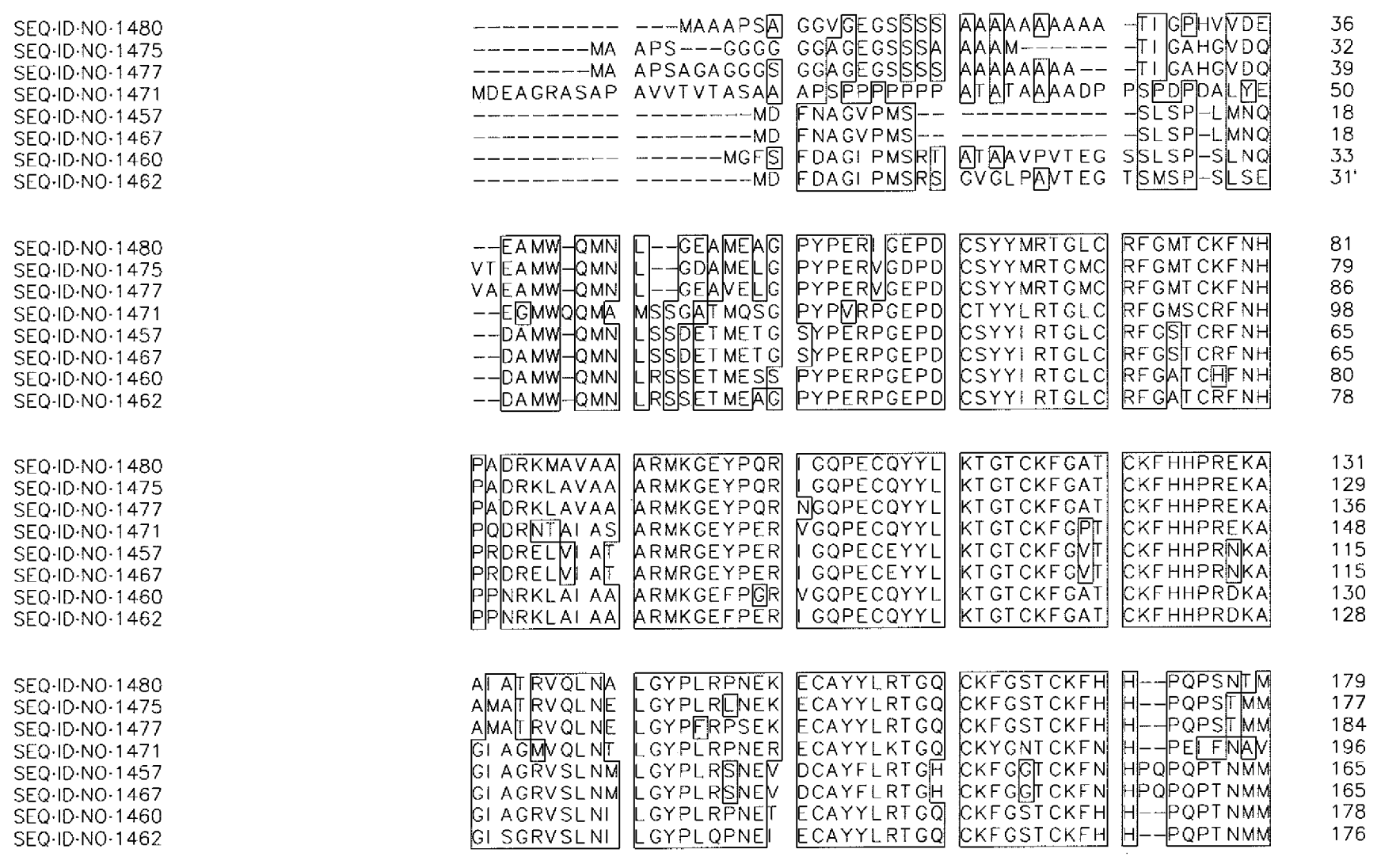

Amino acid sequences of functional homologs of the polypeptide set forth in SEQ ID NO:1457 are provided in FIG. 17. Such functional homologs include Ceres CLONE ID no.1924904 (SEQ ID NO:1460), Ceres ANNOT ID no.1543346 (SEQ ID NO:1462), Public GI ID no.18396338 (SEQ ID NO:1467), Ceres CLONE ID no.833872 (SEQ ID NO:1471), Ceres CLONE ID no.1579587 (SEQ ID NO:1475), Ceres CLONE ID no.1786411 (SEQ ID NO:1477), and Public GI ID no.108864370 (SEQ ID NO:1480). Other functional homologs of SEQ ID NO:1457 include SEQ ID NO:1458, Ceres ANNOT ID no.1532932 (SEQ ID NO:1464), Ceres ANNOT ID no.1489955 (SEQ ID NO:1466), Public GI ID no.4928917 (SEQ ID NO:1468), Public GI ID no.6728979 (SEQ ID NO:1469), Ceres CLONE ID no.285780 (SEQ ID NO:1473), Public GI ID no.125528863 (SEQ ID NO:1478), Public GI ID no.125536365 (SEQ ID NO:1479), Public GI ID no.108864369 (SEQ ID NO:1481), Public GI ID no.115488274 (SEQ ID NO:1482), Public GI ID no.125577099 (SEQ ID NO:1483), Public GI ID no.125573110 (SEQ ID NO:1484), Public GI ID no.124359159 (SEQ ID NO:1485), Public GI ID no.62901479 (SEQ ID NO:1486), Ceres ANNOT ID no.6016783 (SEQ ID NO:1488), Ceres ANNOT ID no.6020759 (SEQ ID NO:1490), Ceres ANNOT ID no.6028676 (SEQ ID NO:1492), Ceres ANNOT ID no.6028677 (SEQ ID NO:1494), and sequences identified as functional homologs of the sequences of FIG. 17, as set forth in the sequence listing. In some cases, a functional homolog of SEQ ID NO:1457 has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1457.

Amino acid sequences of functional homologs of the polypeptide set forth in SEQ ID NO:1497 are provided in FIG. 18. Such functional homologs include Ceres ANNOT ID no.1443463 (SEQ ID NO:1499), Public GI ID no.13605525 (SEQ ID NO:1502), Public GI ID no.94965681 (SEQ ID NO:1506), and Public GI ID no.28201254 (SEQ ID NO:1512). Other functional homologs of SEQ ID NO:1497 include Ceres ANNOT ID no.1504954 (SEQ ID NO:1501), Public GI ID no.2499553 (SEQ ID NO:1503), Public GI ID no.738308 (SEQ ID NO:1504), Public GI ID no.4325368 (SEQ ID NO:1505), Ceres CLONE ID no.919923 (SEQ ID NO:1508), Ceres CLONE ID no.1659764 (SEQ ID NO:1510), Public GI ID no.125539984 (SEQ ID NO:1511), Public GI ID no.21740729 (SEQ ID NO:1513), Public GI ID no.115458700 (SEQ ID NO:1514), Public GI ID no.125590574 (SEQ ID NO:1515), Public GI ID no.16444957 (SEQ ID NO:1516), Ceres CLONE ID no.1784494 (SEQ ID NO:1518), Public GI ID no.77963980 (SEQ ID NO:1519), Public GI ID no.124361190 (SEQ ID NO:1520), Public GI ID no.37725007 (SEQ ID NO:1521), Public GI ID no.45935258 (SEQ ID NO:1522), Public GI ID no.15559008 (SEQ ID NO:1523), Public GI ID no.38037416 (SEQ ID NO:1524), Public GI ID no.77963974 (SEQ ID NO:1525), Ceres ANNOT ID no.6112581 (SEQ ID NO:1527), Public GI ID no.56553448 (SEQ ID NO:1528), Public GI ID no.23506659 (SEQ ID NO:1529), Ceres ANNOT ID no.6118060 (SEQ ID NO:1531), Public GI ID no.46446306 (SEQ ID NO:1532), Public GI ID no.114321405 (SEQ ID NO:1533), Public GI ID no.83858274 (SEQ ID NO:1534), Public GI ID no.154250969 (SEQ ID NO:1535), Public GI ID no.83594235 (SEQ ID NO:1536), and sequences identified as functional homologs of the sequences of FIG. 18, as set forth in the sequence listing. In some cases, a functional homolog of SEQ ID NO:1497 has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1497.

Figure 19:
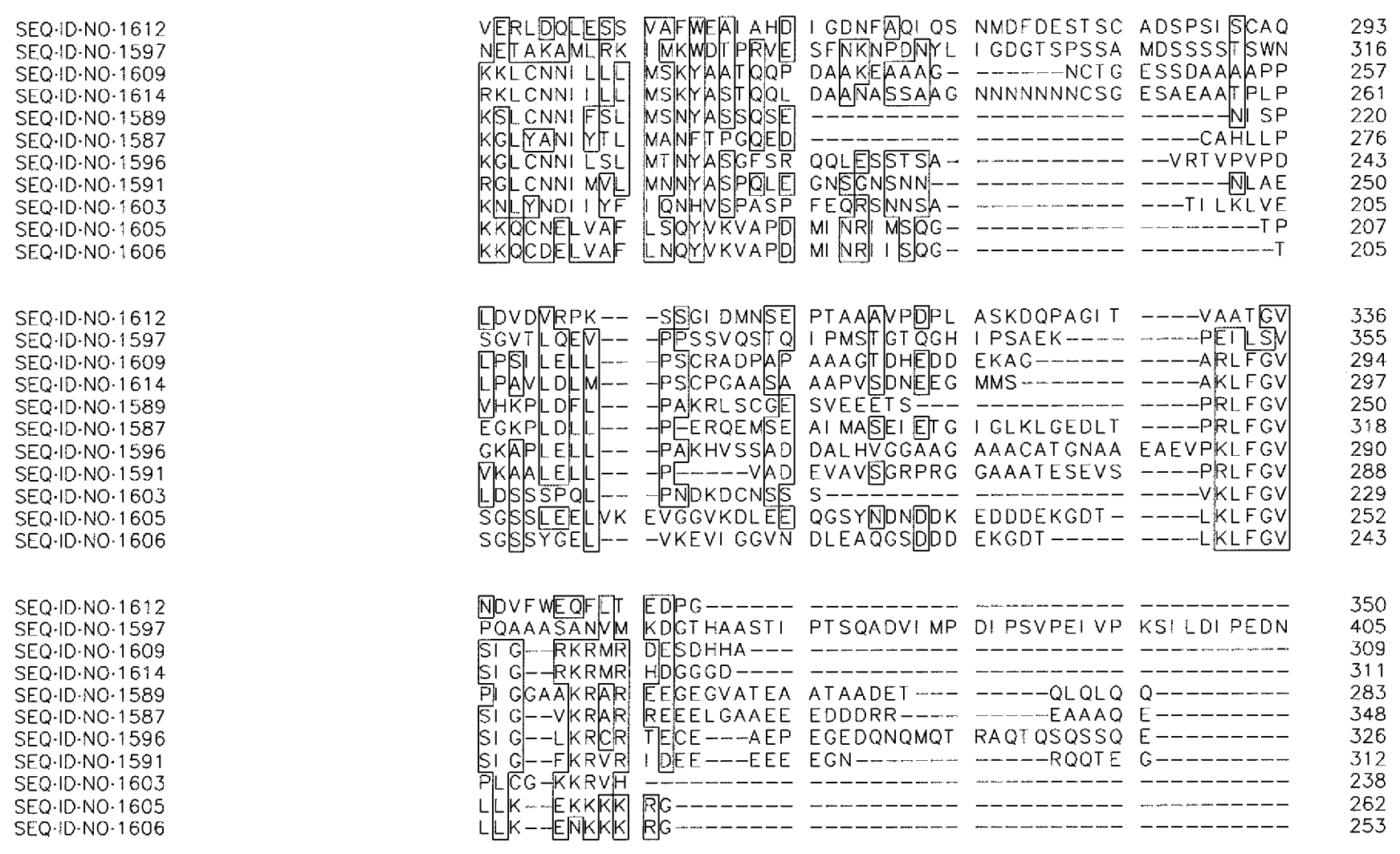

Amino acid sequences of functional homologs of the polypeptide set forth in SEQ ID NO:1587 are provided in FIG. 19. Such functional homologs include Ceres CLONE ID no.1839577 (SEQ ID NO:1589), Ceres ANNOT ID no.1491567 (SEQ ID NO:1591), Ceres CLONE ID no.574505 (SEQ ID NO:1596), Public GI ID no.56117815 (SEQ ID NO:1597), Public GI ID no.92874021 (SEQ ID NO:1603), Public GI ID no.123684 (SEQ ID NO:1605), Public GI ID no.5821136 (SEQ ID NO:1606), Ceres CLONE ID no.283366 (SEQ ID NO:1609), Public GI ID no.16118447 (SEQ ID NO:1612), and Public GI ID no.125562434 (SEQ ID NO:1614). Other functional homologs of SEQ ID NO:1587 include Ceres ANNOT ID no.1438739 (SEQ ID NO:1593), Public GI ID no.89274218 (SEQ ID NO:1594), Public GI ID no.115521211 (SEQ ID NO:1598), Public GI ID no.115521213 (SEQ ID NO:1599), Public GI ID no.115521217 (SEQ ID NO:1600), Public GI ID no.115521209 (SEQ ID NO:1601), Public GI ID no.115521215 (SEQ ID NO:1602), Public GI ID no.11386827 (SEQ ID NO:1604), Public GI ID no.25052685 (SEQ ID NO:1607), Ceres CLONE ID no.1440437 (SEQ ID NO:1611), Public GI ID no.125564440 (SEQ ID NO:1613), Public GI ID no.116309817 (SEQ ID NO:1615), Public GI ID no.125549382 (SEQ ID NO:1616), Public GI ID no.52077317 (SEQ ID NO:1617), Public GI ID no.115477655 (SEQ ID NO:1618), Public GI ID no.42408097 (SEQ ID NO:1619), Public GI ID no.115459982 (SEQ ID NO:1620), Public GI ID no.33591096 (SEQ ID NO:1621), Ceres CLONE ID no.484753 (SEQ ID NO:1623), Ceres ANNOT ID no.6035291 (SEQ ID NO:1625), and sequences identified as functional homologs of the sequences of FIG. 19, as set forth in the sequence listing. In some cases, a functional homolog of SEQ ID NO:1587 has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1587.

Figure 20:
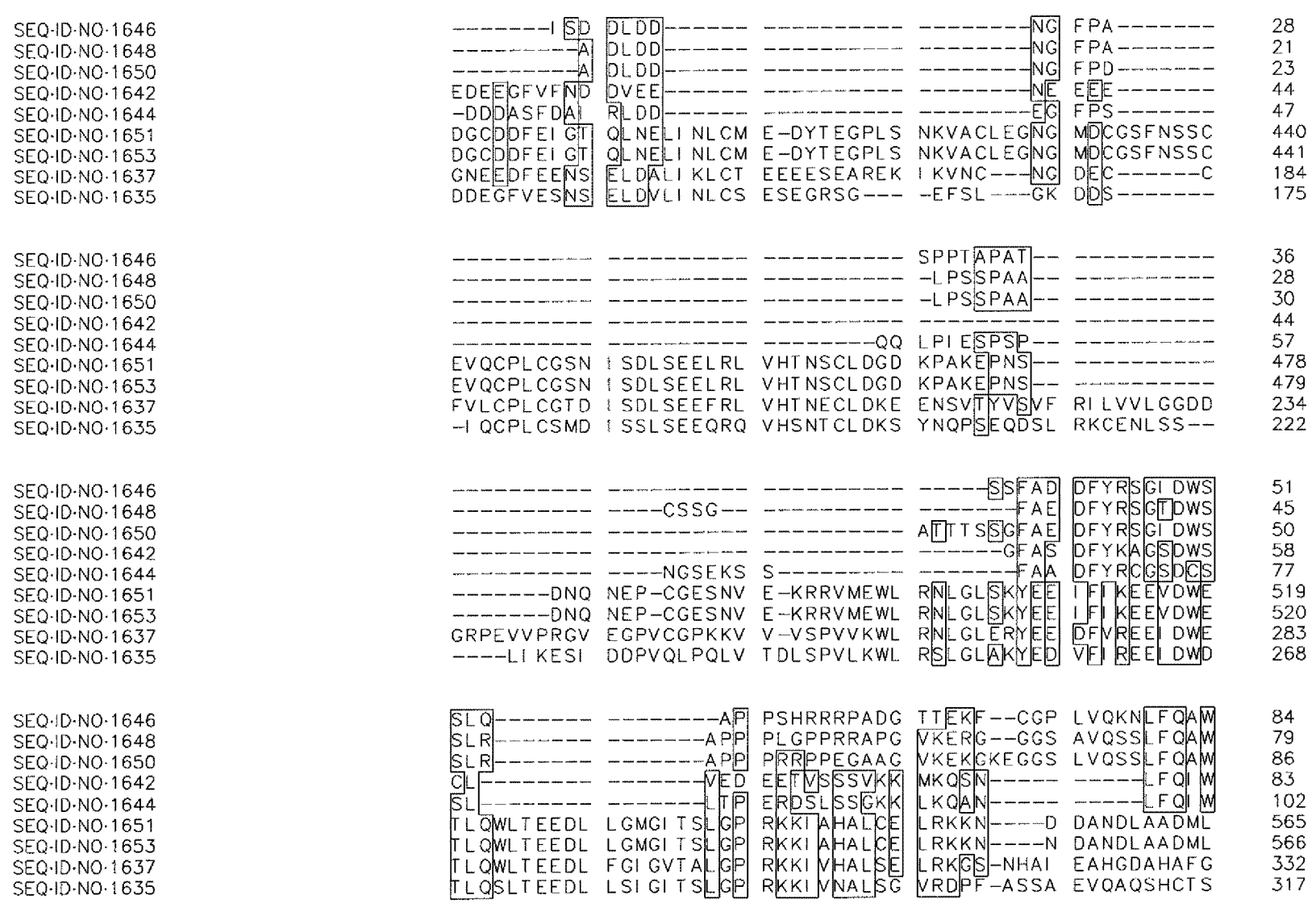
Figure 20:
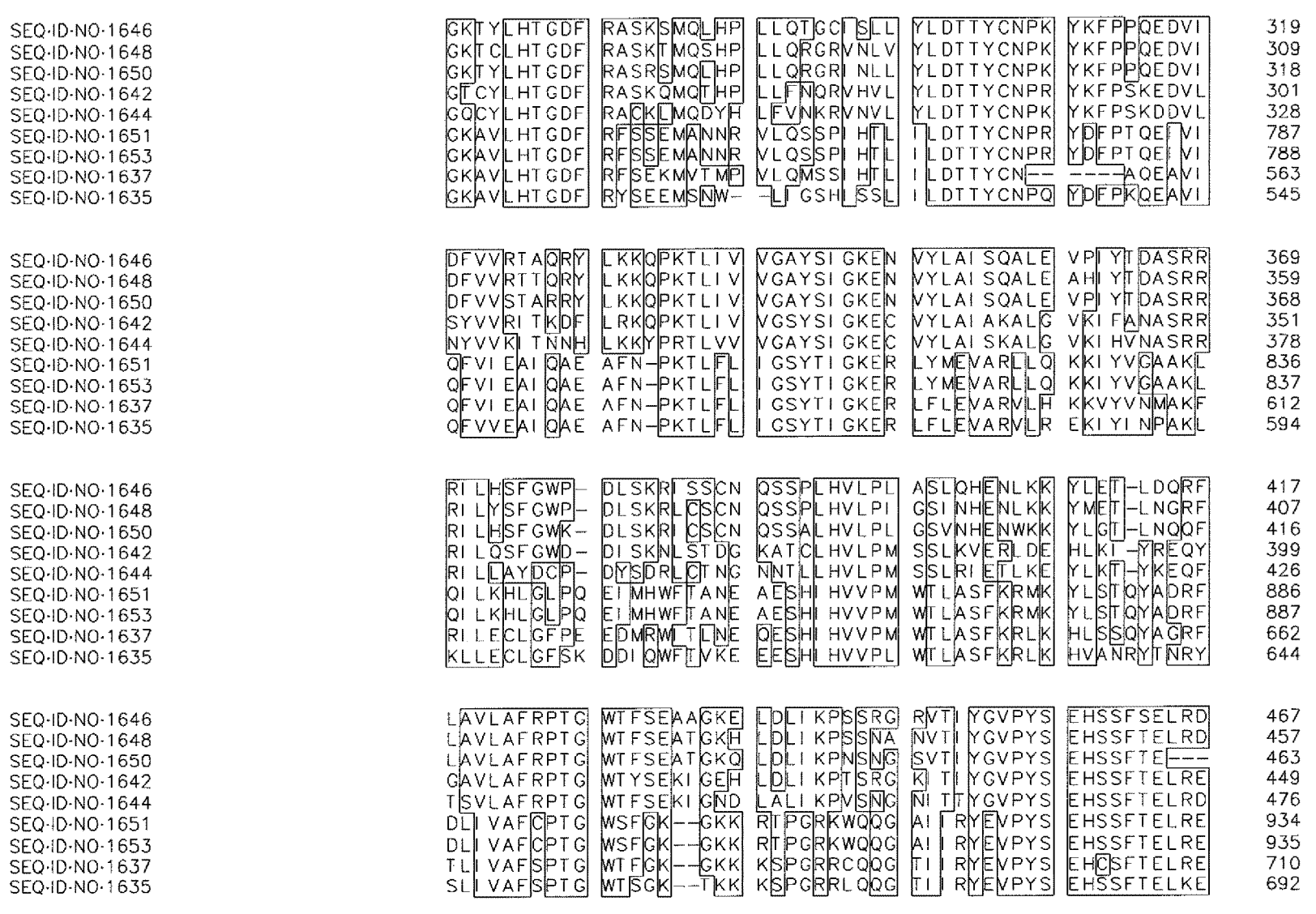
Figure 20:
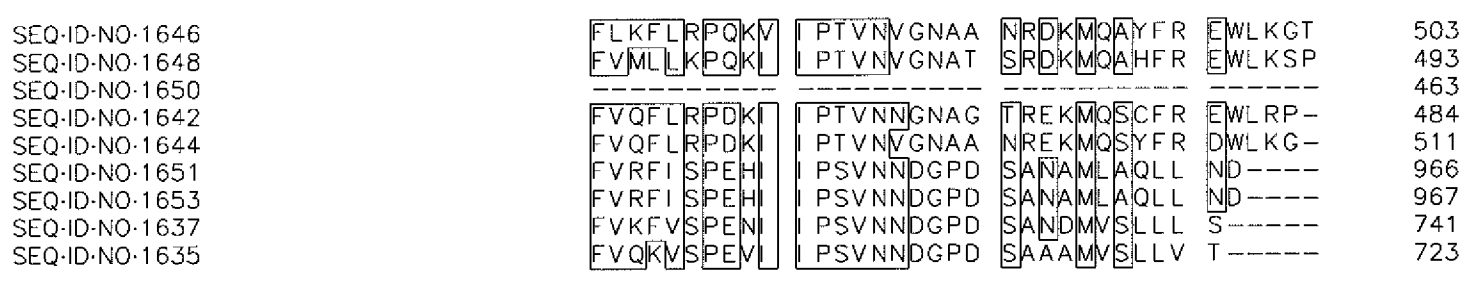

Amino acid sequences of functional homologs of the polypeptide set forth in SEQ ID NO:1635 are provided in FIG. 20. Such functional homologs include Ceres ANNOT ID no.1508307 (SEQ ID NO:1637), Public GI ID no.1495267 (SEQ ID NO:1642), Public GI ID no.87241310 (SEQ ID NO:1644), Ceres CLONE ID no.938390 (SEQ ID NO:1646), Ceres CLONE ID no.272338 (SEQ ID NO:1648), Ceres CLONE ID no.1993510 (SEQ ID NO:1650), Public GI ID no.125563862 (SEQ ID NO:1651), and Public GI ID no.125605833 (SEQ ID NO:1653). Other functional homologs of SEQ ID NO:1635 include Public GI ID no.6899919 (SEQ ID NO:1632), Ceres ANNOT ID no.1455110 (SEQ ID NO:1639), Ceres ANNOT ID no.1525218 (SEQ ID NO:1641), Public GI ID no.15231597 (SEQ ID NO:1643), Public GI ID no.125548147 (SEQ ID NO:1652), Public GI ID no.51091343 (SEQ ID NO:1654), Public GI ID no.115479355 (SEQ ID NO:1655), Ceres ANNOT ID no.6042086 (SEQ ID NO:1657), Ceres ANNOT ID no.6029903 (SEQ ID NO:1659), and sequences identified as functional homologs of the sequences of FIG. 20, as set forth in the sequence listing. In some cases, a functional homolog of SEQ ID NO:1635 has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1635.

Amino acid sequences of functional homologs of the polypeptide set forth in SEQ ID NO:1540 are provided in FIG. 21. Such functional homologs include Ceres CLONE ID no.1943265 (SEQ ID NO:1543), Ceres ANNOT ID no.1454522 (SEQ ID NO:1547), Public GI ID no.31323447 (SEQ ID NO:1556), Ceres CLONE ID no.1583941 (SEQ ID NO:1561), Ceres CLONE ID no.1792942 (SEQ ID NO:1563), Public GI ID no.77548772 (SEQ ID NO:1565), and Public GI ID no.84453182 (SEQ ID NO:1567). Other functional homologs of SEQ ID NO:1540 include Public GI ID no.31746344 (SEQ ID NO:1541), Ceres CLONE ID no.1926640 (SEQ ID NO:1545), Ceres ANNOT ID no.1475125 (SEQ ID NO:1549), Ceres ANNOT ID no.1439653 (SEQ ID NO:1551), Ceres ANNOT ID no.1461995 (SEQ ID NO:1553), Public GI ID no.13877517 (SEQ ID NO:1554), Public GI ID no.7239157 (SEQ ID NO:1555), Public GI ID no.22652125 (SEQ ID NO:1557), Public GI ID no.22652115 (SEQ ID NO:1558), Public GI ID no.22652117 (SEQ ID NO:1559), Public GI ID no.125535858 (SEQ ID NO:1564), Public GI ID no.125578581 (SEQ ID NO:1566), Public GI ID no.13752407 (SEQ ID NO:1568), Ceres ANNOT ID no.6098817 (SEQ ID NO:1570), Ceres ANNOT ID no.6039430 (SEQ ID NO:1572), Ceres ANNOT ID no.6068141 (SEQ ID NO:1574), Ceres ANNOT ID no.6033916 (SEQ ID NO:1576), Ceres ANNOT ID no.6034399 (SEQ ID NO:1578), Ceres ANNOT ID no.6068617 (SEQ ID NO:1580), Ceres ANNOT ID no.6026318 (SEQ ID NO:1582), Ceres ANNOT ID no.6107650 (SEQ ID NO:1584), and sequences identified as functional homologs of the sequences of FIG. 21, as set forth in the sequence listing. In some cases, a functional homolog of SEQ ID NO:1540 has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1540.

Figure 22:
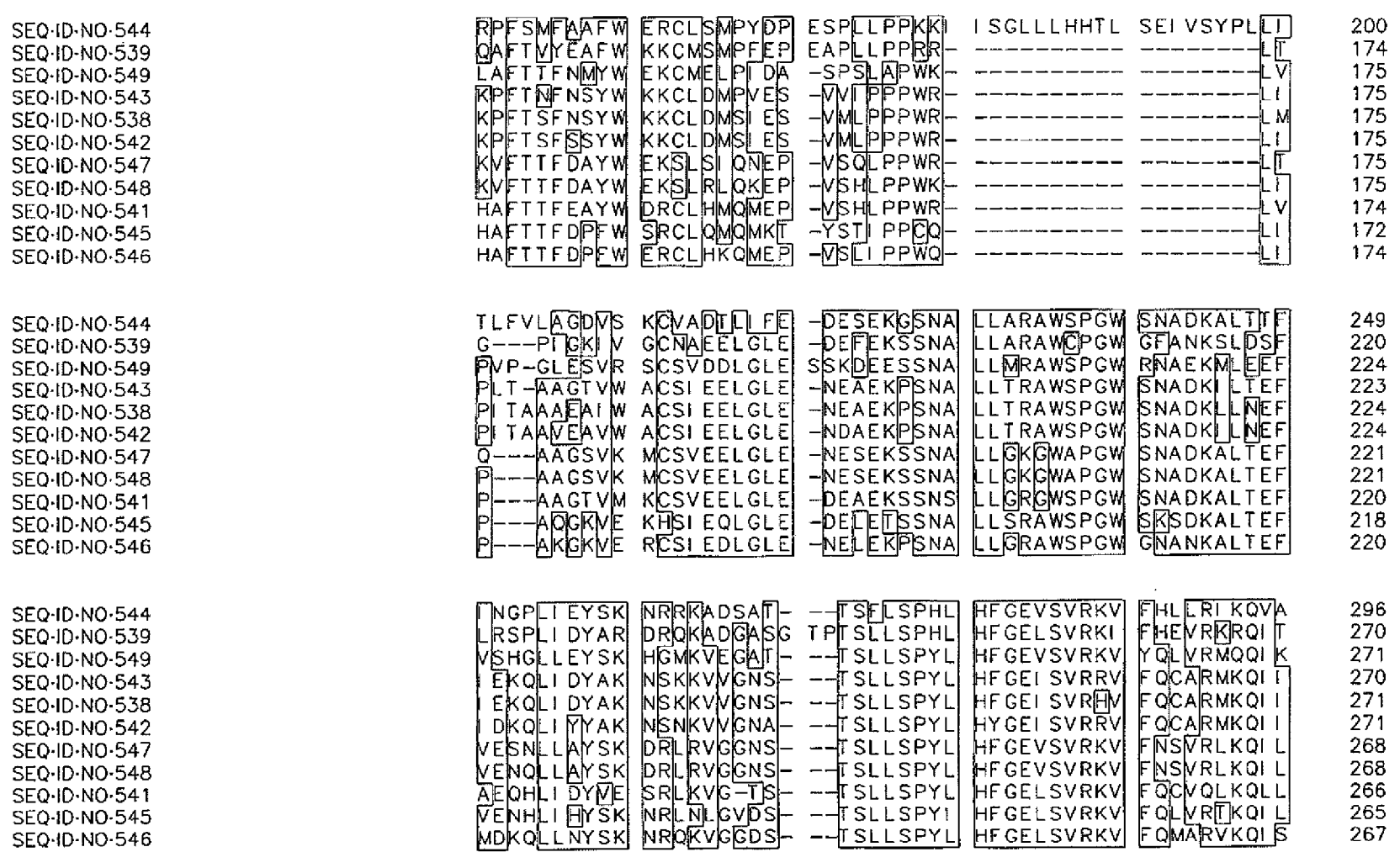
Figure 22:
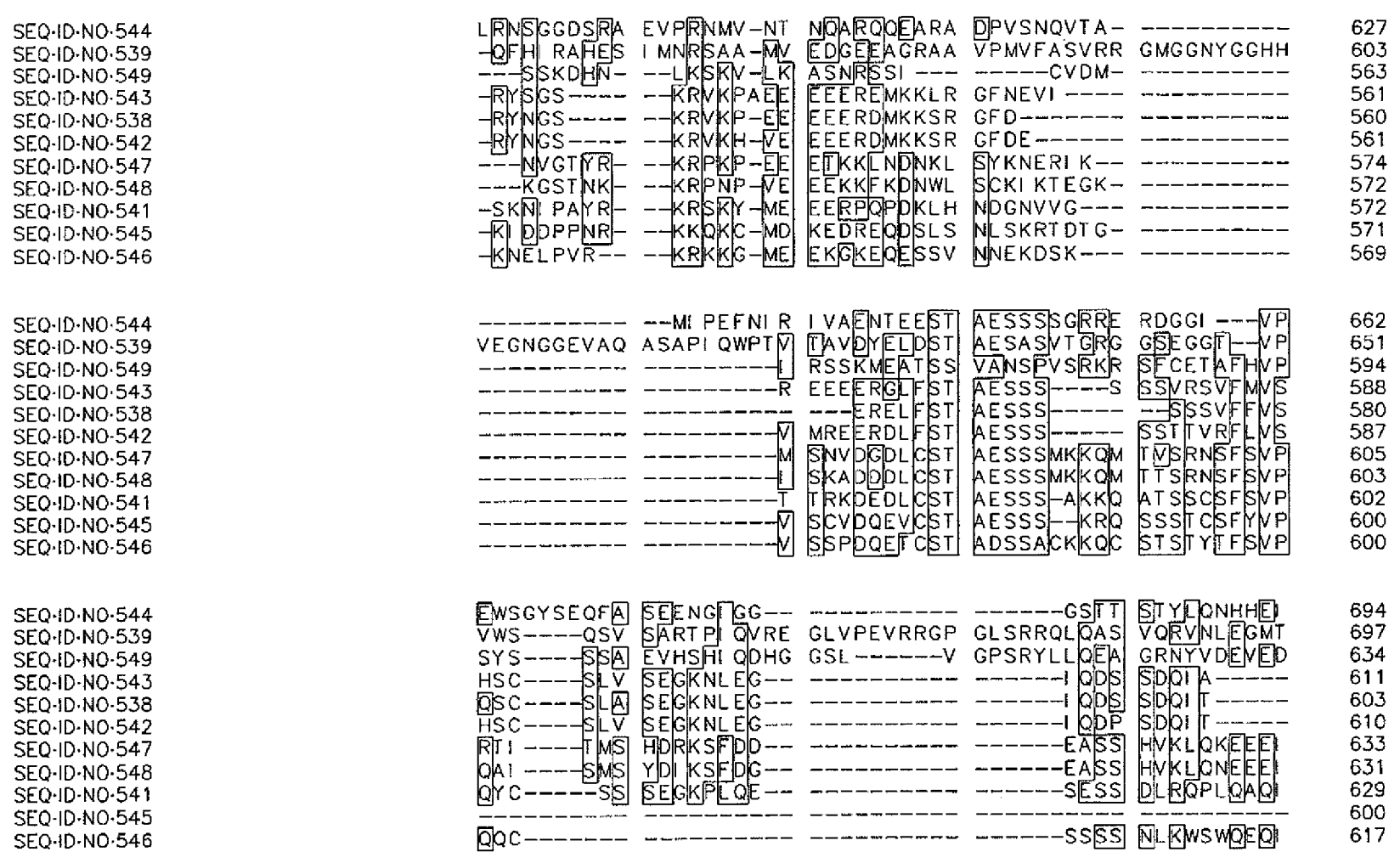

Amino acid sequences of functional homologs of the polypeptide set forth in SEQ ID NO:538 are provided in FIG. 22. Such functional homologs include Public GI ID no.5731739 (SEQ ID NO:539), Ceres ANNOT ID no.1538045 (SEQ ID NO:541), Public GI ID no.29467479 (SEQ ID NO:542), Public GI ID no.133921974 (SEQ ID NO:543), Public GI ID no.113197027 (SEQ ID NO:544), Public GI ID no.92879277 (SEQ ID NO:545), Public GI ID no.45935260 (SEQ ID NO:546), Public GI ID no.8101444 (SEQ ID NO:547), Public GI ID no.78217443 (SEQ ID NO:548), and Public GI ID no.28372347 (SEQ ID NO:549). Other functional homologs of SEQ ID NO:538 include Public GI ID no.16416405 (SEQ ID NO:550), Ceres ANNOT ID no.1484634 (SEQ ID NO:552), Ceres ANNOT ID no.1451869 (SEQ ID NO:554), Public GI ID no.25407462 (SEQ ID NO:555), Public GI ID no.29467481 (SEQ ID NO:556), Public GI ID no.29467477 (SEQ ID NO:557), Public GI ID no.45935264 (SEQ ID NO:558), Public GI ID no.5524201 (SEQ ID NO:559), Public GI ID no.78217441 (SEQ ID NO:560), Public GI ID no.3551221 (SEQ ID NO:561), Public GI ID no.3551219 (SEQ ID NO:562), Public GI ID no.23954324 (SEQ ID NO:563), Public GI ID no.125582937 (SEQ ID NO:564), Public GI ID no.83764373 (SEQ ID NO:565), Ceres ANNOT ID no.6045327 (SEQ ID NO:567), and sequences identified as functional homologs of the sequences of FIG. 22, as set forth in the sequence listing. In some cases, a functional homolog of SEQ ID NO:538 has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:538.

Amino acid sequences of functional homologs of the polypeptide set forth in SEQ ID NO:606 are provided in FIG. 23. Such functional homologs include Public GI ID no.92873064 (SEQ ID NO:607), Public GI ID no.37051125 (SEQ ID NO:608), and Public GI ID no.112363376 (SEQ ID NO:609). Other functional homologs of SEQ ID NO:606 include Ceres CLONE ID no.1938524 (SEQ ID NO:611), Ceres ANNOT ID no.1473601 (SEQ ID NO:613), Ceres ANNOT ID no.1468397 (SEQ ID NO:615), Public GI ID no.21554185 (SEQ ID NO:616), Public GI ID no.18424330 (SEQ ID NO:617), Public GI ID no.8885571 (SEQ ID NO:618), Ceres CLONE ID no.20852 (SEQ ID NO:620), Public GI ID no.21553763 (SEQ ID NO:621), Public GI ID no.18401763 (SEQ ID NO:622), Ceres CLONE ID no.16423 (SEQ ID NO:624), Public GI ID no.112363380 (SEQ ID NO:625), Public GI ID no.6092016 (SEQ ID NO:626), Ceres CLONE ID no.770468 (SEQ ID NO:628), Public GI ID no.113205234 (SEQ ID NO:629), Ceres ANNOT ID no.6094775 (SEQ ID NO:631), and sequences identified as functional homologs of the sequences of FIG. 23, as set forth in the sequence listing. In some cases, a functional homolog of SEQ ID NO:606 has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:606.

Figure 24:
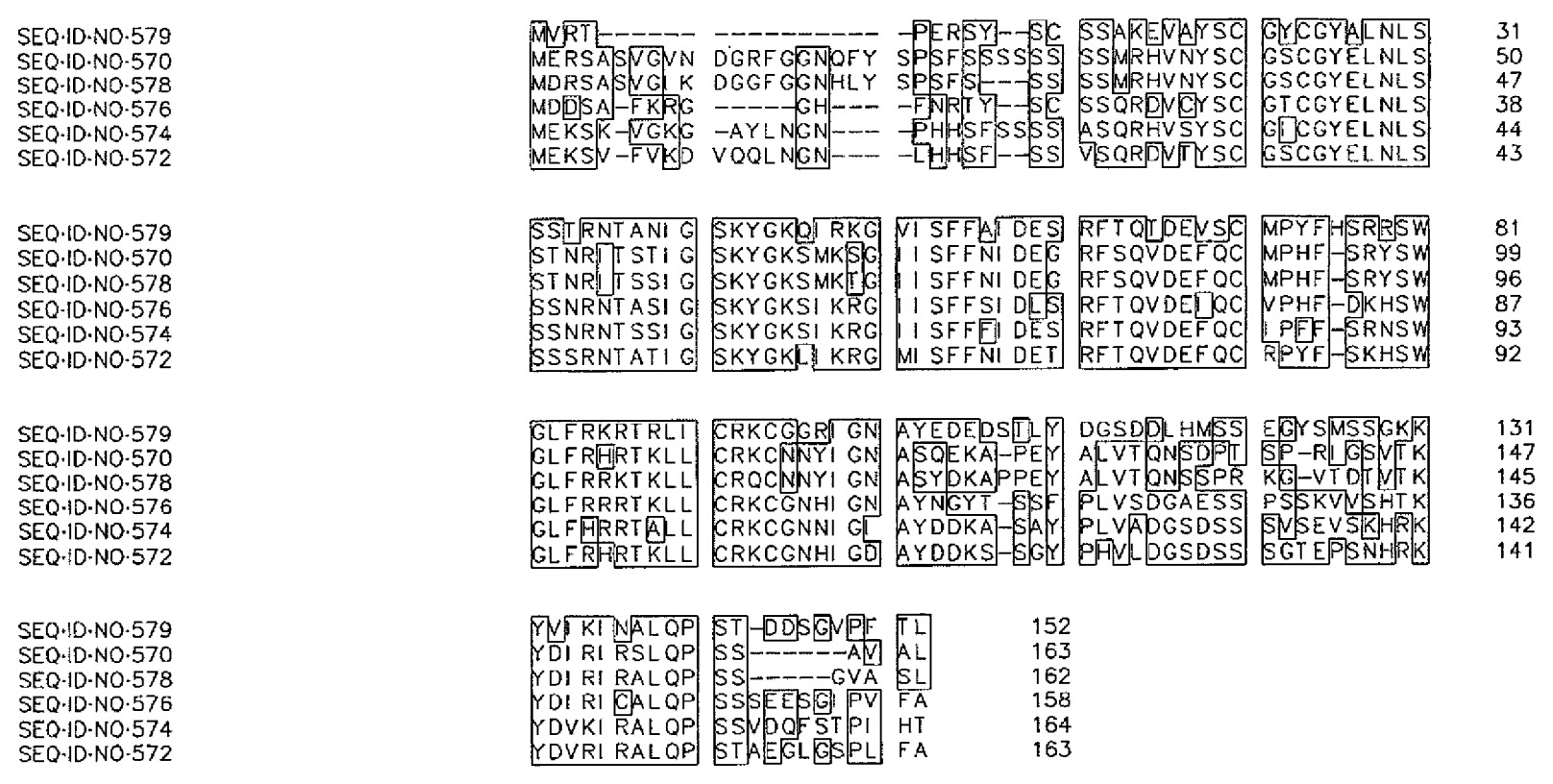

Amino acid sequences of functional homologs of the polypeptide set forth in SEQ ID NO:570 are provided in FIG. 24. Such functional homologs include Ceres CLONE ID no.1919714 (SEQ ID NO:572), Ceres ANNOT ID no.1443290 (SEQ ID NO:574), Ceres CLONE ID no.1042157 (SEQ ID NO:576), Ceres CLONE ID no.1384304 (SEQ ID NO:578), and Public GI ID no.115464375 (SEQ ID NO:579). Other functional homologs of SEQ ID NO:570 include Ceres CLONE ID no.100028078 (SEQ ID NO:580), Ceres ANNOT ID no.1452096 (SEQ ID NO:582), Ceres ANNOT ID no.1503869 (SEQ ID NO:584), Ceres ANNOT ID no.1525651 (SEQ ID NO:586), Ceres CLONE ID no.1645639 (SEQ ID NO:588), Ceres CLONE ID no.603237 (SEQ ID NO:590), Ceres CLONE ID no.340925 (SEQ ID NO:592), Ceres CLONE ID no.293238 (SEQ ID NO:594), Ceres CLONE ID no.483742 (SEQ ID NO:596), Ceres CLONE ID no.1460255 (SEQ ID NO:598), Ceres CLONE ID no.1400107 (SEQ ID NO:600), Public GI ID no.115440865 (SEQ ID NO:601), Ceres ANNOT ID no.6016008 (SEQ ID NO:603), and sequences identified as functional homologs of the sequences of FIG. 24, as set forth in the sequence listing. In some cases, a functional homolog of SEQ ID NO:570 has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:570.

The identification of conserved regions in an SD+EODFR and/or low light tolerance polypeptide facilitates production of variants of SD+EODFR and/or low light tolerance polypeptides. Variants of SD+EODFR and/or low light tolerance polypeptides typically have 10 or fewer conservative amino acid substitutions within the primary amino acid sequence, e.g., 7 or fewer conservative amino acid substitutions, 5 or fewer conservative amino acid substitutions, or between 1 and 5 conservative substitutions. A useful variant polypeptide can be constructed based on one of the alignments set forth in FIGS. 1-24. Such a polypeptide includes the conserved regions, arranged in the order depicted in the Figure from amino-terminal end to carboxy-terminal end. Such a polypeptide may also include zero, one, or more than one amino acid in positions marked by dashes. When no amino acids are present at positions marked by dashes, the length of such a polypeptide is the sum of the amino acid residues in all conserved regions. When amino acids are present at all positions marked by dashes, such a polypeptide has a length that is the sum of the amino acid residues in all conserved regions and all dashes.

D. Functional Homologs Identified by HMMER

In some embodiments, useful SD+EODFR and/or low light tolerance polypeptides include those that fit a Hidden Markov Model based on the polypeptides set forth in any one of FIGS. 1-24. A Hidden Markov Model (HMM) is a statistical model of a consensus sequence for a group of functional homologs. See, Durbin et al., *Biological Sequence Analysis: Probabilistic Models of Proteins and Nucleic Acids*, Cambridge University Press, Cambridge, UK (1998). An HMM is generated by the program HMMER 2.3.2 with default program parameters, using the sequences of the group of functional homologs as input. The multiple sequence alignment is generated by ProbCons (Do et al., Genome Res., 15(2):330-40 (2005)) version 1.11 using a set of default parameters: -c, -consistency REPS of 2; -ir, -iterative-refinement REPS of 100; -pre, -pre-training REPS of 0. ProbCons is a public domain software program provided by Stanford University.

The default parameters for building an HMM (hmmbuild) are as follows: the default "architecture prior" (archpri) used by MAP architecture construction is 0.85, and the default cutoff threshold (idlevel) used to determine the effective sequence number is 0.62. HMMER 2.3.2 was released Oct. 3, 2003 under a GNU general public license, and is available from various sources on the World Wide Web such as hmmer.janelia.org; hmmer wustl.edu; and fr.com/hmmer232/. Hmmbuild outputs the model as a text file.

The HMM for a group of functional homologs can be used to determine the likelihood that a candidate SD+EODFR and/or low light tolerance polypeptide sequence is a better fit to that particular HMM than to a null HMM generated using a group of sequences that are not structurally or functionally related. The likelihood that a candidate polypeptide sequence is a better fit to an HMM than to a null HMM is indicated by the HMM bit score, a number generated when the candidate sequence is fitted to the HMM profile using the HMMER hmmsearch program. The following default parameters are used when running hmmsearch: the default E-value cutoff (E) is 10.0, the default bit score cutoff (T) is negative infinity, the default number of sequences in a database (Z) is the real number of sequences in the database, the default E-value cutoff for the per-domain ranked hit list (domE) is infinity, and the default bit score cutoff for the per-domain ranked hit list (domT) is negative infinity. A high HMM bit score indicates a greater likelihood that the candidate sequence carries out one or more of the biochemical or physiological function(s) of the polypeptides used to generate the HMM. A high HMM bit score is at least 20, and often is higher. Slight variations in the HMM bit score of a particular sequence can occur due to factors such as the order in which sequences are processed for alignment by multiple sequence alignment algorithms such as the ProbCons program. Nevertheless, such HMM bit score variation is minor.

The SD+EODFR and/or low light tolerance polypeptides discussed below fit the indicated HMM with an HMM bit score greater than 20 (e.g., greater than 30, 40, 50, 60, 70, 80, 90, 100, 200, 300, 400, or 500). In some embodiments, the HMM bit score of an SD+EODFR and/or low light tolerance polypeptide discussed below is about 50%, 60%, 70%, 80%, 90%, or 95% of the HMM bit score of a functional homolog provided in the Sequence Listing. In some embodiments, an SD+EODFR and/or low light tolerance polypeptide discussed below fits the indicated HMM with an HMM bit score greater than 20, and has a domain indicative of an SD+EODFR and/or low light tolerance polypeptide. In some embodiments, an SD+EODFR and/or low light tolerance polypeptide discussed below fits the indicated HMM with an HMM bit score greater than 20, and has 70% or greater sequence identity (e.g., 75%, 80%, 85%, 90%, 95%, or 100% sequence identity) to an amino acid sequence shown in any one of FIGS. 1-24.

Polypeptides are shown in the sequence listing that have HMM bit scores greater than 170 when fitted to an HMM generated from the amino acid sequences set forth in FIG. 1. Such polypeptides include At4g37295 (SEQ ID NO:3), Ceres CLONE ID no. 1844057 (SEQ ID NO:7), Ceres ANNOT ID no. 1469148 (SEQ ID NO:22), Public GI ID no. 18390998 (SEQ ID NO:25), Ceres CLONE ID no. 1065656 (SEQ ID NO:32), Ceres CLONE ID no. 1652677 (SEQ ID NO:36), Public GI ID no. 92874556 (SEQ ID NO:49), Ceres CLONE ID no. 1329161 (SEQ ID NO:53), Ceres CLONE ID no. 1030378 (SEQ ID NO:55), Ceres CLONE ID no. 1413787 (SEQ ID NO:57), Public GI ID no. 125543598 (SEQ ID NO:60), Ceres CLONE ID no. 1793691 (SEQ ID NO:5), Ceres CLONE ID no. 1933784 (SEQ ID NO:9), Ceres CLONE ID no. 100030408 (SEQ ID NO:10), Ceres CLONE ID no. 1837059 (SEQ ID NO:12), Ceres CLONE ID no. 1793801 (SEQ ID NO:14), Ceres CLONE ID no. 1855480 (SEQ ID NO:16), Ceres CLONE ID no. 1915644 (SEQ ID NO:18), Ceres CLONE ID no. 1898104 (SEQ ID NO:20), Ceres ANNOT ID no. 1464241 (SEQ ID NO:24), Public GI ID no. 18697627 (SEQ ID NO:26), Ceres CLONE ID no. 9391 (SEQ ID NO:28), Ceres CLONE ID no. 111154 (SEQ ID NO:30), Ceres CLONE ID no. 973975 (SEQ ID NO:34), Ceres CLONE ID no. 676695 (SEQ ID NO:38), Ceres CLONE ID no. 680331 (SEQ ID NO:40), Ceres CLONE ID no. 654515 (SEQ ID NO:42), Ceres CLONE ID no. 626154 (SEQ ID NO:44), Ceres CLONE ID no. 710603 (SEQ ID NO:46), Ceres CLONE ID no. 648076 (SEQ ID NO:48), Ceres CLONE ID no. 749439 (SEQ ID NO:51), Ceres CLONE ID no. 295936 (SEQ ID NO:59), Public GI ID no. 125525139 (SEQ ID NO:61), Public GI ID no. 115452643 (SEQ ID NO:62), Public GI ID no. 24059889 (SEQ ID NO:63), Ceres ANNOT ID no. 6012747 (SEQ ID NO:65), Ceres ANNOT ID no. 6027628 (SEQ ID NO:67), and sequences identified as functional homologs of the sequences of FIG. 1, as set forth in the sequence listing.

Polypeptides are shown in the sequence listing that have HMM bit scores greater than 80 when fitted to an HMM generated from the amino acid sequences set forth in FIG. 2. Such polypeptides include At2g32710 (SEQ ID NO:70), Ceres CLONE ID no. 1975934 (SEQ ID NO:72), Ceres ANNOT ID no. 1529913 (SEQ ID NO:80), Ceres CLONE ID no. 977794 (SEQ ID NO:93), Public GI ID no. 42362378 (SEQ ID NO:96), Public GI ID no. 23899378 (SEQ ID NO:99), Public GI ID no. 15963346 (SEQ ID NO:101), Public GI ID no. 15963344+B816 (SEQ ID NO:102), Public GI ID no. 92429657 (SEQ ID NO:103), Ceres CLONE ID no. 746644 (SEQ ID NO:105), Ceres CLONE ID no. 623089 (SEQ ID NO:109), Ceres CLONE ID no. 1913678 (SEQ ID NO:115), Public GI ID no. 115450609 (SEQ ID NO:119), Ceres CLONE ID no. 1835084 (SEQ ID NO:74), Ceres CLONE ID no. 1846153 (SEQ ID NO:76), Ceres CLONE ID no. 1930884 (SEQ ID NO:78), Ceres ANNOT ID no. 1493858 (SEQ ID NO:82), Ceres ANNOT ID no. 1498646 (SEQ ID NO:84), Ceres ANNOT ID no. 1440974 (SEQ ID NO:86), Ceres CLONE ID no. 1189183 (SEQ ID NO:88), Public GI ID no. 26450253 (SEQ ID NO:89), Public GI ID no. 15239719 (SEQ ID NO:90), Public GI ID no. 15230194 (SEQ ID NO:91), Ceres CLONE ID no. 630905 (SEQ ID NO:95), Public GI ID no. 42362389 (SEQ ID NO:97), Public GI ID no. 70906129 (SEQ ID NO:98), Public GI ID no. 23899381 (SEQ ID NO:100), Ceres CLONE ID no. 298166 (SEQ ID NO:107), Ceres CLONE ID no. 1448390 (SEQ ID NO:111), Ceres CLONE ID no. 1734216 (SEQ ID NO:113), Public GI ID no. 125542322 (SEQ ID NO:116), Public GI ID no. 125532331 (SEQ ID NO:117), Public GI ID no. 125541233 (SEQ ID NO:118), Public GI ID no. 125584844 (SEQ ID NO:120), Public GI ID no. 115482472 (SEQ ID NO:121), Public GI ID no. 125575112 (SEQ ID NO:122), Ceres ANNOT ID no.6003994 (SEQ ID NO:124), Ceres ANNOT ID no. 6068427 (SEQ ID NO:126), and sequences identified as functional homologs of the sequences of FIG. 2, as set forth in the sequence listing.

Polypeptides are shown in the sequence listing that have HMM bit scores greater than 80 when fitted to an HMM generated from the amino acid sequences set forth in FIG. 3. Such polypeptides include Public GI ID no. 34550779 (SEQ ID NO:133), Ceres CLONE ID no. 1932235 (SEQ ID NO:137), Ceres CLONE ID no. 981738 (SEQ ID NO:201), Ceres CLONE ID no. 565974 (SEQ ID NO:209), Public GI ID no. 1352058 (SEQ ID NO:231), Public GI ID no. 11131101 (SEQ ID NO:234), Public GI ID no. 4887018 (SEQ ID NO:236), Public GI ID no. 4887018 (SEQ ID NO:236), Ceres CLONE ID no. 644455 (SEQ ID NO:247), Ceres CLONE ID no. 1731500 (SEQ ID NO:270), Public GI ID no. 20269063 (SEQ ID NO:300), Public GI ID no. 50404477 (SEQ ID NO:302), Public GI ID no. 62125392 (SEQ ID NO:303), Public GI ID no. 32396293 (SEQ ID NO:130), Public GI ID no. 32396299 (SEQ ID NO:131), Public GI ID no. 32396295 (SEQ ID NO:132), Ceres CLONE ID no. 1855369 (SEQ ID NO:135), Ceres CLONE ID no. 1948456 (SEQ ID NO:139), Ceres CLONE ID no. 1920182 (SEQ ID NO:141), Ceres CLONE ID no. 1835797 (SEQ ID NO:143), Ceres CLONE ID no. 1794204 (SEQ ID NO:145), Ceres CLONE ID no. 1853542 (SEQ ID NO:147), Ceres CLONE ID no. 1838776 (SEQ ID NO:149), Ceres CLONE ID no. 1854675 (SEQ ID NO:151), Ceres CLONE ID no. 1833078 (SEQ ID NO:153), Ceres CLONE ID no. 1850667 (SEQ ID NO:155), Ceres CLONE ID no. 1918745 (SEQ ID NO:157), Ceres CLONE ID no. 1929487 (SEQ ID NO:159), Ceres ANNOT ID no. 1497918 (SEQ ID NO:161), Ceres ANNOT ID no. 1459563 (SEQ ID NO:163), Ceres ANNOT ID no. 1452610 (SEQ ID NO:165), Ceres ANNOT ID no. 1496539 (SEQ ID NO:167), Ceres ANNOT ID no. 1498819 (SEQ ID NO:169), Ceres ANNOT ID no. 1446583 (SEQ ID NO:171), Ceres ANNOT ID no. 1535123 (SEQ ID NO:173), Ceres ANNOT ID no. 1463397 (SEQ ID NO:175), Ceres ANNOT ID no. 1499563 (SEQ ID NO:177), Ceres ANNOT ID no. 1495753 (SEQ ID NO:179), Ceres ANNOT ID no. 1488767 (SEQ ID NO:181), Ceres ANNOT ID no. 1522920 (SEQ ID NO:185), Ceres ANNOT ID no. 1469532 (SEQ ID NO:187), Public GI ID no. 15219692 (SEQ ID NO:188), Public GI ID no. 18420964 (SEQ ID NO:189), Ceres CLONE ID no. 1342080 (SEQ ID NO:191), Ceres CLONE ID no. 123105 (SEQ ID NO:193), Ceres CLONE ID no. 32727 (SEQ ID NO:195), Ceres CLONE ID no. 41161 (SEQ ID NO:197), Ceres CLONE ID no. 37274 (SEQ ID NO:199), Ceres CLONE ID no. 538020 (SEQ ID NO:203), Ceres CLONE ID no. 476244 (SEQ ID NO:205), Ceres CLONE ID no. 1623662 (SEQ ID NO:207), Ceres CLONE ID no. 626817 (SEQ ID NO:211), Ceres CLONE ID no. 537469 (SEQ ID NO:213), Ceres CLONE ID no. 582463 (SEQ ID NO:215), Ceres CLONE ID no.1069818 (SEQ ID NO:217), Ceres CLONE ID no. 511737 (SEQ ID NO:219), Ceres CLONE ID no. 565422 (SEQ ID NO:221), Ceres CLONE ID no. 514595 (SEQ ID NO:223), Ceres CLONE ID no. 566396 (SEQ ID NO:225), Ceres CLONE ID no. 612705 (SEQ ID NO:227), Ceres CLONE ID no. 564134 (SEQ ID NO:229), Public GI ID no. 92872146 (SEQ ID NO:230), Public GI ID no. 11131103 (SEQ ID NO:232), Public GI ID no. 416641 (SEQ ID NO:233), Public GI ID no. 11131105 (SEQ ID NO:235), Public GI ID no. 4887016 (SEQ ID NO:237), Public GI ID no. 4887022 (SEQ ID NO:238), Public GI ID no. 81074526 (SEQ ID NO:239), Ceres CLONE ID no. 742023 (SEQ ID NO:241), Ceres CLONE ID no. 576268 (SEQ ID NO:243), Ceres CLONE ID no. 615386 (SEQ ID NO:245), Ceres CLONE ID no. 756966 (SEQ ID NO:249), Ceres CLONE ID no. 1052710 (SEQ ID NO:251), Ceres CLONE ID no. 697018 (SEQ ID NO:253), Ceres CLONE ID no. 618577 (SEQ ID NO:255), Ceres CLONE ID no. 935194 (SEQ ID NO:257), Ceres CLONE ID no. 1557429 (SEQ ID NO:259), Ceres CLONE ID no. 305337 (SEQ ID NO:261), Ceres CLONE ID no. 100872943 (SEQ ID NO:262), Ceres CLONE ID no. 305454 (SEQ ID NO:264), Ceres CLONE ID no. 1534670 (SEQ ID NO:266), Ceres CLONE ID no. 207963 (SEQ ID NO:268), Public GI ID no. 20257219 (SEQ ID NO:271), Ceres CLONE ID no. 1876818 (SEQ ID NO:273), Ceres CLONE ID no. 1817533 (SEQ ID NO:275), Ceres CLONE ID no. 1958631 (SEQ ID NO:277), Ceres CLONE ID no. 1963215 (SEQ ID NO:279), Ceres CLONE ID no. 1770022 (SEQ ID NO:281), Ceres CLONE ID no. 1796223 (SEQ ID NO:283), Ceres CLONE ID no. 2016695 (SEQ ID NO:285), Ceres CLONE ID no. 1757085 (SEQ ID NO:287), Ceres CLONE ID no. 1769256 (SEQ ID NO:289), Ceres CLONE ID no. 1994871 (SEQ ID NO:291), Public GI ID no. 17154533 (SEQ ID NO:292), Public GI ID no. 125557426 (SEQ ID NO:293), Public GI ID no. 125524736 (SEQ ID NO:294), Public GI ID no. 125527656 (SEQ ID NO:295), Public GI ID no. 125599342 (SEQ ID NO:296), Public GI ID no. 125569626 (SEQ ID NO:297), Public GI ID no. 115465401 (SEQ ID NO:298), Public GI ID no. 40539038 (SEQ ID NO:299), Public GI ID no. 20269059 (SEQ ID NO:301), Public GI ID no. 110826446 (SEQ ID NO:304), Ceres ANNOT ID no. 6029073 (SEQ ID NO:306), Ceres ANNOT ID no. 6011329 (SEQ ID NO:308), Ceres ANNOT ID no. 6034498 (SEQ ID NO:310), Ceres ANNOT ID no. 6095057 (SEQ ID NO:312), Ceres ANNOT ID no. 6095058 (SEQ ID NO:314), and sequences identified as functional homologs of the sequences of FIG. 3, as set forth in the sequence listing.

Polypeptides are shown in the sequence listing that have HMM bit scores greater than 200 when fitted to an HMM generated from the amino acid sequences set forth in FIG. 4. Such polypeptides include At4g03250 (Ceres Seedline ME10007; SEQ ID NO:317), Ceres CLONE ID no. 1842125 (SEQ ID NO:319), Ceres ANNOT ID no. 1461360 (SEQ ID NO:321), Ceres CLONE ID no. 480906 (SEQ ID NO:327), Public GI ID no. 92889352 (SEQ ID NO:330), Public GI ID no. 56201850 (SEQ ID NO:330), Ceres ANNOT ID no. 1440334 (SEQ ID NO:323), Ceres ANNOT ID no. 1493205 (SEQ ID NO:325), Ceres CLONE ID no. 482270 (SEQ ID NO:329), Public GI ID no. 125571531 (SEQ ID NO:332), Ceres ANNOT ID no. 6042411 (SEQ ID NO:334), and sequences identified as functional homologs of the sequences of FIG. 4, as set forth in the sequence listing.

Polypeptides are shown in the sequence listing that have HMM bit scores greater than 80 when fitted to an HMM generated from the amino acid sequences set forth in FIG. 5. Such polypeptides include At2g04240 (SEQ ID NO:337), Ceres CLONE ID no. 952050 (SEQ ID NO:339), Public GI ID no. 115477050 (SEQ ID NO:349), Public GI ID no. 87162911 (SEQ ID NO:355), Ceres CLONE ID no. 1790901 (SEQ ID NO:357), Ceres CLONE ID no. 1460088 (SEQ ID NO:370), Ceres CLONE ID no. 1734065 (SEQ ID NO:393), Ceres CLONE ID no. 473509 (SEQ ID NO:395), Ceres CLONE ID no. 849918 (SEQ ID NO:401), Ceres CLONE ID no. 633470 (SEQ ID NO:409), Ceres CLONE ID no. 1808334 (SEQ ID NO:417), Ceres ANNOT ID no. 1525600 (SEQ ID NO:437), Ceres CLONE ID no. 1265097 (SEQ ID NO:341), Ceres CLONE ID no. 942980 (SEQ ID NO:343), Public GI ID no. 37901055 (SEQ ID NO:344), Ceres CLONE ID no. 1609912 (SEQ ID NO:346), Public GI ID no. 76446335 (SEQ ID NO:347), Public GI ID no. 125560204 (SEQ ID NO:348), Public GI ID no. 125303087 (SEQ ID NO:350), Public GI ID no. 115460088 (SEQ ID NO:351), Public GI ID no. 125591385 (SEQ ID NO:352), Public GI ID no. 115447931 (SEQ ID NO:353), Public GI ID no. 92893514 (SEQ ID NO:354), Ceres CLONE ID no. 2019320 (SEQ ID NO:359), Ceres CLONE ID no. 1890013 (SEQ ID NO:361), Public GI ID no. 20340241 (SEQ ID NO:362), Ceres CLONE ID no. 25801 (SEQ ID NO:364), Public GI ID no. 9743343 (SEQ ID NO:365), Public GI ID no. 15238072 (SEQ ID NO:366), Public GI ID no. 15222553 (SEQ ID NO:367), Public GI ID no. 21554155 (SEQ ID NO:368), Ceres CLONE ID no. 374439 (SEQ ID NO:372), Ceres CLONE ID no. 1465572 (SEQ ID NO:374), Ceres CLONE ID no. 1565524 (SEQ ID NO:376), Ceres CLONE ID no. 322302 (SEQ ID NO:378), Public GI ID no. 101136485 (SEQ ID NO:379), Ceres CLONE ID no. 1376133 (SEQ ID NO:381), Ceres CLONE ID no. 1374381 (SEQ ID NO:383), Ceres CLONE ID no. 1566473 (SEQ ID NO:385), Ceres CLONE ID no. 318088 (SEQ ID NO:387), Ceres CLONE ID no. 1452604 (SEQ ID NO:389), Ceres CLONE ID no. 337906 (SEQ ID NO:391), Ceres CLONE ID no. 1662513 (SEQ ID NO:397), Ceres CLONE ID no. 1662527 (SEQ ID NO:399), Ceres CLONE ID no. 571184 (SEQ ID NO:403), Ceres CLONE ID no. 665689 (SEQ ID NO:405), Ceres CLONE ID no. 1365853 (SEQ ID NO:407), Ceres CLONE ID no. 1052457 (SEQ ID NO:411), Ceres CLONE ID no. 579918 (SEQ ID NO:413), Ceres CLONE ID no. 863299 (SEQ ID NO:415), Ceres CLONE ID no. 1855611 (SEQ ID NO:419), Ceres CLONE ID no. 1845975 (SEQ ID NO:421), Ceres CLONE ID no. 1808298 (SEQ ID NO:423), Ceres CLONE ID no. 1841236 (SEQ ID NO:425), Ceres CLONE ID no. 1808269 (SEQ ID NO:427), Ceres CLONE ID no. 1850628 (SEQ ID NO:429), Ceres CLONE ID no. 1846911 (SEQ ID NO:431), Ceres CLONE ID no. 1916014 (SEQ ID NO:433), Ceres CLONE ID no. 1842594 (SEQ ID NO:435), Ceres ANNOT ID no. 1472192 (SEQ ID NO:439), Ceres ANNOT ID no. 1447489 (SEQ ID NO:441), Ceres ANNOT ID no. 1513000 (SEQ ID NO:443), Ceres ANNOT ID no. 1438658 (SEQ ID NO:445), Ceres ANNOT ID no. 1497255 (SEQ ID NO:447), Ceres ANNOT ID no. 6092104 (SEQ ID NO:449), Ceres ANNOT ID no. 6041700 (SEQ ID NO:451), Ceres ANNOT ID no. 6007297 (SEQ ID NO:453), and sequences identified as functional homologs of the sequences of FIG. 5, as set forth in the sequence listing.

Polypeptides are shown in the sequence listing that have HMM bit scores greater than 60 when fitted to an HMM generated from the amino acid sequences set forth in FIG. 6. Such polypeptides include At5g14370 (SEQ ID NO:456), Public GI ID no. 58430585 (SEQ ID NO:457), Ceres CLONE ID no. 1842825 (SEQ ID NO:466), Ceres ANNOT ID no. 1449721 (SEQ ID NO:474), Public GI ID no. 41323978 (SEQ ID NO:475), Public GI ID no. 2895186 (SEQ ID NO:478), Public GI ID no. 22854950 (SEQ ID NO:481), Public GI ID no. 116010474 (SEQ ID NO:485), Public GI ID no. 4091804 (SEQ ID NO:488), Public GI ID no. 60459257 (SEQ ID NO:494), Public GI ID no. 45544881 (SEQ ID NO:496), Public GI ID no. 36789802 (SEQ ID NO:498), Public GI ID no. 92875402 (SEQ ID NO:508), Public GI ID no. 118406898 (SEQ ID NO:510), Public GI ID no. 107770485 (SEQ ID NO:511), Public GI ID no. 90657642 (SEQ ID NO:536), Ceres CLONE ID no. 1569555 (SEQ ID NO:1842) Public GI ID no. 66841018 (SEQ ID NO:458), Public GI ID no. 66841020 (SEQ ID NO:459), Public GI ID no. 108859343 (SEQ ID NO:460), Ceres CLONE ID no. 1937613 (SEQ ID NO:462), Ceres CLONE ID no. 1834027 (SEQ ID NO:464), Ceres ANNOT ID no. 1477832 (SEQ ID NO:468), Ceres ANNOT ID no. 1482536 (SEQ ID NO:470), Ceres ANNOT ID no. 1478227 (SEQ ID NO:472), Ceres CLONE ID no. 19906 (SEQ ID NO:478), Public GI ID no. 2895184 (SEQ ID NO:479), Public GI ID no. 2895188 (SEQ ID NO:480), Public GI ID no. 11037313 (SEQ ID NO:482), Public GI ID no. 22854908 (SEQ ID NO:483), Public GI ID no. 40787165 (SEQ ID NO:484), Public GI ID no. 116010475 (SEQ ID NO:486), Public GI ID no. 3341723 (SEQ ID NO:487), Public GI ID no. 4091806 (SEQ ID NO:489), Ceres CLONE ID no. 523203 (SEQ ID NO:491), Ceres CLONE ID no.

463157 (SEQ ID NO:493), Public GI ID no. 61611678 (SEQ ID NO:495), Public GI ID no. 45544887 (SEQ ID NO:497), Public GI ID no. 36789793 (SEQ ID NO:481), Ceres CLONE ID no. 907473 (SEQ ID NO:501), Ceres CLONE ID no. 1674443 (SEQ ID NO:503), Ceres CLONE ID no. 1559496 (SEQ ID NO:505), Ceres CLONE ID no. 530984 (SEQ ID NO:507), Public GI ID no. 61611682 (SEQ ID NO:509), Public GI ID no. 36789785 (SEQ ID NO:512), Ceres CLONE ID no. 702632 (SEQ ID NO:514), Public GI ID no. 61657299 (SEQ ID NO:515), Public GI ID no. 10946337 (SEQ ID NO:516), Ceres CLONE ID no. 1996408 (SEQ ID NO:518), Ceres CLONE ID no. 1725313 (SEQ ID NO:520), Public GI ID no. 78058606 (SEQ ID NO:521), Public GI ID no. 125538317 (SEQ ID NO:522), Public GI ID no. 125556324 (SEQ ID NO:523), Public GI ID no. 125548890 (SEQ ID NO:524), Public GI ID no. 93211100 (SEQ ID NO:525), Public GI ID no. 115444217 (SEQ ID NO:526), Public GI ID no. 115467558 (SEQ ID NO:527), Public GI ID no. 11094209 (SEQ ID NO:528), Public GI ID no. 125596830 (SEQ ID NO:529), Public GI ID no. 115469296 (SEQ ID NO:530), Public GI ID no. 115447239 (SEQ ID NO:531), Public GI ID no. 21655154 (SEQ ID NO:532), Public GI ID no. 21667485 (SEQ ID NO:533), Public GI ID no. 21667475 (SEQ ID NO:534), Public GI ID no. 21655158 (SEQ ID NO:535), and sequences identified as functional homologs of the sequences of FIG. 6, as set forth in the sequence listing.

Polypeptides are shown in the sequence listing that have HMM bit scores greater than 20 when fitted to an HMM generated from the amino acid sequences set forth in FIG. 7. Such polypeptides include At1g70270 (SEQ ID NO:634), Public GI ID no. 98961985 (SEQ ID NO:637), Ceres CLONE ID no. 1916112 (SEQ ID NO:636), Public GI ID no. 9369405 (SEQ ID NO:638), Public GI ID no. 9369406 (SEQ ID NO:639), Ceres CLONE ID no. 1238706 (SEQ ID NO:641), and sequences identified as functional homologs of the sequences of FIG. 7, as set forth in the sequence listing.

Polypeptides are shown in the sequence listing that have HMM bit scores greater than 80 when fitted to an HMM generated from the amino acid sequences set forth in FIG. 8. Such polypeptides include At4g25480 (SEQ ID NO:644), SEQ ID NO:645, Ceres CLONE ID no. 1849479 (SEQ ID NO:767), Public GI ID no. 89275008 (SEQ ID NO:796), Public GI ID no. 120400525 (SEQ ID NO:797), Public GI ID no. 98980426 (SEQ ID NO:804), Public GI ID no. 71983373 (SEQ ID NO:808), Public GI ID no. 41351817 (SEQ ID NO:809), Public GI ID no. 76446191 (SEQ ID NO:811), Public GI ID no. 5616086 (SEQ ID NO:813), Ceres CLONE ID no. 1052602 (SEQ ID NO:826), Public GI ID no. 72068957 (SEQ ID NO:830), Public GI ID no. 71534113 (SEQ ID NO:831), Public GI ID no. 37147896 (SEQ ID NO:832), Public GI ID no. 92918850 (SEQ ID NO:834), Public GI ID no. 40647095 (SEQ ID NO:835), Ceres ANNOT ID no. 1527711 (SEQ ID NO:837), Public GI ID no. 71041116 (SEQ ID NO:838), Public GI ID no. 12003384 (SEQ ID NO:839), Public GI ID no. 18535580 (SEQ ID NO:840), Ceres CLONE ID no. 991178 (SEQ ID NO:647), Ceres CLONE ID no. 1626038 (SEQ ID NO:649), Ceres CLONE ID no. 341615 (SEQ ID NO:651), Ceres CLONE ID no. 1832518 (SEQ ID NO:653), Ceres CLONE ID no. 1832588 (SEQ ID NO:655), Ceres CLONE ID no. 1936806 (SEQ ID NO:657), Ceres CLONE ID no. 973892 (SEQ ID NO:659), Ceres CLONE ID no. 565251 (SEQ ID NO:661), Ceres CLONE ID no. 681088 (SEQ ID NO:663), Ceres CLONE ID no. 707775 (SEQ ID NO:665), Ceres CLONE ID no. 453357 (SEQ ID NO:667), Ceres CLONE ID no. 1916958 (SEQ ID NO:669), Ceres CLONE ID no. 1940632 (SEQ ID NO:671), Ceres CLONE ID no. 476784 (SEQ ID NO:673), Ceres CLONE ID no. 1869284 (SEQ ID NO:675), Public GI ID no. 125540662 (SEQ ID NO:676), Ceres CLONE ID no. 1648272 (SEQ ID NO:678), Ceres CLONE ID no. 1987804 (SEQ ID NO:680), Ceres CLONE ID no. 1675695 (SEQ ID NO:682), Ceres CLONE ID no. 1169111 (SEQ ID NO:684), Ceres CLONE ID no. 572121 (SEQ ID NO:686), Ceres CLONE ID no. 1674836 (SEQ ID NO:688), Ceres ANNOT ID no. 1486207 (SEQ ID NO:690), Ceres CLONE ID no. 2023610 (SEQ ID NO:692), Ceres ANNOT ID no. 1496976 (SEQ ID NO:694), Public GI ID no. 116310031 (SEQ ID NO:695), Ceres CLONE ID no. 1626363 (SEQ ID NO:697), Ceres ANNOT ID no. 1483747 (SEQ ID NO:699), Ceres ANNOT ID no. 1471330 (SEQ ID NO:701), Ceres CLONE ID no. 101144964 (SEQ ID NO:702), Ceres ANNOT ID no. 1439439 (SEQ ID NO:704), Ceres CLONE ID no. 1446565 (SEQ ID NO:706), Ceres CLONE ID no. 1951962 (SEQ ID NO:708), Ceres CLONE ID no. 100960656 (SEQ ID NO:709), Ceres CLONE ID no. 285154 (SEQ ID NO:711), Public GI ID no. 61968916 (SEQ ID NO:712), Public GI ID no. 118026854 (SEQ ID NO:713), Public GI ID no. 63098612 (SEQ ID NO:714), Ceres ANNOT ID no. 1522310 (SEQ ID NO:716), Ceres CLONE ID no. 1854375 (SEQ ID NO:718), Ceres CLONE ID no. 709819 (SEQ ID NO:720), Public GI ID no. 115447695 (SEQ ID NO:721), Ceres CLONE ID no. 1726356 (SEQ ID NO:723), Ceres CLONE ID no. 1762419 (SEQ ID NO:725), Public GI ID no. 63098606 (SEQ ID NO:726), Ceres CLONE ID no. 1766572 (SEQ ID NO:728), Ceres CLONE ID no. 281871 (SEQ ID NO:730), Ceres CLONE ID no. 1560970 (SEQ ID NO:732), Ceres CLONE ID no. 1760747 (SEQ ID NO:734), Ceres ANNOT ID no. 1438772 (SEQ ID NO:736), Ceres ANNOT ID no. 1447378 (SEQ ID NO:738), Ceres ANNOT ID no. 1453360 (SEQ ID NO:740), Public GI ID no. 33637698 (SEQ ID NO:741), Public GI ID no. 118026860 (SEQ ID NO:742), Public GI ID no. 60116232 (SEQ ID NO:743), Public GI ID no.115477639 (SEQ ID NO:744), Public GI ID no.126567023 (SEQ ID NO:745), Ceres CLONE ID no.988971 (SEQ ID NO:747), Ceres CLONE ID no.1464521 (SEQ ID NO:749), Public GI ID no.63098610 (SEQ ID NO:750), Public GI ID no.126566972 (SEQ ID NO:751), Ceres CLONE ID no.1556129 (SEQ ID NO:753), Ceres CLONE ID no.1761385 (SEQ ID NO:755), Ceres ANNOT ID no.1488325 (SEQ ID NO:757), Ceres ANNOT ID no.1460483 (SEQ ID NO:759), Ceres CLONE ID no.1837825 (SEQ ID NO:761), Public GI ID no.27228310 (SEQ ID NO:762), Public GI ID no.117653881 (SEQ ID NO:763), Public GI ID no.115480233 (SEQ ID NO:764), Public GI ID no.37694048 (SEQ ID NO:765), Ceres CLONE ID no.1934653 (SEQ ID NO:769), Ceres CLONE ID no.1608106 (SEQ ID NO:771), Ceres CLONE ID no.1604576 (SEQ ID NO:773), Public GI ID no.55824656 (SEQ ID NO:774), Ceres CLONE ID no.1620272 (SEQ ID NO:776), Ceres CLONE ID no.1853170 (SEQ ID NO:778), Public GI ID no.79013962 (SEQ ID NO:779), Public GI ID no.98975385 (SEQ ID NO:780), Ceres ANNOT ID no.1438775 (SEQ ID NO:782), Public GI ID no.23495460 (SEQ ID NO:783), Public GI ID no.98975377 (SEQ ID NO:784), Ceres ANNOT ID no.1438776 (SEQ ID NO:786), Ceres CLONE ID no.1853601 (SEQ ID NO:788), Ceres CLONE ID no.1609048 (SEQ ID NO:790), Ceres CLONE ID no.322305 (SEQ ID NO:792), Ceres CLONE ID no.1823713 (SEQ ID NO:794), Public GI ID no.3660548 (SEQ ID NO:795), Public GI ID no.56154991 (SEQ ID NO:798), Public GI ID no.2980802 (SEQ ID NO:799), Public GI ID no.7269398 (SEQ ID NO:800), Public GI ID no.18416557 (SEQ ID NO:801), Public GI ID no.56154992 (SEQ ID NO:802), Public GI ID no.4091984 (SEQ ID NO:803), Public GI ID no.1899058 (SEQ ID NO:805), Public GI ID no.56154990 (SEQ ID NO:806), Public GI ID no.18416562 (SEQ ID NO:807), Public GI ID no.38683266 (SEQ ID NO:810), Public GI ID no.39983638 (SEQ ID NO:812), Public GI ID no.38426954 (SEQ ID NO:814), Public GI ID no.38426948 (SEQ ID NO:815), Public GI ID no.38146944 (SEQ ID NO:816), Public GI ID no.38426952 (SEQ ID NO:817), Public GI ID no.20303011 (SEQ ID NO:818), Public GI ID no.66269982 (SEQ ID NO:819), Public GI ID no.89212816 (SEQ ID NO:820), Public GI ID no.20303015 (SEQ ID NO:821), Public GI ID no.38426950 (SEQ ID NO:822), Public GI ID no.15242244 (SEQ ID NO:823), Public GI ID no.116831599 (SEQ ID NO:824), Public GI ID no.66269671 (SEQ ID NO:827), Ceres ANNOT ID no.1468919 (SEQ ID NO:829), Public GI ID no.57903606 (SEQ ID NO:833), Public GI ID no.45826358 (SEQ ID NO:841), Ceres ANNOT ID no.6085912 (SEQ ID NO:843), Ceres ANNOT ID no.6026171 (SEQ ID NO:845), Ceres ANNOT ID no.6031706 (SEQ ID NO:847), Public GI ID no. 115353971 (SEQ ID NO:1843), and sequences identified as functional homologs of the sequences of FIG. 8, as set forth in the sequence listing.

Polypeptides are shown in the sequence listing that have HMM bit scores greater than 170 when fitted to an HMM generated from the amino acid sequences set forth in FIG. 9. Such polypeptides include A2g33780 (SEQ ID NO:850), Ceres CLONE ID no.1833093 (SEQ ID NO:853), Ceres ANNOT ID no.1502190 (SEQ ID NO:857), Ceres CLONE ID no.565641 (SEQ ID NO:876), Public GI ID no.87240507 (SEQ ID NO:877), Ceres CLONE ID no.1325382 (SEQ ID NO:881), Ceres CLONE ID no.1558265 (SEQ ID NO:885), Ceres CLONE ID no.1823669 (SEQ ID NO:895), Public GI ID no.115464921 (SEQ ID NO:898), Ceres CLONE ID no.100040598 (SEQ ID NO:851), Ceres CLONE ID no.1847967 (SEQ ID NO:855), Ceres ANNOT ID no.1449186 (SEQ ID NO:859), Ceres ANNOT ID no.1466723 (SEQ ID NO:861), Public GI ID no.21805688 (SEQ ID NO:862), Public GI ID no.9795609 (SEQ ID NO:863), Public GI ID no.13877535 (SEQ ID NO:864), Public GI ID no.15232547 (SEQ ID NO:865), Public GI ID no.15238851 (SEQ ID NO:866), Ceres CLONE ID no.123863 (SEQ ID NO:868), Ceres CLONE ID no.652496 (SEQ ID NO:870), Ceres CLONE ID no.1656707 (SEQ ID NO:872), Ceres CLONE ID no.1660346 (SEQ ID NO:874), Ceres CLONE ID no.678878 (SEQ ID NO:879), Ceres CLONE ID no.340102 (SEQ ID NO:883), Ceres CLONE ID no.330491 (SEQ ID NO:887), Ceres CLONE ID no.992304 (SEQ ID NO:889), Ceres CLONE ID no.1509925 (SEQ ID NO:891), Ceres CLONE ID no.1543852 (SEQ ID NO:893), Ceres CLONE ID no.1785736 (SEQ ID NO:897), Ceres ANNOT ID no.6079909 (SEQ ID NO:900), Ceres ANNOT ID no.6040353 (SEQ ID NO:902), Ceres ANNOT ID no.6100173 (SEQ ID NO:904), and sequences identified as functional homologs of the sequences of FIG. 9, as set forth in the sequence listing.

Polypeptides are shown in the sequence listing that have HMM bit scores greater than 80 when fitted to an HMM generated from the amino acid sequences set forth in FIG. 10. Such polypeptides include At4g17810 (SEQ ID NO:907), Ceres CLONE ID no.1940797 (SEQ ID NO:909), Ceres ANNOT ID no.1538900 (SEQ ID NO:911), Ceres CLONE ID no.1126868 (SEQ ID NO:922), Public GI ID no.89257684 (SEQ ID NO:923), Public GI ID no.124360460 (SEQ ID NO:929), Public GI ID no.62865694 (SEQ ID NO:931), Public GI ID no.62865692 (SEQ ID NO:932), Ceres CLONE ID no.260368 (SEQ ID NO:936), Ceres CLONE ID no.1873510 (SEQ ID NO:947), Public GI ID no.125541662 (SEQ ID NO:948), Public GI ID no.48716268 (SEQ ID NO:950), Ceres ANNOT ID no.1529131 (SEQ ID NO:913), Ceres ANNOT ID no.1454060 (SEQ ID NO:915), Ceres ANNOT ID no.1442787 (SEQ ID NO:917), Ceres ANNOT ID no.1452648 (SEQ ID NO:919), Public GI ID no.2245140 (SEQ ID NO:920), Public GI ID no.89274212 (SEQ ID NO:924), Ceres CLONE ID no.1104523 (SEQ ID NO:926), Ceres CLONE ID no.654265 (SEQ ID NO:928), Public GI ID no.42627704 (SEQ ID NO:930), Ceres CLONE ID no.887222 (SEQ ID NO:934), Public GI ID no.62865690 (SEQ ID NO:937), Public GI ID no.64175600 (SEQ ID NO:938), Public GI ID no.64175634 (SEQ ID NO:939), Public GI ID no.64175606 (SEQ ID NO:940), Public GI ID no.64175648 (SEQ ID NO:941), Ceres CLONE ID no.312184 (SEQ ID NO:943), Ceres CLONE ID no.380740 (SEQ ID NO:945), Public GI ID no.125531536 (SEQ ID NO:949), Public GI ID no. 62865696 (SEQ ID NO:1844), and sequences identified as functional homologs of the sequences of FIG. 10, as set forth in the sequence listing.

Polypeptides are shown in the sequence listing that have HMM bit scores greater than 60 when fitted to an HMM generated from the amino acid sequences set forth in FIG. 11. Such polypeptides include At1g13360 (SEQ ID NO:951), Ceres CLONE ID no.1798705 (SEQ ID NO:955), Ceres ANNOT ID no.1458907 (SEQ ID NO:963), Ceres CLONE ID no.1090409 (SEQ ID NO:971), Ceres CLONE ID no.479817 (SEQ ID NO:977), Ceres CLONE ID no.1041793 (SEQ ID NO:979), Ceres CLONE ID no.684633 (SEQ ID NO:985), Ceres CLONE ID no.371815 (SEQ ID NO:991), Ceres CLONE ID no.1686460 (SEQ ID NO:993), Ceres CLONE ID no.1448595 (SEQ ID NO:995), Ceres CLONE ID no.1734477 (SEQ ID NO:999), Ceres CLONE ID no.1605693 (SEQ ID NO:1005), Ceres CLONE ID no.1757400 (SEQ ID NO:1009), Public GI ID no.115434334 (SEQ ID NO:1015), Ceres CLONE ID no.1793754 (SEQ ID NO:957), Ceres CLONE ID no.1938045 (SEQ ID NO:959), Ceres CLONE ID no.1850004 (SEQ ID NO:961), Ceres ANNOT ID no.1489548 (SEQ ID NO:965), Public GI ID no.22329538 (SEQ ID NO:966), Public GI ID no.18404714 (SEQ ID NO:967), Ceres CLONE ID no.1110032 (SEQ ID NO:969), Ceres CLONE ID no.1095353 (SEQ ID NO:973), Ceres CLONE ID no.872121 (SEQ ID NO:975), Ceres CLONE ID no.562208 (SEQ ID NO:981), Ceres CLONE ID no.1042364 (SEQ ID NO:983), Ceres CLONE ID no.1031873 (SEQ ID NO:987), Ceres CLONE ID no.1377698 (SEQ ID NO:989), Ceres CLONE ID no.1742945 (SEQ ID NO:997), Ceres CLONE ID no.1742053 (SEQ ID NO:1001), Ceres CLONE ID no.1728365 (SEQ ID NO:1003), Ceres CLONE ID no.1609807 (SEQ ID NO:1007), Ceres CLONE ID no.1778566 (SEQ ID NO:1011), Ceres CLONE ID no.2020580 (SEQ ID NO:1013), Public GI ID no.125524285 (SEQ ID NO:1014), Public GI ID no.125568898 (SEQ ID NO:1016), Ceres ANNOT ID no.6055303 (SEQ ID NO:1018), and sequences identified as functional homologs of the sequences of FIG. 11, as set forth in the sequence listing.

Polypeptides are shown in the sequence listing that have HMM bit scores greater than 140 when fitted to an HMM generated from the amino acid sequences set forth in FIG. 12. Such polypeptides include At1g75860 (SEQ ID NO:1024), Ceres ANNOT ID no.1452905 (SEQ ID NO:1029), Ceres CLONE ID no.956176 (SEQ ID NO:1039), Public GI ID no.92870366 (SEQ ID NO:1040), Ceres CLONE ID no.294166 (SEQ ID NO:1042), Public GI ID no.125543067 (SEQ ID NO:1043), SEQ ID NO:1025, Ceres ANNOT ID no.1442522 (SEQ ID NO:1027), Public GI ID no.8778818 (SEQ ID NO:1030), Ceres CLONE ID no.108095 (SEQ ID NO:1032), Public GI ID no.18394821 (SEQ ID NO:1033), Ceres CLONE ID no.6332 (SEQ ID NO:1035), Ceres CLONE ID no.1069047 (SEQ ID NO:1037), Public GI ID no.115480956 (SEQ ID NO:1044), and sequences identified as functional homologs of the sequences of FIG. 12, as set forth in the sequence listing.

Polypeptides are shown in the sequence listing that have HMM bit scores greater than 80 when fitted to an HMM generated from the amino acid sequences set forth in FIG. 13. Such polypeptides include At4g19700 (SEQ ID NO:1047), Ceres CLONE ID no.1837694 (SEQ ID NO:1053), Ceres ANNOT ID no.1483367 (SEQ ID NO:1057), Ceres CLONE ID no.1077781 (SEQ ID NO:1083), Ceres CLONE ID no.471026 (SEQ ID NO:1085), Public GI ID no.92888885 (SEQ ID NO:1099), Public GI ID no.45544873 (SEQ ID NO:1100), Public GI ID no.45758663 (SEQ ID NO:1101), Ceres CLONE ID no.772927 (SEQ ID NO:1105), Ceres CLONE ID no.895080 (SEQ ID NO:1111), Ceres CLONE ID no.1806128 (SEQ ID NO:1131), Public GI ID no.115458192 (SEQ ID NO:1134), Public GI ID no.82470795 (SEQ ID NO:1139), Ceres CLONE ID no.1837746 (SEQ ID NO:1049), Ceres CLONE ID no.1834764 (SEQ ID NO:1051), Ceres CLONE ID no.1853547 (SEQ ID NO:1055), Ceres ANNOT ID no.1474088 (SEQ ID NO:1059), Ceres ANNOT ID no.1536919 (SEQ ID NO:1061), Ceres ANNOT ID no.1467033 (SEQ ID NO:1063), Ceres ANNOT ID no.1485401 (SEQ ID NO:1065), Ceres ANNOT ID no.1486505 (SEQ ID NO:1067), Public GI ID no.17065054 (SEQ ID NO:1068), Public GI ID no.30694690 (SEQ ID NO:1069), Ceres CLONE ID no.12997 (SEQ ID NO:1071), Public GI ID no.30694694 (SEQ ID NO:1072), Public GI ID no.42572167 (SEQ ID NO:1073), Public GI ID no.110739742 (SEQ ID NO:1074), Public GI ID no.18412263 (SEQ ID NO:1075), Ceres CLONE ID no.36412 (SEQ ID NO:1077), Public GI ID no.18399792 (SEQ ID NO:1078), Ceres CLONE ID no.924 (SEQ ID NO:1080), Public GI ID no.15238000 (SEQ ID NO:1081), Ceres CLONE ID no.1626330 (SEQ ID NO:1087), Ceres CLONE ID no.1650419 (SEQ ID NO:1089), Ceres CLONE ID no.1641329 (SEQ ID NO:1091), Ceres CLONE ID no.1620406 (SEQ ID NO:1093), Ceres CLONE ID no.546832 (SEQ ID NO:1095), Ceres CLONE ID no.1243138 (SEQ ID NO:1097), Public GI ID no.92887260 (SEQ ID NO:1098), Ceres CLONE ID no.885628 (SEQ ID NO:1103), Ceres CLONE ID no.1376391 (SEQ ID NO:1107), Ceres CLONE ID no.465893 (SEQ ID NO:1109), Ceres CLONE ID no.218243 (SEQ ID NO:1113), Ceres CLONE ID no.1558456 (SEQ ID NO:1115), Ceres CLONE ID no.343008 (SEQ ID NO:1117), Ceres CLONE ID no.218463 (SEQ ID NO:1119), Ceres CLONE ID no.1565409 (SEQ ID NO:1121), Ceres CLONE ID no.1060968 (SEQ ID NO:1123), Ceres CLONE ID no.236111 (SEQ ID NO:1125), Ceres CLONE ID no.285598 (SEQ ID NO:1127), Ceres CLONE ID no.225881 (SEQ ID NO:1129), Ceres CLONE ID no.1811383 (SEQ ID NO:1133), Public GI ID no.49388268 (SEQ ID NO:1135), Public GI ID no.125590268 (SEQ ID NO:1136), Public GI ID no.115444009 (SEQ ID NO:1137), Public GI ID no.115447993 (SEQ ID NO:1138), Ceres ANNOT ID no.6033842 (SEQ ID NO:1141), Ceres ANNOT ID no.6029952 (SEQ ID NO:1143), Ceres ANNOT ID no.6035837 (SEQ ID NO:1145), Ceres ANNOT ID no.6035830 (SEQ ID NO:1147), Ceres ANNOT ID no.6029981 (SEQ ID NO:1149), and sequences identified as functional homologs of the sequences of FIG. 13, as set forth in the sequence listing.

Polypeptides are shown in the sequence listing that have HMM bit scores greater than 80 when fitted to an HMM generated from the amino acid sequences set forth in FIG. 14. Such polypeptides include At1g58100 (SEQ ID NO:1151), Ceres CLONE ID no.1851526 (SEQ ID NO:1155), Ceres ANNOT ID no.1486769 (SEQ ID NO:1172), Public GI ID no.83032232 (SEQ ID NO:1209), Ceres CLONE ID no.1620420 (SEQ ID NO:1211), Public GI ID no.92892428 (SEQ ID NO:1215), Ceres CLONE ID no.884742 (SEQ ID NO:1223), Ceres CLONE ID no.1821559 (SEQ ID NO:1246), Public GI ID no.51535021 (SEQ ID NO:1258), Public GI ID no.113205304 (SEQ ID NO:1263), Public GI ID no.37719051 (SEQ ID NO:1264), Ceres CLONE ID no.1918070 (SEQ ID NO:1153), Ceres CLONE ID no.1948426 (SEQ ID NO:1157), Ceres CLONE ID no.1937875 (SEQ ID NO:1159), Ceres CLONE ID no.100056542 (SEQ ID NO:1160), Public GI ID no.5731257 (SEQ ID NO:1161), Ceres CLONE ID no.100058043 (SEQ ID NO:1162), Ceres CLONE ID no.1838288 (SEQ ID NO:1164), Ceres CLONE ID no.1793597 (SEQ ID NO:1166), Ceres ANNOT ID no.1543031 (SEQ ID NO:1168), Ceres ANNOT ID no.1489643 (SEQ ID NO:1170), Ceres ANNOT ID no.1479721 (SEQ ID NO:1174), Ceres ANNOT ID no.1449170 (SEQ ID NO:1176), Ceres ANNOT ID no.1493696 (SEQ ID NO:1178), Ceres ANNOT ID no.1543534 (SEQ ID NO:1180), Ceres ANNOT ID no.1440815 (SEQ ID NO:1182), Ceres ANNOT ID no.1490137 (SEQ ID NO:1184), Ceres ANNOT ID no.1451054 (SEQ ID NO:1186), Ceres ANNOT ID no.1456669 (SEQ ID NO:1188), Ceres ANNOT ID no.1509865 (SEQ ID NO:1190), Ceres ANNOT ID no.1447910 (SEQ ID NO:1192), Ceres ANNOT ID no.1471068 (SEQ ID NO:1194), Ceres ANNOT ID no.1504118 (SEQ ID NO:1196), Ceres CLONE ID no.1343621 (SEQ ID NO:1198), Public GI ID no.15218305 (SEQ ID NO:1199), Public GI ID no.15219640 (SEQ ID NO:1200), Public GI ID no.18409345 (SEQ ID NO:1201), Public GI ID no.6522545 (SEQ ID NO:1202), Public GI ID no.15237274 (SEQ ID NO:1203), Public GI ID no.26452377 (SEQ ID NO:1204), Ceres CLONE ID no.33629 (SEQ ID NO:1206), Ceres CLONE ID no.1064407 (SEQ ID NO:1208), Ceres CLONE ID no.1656310 (SEQ ID NO:1213), Public GI ID no.92885257 (SEQ ID NO:1214), Public GI ID no.92868571 (SEQ ID NO:1216), Public GI ID no.53689778 (SEQ ID NO:1217), Ceres CLONE ID no.835598 (SEQ ID NO:1219), Ceres CLONE ID no.575649 (SEQ ID NO:1221), Ceres CLONE ID no.376567 (SEQ ID NO:1225), Ceres CLONE ID no.1284191 (SEQ ID NO:1227), Ceres CLONE ID no.367175 (SEQ ID NO:1229), Ceres CLONE ID no.100748296 (SEQ ID NO:1230), Ceres CLONE ID no.1597176 (SEQ ID NO:1232), Ceres CLONE ID no.375636 (SEQ ID NO:1234), Ceres CLONE ID no.288123 (SEQ ID NO:1236), Ceres CLONE ID no.303582 (SEQ ID NO:1238), Ceres CLONE ID no.1604759 (SEQ ID NO:1240), Ceres CLONE ID no.1955192 (SEQ ID NO:1242), Ceres CLONE ID no.2008687 (SEQ ID NO:1244), Ceres CLONE ID no.1995843 (SEQ ID NO:1248), Ceres CLONE ID no.2008591 (SEQ ID NO:1250), Ceres CLONE ID no.2046826 (SEQ ID NO:1252), Ceres CLONE ID no.1985573 (SEQ ID NO:1254), Public GI ID no.125541129 (SEQ ID NO:1255), Public GI ID no.125528922 (SEQ ID NO:1256), Public GI ID no.115487590 (SEQ ID NO:1257), Public GI ID no.115448671 (SEQ ID NO:1259), Public GI ID no.125596564 (SEQ ID NO:1260), Public GI ID no.125573161 (SEQ ID NO:1261), Public GI ID no.48716463 (SEQ ID NO:1262), Ceres ANNOT ID no.6054246 (SEQ ID NO:1266), Ceres ANNOT ID no.6086570 (SEQ ID NO:1268), Ceres ANNOT ID no.6024957 (SEQ ID NO:1270), Ceres ANNOT ID no.6016867 (SEQ ID NO:1272), Ceres ANNOT ID no.6091369 (SEQ ID NO:1274), and sequences identified as functional homologs of the sequences of FIG. 14, as set forth in the sequence listing.

Polypeptides are shown in the sequence listing that have HMM bit scores greater than 180 when fitted to an HMM generated from the amino acid sequences set forth in FIG. 15. Such polypeptides include At5g46170 (SEQ ID NO:1277), Ceres CLONE ID no.1926352 (SEQ ID NO:1279), Ceres ANNOT ID no.1448905 (SEQ ID NO:1285), Public GI ID no.15236865 (SEQ ID NO:1294), Ceres CLONE ID no.934771 (SEQ ID NO:1301), Ceres CLONE ID no.338386 (SEQ ID NO:1303), Ceres CLONE ID no.1780691 (SEQ ID NO:1317), Public GI ID no.115464819 (SEQ ID NO:1326), Ceres CLONE ID no.1848576 (SEQ ID NO:1281), Ceres CLONE ID no.1981528 (SEQ ID NO:1283), Ceres ANNOT ID no.1465978 (SEQ ID NO:1287), Ceres ANNOT ID no.1504997 (SEQ ID NO:1289), Ceres ANNOT ID no.1451909 (SEQ ID NO:1291), Ceres ANNOT ID no.1461635 (SEQ ID NO:1293), Public GI ID no.18397400 (SEQ ID NO:1295), Ceres CLONE ID no.16226 (SEQ ID NO:1297), Public GI ID no.18411823 (SEQ ID NO:1298), Public GI ID no.15219845 (SEQ ID NO:1299), Ceres CLONE ID no.1276710 (SEQ ID NO:1305), Ceres CLONE ID no.1479310 (SEQ ID NO:1307), Ceres CLONE ID no.376230 (SEQ ID NO:1309), Ceres CLONE ID no.1290713 (SEQ ID NO:1311), Ceres CLONE ID no.321681 (SEQ ID NO:1313), Ceres CLONE ID no.1869072 (SEQ ID NO:1315), Ceres CLONE ID no.1818502 (SEQ ID NO:1319), Ceres CLONE ID no.1750477 (SEQ ID NO:1321), Public GI ID no.125552947 (SEQ ID NO:1322), Public GI ID no.125527862 (SEQ ID NO:1323), Public GI ID no.125543660 (SEQ ID NO:1324), Public GI ID no.125528123 (SEQ ID NO:1325), Public GI ID no.115440195 (SEQ ID NO:1327), Public GI ID no.115452717 (SEQ ID NO:1328), Public GI ID no.115440629 (SEQ ID NO:1329), Public GI ID no.115464599 (SEQ ID NO:1330), Public GI ID no.20161462 (SEQ ID NO:1331), Public GI ID no.125586076 (SEQ ID NO:1332), Ceres CLONE ID no.1823216 (SEQ ID NO:1334), Ceres ANNOT ID no.6040230 (SEQ ID NO:1336), Ceres ANNOT ID no.6015489 (SEQ ID NO:1338), Ceres ANNOT ID no.6042890 (SEQ ID NO:1340), Ceres ANNOT ID no.6040033 (SEQ ID NO:1342), Ceres ANNOT ID no.6018414 (SEQ ID NO:1344), and sequences identified as functional homologs of the sequences of FIG. 15, as set forth in the sequence listing.

Polypeptides are shown in the sequence listing that have HMM bit scores greater than 60 when fitted to an HMM generated from the amino acid sequences set forth in FIG. 16. Such polypeptides include At4g32280 (SEQ ID NO:1347), Ceres CLONE ID no.285028 (SEQ ID NO:1419), Ceres CLONE ID no.100969565 (SEQ ID NO:1422), Public GI ID no.1352057 (SEQ ID NO:1427), Ceres ANNOT ID no.1453784 (SEQ ID NO:1429), Public GI ID no.452777 (SEQ ID NO:1430), Public GI ID no.92873297 (SEQ ID NO:1431), Ceres ANNOT ID no.1452612 (SEQ ID NO:1349), Ceres CLONE ID no.520455 (SEQ ID NO:1351), Public GI ID no.75271810 (SEQ ID NO:1352), Public GI ID no.115489446 (SEQ ID NO:1353), Ceres CLONE ID no.499878 (SEQ ID NO:1355), Ceres ANNOT ID no.1491840 (SEQ ID NO:1357), Public GI ID no.125587204 (SEQ ID NO:1358), Ceres CLONE ID no.320997 (SEQ ID NO:1360), Ceres ANNOT ID no.1455585 (SEQ ID NO:1362), Ceres ANNOT ID no.1499460 (SEQ ID NO:1364), Ceres CLONE ID no.334484 (SEQ ID NO:1366), Ceres CLONE ID no.100819481 (SEQ ID NO:1367), Public GI ID no.115462401 (SEQ ID NO:1368), Ceres CLONE ID no.1448136 (SEQ ID NO:1370), Ceres CLONE ID no.277751 (SEQ ID NO:1372), Ceres ANNOT ID no.1491839 (SEQ ID NO:1374), Ceres CLONE ID no.100913241 (SEQ ID NO:1375), Ceres CLONE ID no.1053224 (SEQ ID NO:1377), Ceres CLONE ID no.425766 (SEQ ID NO:1379), Ceres CLONE ID no.485480 (SEQ ID NO:1381), Ceres CLONE ID no.474845 (SEQ ID NO:1383), Ceres CLONE ID no.354561 (SEQ ID NO:1385), Ceres CLONE ID no.540858 (SEQ ID NO:1387), Ceres CLONE ID no.2032994 (SEQ ID NO:1389), Ceres CLONE ID no.2015315 (SEQ ID NO:1391), Ceres CLONE ID no.2016149 (SEQ ID NO:1393), Ceres CLONE ID no.1922843 (SEQ ID NO:1395), Ceres CLONE ID no.2000263 (SEQ ID NO:1397), Ceres CLONE ID no.1943510 (SEQ ID NO:1399), Ceres CLONE ID no.1835498 (SEQ ID NO:1401), Ceres CLONE ID no.101116694 (SEQ ID NO:1402), Ceres CLONE ID no.1930596 (SEQ ID NO:1404), Ceres CLONE ID no.846036 (SEQ ID NO:1406), Ceres CLONE ID no.941614 (SEQ ID NO:1408), Ceres CLONE ID no.238788 (SEQ ID NO:1410), Public GI ID no.125554220 (SEQ ID NO:1411), Public GI ID no.125559895 (SEQ ID NO:1412), Public GI ID no.75252070 (SEQ ID NO:1413), Public GI ID no.115466632 (SEQ ID NO:1414), Public GI ID no.125541525 (SEQ ID NO:1415), Ceres CLONE ID no.1805110 (SEQ ID NO:1417), Ceres CLONE ID no.1725309 (SEQ ID NO:1421), Ceres CLONE ID no.100861679 (SEQ ID NO:1423), Public GI ID no.75226278 (SEQ ID NO:1424), Public GI ID no.125525030 (SEQ ID NO:1425), Public GI ID no.115435474 (SEQ ID NO:1426), Ceres CLONE ID no.1728516 (SEQ ID NO:1433), Public GI ID no.115467910 (SEQ ID NO:1434), Public GI ID no.15239950 (SEQ ID NO:1435), Public GI ID no.4887012 (SEQ ID NO:1436), Ceres ANNOT ID no.1478544 (SEQ ID NO:1438), Public GI ID no.90811713 (SEQ ID NO:1439), Public GI ID no.25989504 (SEQ ID NO:1440), Ceres CLONE ID no.1113354 (SEQ ID NO:1442), Ceres CLONE ID no.1113630 (SEQ ID NO:1444), Ceres ANNOT ID no.6072030 (SEQ ID NO:1446), Ceres ANNOT ID no.6025654 (SEQ ID NO:1448), Ceres ANNOT ID no.6091150 (SEQ ID NO:1450), Ceres ANNOT ID no.6100390 (SEQ ID NO:1452), and sequences identified as functional homologs of the sequences of FIG. 16, as set forth in the sequence listing.

Polypeptides are shown in the sequence listing that have HMM bit scores greater than 270 when fitted to an HMM generated from the amino acid sequences set forth in FIG. 17. Such polypeptides include At3g02830 (SEQ ID NO:1457), Ceres CLONE ID no.1924904 (SEQ ID NO:1460), Ceres ANNOT ID no.1543346 (SEQ ID NO:1462), Public GI ID no.18396338 (SEQ ID NO:1467), Ceres CLONE ID no.833872 (SEQ ID NO:1471), Ceres CLONE ID no.1579587 (SEQ ID NO:1475), Ceres CLONE ID no.1786411 (SEQ ID NO:1477), Public GI ID no.108864370 (SEQ ID NO:1480), SEQ ID NO:1458, Ceres ANNOT ID no.1532932 (SEQ ID NO:1464), Ceres ANNOT ID no.1489955 (SEQ ID NO:1466), Public GI ID no.4928917 (SEQ ID NO:1468), Public GI ID no.6728979 (SEQ ID NO:1469), Ceres CLONE ID no.285780 (SEQ ID NO:1473), Public GI ID no.125528863 (SEQ ID NO:1478), Public GI ID no.125536365 (SEQ ID NO:1479), Public GI ID no.108864369 (SEQ ID NO:1481), Public GI ID no.115488274 (SEQ ID NO:1482), Public GI ID no.125577099 (SEQ ID NO:1483), Public GI ID no.125573110 (SEQ ID NO:1484), Public GI ID no.124359159 (SEQ ID NO:1485), Public GI ID no.62901479 (SEQ ID NO:1486), Ceres ANNOT ID no.6016783 (SEQ ID NO:1488), Ceres ANNOT ID no.6020759 (SEQ ID NO:1490), Ceres ANNOT ID no.6028676 (SEQ ID NO:1492), Ceres ANNOT ID no.6028677 (SEQ ID NO:1494), and sequences identified as functional homologs of the sequences of FIG. 17, as set forth in the sequence listing.

Polypeptides are shown in the sequence listing that have HMM bit scores greater than 70 when fitted to an HMM generated from the amino acid sequences set forth in FIG. 18. Such polypeptides include At4g08920 (SEQ ID NO:1497), Ceres ANNOT ID no.1443463 (SEQ ID NO:1499), Public GI ID no.13605525 (SEQ ID NO:1502), Public GI ID no.94965681 (SEQ ID NO:1506), Public GI ID no.28201254 (SEQ ID NO:1512), Ceres ANNOT ID no.1504954 (SEQ ID NO:1501), Public GI ID no.2499553 (SEQ ID NO:1503), Public GI ID no.738308 (SEQ ID NO:1504), Public GI ID no.4325368 (SEQ ID NO:1505), Ceres CLONE ID no.919923 (SEQ ID NO:1508), Ceres CLONE ID no.1659764 (SEQ ID NO:1510), Public GI ID no.125539984 (SEQ ID NO:1511), Public GI ID no.21740729 (SEQ ID NO:1513), Public GI ID no.115458700 (SEQ ID NO:1514), Public GI ID no.125590574 (SEQ ID NO:1515), Public GI ID no.16444957 (SEQ ID NO:1516), Ceres CLONE ID no.1784494 (SEQ ID NO:1518), Public GI ID no.77963980 (SEQ ID NO:1519), Public GI ID 110.124361190 (SEQ ID NO:1520), Public GI ID no.37725007 (SEQ ID NO:1521), Public GI ID no.45935258 (SEQ ID NO:1522), Public GI ID no.15559008 (SEQ ID NO:1523), Public GI ID no.38037416 (SEQ ID NO:1524), Public GI ID no.77963974 (SEQ ID NO:1525), Ceres ANNOT ID no.6112581 (SEQ ID NO:1527), Public GI ID no.56553448 (SEQ ID NO:1528), Public GI ID no.23506659 (SEQ ID NO:1529), Ceres ANNOT ID no.6118060 (SEQ ID NO:1531), Public GI ID no.46446306 (SEQ ID NO:1532), Public GI ID no.114321405 (SEQ ID NO:1533), Public GI ID no.83858274 (SEQ ID NO:1534), Public GI ID no.154250969 (SEQ ID NO:1535), Public GI ID no.83594235 (SEQ ID NO:1536), and sequences identified as functional homologs of the sequences of FIG. 18, as set forth in the sequence listing.

Polypeptides are shown in the sequence listing that have HMM bit scores greater than 130 when fitted to an HMM generated from the amino acid sequences set forth in FIG. 19. Such polypeptides include At4g11660 (SEQ ID NO:1587), Ceres CLONE ID no.1839577 (SEQ ID NO:1589), Ceres ANNOT ID no.1491567 (SEQ ID NO:1591), Ceres CLONE ID no.574505 (SEQ ID NO:1596), Public GI ID no.56117815 (SEQ ID NO:1597), Public GI ID no.92874021 (SEQ ID NO:1603), Public GI ID no.123684 (SEQ ID NO:1605), Public GI ID no.5821136 (SEQ ID NO:1606), Ceres CLONE ID no.283366 (SEQ ID NO:1609), Public GI ID no.16118447 (SEQ ID NO:1612), Public GI ID no.125562434 (SEQ ID NO:1614), Ceres ANNOT ID no.1438739 (SEQ ID NO:1593), Public GI ID no.89274218 (SEQ ID NO:1594), Public GI ID no.115521211 (SEQ ID NO:1598), Public GI ID no.115521213 (SEQ ID NO:1599), Public GI ID no.115521217 (SEQ ID NO:1600), Public GI ID no.115521209 (SEQ ID NO:1601), Public GI ID no.115521215 (SEQ ID NO:1602), Public GI ID no.11386827 (SEQ ID NO:1604), Public GI ID no.25052685 (SEQ ID NO:1607), Ceres CLONE ID no.1440437 (SEQ ID NO:1611), Public GI ID no.125564440 (SEQ ID NO:1613), Public GI ID no.116309817 (SEQ ID NO:1615), Public GI ID no.125549382 (SEQ ID NO:1616), Public GI ID no.52077317 (SEQ ID NO:1617), Public GI ID no.115477655 (SEQ ID NO:1618), Public GI ID no.42408097 (SEQ ID NO:1619), Public GI ID no.115459982 (SEQ ID NO:1620), Public GI ID no.33591096 (SEQ ID NO:1621), Ceres CLONE ID no.484753 (SEQ ID NO:1623), Ceres ANNOT ID no.6035291 (SEQ ID NO:1625), and sequences identified as functional homologs of the sequences of FIG. 19, as set forth in the sequence listing.

Polypeptides are shown in the sequence listing that have HMM bit scores greater than 570 when fitted to an HMM generated from the amino acid sequences set forth in FIG. 20. Such polypeptides include At2g45700 (SEQ ID NO:1635), Ceres ANNOT ID no.1508307 (SEQ ID NO:1637), Public GI ID no.1495267 (SEQ ID NO:1642), Public GI ID no.87241310 (SEQ ID NO:1644), Ceres CLONE ID no.938390 (SEQ ID NO:1646), Ceres CLONE ID no.272338 (SEQ ID NO:1648), Ceres CLONE ID no.1993510 (SEQ ID NO:1650), Public GI ID no.125563862 (SEQ ID NO:1651), Public GI ID no.125605833 (SEQ ID NO:1653), Public GI ID no.6899919 (SEQ ID NO:1632), Ceres ANNOT ID no.1455110 (SEQ ID NO:1639), Ceres ANNOT ID no.1525218 (SEQ ID NO:1641), Public GI ID no.15231597 (SEQ ID NO:1643), Public GI ID no.125548147 (SEQ ID NO:1652), Public GI ID no.51091343 (SEQ ID NO:1654), Public GI ID no.115479355 (SEQ ID NO:1655), Ceres ANNOT ID no.6042086 (SEQ ID NO:1657), Ceres ANNOT ID no.6029903 (SEQ ID NO:1659), and sequences identified as functional homologs of the sequences of FIG. 20, as set forth in the sequence listing.

Polypeptides are shown in the sequence listing that have HMM bit scores greater than 150 when fitted to an HMM generated from the amino acid sequences set forth in FIG. 21. Such polypeptides include At2g35940 (SEQ ID NO:1540), Ceres CLONE ID no.1943265 (SEQ ID NO:1543), Ceres ANNOT ID no.1454522 (SEQ ID NO:1547), Public GI ID no.31323447 (SEQ ID NO:1556), Ceres CLONE ID no.1583941 (SEQ ID NO:1561), Ceres CLONE ID no.1792942 (SEQ ID NO:1563), Public GI ID no.77548772 (SEQ ID NO:1565), Public GI ID no.84453182 (SEQ ID NO:1567), Public GI ID no.31746344 (SEQ ID NO:1541), Ceres CLONE ID no.1926640 (SEQ ID NO:1545), Ceres ANNOT ID no.1475125 (SEQ ID NO:1549), Ceres ANNOT ID no.1439653 (SEQ ID NO:1551), Ceres ANNOT ID no.1461995 (SEQ ID NO:1553), Public GI ID no.13877517 (SEQ ID NO:1554), Public GI ID no.7239157 (SEQ ID NO:1555), Public GI ID no.22652125 (SEQ ID NO:1557), Public GI ID no.22652115 (SEQ ID NO:1558), Public GI ID no.22652117 (SEQ ID NO:1559), Public GI ID no.125535858 (SEQ ID NO:1564), Public GI ID no.125578581 (SEQ ID NO:1566), Public GI ID no.13752407 (SEQ ID NO:1568), Ceres ANNOT ID no.6098817 (SEQ ID NO:1570), Ceres ANNOT ID no.6039430 (SEQ ID NO:1572), Ceres ANNOT ID no.6068141 (SEQ ID NO:1574), Ceres ANNOT ID no.6033916 (SEQ ID NO:1576), Ceres ANNOT ID no.6034399 (SEQ ID NO:1578), Ceres ANNOT ID no.6068617 (SEQ ID NO:1580), Ceres ANNOT ID no.6026318 (SEQ ID NO:1582), Ceres ANNOT ID no.6107650 (SEQ ID NO:1584), and sequences identified as functional homologs of the sequences of FIG. 21, as set forth in the sequence listing.

Polypeptides are shown in the sequence listing that have HMM bit scores greater than 1340 when fitted to an HMM generated from the amino acid sequences set forth in FIG. 22. Such polypeptides include At1g04400 (SEQ ID NO:538), Public GI ID no.5731739 (SEQ ID NO:539), Ceres ANNOT ID no.1538045 (SEQ ID NO:541), Public GI ID no.29467479 (SEQ ID NO:542), Public GI ID no.133921974 (SEQ ID NO:543), Public GI ID no.113197027 (SEQ ID NO:544), Public GI ID no.92879277 (SEQ ID NO:545), Public GI ID no.45935260 (SEQ ID NO:546), Public GI ID no.8101444 (SEQ ID NO:547), Public GI ID no.78217443 (SEQ ID NO:548), Public GI ID no.28372347 (SEQ ID NO:549), Public GI ID no.16416405 (SEQ ID NO:550), Ceres ANNOT ID no.1484634 (SEQ ID NO:552), Ceres ANNOT ID no.1451869 (SEQ ID NO:554), Public GI ID no.25407462 (SEQ ID NO:555), Public GI ID no.29467481 (SEQ ID NO:556), Public GI ID no.29467477 (SEQ ID NO:557), Public GI ID no.45935264 (SEQ ID NO:558), Public GI ID no.5524201 (SEQ ID NO:559), Public GI ID no.78217441 (SEQ ID NO:560), Public GI ID no.3551221 (SEQ ID NO:561), Public GI ID no.3551219 (SEQ ID NO:562), Public GI ID no.23954324 (SEQ ID NO:563), Public GI ID no.125582937 (SEQ ID NO:564), Public GI ID no.83764373 (SEQ ID NO:565), Ceres ANNOT ID no.6045327 (SEQ ID NO:567), and sequences identified as functional homologs of the sequences of FIG. 22, as set forth in the sequence listing.

Polypeptides are shown in the sequence listing that have HMM bit scores greater than 80 when fitted to an HMM generated from the amino acid sequences set forth in FIG. 23. Such polypeptides include At3g45610 (SEQ ID NO:606), Public GI ID no.92873064 (SEQ ID NO:607), Public GI ID no.37051125 (SEQ ID NO:608), Public GI ID no.112363376 (SEQ ID NO:609), Ceres CLONE ID no.1938524 (SEQ ID NO:611), Ceres ANNOT ID no.1473601 (SEQ ID NO:613), Ceres ANNOT ID no.1468397 (SEQ ID NO:615), Public GI ID no.21554185 (SEQ ID NO:616), Public GI ID no.18424330 (SEQ ID NO:617), Public GI ID no.8885571 (SEQ ID NO:618), Ceres CLONE ID no.20852 (SEQ ID NO:620), Public GI ID no.21553763 (SEQ ID NO:621), Public GI ID no.18401763 (SEQ ID NO:622), Ceres CLONE ID no.16423 (SEQ ID NO:624), Public GI ID no.112363380 (SEQ ID NO:625), Public GI ID no.6092016 (SEQ ID NO:626), Ceres CLONE ID no.770468 (SEQ ID NO:628), Public GI ID no.113205234 (SEQ ID NO:629), Ceres ANNOT ID no.6094775 (SEQ ID NO:631), and sequences identified as functional homologs of the sequences of FIG. 23, as set forth in the sequence listing.

Polypeptides are shown in the sequence listing that have HMM bit scores greater than 110 when fitted to an HMM generated from the amino acid sequences set forth in FIG. 24. Such polypeptides include At4g08330 (SEQ ID NO:570), Ceres CLONE ID no.1919714 (SEQ ID NO:572), Ceres ANNOT ID no.1443290 (SEQ ID NO:574), Ceres CLONE ID no.1042157 (SEQ ID NO:576), Ceres CLONE ID no.1384304 (SEQ ID NO:578), Public GI ID no.115464375 (SEQ ID NO:579), Ceres CLONE ID no.100028078 (SEQ ID NO:580), Ceres ANNOT ID no.1452096 (SEQ ID NO:582), Ceres ANNOT ID no.1503869 (SEQ ID NO:584), Ceres ANNOT ID no.1525651 (SEQ ID NO:586), Ceres CLONE ID no.1645639 (SEQ ID NO:588), Ceres CLONE ID no.603237 (SEQ ID NO:590), Ceres CLONE ID no.340925 (SEQ ID NO:592), Ceres CLONE ID no.293238 (SEQ ID NO:594), Ceres CLONE ID no.483742 (SEQ ID NO:596), Ceres CLONE ID no.1460255 (SEQ ID NO:598), Ceres CLONE ID no.1400107 (SEQ ID NO:600), Public GI ID no.115440865 (SEQ ID NO:601), Ceres ANNOT ID no.6016008 (SEQ ID NO:603), and sequences identified as functional homologs of the sequences of FIG. 24, asset forth in the sequence listing.

E. Percent Identity

In some embodiments, an SD+EODFR and/or low light-tolerance polypeptide has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to one of the amino acid sequences set forth in SEQ ID NO:3, SEQ ID NO:70, SEQ ID NO:129, SEQ ID NO:317, SEQ ID NO:337, SEQ ID NO:456, SEQ ID NO:538, SEQ ID NO:570, SEQ ID NO:606, SEQ ID NO:634, SEQ ID NO:644, SEQ ID NO:850, SEQ ID NO:907, SEQ ID NO:953, SEQ ID NO:1024, SEQ ID NO:1047, SEQ ID NO:1151, SEQ ID NO:1277, SEQ ID NO:1347, SEQ ID NO:1457, SEQ ID NO:1497, SEQ ID NO:1540, SEQ ID NO:1587, SEQ ID NO:1630, and SEQ ID NO:1635. Polypeptides having such a percent sequence identity often have a domain indicative of an SD+EODFR and/or low light-tolerance polypeptide and/or have an HMM bit score that is greater than 20, as discussed above. Amino acid sequences of SD+EODFR and/or low light-tolerance polypeptides having at least 40% sequence identity to one of the amino acid sequences set forth in SEQ ID NO:3, SEQ ID NO:70, SEQ ID NO:129, SEQ ID NO:317, SEQ ID NO:337, SEQ ID NO:456, SEQ ID NO:538, SEQ ID NO:570, SEQ ID NO:606, SEQ ID NO:634, SEQ ID NO:644, SEQ ID NO:850, SEQ ID NO:907, SEQ ID NO:953, SEQ ID NO:1024, SEQ ID NO:1047, SEQ ID NO:1151, SEQ ID NO:1277, SEQ ID NO:1347, SEQ ID NO:1457, SEQ ID NO:1497, SEQ ID NO:1540, SEQ ID NO:1587, and SEQ ID NO:1635 are provided in FIGS. 1-24.

"Percent sequence identity" refers to the degree of sequence identity between any given reference sequence, e.g., SEQ ID NO:3, and a candidate SD+EODFR and/or low light-tolerance sequence. A candidate sequence typically has a length that is from 80 percent to 200 percent of the length of the reference sequence, e.g., 82, 85, 87, 89, 90, 93, 95, 97, 99, 100, 105, 110, 115, 120, 130, 140, 150, 160, 170, 180, 190, or 200 percent of the length of the reference sequence. A percent identity for any candidate nucleic acid or polypeptide relative to a reference nucleic acid or polypeptide can be determined as follows. A reference sequence (e.g., a nucleic acid sequence or an amino acid sequence) is aligned to one or more candidate sequences using the computer program ClustalW (version 1.83, default parameters), which allows alignments of nucleic acid or polypeptide sequences to be carried out across their entire length (global alignment). Chenna et al., Nucleic Acids Res., 31(13):3497-500 (2003).

ClustalW calculates the best match between a reference and one or more candidate sequences, and aligns them so that identities, similarities and differences can be determined. Gaps of one or more residues can be inserted into a reference sequence, a candidate sequence, or both, to maximize sequence alignments. For fast pairwise alignment of nucleic acid sequences, the following default parameters are used: word size: 2; window size: 4; scoring method: percentage; number of top diagonals: 4; and gap penalty: 5. For multiple sequence alignment of nucleic acid sequences, the following parameters are used: gap opening penalty: 10.0; gap extension penalty: 5.0; and weight transitions: yes. For fast pairwise alignment of protein sequences, the following parameters are used: word size: 1; window size: 5; scoring method: percentage; number of top diagonals: 5; gap penalty: 3. For multiple alignment of protein sequences, the following parameters are used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; residue-specific gap penalties: on. The ClustalW output is a sequence alignment that reflects the relationship between sequences. ClustalW can be run, for example, at the Baylor College of Medicine Search Launcher site (searchlauncher.bcm.tmc.edu/multi-align/multi-align.html) and at the European Bioinformatics Institute site on the World Wide Web (ebi.ac.uk/clustalw).

To determine percent identity of a candidate nucleic acid or amino acid sequence to a reference sequence, the sequences are aligned using ClustalW, the number of identical matches in the alignment is divided by the length of the reference sequence, and the result is multiplied by 100. It is noted that the percent identity value can be rounded to the nearest tenth. For example, 78.11, 78.12, 78.13, and 78.14 are rounded down to 78.1, while 78.15, 78.16, 78.17, 78.18, and 78.19 are rounded up to 78.2.

In some cases, an SD+EODFR and/or low light-tolerance polypeptide has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:3. Amino acid sequences of polypeptides having greater than 40% sequence identity to the polypeptide set forth in SEQ ID NO:3 are provided in FIG. 1. Such polypeptides include Ceres CLONE ID no. 1844057 (SEQ ID NO:7), Ceres ANNOT ID no. 1469148 (SEQ ID NO:22), Public GI ID no. 18390998 (SEQ ID NO:25), Ceres CLONE ID no. 1065656 (SEQ ID NO:32), Ceres CLONE ID no. 1652677 (SEQ ID NO:36), Public GI ID no. 92874556 (SEQ ID NO:49), Ceres CLONE ID no. 1329161 (SEQ ID NO:53), Ceres CLONE ID no. 1030378 (SEQ ID NO:55), Ceres CLONE ID no. 1413787 (SEQ ID NO:57), and Public GI ID no. 125543598 (SEQ ID NO:60).

In some cases, a SD+EODFR and/or low light-tolerance polypeptide has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:70. Amino acid sequences of polypeptides having greater than 40% sequence identity to the polypeptide set forth in SEQ ID NO:70 are provided in FIG. 2. Such polypeptides include Ceres CLONE ID no. 1975934 (SEQ ID NO:72), Ceres ANNOT ID no. 1529913 (SEQ ID NO:80), Ceres CLONE ID no. 977794 (SEQ ID NO:93), Public GI ID no. 42362378 (SEQ ID NO:96), Public GI ID no. 23899378 (SEQ ID NO:99), Public GI ID no. 15963346 (SEQ ID NO:101), Public GI ID no. 15963344+B816 (SEQ ID NO:102), Public GI ID no. 92429657 (SEQ ID NO:103), Ceres CLONE ID no. 746644 (SEQ ID NO:105), Ceres CLONE ID no. 623089 (SEQ ID NO:109), Ceres CLONE ID no. 1913678 (SEQ ID NO:115), and Public GI ID no. 115450609 (SEQ ID NO:119).

In some cases, a SD+EODFR and/or low light-tolerance polypeptide has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:129. Amino acid sequences of polypeptides having greater than 40% sequence identity to the polypeptide set forth in SEQ ID NO:129 are provided in FIG. 3. Such polypeptides include Public GI ID no. 34550779 (SEQ ID NO:133), Ceres CLONE ID no. 1932235 (SEQ ID NO:137), Ceres CLONE ID no. 981738 (SEQ ID NO:201), Ceres CLONE ID no. 565974 (SEQ ID NO:209), Public GI ID no. 1352058 (SEQ ID NO:231), Public GI ID no. 11131101 (SEQ ID NO:234), Public GI ID no. 4887018 (SEQ ID NO:236), Public GI ID no. 4887018 (SEQ ID NO:236), Ceres CLONE ID no. 644455 (SEQ ID NO:247), Ceres CLONE ID no. 1731500 (SEQ ID NO:270), Public GI ID no. 20269063 (SEQ ID NO:300), Public GI ID no. 50404477 (SEQ ID NO:302), and Public GI ID no. 62125392 (SEQ ID NO:303).

In some cases, a SD+EODFR and/or low light-tolerance polypeptide has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:317. Amino acid sequences of polypeptides having greater than 40% sequence identity to the polypeptide set forth in SEQ ID NO:317 are provided in FIG. 4. Such polypeptides include Ceres CLONE ID no. 1842125 (SEQ ID NO:319), Ceres ANNOT ID no. 1461360 (SEQ ID NO:321), Ceres CLONE ID no. 480906 (SEQ ID NO:327), Public GI ID no. 92889352 (SEQ ID NO:330), and Public GI ID no. 56201850 (SEQ ID NO:330).

In some cases, a SD+EODFR and/or low light-tolerance polypeptide has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:337. Amino acid sequences of polypeptides having greater than 40% sequence identity to the polypeptide set forth in SEQ ID NO:337 are provided in FIG. 5. Such polypeptides include At2g04240 Ceres CLONE ID no. 952050 (SEQ ID NO:339), Public GI ID no. 115477050 (SEQ ID NO:349), Public GI ID no. 87162911 (SEQ ID NO:355), Ceres CLONE ID no. 1790901 (SEQ ID NO:357), Ceres CLONE ID no. 1460088 (SEQ ID NO:370), Ceres CLONE ID no. 1734065 (SEQ ID NO:393), Ceres CLONE ID no. 473509 (SEQ ID NO:395), Ceres CLONE ID no. 849918 (SEQ ID NO:401), Ceres CLONE ID no. 633470 (SEQ ID NO:409), Ceres CLONE ID no. 1808334 (SEQ ID NO:417), and Ceres ANNOT ID no. 1525600 (SEQ ID NO:437).

In some cases, a SD+EODFR and/or low light-tolerance polypeptide has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:456. Amino acid sequences of polypeptides having greater than 40% sequence identity to the polypeptide set forth in SEQ ID NO:456 are provided in FIG. 6. Such polypeptides include Public GI ID no. 58430585 (SEQ ID NO:457), Ceres CLONE ID no. 1842825 (SEQ ID NO:466), Ceres ANNOT ID no. 1449721 (SEQ ID NO:474), Public GI ID no. 41323978 (SEQ ID NO:475), Public GI ID no. 2895186 (SEQ ID NO:478), Public GI ID no. 22854950 (SEQ ID NO:481), Public GI ID no. 116010474 (SEQ ID NO:485), Public GI ID no. 4091804 (SEQ ID NO:488), Public GI ID no. 60459257 (SEQ ID NO:494), Public GI ID no. 45544881 (SEQ ID NO:496), Public GI ID no. 36789802 (SEQ ID NO:498), Public GI ID no. 92875402 (SEQ ID NO:508), Public GI ID no. 118406898 (SEQ ID NO:510), Public GI ID no. 107770485 (SEQ ID NO:511), Public GI ID no. 21655154 (SEQ ID NO:532), Public GI ID no. 90657642 (SEQ ID NO:536), and Ceres CLONE ID no. 1569555 (SEQ ID NO:1842).

In some cases, a SD+EODFR and/or low light-tolerance polypeptide has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:634. Amino acid sequences of polypeptides having greater than 40% sequence identity to the polypeptide set forth in SEQ ID NO:634 are provided in FIG. 7. Such polypeptides include Public GI ID no. 98961985 (SEQ ID NO:637).

In some cases, a SD+EODFR and/or low light-tolerance polypeptide has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:644. Amino acid sequences of polypeptides having greater than 40% sequence identity to the polypeptide set forth in SEQ ID NO:644 are provided in FIG. 8. Such polypeptides include SEQ ID NO:645, Ceres CLONE ID no. 1849479 (SEQ ID NO:767), Public GI ID no. 89275008 (SEQ ID NO:796), Public GI ID no. 120400525 (SEQ ID NO:797), Public GI ID no. 98980426 (SEQ ID NO:804), Public GI ID no. 71983373 (SEQ ID NO:808), Public GI ID no. 41351817 (SEQ ID NO:809), Public GI ID no. 76446191 (SEQ ID NO:811), Public GI ID no. 5616086 (SEQ ID NO:813), Ceres CLONE ID no. 1052602 (SEQ ID NO:826), Public GI ID no. 72068957 (SEQ ID NO:830), Public GI ID no. 71534113 (SEQ ID NO:831), Public GI ID no. 37147896 (SEQ ID NO:832), Public GI ID no. 92918850 (SEQ ID NO:834), Public GI ID no. 40647095 (SEQ ID NO:835), Ceres ANNOT ID no. 1527711 (SEQ ID NO:837), Public GI ID no. 71041116 (SEQ ID NO:838), Public GI ID no. 12003384 (SEQ ID NO:839), Public GI ID no. 18535580 (SEQ ID NO:840), and Public GI ID no. 115353971 (SEQ ID NO:1843).

In some cases, a SD+EODFR and/or low light-tolerance polypeptide has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:850. Amino acid sequences of polypeptides having greater than 40% sequence identity to the polypeptide set forth in SEQ ID NO:850 are provided in FIG. 9. Such polypeptides include Ceres CLONE ID no.1833093 (SEQ ID NO:853), Ceres ANNOT ID no.1502190 (SEQ ID NO:857), Ceres CLONE ID no.565641 (SEQ ID NO:876), Public GI ID no.87240507 (SEQ ID NO:877), Ceres CLONE ID no.1325382 (SEQ ID NO:881), Ceres CLONE ID no.1558265 (SEQ ID NO:885), Ceres CLONE ID no.1823669 (SEQ ID NO:895), and Public GI ID no.115464921 (SEQ ID NO:898).

In some cases, a SD+EODFR and/or low light-tolerance polypeptide has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:907. Amino acid sequences of polypeptides having greater than 40% sequence identity to the polypeptide set forth in SEQ ID NO:907 are provided in FIG. 10. Such polypeptides include Ceres CLONE ID no.1940797 (SEQ ID NO:909), Ceres ANNOT ID no.1538900 (SEQ ID NO:911), Ceres CLONE ID no.1126868 (SEQ ID NO:922), Public GI ID no.89257684 (SEQ ID NO:923), Public GI ID no.124360460 (SEQ ID NO:929), Public GI ID no.62865694 (SEQ ID NO:931), Public GI ID no.62865692 (SEQ ID NO:932), Ceres CLONE ID no.260368 (SEQ ID NO:936), Ceres CLONE ID no.1873510 (SEQ ID NO:947), Public GI ID no.125541662 (SEQ ID NO:948), Public GI ID no.48716268 (SEQ ID NO:950), and Public GI ID no. 62865696 (SEQ ID NO:1844).

In some cases, a SD+EODFR and/or low light-tolerance polypeptide has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:953. Amino acid sequences of polypeptides having greater than 40% sequence identity to the polypeptide set forth in SEQ ID NO:953 are provided in FIG. 11. Such polypeptides include Ceres CLONE ID no.1798705 (SEQ ID NO:955), Ceres ANNOT ID no.1458907 (SEQ ID NO:963), Ceres CLONE ID no.1090409 (SEQ ID NO:971), Ceres CLONE ID no.479817 (SEQ ID NO:977), Ceres CLONE ID no.1041793 (SEQ ID NO:979), Ceres CLONE ID no.684633 (SEQ ID NO:985), Ceres CLONE ID no.371815 (SEQ ID NO:991), Ceres CLONE ID no.1686460 (SEQ ID NO:993), Ceres CLONE ID no.1448595 (SEQ ID NO:995), Ceres CLONE ID no.1734477 (SEQ ID NO:999), Ceres CLONE ID no.1605693 (SEQ ID NO:1005), Ceres CLONE ID no.1757400 (SEQ ID NO:1009), and Public GI ID no.115434334 (SEQ ID NO:1015).

In some cases, a SD+EODFR and/or low light-tolerance polypeptide has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1024 Amino acid sequences of polypeptides having greater than 40% sequence identity to the polypeptide set forth in SEQ ID NO:1024 are provided in FIG. 12. Such polypeptides include Ceres ANNOT ID no.1452905 (SEQ ID NO:1029), Ceres CLONE ID no.956176 (SEQ ID NO:1039), Public GI ID no.92870366 (SEQ ID NO:1040), Ceres CLONE ID no.294166 (SEQ ID NO:1042), and Public GI ID no.125543067 (SEQ ID NO:1043).

In some cases, an SD+EODFR and/or low light-tolerance polypeptide has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1047 Amino acid sequences of polypeptides having greater than 40% sequence identity to the polypeptide set forth in SEQ ID NO:1047 are provided in FIG. 13. Such polypeptides include Ceres CLONE ID no.1837694 (SEQ ID NO:1053), Ceres ANNOT ID no.1483367 (SEQ ID NO:1057), Ceres CLONE ID no.1077781 (SEQ ID NO:1083), Ceres CLONE ID no.471026 (SEQ ID NO:1085), Public GI ID no.92888885 (SEQ ID NO:1099), Public GI ID no.45544873 (SEQ ID NO:1100), Public GI ID no.45758663 (SEQ ID NO:1101), Ceres CLONE ID no.772927 (SEQ ID NO:1105), Ceres CLONE ID no.895080 (SEQ ID NO:1111), Ceres CLONE ID no.1806128 (SEQ ID NO:1131), Public GI ID no.115458192 (SEQ ID NO:1134), and Public GI ID no.82470795 (SEQ ID NO:1139).

In some cases, a SD+EODFR and/or low light-tolerance polypeptide has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1151 Amino acid sequences of polypeptides having greater than 40% sequence identity to the polypeptide set forth in SEQ ID NO:1151 are provided in FIG. 14. Such polypeptides include Ceres CLONE ID no.1851526 (SEQ ID NO:1155), Ceres ANNOT ID no.1486769 (SEQ ID NO:1172), Public GI ID no.83032232 (SEQ ID NO:1209), Ceres CLONE ID no.1620420 (SEQ ID NO:1211), Public GI ID no.92892428 (SEQ ID NO:1215), Ceres CLONE ID no.884742 (SEQ ID NO:1223), Ceres CLONE ID no.1821559 (SEQ ID NO:1246), Public GI ID no.51535021 (SEQ ID NO:1258), Public GI ID no.113205304 (SEQ ID NO:1263), and Public GI ID no.37719051 (SEQ ID NO:1264).

In some cases, a SD+EODFR and/or low light-tolerance polypeptide has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1277 Amino acid sequences of polypeptides having greater than 40% sequence identity to the polypeptide set forth in SEQ ID NO:1277 are provided in FIG. 15. Such polypeptides include Ceres CLONE ID no.1926352 (SEQ ID NO:1279), Ceres ANNOT ID no.1448905 (SEQ ID NO:1285), Public GI ID no.15236865 (SEQ ID NO:1294), Ceres CLONE ID no.934771 (SEQ ID NO:1301), Ceres CLONE ID no.338386 (SEQ ID NO:1303), Ceres CLONE ID no.1780691 (SEQ ID NO:1317), and Public GI ID no.115464819 (SEQ ID NO:1326).

In some cases, a SD+EODFR and/or low light-tolerance polypeptide has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1347 Amino acid sequences of polypeptides having greater than 40% sequence identity to the polypeptide set forth in SEQ ID NO:1347 are provided in FIG. 16. Such polypeptides include Ceres CLONE ID no.285028 (SEQ ID NO:1419), Ceres CLONE ID no.100969565 (SEQ ID NO:1422), Public GI ID no.1352057 (SEQ ID NO:1427), Ceres ANNOT ID no.1453784 (SEQ ID NO:1429), Public GI ID no.452777 (SEQ ID NO:1430), and Public GI ID no.92873297 (SEQ ID NO:1431).

In some cases, a SD+EODFR and/or low light-tolerance polypeptide has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1457 Amino acid sequences of polypeptides having greater than 40% sequence identity to the polypeptide set forth in SEQ ID NO:1457 are provided in FIG. 17. Such polypeptides include Ceres CLONE ID no.1924904 (SEQ ID NO:1460), Ceres ANNOT ID no.1543346 (SEQ ID NO:1462), Public GI ID no.18396338 (SEQ ID NO:1467), Ceres CLONE ID no.833872 (SEQ ID NO:1471), Ceres CLONE ID no.1579587 (SEQ ID NO:1475), Ceres CLONE ID no.1786411 (SEQ ID NO:1477), and Public GI ID no.108864370 (SEQ ID NO:1480).

In some cases, a SD+EODFR and/or low light-tolerance polypeptide has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1497 Amino acid sequences of polypeptides having greater than 40% sequence identity to the polypeptide set forth in SEQ ID NO:1497 are provided in FIG. 18. Such polypeptides include Ceres ANNOT ID no.1443463 (SEQ ID NO:1499), Public GI ID no.13605525 (SEQ ID NO:1502), Public GI ID no.94965681 (SEQ ID NO:1506), and Public GI ID no.28201254 (SEQ ID NO:1512).

In some cases, a SD+EODFR and/or low light-tolerance polypeptide has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1587 Amino acid sequences of polypeptides having greater than 40% sequence identity to the polypeptide set forth in SEQ ID NO:1587 are provided in FIG. 19. Such polypeptides include Ceres CLONE ID no.1839577 (SEQ ID NO:1589), Ceres ANNOT ID no.1491567 (SEQ ID NO:1591), Ceres CLONE ID no.574505 (SEQ ID NO:1596), Public GI ID no.56117815 (SEQ ID NO:1597), Public GI ID no.92874021 (SEQ ID NO:1603), Public GI ID no.123684 (SEQ ID NO:1605), Public GI ID no.5821136 (SEQ ID NO:1606), Ceres CLONE ID no.283366 (SEQ ID NO:1609), Public GI ID no.16118447 (SEQ ID NO:1612), and Public GI ID no.125562434 (SEQ ID NO:1614).

In some cases, a SD+EODFR and/or low light-tolerance polypeptide has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1635 Amino acid sequences of polypeptides having greater than 40% sequence identity to the polypeptide set forth in SEQ ID NO:1635 are provided in FIG. 20. Such polypeptides include Ceres ANNOT ID no.1508307 (SEQ ID NO:1637), Public GI ID no.1495267 (SEQ ID NO:1642), Public GI ID no.87241310 (SEQ ID NO:1644), Ceres CLONE ID no.938390 (SEQ ID NO:1646), Ceres CLONE ID no.272338 (SEQ ID NO:1648), Ceres CLONE ID no.1993510 (SEQ ID NO:1650), Public GI ID no.125563862 (SEQ ID NO:1651), and Public GI ID no.125605833 (SEQ ID NO:1653).

In some cases, a SD+EODFR and/or low light-tolerance polypeptide has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1540 Amino acid sequences of polypeptides having greater than 40% sequence identity to the polypeptide set forth in SEQ ID NO:1540 are provided in FIG. 21. Such polypeptides include Ceres CLONE ID no.1943265 (SEQ ID NO:1543), Ceres ANNOT ID no.1454522 (SEQ ID NO:1547), Public GI ID no.31323447 (SEQ ID NO:1556), Ceres CLONE ID no.1583941 (SEQ ID NO:1561), Ceres CLONE ID no.1792942 (SEQ ID NO:1563), Public GI ID no.77548772 (SEQ ID NO:1565), and Public GI ID no.84453182 (SEQ ID NO:1567).

In some cases, a SD+EODFR and/or low light-tolerance polypeptide has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:538. Amino acid sequences of polypeptides having greater than 40% sequence identity to the polypeptide set forth in SEQ ID NO:538 are provided in FIG. 22. Such polypeptides include Public GI ID no.5731739 (SEQ ID NO:539), Ceres ANNOT ID no.1538045 (SEQ ID NO:541), Public GI ID no.29467479 (SEQ ID NO:542), Public GI ID no.133921974 (SEQ ID NO:543), Public GI ID no.113197027 (SEQ ID NO:544), Public GI ID no.92879277 (SEQ ID NO:545), Public GI ID no.45935260 (SEQ ID NO:546), Public GI ID no.8101444 (SEQ ID NO:547), Public GI ID no.78217443 (SEQ ID NO:548), and Public GI ID no.28372347 (SEQ ID NO:549).

In some cases, a SD+EODFR and/or low light-tolerance polypeptide has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:606. Amino acid sequences of polypeptides having greater than 40% sequence identity to the polypeptide set forth in SEQ ID NO:606 are provided in FIG. 23. Such polypeptides include Public GI ID no.92873064 (SEQ ID NO:607), Public GI ID no.37051125 (SEQ ID NO:608), and Public GI ID no.112363376 (SEQ ID NO:609).

In some cases, a SD+EODFR and/or low light-tolerance polypeptide has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:570. Amino acid sequences of polypeptides having greater than 40% sequence identity to the polypeptide set forth in SEQ ID NO:570 are provided in FIG. 24. Such polypeptides include Ceres CLONE ID no.1919714 (SEQ ID NO:572), Ceres ANNOT ID no.1443290 (SEQ ID NO:574), Ceres CLONE ID no.1042157 (SEQ ID NO:576), Ceres CLONE ID no.1384304 (SEQ ID NO:578), and Public GI ID no.115464375 (SEQ ID NO:579).

In some cases, a red light specific response pathway polypeptide has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:456. Amino acid sequences of polypeptides having greater than 40% sequence identity to the polypeptide set forth in SEQ ID NO:456 are provided in FIG. 6. Such polypeptides include Public GI ID no. 58430585 (SEQ ID NO:457), Ceres CLONE ID no. 1842825 (SEQ ID NO:466), Ceres ANNOT ID no. 1449721 (SEQ ID NO:474), Public GI ID no. 41323978 (SEQ ID NO:475), Public GI ID no. 2895186 (SEQ ID NO:478), Public GI ID no. 22854950 (SEQ ID NO:481), Public GI ID no. 116010474 (SEQ ID NO:485), Public GI ID no. 4091804 (SEQ ID NO:488), Public GI ID no. 60459257 (SEQ ID NO:494), Public GI ID no. 45544881 (SEQ ID NO:496), Public GI ID no. 36789802 (SEQ ID NO:498), Public GI ID no. 92875402 (SEQ ID NO:508), Public GI ID no. 118406898 (SEQ ID NO:510), Public GI ID no. 107770485 (SEQ ID NO:511), Public GI ID no. 21655154 (SEQ ID NO:532), Public GI ID no. 90657642 (SEQ ID NO:536), and Ceres CLONE ID no. 1569555 (SEQ ID NO:1842).

In some cases, red light specific response pathway polypeptide has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:953. Amino acid sequences of polypeptides having greater than 40% sequence identity to the polypeptide set forth in SEQ ID NO:953 are provided in FIG. 11. Such polypeptides include Ceres CLONE ID no.1798705 (SEQ ID NO:955), Ceres ANNOT ID no.1458907 (SEQ ID NO:963), Ceres CLONE ID no.1090409 (SEQ ID NO:971), Ceres CLONE ID no.479817 (SEQ ID NO:977), Ceres CLONE ID no.1041793 (SEQ ID NO:979), Ceres CLONE ID no.684633 (SEQ ID NO:985), Ceres CLONE ID no.371815 (SEQ ID NO:991), Ceres CLONE ID no.1686460 (SEQ ID NO:993), Ceres CLONE ID no.1448595 (SEQ ID NO:995), Ceres CLONE ID no.1734477 (SEQ ID NO:999), Ceres CLONE ID no.1605693 (SEQ ID NO:1005), Ceres CLONE ID no.1757400 (SEQ ID NO:1009), and Public GI ID no.115434334 (SEQ ID NO:1015).

In some cases, a red light specific response pathway polypeptide has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1540 Amino acid sequences of polypeptides having greater than 40% sequence identity to the polypeptide set forth in SEQ ID NO:1540 are provided in FIG. 21. Such polypeptides include Ceres CLONE ID no.1943265 (SEQ ID NO:1543), Ceres ANNOT ID no.1454522 (SEQ ID NO:1547), Public GI ID no.31323447 (SEQ ID NO:1556), Ceres CLONE ID no.1583941 (SEQ ID NO:1561), Ceres CLONE ID no.1792942 (SEQ ID NO:1563), Public GI ID no.77548772 (SEQ ID NO:1565), and Public GI ID no.84453182 (SEQ ID NO:1567).

F. Other Sequences

It should be appreciated that an SD+EODFR and/or low light-tolerance polypeptide and red light specific response pathway polypeptide can include additional amino acids that are not involved in an SD+EODFR and/or low light tolerance, or a red light specific response pathway, and thus such a polypeptide can be longer than would otherwise be the case. For example, an SD+EODFR and/or low light-tolerance polypeptide can include a purification tag, a chloroplast transit peptide, a mitochondrial transit peptide, an amyloplast peptide, or a leader sequence added to the amino or carboxy terminus. In some embodiments, an SD+EODFR and/or low light-tolerance polypeptide includes an amino acid sequence that functions as a reporter, e.g., a green fluorescent protein or yellow fluorescent protein.

III. Nucleic Acids

Nucleic acids described herein include nucleic acids that are effective to modulate SD+EODFR and/or low light tolerance when transcribed in a plant or plant cell. Such nucleic acids include, without limitation, those that encode an SD+EODFR and/or low light-tolerance polypeptide and those that can be used to inhibit expression of an SD+EODFR and/or low light-tolerance polypeptide or a red light specific response pathway polypeptide via a nucleic acid based method.

A. Nucleic Acids Encoding SD+EODFR and/or Low Light-Tolerance Polypeptides

Nucleic acids encoding SD+EODFR and/or low light-tolerance polypeptides are described herein. Such nucleic acids include SEQ ID NOs:1, 2, 4, 6, 8, 11, 13, 15, 17, 19, 21, 23, 27, 29, 31, 33, 35, 37, 39, 41, 43, 45, 47, 50, 52, 54, 56, 58, 64, 66, 68, 69, 71, 73, 75, 77, 79, 81, 83, 85, 87, 92, 94, 104, 106, 108, 110, 112, 114, 123, 125, 127, 128, 134, 136, 138, 140, 142, 144, 146, 148, 150, 152, 154, 156, 158, 160, 162, 164, 166, 168, 170, 172, 174, 176, 178, 180, 182, 184, 186, 190, 192, 194, 196, 198, 200, 202, 204, 206, 208, 210, 212, 214, 216, 218, 220, 222, 224, 226, 228, 240, 242, 244, 246, 248, 250, 252, 254, 256, 258, 260, 263, 265, 267, 269, 272, 274, 276, 278, 280, 282, 284, 286, 288, 290, 305, 307, 309, 311, 313, 315, 316, 318, 320, 322, 324, 326, 328, 333, 335, 336, 338, 340, 342, 345, 356, 358, 360, 363, 369, 371, 373, 375, 377, 380, 382, 384, 386, 388, 390, 392, 394, 396, 398, 400, 402, 404, 406, 408, 410, 412, 414, 416, 418, 420, 422, 424, 426, 428, 430, 432, 434, 436, 438, 440, 442, 444, 446, 448, 450, 452, 454, 455, 461, 463, 465, 467, 469, 471, 473, 476, 490, 492, 500, 502, 504, 506, 513, 517, 519, 537, 540, 551, 553, 566, 568, 569, 571, 573, 575, 577, 581, 583, 585, 587, 589, 591, 593, 595, 597, 599, 602, 604, 605, 610, 612, 614, 619, 623, 627, 630, 632, 633, 635, 640, 642, 643, 646, 648, 650, 652, 654, 656, 658, 660, 662, 664, 666, 668, 670, 672, 674, 677, 679, 681, 683, 685, 687, 689, 691, 693, 696, 698, 700, 703, 705, 707, 710, 715, 717, 719, 722, 724, 727, 729, 731, 733, 735, 737, 739, 746, 748, 752, 754, 756, 758, 760, 766, 768, 770, 772, 775, 777, 781, 785, 787, 789, 791, 793, 825, 828, 836, 842, 844, 846, 848, 849, 852, 854, 856, 858, 860, 867, 869, 871, 873, 875, 878, 880, 882, 884, 886, 888, 890, 892, 894, 896, 899, 901, 903, 905, 906, 908, 910, 912, 914, 916, 918, 921, 925, 927, 933, 935, 942, 944, 946, 951, 952, 954, 956, 958, 960, 962, 964, 968, 970, 972, 974, 976, 978, 980, 982, 984, 986, 988, 990, 992, 994, 996, 998, 1000, 1002, 1004, 1006, 1008, 1010, 1012, 1017, 1019, 1020, 1021, 1022, 1023, 1026, 1028, 1031, 1034, 1036, 1038, 1041, 1045, 1046, 1048, 1050, 1052, 1054, 1056, 1058, 1060, 1062, 1064, 1066, 1070, 1076, 1079, 1082, 1084, 1086, 1088, 1090, 1092, 1094, 1096, 1102, 1104, 1106, 1108, 1110, 1112, 1114, 1116, 1118, 1120, 1122, 1124, 1126, 1128, 1130, 1132, 1140, 1142, 1144, 1146, 1148, 1150, 1152, 1154, 1156, 1158, 1163, 1165, 1167, 1169, 1171, 1173, 1175, 1177, 1179, 1181, 1183, 1185, 1187, 1189, 1191, 1193, 1195, 1197, 1205, 1207, 1210, 1212, 1218, 1220, 1222, 1224, 1226, 1228, 1231, 1233, 1235, 1237, 1239, 1241, 1243, 1245, 1247, 1249, 1251, 1253, 1265, 1267, 1269, 1271, 1273, 1275, 1276, 1278, 1280, 1282, 1284, 1286, 1288, 1290, 1292, 1296, 1300, 1302, 1304, 1306, 1308, 1310, 1312, 1314, 1316, 1318, 1320, 1333, 1335, 1337, 1339, 1341, 1343, 1345, 1346, 1348, 1350, 1354, 1356, 1359, 1361, 1363, 1365, 1369, 1371, 1373, 1376, 1378, 1380, 1382, 1384, 1386, 1388, 1390, 1392, 1394, 1396, 1398, 1400, 1403, 1405, 1407, 1409, 1416, 1418, 1420, 1428, 1432, 1437, 1441, 1443, 1445, 1447, 1449, 1451, 1453, 1454, 1455, 1456, 1459, 1461, 1463, 1465, 1470, 1472, 1474, 1476, 1487, 1489, 1491, 1493, 1495, 1496, 1498, 1500, 1507, 1509, 1517, 1526, 1530, 1537, 1538, 1539, 1542, 1544, 1546, 1548, 1550, 1552, 1560, 1562, 1569, 1571, 1573, 1575, 1577, 1579, 1581, 1583, 1585, 1586, 1588, 1590, 1592, 1595, 1608, 1610, 1622, 1624, 1626, 1627, 1628, 1629, 1633, 1634, 1636, 1638, 1640, 1645, 1647, 1649, 1656, 1658, 1660, 1662, 1664, 1666, 1668, 1670, 1672, 1674, 1676, 1678, 1680, 1683, 1685, 1687, 1689, 1691, 1693, 1695, 1697, 1706, 1708, 1710, 1712, 1714, 1716, 1718, 1724, 1726, 1728, 1731, 1733, 1735, 1737, 1747, 1749, 1753, 1755, 1757, 1759, 1761, 1763, 1765, 1779, 1781, 1783, 1785, 1787, 1789, 1791, 1793, 1795, 1797, 1799, 1801, 1803, 1841, 1849, 1851, 1853, 1855, 1857, 1868, 1872, 1874, 1876, 1878, 1880, 1882, 1884, 1886, 1888, 1890, 1892, 1894, 1896, 1898, 1900, 1902, 1904, 1906, 1908, 1910, 1912, 1914, 1916, 1918, 1920, 1922, 1924, 1926, 1928, 1930, 1932, 1934, 1936, 1938, 1940, 1942, 1944, 1946, 1948, 1950, 1952, 1954, 1956, 1958, 1960, 1962, 1964, 1966, 1968, 1970, 1972, 1974, 1976, 1978, 1980, 1982, 1984, 1986, 1988, 1990, 1992, 1994, 1996, 1998, 2000, 2002, 2004, 2006, 2008, 2010, 2012, 2014, 2016, 2018, 2020, 2022, 2024, 2026, 2028, 2068, 2071, 2073, 2075, 2077, 2079, 2082, 2086, 2088, 2090, 2092, 2094, 2096, 2098, 2100, 2102, 2104, 2106, 2108, 2110, 2112, 2122, 2124, 2126, 2128, 2130, 2132, 2134, 2145, 2147, 2149, 2151, 2153, 2155, 2157, 2159, 2161, 2163, 2165, 2167, 2169, 2171, 2173, 2175, 2177, 2179, 2181, 2265, 2267, 2279, 2281, 2283, 2285, 2287, 2289, 2291, 2293, 2295, 2297, 2299, 2301, 2303, 2305, 2307, 2309, 2311, 2313, 2315, 2317, 2319, 2321, 2349, 2351, 2353, 2355, 2357, 2359, 2361, 2363, 2365, 2367, 2369, 2371, and 2373 as described in more detail below. A nucleic acid also can be a fragment that is at least 40% (e.g., at least 45, 50, 55, 60, 65, 70, 75, 80, 85, 90, 95, or 99%) of the length of the full-length nucleic acid set forth in SEQ ID NOs:1, 2, 4, 6, 8, 11, 13, 15, 17, 19, 21, 23, 27, 29, 31, 33, 35, 37, 39, 41, 43, 45, 47, 50, 52, 54, 56, 58, 64, 66, 68, 69, 71, 73, 75, 77, 79, 81, 83, 85, 87, 92, 94, 104, 106, 108, 110, 112, 114, 123, 125, 127, 128, 134, 136, 138, 140, 142, 144, 146, 148, 150, 152, 154, 156, 158, 160, 162, 164, 166, 168, 170, 172, 174, 176, 178, 180, 182, 184, 186, 190, 192, 194, 196, 198, 200, 202, 204, 206, 208, 210, 212, 214, 216, 218, 220, 222, 224, 226, 228, 240, 242, 244, 246, 248, 250, 252, 254, 256, 258, 260, 263, 265, 267, 269, 272, 274, 276, 278, 280, 282, 284, 286, 288, 290, 305, 307, 309, 311, 313, 315, 316, 318, 320, 322, 324, 326, 328, 333, 335, 336, 338, 340, 342, 345, 356, 358, 360, 363, 369, 371, 373, 375, 377, 380, 382, 384, 386, 388, 390, 392, 394, 396, 398, 400, 402, 404, 406, 408, 410, 412, 414, 416, 418, 420, 422, 424, 426, 428, 430, 432, 434, 436, 438, 440, 442, 444, 446, 448, 450, 452, 454, 455, 461, 463, 465, 467, 469, 471, 473, 476, 490, 492, 500, 502, 504, 506, 513, 517, 519, 537, 540, 551, 553, 566, 568, 569, 571, 573, 575, 577, 581, 583, 585, 587, 589, 591, 593, 595, 597, 599, 602, 604, 605, 610, 612, 614, 619, 623, 627, 630, 632, 633, 635, 640, 642, 643, 646, 648, 650, 652, 654, 656, 658, 660, 662, 664, 666, 668, 670, 672, 674, 677, 679, 681, 683, 685, 687, 689, 691, 693, 696, 698, 700, 703, 705, 707, 710, 715, 717, 719, 722, 724, 727, 729, 731, 733, 735, 737, 739, 746, 748, 752, 754, 756, 758, 760, 766, 768, 770, 772, 775, 777, 781, 785, 787, 789, 791, 793, 825, 828, 836, 842, 844, 846, 848, 849, 852, 854, 856, 858, 860, 867, 869, 871, 873, 875, 878, 880, 882, 884, 886, 888, 890, 892, 894, 896, 899, 901, 903, 905, 906, 908, 910, 912, 914, 916, 918, 921, 925, 927, 933, 935, 942, 944, 946, 951, 952, 954, 956, 958, 960, 962, 964, 968, 970, 972, 974, 976, 978, 980, 982, 984, 986, 988, 990, 992, 994, 996, 998, 1000, 1002, 1004, 1006, 1008, 1010, 1012, 1017, 1019, 1020, 1021, 1022, 1023, 1026, 1028, 1031, 1034, 1036, 1038, 1041, 1045, 1046, 1048, 1050, 1052, 1054, 1056, 1058, 1060, 1062, 1064, 1066, 1070, 1076, 1079, 1082, 1084, 1086, 1088, 1090, 1092, 1094, 1096, 1102, 1104, 1106, 1108, 1110, 1112, 1114, 1116, 1118, 1120, 1122, 1124, 1126, 1128, 1130, 1132, 1140, 1142, 1144, 1146, 1148, 1150, 1152, 1154, 1156, 1158, 1163, 1165, 1167, 1169, 1171, 1173, 1175, 1177, 1179, 1181, 1183, 1185, 1187, 1189, 1191, 1193, 1195, 1197, 1205, 1207, 1210, 1212, 1218, 1220, 1222, 1224, 1226, 1228, 1231, 1233, 1235, 1237, 1239, 1241, 1243, 1245, 1247, 1249, 1251, 1253, 1265, 1267, 1269, 1271, 1273, 1275, 1276, 1278, 1280, 1282, 1284, 1286, 1288, 1290, 1292, 1296, 1300, 1302, 1304, 1306, 1308, 1310, 1312, 1314, 1316, 1318, 1320, 1333, 1335, 1337, 1339, 1341, 1343, 1345, 1346, 1348, 1350, 1354, 1356, 1359, 1361, 1363, 1365, 1369, 1371, 1373, 1376, 1378, 1380, 1382, 1384, 1386, 1388, 1390, 1392, 1394, 1396, 1398, 1400, 1403, 1405, 1407, 1409, 1416, 1418, 1420, 1428, 1432, 1437, 1441, 1443, 1445, 1447, 1449, 1451, 1453, 1454, 1455, 1456, 1459, 1461, 1463, 1465, 1470, 1472, 1474, 1476, 1487, 1489, 1491, 1493, 1495, 1496, 1498, 1500, 1507, 1509, 1517, 1526, 1530, 1537, 1538, 1539, 1542, 1544, 1546, 1548, 1550, 1552, 1560, 1562, 1569, 1571, 1573, 1575, 1577, 1579, 1581, 1583, 1585, 1586, 1588, 1590, 1592, 1595, 1608, 1610, 1622, 1624, 1626, 1627, 1628, 1629, 1633, 1634, 1636, 1638, 1640, 1645, 1647, 1649, 1656, 1658, 1660, 1662, 1664, 1666, 1668, 1670, 1672, 1674, 1676, 1678, 1680, 1683, 1685, 1687, 1689, 1691, 1693, 1695, 1697, 1706, 1708, 1710, 1712, 1714, 1716, 1718, 1724, 1726, 1728, 1731, 1733, 1735, 1737, 1747, 1749, 1753, 1755, 1757, 1759, 1761, 1763, 1765, 1779, 1781, 1783, 1785, 1787, 1789, 1791, 1793, 1795, 1797, 1799, 1801, 1803, 1841, 1849, 1851, 1853, 1855, 1857, 1868, 1872, 1874, 1876, 1878, 1880, 1882, 1884, 1886, 1888, 1890, 1892, 1894, 1896, 1898, 1900, 1902, 1904, 1906, 1908, 1910, 1912, 1914, 1916, 1918, 1920, 1922, 1924, 1926, 1928, 1930, 1932, 1934, 1936, 1938, 1940, 1942, 1944, 1946, 1948, 1950, 1952, 1954, 1956, 1958, 1960, 1962, 1964, 1966, 1968, 1970, 1972, 1974, 1976, 1978, 1980, 1982, 1984, 1986, 1988, 1990, 1992, 1994, 1996, 1998, 2000, 2002, 2004, 2006, 2008, 2010, 2012, 2014, 2016, 2018, 2020, 2022, 2024, 2026, 2028, 2068, 2071, 2073, 2075, 2077, 2079, 2082, 2086, 2088, 2090, 2092, 2094, 2096, 2098, 2100, 2102, 2104, 2106, 2108, 2110, 2112, 2122, 2124, 2126, 2128, 2130, 2132, 2134, 2145, 2147, 2149, 2151, 2153, 2155, 2157, 2159, 2161, 2163, 2165, 2167, 2169, 2171, 2173, 2175, 2177, 2179, 2181, 2265, 2267, 2279, 2281, 2283, 2285, 2287, 2289, 2291, 2293, 2295, 2297, 2299, 2301, 2303, 2305, 2307, 2309, 2311, 2313, 2315, 2317, 2319, 2321, 2349, 2351, 2353, 2355, 2357, 2359, 2361, 2363, 2365, 2367, 2369, 2371, and 2373.

An SD+EODFR and/or low light-tolerance nucleic acid can comprise the nucleotide sequence set forth in SEQ ID NO:1 or SEQ ID NO:2. Alternatively, an SD+EODFR and/or low light-tolerance nucleic acid can be a variant of the nucleic acid having the nucleotide sequence set forth in SEQ ID NO:1 or SEQ ID NO:2. For example, an SD+EODFR and/or low light-tolerance nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1 or SEQ ID NO:2.

An SD+EODFR and/or low light-tolerance nucleic acid can comprise the nucleotide sequence set forth in SEQ ID NO:68 or SEQ ID NO:69. Alternatively, an SD+EODFR and/or low light-tolerance nucleic acid can be a variant of the nucleic acid having the nucleotide sequence set forth in SEQ ID NO:68 or SEQ ID NO:69. For example, an SD+EODFR and/or low light-tolerance nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:68 or SEQ ID NO:69.

An SD+EODFR and/or low light-tolerance nucleic acid can comprise the nucleotide sequence set forth in SEQ ID NO:127 or SEQ ID NO:128. Alternatively, an SD+EODFR and/or low light-tolerance nucleic acid can be a variant of the nucleic acid having the nucleotide sequence set forth in SEQ ID NO:127 or SEQ ID NO:128. For example, an SD+EODFR and/or low light-tolerance nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:127 or SEQ ID NO:128.

An SD+EODFR and/or low light-tolerance nucleic acid can comprise the nucleotide sequence set forth in SEQ ID NO:315 or SEQ ID NO:316. Alternatively, an SD+EODFR and/or low light-tolerance nucleic acid can be a variant of the nucleic acid having the nucleotide sequence set forth in SEQ ID NO:315 or SEQ ID NO:316. For example, an SD+EODFR and/or low light-tolerance nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:315 or SEQ ID NO:316.

An SD+EODFR and/or low light-tolerance nucleic acid can comprise the nucleotide sequence set forth in SEQ ID NO:335 or SEQ ID NO:336. Alternatively, an SD+EODFR and/or low light-tolerance nucleic acid can be a variant of the nucleic acid having the nucleotide sequence set forth in SEQ ID NO:335 or SEQ ID NO:336. For example, an SD+EODFR and/or low light-tolerance nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:335 or SEQ ID NO:336.

An SD+EODFR and/or low light-tolerance nucleic acid can comprise the nucleotide sequence set forth in SEQ ID NO:454 or SEQ ID NO:455. Alternatively, an SD+EODFR and/or low light-tolerance nucleic acid can be a variant of the nucleic acid having the nucleotide sequence set forth in SEQ ID NO:454 or SEQ ID NO:455. For example, an SD+EODFR and/or low light-tolerance nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:454 or SEQ ID NO:455.

An SD+EODFR and/or low light-tolerance nucleic acid can comprise the nucleotide sequence set forth in SEQ ID NO:537. Alternatively, an SD+EODFR and/or low light-tolerance nucleic acid can be a variant of the nucleic acid having the nucleotide sequence set forth in SEQ ID NO:537. For example, an SD+EODFR and/or low light-tolerance nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:537.

An SD+EODFR and/or low light-tolerance nucleic acid can comprise the nucleotide sequence set forth in SEQ ID NO:568 or SEQ ID NO:569. Alternatively, an SD+EODFR and/or low light-tolerance nucleic acid can be a variant of the nucleic acid having the nucleotide sequence set forth in SEQ ID NO:568 or SEQ ID NO:569. For example, an SD+EODFR and/or low light-tolerance nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:568 or SEQ ID NO:569.

An SD+EODFR and/or low light-tolerance nucleic acid can comprise the nucleotide sequence set forth in SEQ ID NO:604 or SEQ ID NO:605. Alternatively, an SD+EODFR and/or low light-tolerance nucleic acid can be a variant of the nucleic acid having the nucleotide sequence set forth in SEQ ID NO:604 or SEQ ID NO:605. For example, an SD+EODFR and/or low light-tolerance nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:604 or SEQ ID NO:605.

An SD+EODFR and/or low light-tolerance nucleic acid can comprise the nucleotide sequence set forth in SEQ ID NO:632 or SEQ ID NO:633. Alternatively, an SD+EODFR and/or low light-tolerance nucleic acid can be a variant of the nucleic acid having the nucleotide sequence set forth in SEQ ID NO:632 or SEQ ID NO:633. For example, an SD+EODFR and/or low light-tolerance nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:632 or SEQ ID NO:633.

An SD+EODFR and/or low light-tolerance nucleic acid can comprise the nucleotide sequence set forth in SEQ ID NO:642 or SEQ ID NO:643. Alternatively, an SD+EODFR and/or low light-tolerance nucleic acid can be a variant of the nucleic acid having the nucleotide sequence set forth in SEQ ID NO:642 or SEQ ID NO:643. For example, an SD+EODFR and/or low light-tolerance nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:642 or SEQ ID NO:643.

An SD+EODFR and/or low light-tolerance nucleic acid can comprise the nucleotide sequence set forth in SEQ ID NO:848 or SEQ ID NO:849. Alternatively, an SD+EODFR and/or low light-tolerance nucleic acid can be a variant of the nucleic acid having the nucleotide sequence set forth in SEQ ID NO:848 or SEQ ID NO:849. For example, an SD+EODFR and/or low light-tolerance nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:848 or SEQ ID NO:849.

An SD+EODFR and/or low light-tolerance nucleic acid can comprise the nucleotide sequence set forth in SEQ ID NO:905 or SEQ ID NO:906. Alternatively, an SD+EODFR and/or low light-tolerance nucleic acid can be a variant of the nucleic acid having the nucleotide sequence set forth in SEQ ID NO:905 or SEQ ID NO:906. For example, an SD+EODFR and/or low light-tolerance nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:905 or SEQ ID NO:906.

An SD+EODFR and/or low light-tolerance nucleic acid can comprise the nucleotide sequence set forth in SEQ ID NO:951 or SEQ ID NO:952. Alternatively, an SD+EODFR and/or low light-tolerance nucleic acid can be a variant of the nucleic acid having the nucleotide sequence set forth in SEQ ID NO:951 or SEQ ID NO:952. For example, an SD+EODFR and/or low light-tolerance nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:951 or SEQ ID NO:952.

An SD+EODFR and/or low light-tolerance nucleic acid can comprise the nucleotide sequence set forth in SEQ ID NO:1019, SEQ ID NO:1020, SEQ ID NO:1021, SEQ ID NO:1022, or SEQ ID NO:1023. Alternatively, an SD+EODFR and/or low light-tolerance nucleic acid can be a variant of the nucleic acid having the nucleotide sequence set forth in SEQ ID NO:1019, SEQ ID NO:1020, SEQ ID NO:1021, SEQ ID NO:1022, or SEQ ID NO:1023. For example, an SD+EODFR and/or low light-tolerance nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1019, SEQ ID NO:1020, SEQ ID NO:1021, SEQ ID NO:1022, or SEQ ID NO:1023.

An SD+EODFR and/or low light-tolerance nucleic acid can comprise the nucleotide sequence set forth in SEQ ID NO:1045 or SEQ ID NO:1046. Alternatively, an SD+EODFR and/or low light-tolerance nucleic acid can be a variant of the nucleic acid having the nucleotide sequence set forth in SEQ ID NO:1045 or SEQ ID NO:1046. For example, an SD+EODFR and/or low light-tolerance nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1045 or SEQ ID NO:1046.

An SD+EODFR and/or low light-tolerance nucleic acid can comprise the nucleotide sequence set forth in SEQ ID NO:1150. Alternatively, an SD+EODFR and/or low light-tolerance nucleic acid can be a variant of the nucleic acid having the nucleotide sequence set forth in SEQ ID NO:1150. For example, an SD+EODFR and/or low light-tolerance nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1150.

An SD+EODFR and/or low light-tolerance nucleic acid can comprise the nucleotide sequence set forth in SEQ ID NO:1275 or SEQ ID NO:1276. Alternatively, an SD+EODFR and/or low light-tolerance nucleic acid can be a variant of the nucleic acid having the nucleotide sequence set forth in SEQ ID NO:1275 or SEQ ID NO:1276. For example, an SD+EODFR and/or low light-tolerance nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1275 or SEQ ID NO:1276.

An SD+EODFR and/or low light-tolerance nucleic acid can comprise the nucleotide sequence set forth in SEQ ID NO:1345 or SEQ ID NO:1346. Alternatively, an SD+EODFR and/or low light-tolerance nucleic acid can be a variant of the nucleic acid having the nucleotide sequence set forth in SEQ ID NO:1345 or SEQ ID NO:1346. For example, an SD+EODFR and/or low light-tolerance nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1345 or SEQ ID NO:1346.

An SD+EODFR and/or low light-tolerance nucleic acid can comprise the nucleotide sequence set forth in SEQ ID NO:1453, SEQ ID NO:1454, SEQ ID NO:1455, or SEQ ID NO:1456. Alternatively, an SD+EODFR and/or low light-tolerance nucleic acid can be a variant of the nucleic acid having the nucleotide sequence set forth in SEQ ID NO:1453, SEQ ID NO:1454, SEQ ID NO:1455, or SEQ ID NO:1456. For example, an SD+EODFR and/or low light-tolerance nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1453, SEQ ID NO:1454, SEQ ID NO:1455, or SEQ ID NO:1456.

An SD+EODFR and/or low light-tolerance nucleic acid can comprise the nucleotide sequence set forth in SEQ ID NO:1495 or SEQ ID NO:1496. Alternatively, an SD+EODFR and/or low light-tolerance nucleic acid can be a variant of the nucleic acid having the nucleotide sequence set forth in SEQ ID NO:1495 or SEQ ID NO:1496. For example, an SD+EODFR and/or low light-tolerance nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1495 or SEQ ID NO:1496.

An SD+EODFR and/or low light-tolerance nucleic acid can comprise the nucleotide sequence set forth in SEQ ID NO:1537, SEQ ID NO:1538, or SEQ ID NO:1539. Alternatively, an SD+EODFR and/or low light-tolerance nucleic acid can be a variant of the nucleic acid having the nucleotide sequence set forth in SEQ ID NO:1537, SEQ ID NO:1538, or SEQ ID NO:1539. For example, an SD+EODFR and/or low light-tolerance nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1537, SEQ ID NO:1538, or SEQ ID NO:1539.

An SD+EODFR and/or low light-tolerance nucleic acid can comprise the nucleotide sequence set forth in SEQ ID NO:1585 or SEQ ID NO:1586. Alternatively, an SD+EODFR and/or low light-tolerance nucleic acid can be a variant of the nucleic acid having the nucleotide sequence set forth in SEQ ID NO:1585 or SEQ ID NO:1586. For example, an SD+EODFR and/or low light-tolerance nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1585 or SEQ ID NO:1586.

An SD+EODFR and/or low light-tolerance nucleic acid can comprise the nucleotide sequence set forth in SEQ ID NO:1626, SEQ ID NO:1627, SEQ ID NO:1628, or SEQ ID NO:1629. Alternatively, an SD+EODFR and/or low light-tolerance nucleic acid can be a variant of the nucleic acid having the nucleotide sequence set forth in SEQ ID NO:1626, SEQ ID NO:1627, SEQ ID NO:1628, or SEQ ID NO:1629. For example, an SD+EODFR and/or low light-tolerance nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1626, SEQ ID NO:1627, SEQ ID NO:1628, or SEQ ID NO:1629.

An SD+EODFR and/or low light-tolerance nucleic acid can comprise the nucleotide sequence set forth in SEQ ID NO:1633 or SEQ ID NO:1634. Alternatively, an SD+EODFR and/or low light-tolerance nucleic acid can be a variant of the nucleic acid having the nucleotide sequence set forth in SEQ ID NO:1633 or SEQ ID NO:1634. For example, an SD+EODFR and/or low light-tolerance nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1633 or SEQ ID NO:1634.

B. Nucleic Acids Encoding Red Light Specific Response Pathway Polypeptides

Nucleic acids encoding red light specific response pathway polypeptides are described herein. Such nucleic acids include SEQ ID NOs: 454, 455, 461, 463, 465, 467, 469, 471, 473, 476, 490, 492, 500, 502, 504, 506, 513, 517, 519, 951, 952, 954, 956, 958, 960, 962, 964, 968, 970, 972, 974, 976, 978, 980, 982, 984, 986, 988, 990, 992, 994, 996, 998, 1000, 1002, 1004, 1006, 1008, 1010, 1012, 1017, 1537, 1538, 1539, 1542, 1544, 1546, 1548, 1550, 1552, 1560, 1562, 1569, 1571, 1573, 1575, 1577, 1579, 1581, 1583, 1660, 1662, 1664, 1666, 1668, 1670, 1672, 1674, 1676, 1779, 1781, 1783, 1785, 1787, 1789, 1791, 1793, 1795, 1797, 1799, 1801, 1803, 1841, and 2267 as described in more detail below. A nucleic acid also can be a fragment that is at least 40% (e.g., at least 45, 50, 55, 60, 65, 70, 75, 80, 85, 90, 95, or 99%) of the length of the full-length nucleic acid set forth in SEQ ID NOs: 454, 455, 461, 463, 465, 467, 469, 471, 473, 476, 490, 492, 500, 502, 504, 506, 513, 517, 519, 951, 952, 954, 956, 958, 960, 962, 964, 968, 970, 972, 974, 976, 978, 980, 982, 984, 986, 988, 990, 992, 994, 996, 998, 1000, 1002, 1004, 1006, 1008, 1010, 1012, 1017, 1537, 1538, 1539, 1542, 1544, 1546, 1548, 1550, 1552, 1560, 1562, 1569, 1571, 1573, 1575, 1577, 1579, 1581, 1583, 1660, 1662, 1664, 1666, 1668, 1670, 1672, 1674, 1676, 1779, 1781, 1783, 1785, 1787, 1789, 1791, 1793, 1795, 1797, 1799, 1801, 1803, 1841, and 2267.

A red light specific response pathway nucleic acid can comprise the nucleotide sequence set forth in SEQ ID NO:454 or SEQ ID NO:455. Alternatively, a red light specific response pathway nucleic acid can be a variant of the nucleic acid having the nucleotide sequence set forth in SEQ ID NO:454 or SEQ ID NO:455. For example, a red light specific response pathway nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:454 or SEQ ID NO:455.

A red light specific response pathway nucleic acid can comprise the nucleotide sequence set forth in SEQ ID NO:951 or SEQ ID NO:952. Alternatively, a red light specific response pathway nucleic acid can be a variant of the nucleic acid having the nucleotide sequence set forth in SEQ ID NO:951 or SEQ ID NO:952. For example, a red light specific response pathway nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:951 or SEQ ID NO:952.

A red light specific response pathway nucleic acid can comprise the nucleotide sequence set forth in SEQ ID NO:1537, SEQ ID NO:1538, or SEQ ID NO:1539. Alternatively, a red light specific response pathway nucleic acid can be a variant of the nucleic acid having the nucleotide sequence set forth in SEQ ID NO:1537, SEQ ID NO:1538, or SEQ ID NO:1539. For example, a red light specific response pathway nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1537, SEQ ID NO:1538, or SEQ ID NO:1539.

Isolated nucleic acid molecules can be produced by standard techniques. For example, polymerase chain reaction (PCR) techniques can be used to obtain an isolated nucleic acid containing a nucleotide sequence described herein. PCR can be used to amplify specific sequences from DNA as well as RNA, including sequences from total genomic DNA or total cellular RNA. Various PCR methods are described, for example, in *PCR Primer: A Laboratory Manual*, Dieffenbach and Dveksler, eds., Cold Spring Harbor Laboratory Press, 1995. Generally, sequence information from the ends of the region of interest or beyond is employed to design oligonucleotide primers that are identical or similar in sequence to opposite strands of the template to be amplified. Various PCR strategies also are available by which site-specific nucleotide sequence modifications can be introduced into a template nucleic acid. Isolated nucleic acids also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector. Isolated nucleic acids of the invention also can be obtained by mutagenesis of, e.g., a naturally occurring DNA.

C. Use of Nucleic Acids to Modulate Expression of Polypeptides Expression of an SD+EODFR and/or Low Light-Tolerance Polypeptide A nucleic acid encoding one of the SD+EODFR and/or low light-tolerance polypeptides described herein can be used to express the polypeptide in a plant species of interest, typically by transforming a plant cell with a nucleic acid having the coding sequence for the polypeptide operably linked in sense orientation to one or more regulatory regions. It will be appreciated that because of the degeneracy of the genetic code, a number of nucleic acids can encode a particular SD+EODFR and/or low light-tolerance polypeptide; i.e., for many amino acids, there is more than one nucleotide triplet that serves as the codon for the amino acid. Thus, codons in the coding sequence for a given SD+EODFR and/or low light-tolerance polypeptide can be modified such that optimal expression in a particular plant species is obtained, using appropriate codon bias tables for that species.

In some cases, expression of an SD+EODFR and/or low light-tolerance polypeptide inhibits one or more functions of an endogenous polypeptide. For example, a nucleic acid that encodes a dominant negative polypeptide can be used to inhibit protein function. A dominant negative polypeptide typically is mutated or truncated relative to an endogenous wild type polypeptide, and its presence in a cell inhibits one or more functions of the wild type polypeptide in that cell, i.e., the dominant negative polypeptide is genetically dominant and confers a loss of function. The mechanism by which a dominant negative polypeptide confers such a phenotype can vary but often involves a protein-protein interaction or a protein-DNA interaction. For example, a dominant negative polypeptide can be an enzyme that is truncated relative to a native wild type enzyme, such that the truncated polypeptide retains domains involved in binding a first protein but lacks domains involved in binding a second protein. The truncated polypeptide is thus unable to properly modulate the activity of the second protein. See, e.g., US 2007/0056058. As another example, a point mutation that results in a non-conservative amino acid substitution in a catalytic domain can result in a dominant negative polypeptide. See, e.g., US 2005/032221. As another example, a dominant negative polypeptide can be a transcription factor that is truncated relative to a native wild type transcription factor, such that the truncated polypeptide retains the DNA binding domain(s) but lacks the activation domain(s). Such a truncated polypeptide can inhibit the wild type transcription factor from binding DNA, thereby inhibiting transcription activation.

D. Use of Nucleic Acids to Inhibit Expression of a Red Light Specific Response Pathway Polypeptide Polynucleotides and recombinant constructs described herein can be used to inhibit expression of a red light specific response pathway polypeptide in a plant species of interest. See, e.g., Matzke and Birchler, *Nature Reviews Genetics*, 6:24-35 (2005); Akashi et al., *Nature Reviews Mol. Cell Biology*, 6:413-422 (2005); Mittal, *Nature Reviews Genetics*, 5:355-365 (2004); and *Nature Reviews RNA interference collection*, October 2005 at nature.com/reviews/focus/mai. A number of nucleic acid based methods, including anti-sense RNA, ribozyme directed RNA cleavage, post-transcriptional gene silencing (PTGS), e.g., RNA interference (RNAi), and transcriptional gene silencing (TGS) are known to inhibit gene expression in plants. Suitable polynucleotides include full-length nucleic acids encoding red light specific response pathway polypeptides or fragments of such full-length nucleic acids. In some embodiments, a complement of the full-length nucleic acid or a fragment thereof can be used. Typically, a fragment is at least 10 nucleotides, e.g., at least 12, 13, 14, 15, 16, 17, 18, 19, 20, 21, 22, 23, 24, 25, 26, 27, 30, 35, 40, 50, 80, 100, 200, 500 nucleotides or more. Generally, higher homology can be used to compensate for the use of a shorter sequence.

Antisense technology is one well-known method. In this method, a nucleic acid of a gene to be repressed is cloned and operably linked to a regulatory region and a transcription termination sequence so that the antisense strand of RNA is transcribed. The recombinant construct is then transformed into plants, as described herein, and the antisense strand of RNA is produced. The nucleic acid need not be the entire sequence of the gene to be repressed, but typically will be substantially complementary to at least a portion of the sense strand of the gene to be repressed.

In another method, a nucleic acid can be transcribed into a ribozyme, or catalytic RNA, that affects expression of an mRNA. See, U.S. Pat. No. 6,423,885. Ribozymes can be designed to specifically pair with virtually any target RNA and cleave the phosphodiester backbone at a specific location, thereby functionally inactivating the target RNA. Heterologous nucleic acids can encode ribozymes designed to cleave particular mRNA transcripts, thus preventing expression of a polypeptide. Hammerhead ribozymes are useful for destroying particular mRNAs, although various ribozymes that cleave mRNA at site-specific recognition sequences can be used. Hammerhead ribozymes cleave mRNAs at locations dictated by flanking regions that form complementary base pairs with the target mRNA. The sole requirement is that the target RNA contains a 5 '-UG-3' nucleotide sequence. The construction and production of hammerhead ribozymes is known in the art. See, for example, U.S. Pat. No. 5,254,678 and WO 02/46449 and references cited therein. Hammerhead ribozyme sequences can be embedded in a stable RNA such as a transfer RNA (tRNA) to increase cleavage efficiency in vivo. Perriman et al., *Proc. Natl. Acad. Sci. USA*, 92(13):6175-6179 (1995); de Feyter and Gaudron, Methods in Molecular Biology, Vol. 74, Chapter 43, "Expressing Ribozymes in Plants", Edited by Turner, P. C., Humana Press Inc., Totowa, N.J. RNA endoribonucleases which have been described, such as the one that occurs naturally in *Tetrahymena thermophila*, can be useful. See, for example, U.S. Pat. Nos. 4,987,071 and 6,423,885.

PTGS, e.g., RNAi, can also be used to inhibit the expression of a gene. For example, a construct can be prepared that includes a sequence that is transcribed into an RNA that can anneal to itself, e.g., a double stranded RNA having a stem-loop structure. In some embodiments, one strand of the stem portion of a double stranded RNA comprises a sequence that is similar or identical to the sense coding sequence or a fragment thereof of a red light specific response pathway polypeptide, and that is from about 10 nucleotides to about 2,500 nucleotides in length. The length of the sequence that is similar or identical to the sense coding sequence can be from 10 nucleotides to 500 nucleotides, from 15 nucleotides to 300 nucleotides, from 20 nucleotides to 100 nucleotides, or from 25 nucleotides to 100 nucleotides. The other strand of the stem portion of a double stranded RNA comprises a sequence that is similar or identical to the antisense strand or a fragment thereof of the coding sequence of the red light specific response pathway polypeptide, and can have a length that is shorter, the same as, or longer than the corresponding length of the sense sequence. In some cases, one strand of the stem portion of a double stranded RNA comprises a sequence that is similar or identical to the 3' or 5' untranslated region, or a fragment thereof, of an mRNA encoding a red light specific response pathway polypeptide, and the other strand of the stem portion of the double stranded RNA comprises a sequence that is similar or identical to the sequence that is complementary to the 3' or 5' untranslated region, respectively, or a fragment thereof, of the mRNA encoding the red light specific response pathway polypeptide. In other embodiments, one strand of the stem portion of a double stranded RNA comprises a sequence that is similar or identical to the sequence of an intron, or a fragment thereof, in the pre-mRNA encoding a red light specific response pathway polypeptide, and the other strand of the stem portion comprises a sequence that is similar or identical to the sequence that is complementary to the sequence of the intron, or a fragment thereof, in the pre-mRNA.

The loop portion of a double stranded RNA can be from 3 nucleotides to 5,000 nucleotides, e.g., from 3 nucleotides to 25 nucleotides, from 15 nucleotides to 1,000 nucleotides, from 20 nucleotides to 500 nucleotides, or from 25 nucleotides to 200 nucleotides. The loop portion of the RNA can include an intron or a fragment thereof. A double stranded RNA can have zero, one, two, three, four, five, six, seven, eight, nine, ten, or more stem-loop structures.

A construct including a sequence that is operably linked to a regulatory region and a transcription termination sequence, and that is transcribed into an RNA that can form a double stranded RNA, is transformed into plants as described herein. Methods for using RNAi to inhibit the expression of a gene are known to those of skill in the art. See, e.g., U.S. Pat. Nos. 5,034,323; 6,326,527; 6,452,067; 6,573,099; 6,753,139; and 6,777,588. See also WO 97/01952; WO 98/53083; WO 99/32619; WO 98/36083; and U.S. Patent Publications 20030175965, 20030175783, 20040214330, and 20030180945.

Constructs containing regulatory regions operably linked to nucleic acid molecules in sense orientation can also be used to inhibit the expression of a gene. The transcription product can be similar or identical to the sense coding sequence, or a fragment thereof, of a red light specific response pathway polypeptide. The transcription product also can be unpolyadenylated, lack a 5' cap structure, or contain an unspliceable intron. Methods of inhibiting gene expression using a full-length cDNA as well as a partial cDNA sequence are known in the art. See, e.g., U.S. Pat. No. 5,231,020.

In some embodiments, a construct containing a nucleic acid having at least one strand that is a template for both sense and antisense sequences that are complementary to each other is used to inhibit the expression of a gene. The sense and antisense sequences can be part of a larger nucleic acid molecule or can be part of separate nucleic acid molecules having sequences that are not complementary. The sense or antisense sequence can be a sequence that is identical or complementary to the sequence of an mRNA, the 3' or 5' untranslated region of an mRNA, or an intron in a pre-mRNA encoding a red light specific response pathway polypeptide, or a fragment of such sequences. In some embodiments, the sense or antisense sequence is identical or complementary to a sequence of the regulatory region that drives transcription of the gene encoding a red light specific response pathway polypeptide. In each case, the sense sequence is the sequence that is complementary to the antisense sequence.

The sense and antisense sequences can be a length greater than about 10 nucleotides (e.g., 12, 13, 14, 15, 16, 17, 18, 19, 20, 21, 22, 23, 24, 25, 26, 27, 28, 29, 30, or more nucleotides). For example, an antisense sequence can be 21 or 22 nucleotides in length. Typically, the sense and antisense sequences range in length from about 15 nucleotides to about 30 nucleotides, e.g., from about 18 nucleotides to about 28 nucleotides, or from about 21 nucleotides to about 25 nucleotides.

In some embodiments, an antisense sequence is a sequence complementary to an mRNA sequence, or a fragment thereof, encoding a red light specific response pathway polypeptide described herein. The sense sequence complementary to the antisense sequence can be a sequence present within the mRNA of the red light specific response pathway polypeptide. Typically, sense and antisense sequences are designed to correspond to a 15-30 nucleotide sequence of a target mRNA such that the level of that target mRNA is reduced.

In some embodiments, a construct containing a nucleic acid having at least one strand that is a template for more than one sense sequence (e.g., 2, 3, 4, 5, 6, 7, 8, 9, 10 or more sense sequences) can be used to inhibit the expression of a gene. Likewise, a construct containing a nucleic acid having at least one strand that is a template for more than one antisense sequence (e.g., 2, 3, 4, 5, 6, 7, 8, 9, 10 or more antisense sequences) can be used to inhibit the expression of a gene. For example, a construct can contain a nucleic acid having at least one strand that is a template for two sense sequences and two antisense sequences. The multiple sense sequences can be identical or different, and the multiple antisense sequences can be identical or different. For example, a construct can have a nucleic acid having one strand that is a template for two identical sense sequences and two identical antisense sequences that are complementary to the two identical sense sequences. Alternatively, an isolated nucleic acid can have one strand that is a template for (1) two identical sense sequences 20 nucleotides in length, (2) one antisense sequence that is complementary to the two identical sense sequences 20 nucleotides in length, (3) a sense sequence 30 nucleotides in length, and (4) three identical antisense sequences that are complementary to the sense sequence 30 nucleotides in length. The constructs provided herein can be designed to have a suitable arrangement of sense and antisense sequences. For example, two identical sense sequences can be followed by two identical antisense sequences or can be positioned between two identical antisense sequences.

A nucleic acid having at least one strand that is a template for one or more sense and/or antisense sequences can be operably linked to a regulatory region to drive transcription of an RNA molecule containing the sense and/or antisense sequence(s). In addition, such a nucleic acid can be operably linked to a transcription terminator sequence, such as the terminator of the nopaline synthase (nos) gene. In some cases, two regulatory regions can direct transcription of two transcripts: one from the top strand, and one from the bottom strand. See, for example, Yan et al., Plant Physiol., 141: 1508-1518 (2006). The two regulatory regions can be the same or different. The two transcripts can form double-stranded RNA molecules that induce degradation of the target RNA. In some cases, a nucleic acid can be positioned within a T-DNA or plant-derived transfer DNA (P-DNA) such that the left and right T-DNA border sequences, or the left and right border-like sequences of the P-DNA, flank or are on either side of the nucleic acid. See, US 2006/0265788. The nucleic acid sequence between the two regulatory regions can be from about 15 to about 300 nucleotides in length. In some embodiments, the nucleic acid sequence between the two regulatory regions is from about 15 to about 200 nucleotides in length, from about 15 to about 100 nucleotides in length, from about 15 to about 50 nucleotides in length, from about 18 to about 50 nucleotides in length, from about 18 to about 40 nucleotides in length, from about 18 to about 30 nucleotides in length, or from about 18 to about 25 nucleotides in length.

In some nucleic-acid based methods for inhibition of gene expression in plants, a suitable nucleic acid can be a nucleic acid analog. Nucleic acid analogs can be modified at the base moiety, sugar moiety, or phosphate backbone to improve, for example, stability, hybridization, or solubility of the nucleic acid. Modifications at the base moiety include deoxyuridine for deoxythymidine, and 5-methyl-2'-deoxycytidine and 5-bromo-2'-deoxycytidine for deoxycytidine. Modifications of the sugar moiety include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six-membered morpholino ring, or peptide nucleic acids, in which the deoxyphosphate backbone is replaced by a pseudopeptide backbone and the four bases are retained. See, for example, Summerton and Weller, 1997, *Antisense Nucleic Acid Drug Dev.*, 7:187-195; Hyrup et al., *Bioorgan. Med. Chem.*, 4:5-23 (1996). In addition, the deoxyphosphate backbone can be replaced with, for example, a phosphorothioate or phosphorodithioate backbone, a phosphoroamidite, or an alkyl phosphotriester backbone.

E. Constructs/Vectors

Recombinant constructs provided herein can be used to transform plants or plant cells in order to modulate SD+EODFR, low light tolerance, and/or red light specific response pathways. A recombinant nucleic acid construct can comprise a nucleic acid encoding an SD+EODFR and/or low light-tolerance polypeptide as described herein, operably linked to a regulatory region suitable for expressing the SD+EODFR and/or low light-tolerance polypeptide in the plant or cell. Thus, a nucleic acid can comprise a coding sequence that encodes any of the SD+EODFR and/or low light-tolerance polypeptides as set forth in SEQ ID NOs:3, 5, 7, 9, 10, 12, 14, 16, 18, 20, 22, 24, 25, 26, 28, 30, 32, 34, 36, 38, 40, 42, 44, 46, 48, 49, 51, 53, 55, 57, 59, 60, 61, 62, 63, 65, 67, 70, 72, 74, 76, 78, 80, 82, 84, 86, 88, 89, 90, 91, 93, 95, 96, 97, 98, 99, 100, 101, 102, 103, 105, 107, 109, 111, 113, 115, 116, 117, 118, 119, 120, 121, 122, 124, 126, 129, 130, 131, 132, 133, 135, 137, 139, 141, 143, 145, 147, 149, 151, 153, 155, 157, 159, 161, 163, 165, 167, 169, 171, 173, 175, 177, 179, 181, 183, 185, 187, 188, 189, 191, 193, 195, 197, 199, 201, 203, 205, 207, 209, 211, 213, 215, 217, 219, 221, 223, 225, 227, 229, 230, 231, 232, 233, 234, 235, 236, 237, 238, 239, 241, 243, 245, 247, 249, 251, 253, 255, 257, 259, 261, 262, 264, 266, 268, 270, 271, 273, 275, 277, 279, 281, 283, 285, 287, 289, 291, 292, 293, 294, 295, 296, 297, 298, 299, 300, 301, 302, 303, 304, 306, 308, 310, 312, 314, 317, 319, 321, 323, 325, 327, 329, 330, 331, 332, 334, 337, 339, 341, 343, 344, 346, 347, 348, 349, 350, 351, 352, 353, 354, 355, 357, 359, 361, 362, 364, 365, 366, 367, 368, 370, 372, 374, 376, 378, 379, 381, 383, 385, 387, 389, 391, 393, 395, 397, 399, 401, 403, 405, 407, 409, 411, 413, 415, 417, 419, 421, 423, 425, 427, 429, 431, 433, 435, 437, 439, 441, 443, 445, 447, 449, 451, 453, 456, 457, 458, 459, 460, 462, 464, 466, 468, 470, 472, 474, 475, 477, 478, 479, 480, 481, 482, 483, 484, 485, 486, 487, 488, 489, 491, 493, 494, 495, 496, 497, 498, 499, 501, 503, 505, 507, 508, 509, 510, 511, 512, 514, 515, 516, 518, 520, 521, 522, 523, 524, 525, 526, 527, 528, 529, 530, 531, 532, 533, 534, 535, 536, 538, 539, 541, 542, 543, 544, 545, 546, 547, 548, 549, 550, 552, 554, 555, 556, 557, 558, 559, 560, 561, 562, 563, 564, 565, 567, 570, 572, 574, 576, 578, 579, 580, 582, 584, 586, 588, 590, 592, 594, 596, 598, 600, 601, 603, 606, 607, 608, 609, 611, 613, 615, 616, 617, 618, 620, 621, 622, 624, 625, 626, 628, 629, 631, 634, 636, 637, 638, 639, 641, 644, 645, 647, 649, 651, 653, 655, 657, 659, 661, 663, 665, 667, 669, 671, 673, 675, 676, 678, 680, 682, 684, 686, 688, 690, 692, 694, 695, 697, 699, 701, 702, 704, 706, 708, 709, 711, 712, 713, 714, 716, 718, 720, 721, 723, 725, 726, 728, 730, 732, 734, 736, 738, 740, 741, 742, 743, 744, 745, 747, 749, 750, 751, 753, 755, 757, 759, 761, 762, 763, 764, 765, 767, 769, 771, 773, 774, 776, 778, 779, 780, 782, 783, 784, 786, 788, 790, 792, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 826, 827, 829, 830, 831, 832, 833, 834, 835, 837, 838, 839, 840, 841, 843, 845, 847, 850, 851, 853, 855, 857, 859, 861, 862, 863, 864, 865, 866, 868, 870, 872, 874, 876, 877, 879, 881, 883, 885, 887, 889, 891, 893, 895, 897, 898, 900, 902, 904, 907, 909, 911, 913, 915, 917, 919, 920, 922, 923, 924, 926, 928, 929, 930, 931, 932, 934, 936, 937, 938, 939, 940, 941, 943, 945, 947, 948, 949, 950, 953, 955, 957, 959, 961, 963, 965, 966, 967, 969, 971, 973, 975, 977, 979, 981, 983, 985, 987, 989, 991, 993, 995, 997, 999, 1001, 1003, 1005, 1007, 1009, 1011, 1013, 1014, 1015, 1016, 1018, 1024, 1025, 1027, 1029, 1030, 1032, 1033, 1035, 1037, 1039, 1040, 1042, 1043, 1044, 1047, 1049, 1051, 1053, 1055, 1057, 1059, 1061, 1063, 1065, 1067, 1068, 1069, 1071, 1072, 1073, 1074, 1075, 1077, 1078, 1080, 1081, 1083, 1085, 1087, 1089, 1091, 1093, 1095, 1097, 1098, 1099, 1100, 1101, 1103, 1105, 1107, 1109, 1111, 1113, 1115, 1117, 1119, 1121, 1123, 1125, 1127, 1129, 1131, 1133, 1134, 1135, 1136, 1137, 1138, 1139, 1141, 1143, 1145, 1147, 1149, 1151, 1153, 1155, 1157, 1159, 1160, 1161, 1162, 1164, 1166, 1168, 1170, 1172, 1174, 1176, 1178, 1180, 1182, 1184, 1186, 1188, 1190, 1192, 1194, 1196, 1198, 1199, 1200, 1201, 1202, 1203, 1204, 1206, 1208, 1209, 1211, 1213, 1214, 1215, 1216, 1217, 1219, 1221, 1223, 1225, 1227, 1229, 1230, 1232, 1234, 1236, 1238, 1240, 1242, 1244, 1246, 1248, 1250, 1252, 1254, 1255, 1256, 1257, 1258, 1259, 1260, 1261, 1262, 1263, 1264, 1266, 1268, 1270, 1272, 1274, 1277, 1279, 1281, 1283, 1285, 1287, 1289, 1291, 1293, 1294, 1295, 1297, 1298, 1299, 1301, 1303, 1305, 1307, 1309, 1311, 1313, 1315, 1317, 1319, 1321, 1322, 1323, 1324, 1325, 1326, 1327, 1328, 1329, 1330, 1331, 1332, 1334, 1336, 1338, 1340, 1342, 1344, 1347, 1349, 1351, 1352, 1353, 1355, 1357, 1358, 1360, 1362, 1364, 1366, 1367, 1368, 1370, 1372, 1374, 1375, 1377, 1379, 1381, 1383, 1385, 1387, 1389, 1391, 1393, 1395, 1397, 1399, 1401, 1402, 1404, 1406, 1408, 1410, 1411, 1412, 1413, 1414, 1415, 1417, 1419, 1421, 1422, 1423, 1424, 1425, 1426, 1427, 1429, 1430, 1431, 1433, 1434, 1435, 1436, 1438, 1439, 1440, 1442, 1444, 1446, 1448, 1450, 1452, 1457, 1458, 1460, 1462, 1464, 1466, 1467, 1468, 1469, 1471, 1473, 1475, 1477, 1478, 1479, 1480, 1481, 1482, 1483, 1484, 1485, 1486, 1488, 1490, 1492, 1494, 1497, 1499, 1501, 1502, 1503, 1504, 1505, 1506, 1508, 1510, 1511, 1512, 1513, 1514, 1515, 1516, 1518, 1519, 1520, 1521, 1522, 1523, 1524, 1525, 1527, 1528, 1529, 1531, 1532, 1533, 1534, 1535, 1536, 1540, 1541, 1543, 1545, 1547, 1549, 1551, 1553, 1554, 1555, 1556, 1557, 1558, 1559, 1561, 1563, 1564, 1565, 1566, 1567, 1568, 1570, 1572, 1574, 1576, 1578, 1580, 1582, 1584, 1587, 1589, 1591, 1593, 1594, 1596, 1597, 1598, 1599, 1600, 1601, 1602, 1603, 1604, 1605, 1606, 1607, 1609, 1611, 1612, 1613, 1614, 1615, 1616, 1617, 1618, 1619, 1620, 1621, 1623, 1625, 1630, 1631, 1632, 1635, 1637, 1639, 1641, 1642, 1643, 1644, 1646, 1648, 1650, 1651, 1652, 1653, 1654, 1655, 1657, 1659, 1661, 1663, 1665, 1667, 1669, 1671, 1673, 1675, 1677, 1679, 1681, 1682, 1684, 1686, 1688, 1690, 1692, 1694, 1696, 1698, 1699, 1700, 1701, 1702, 1703, 1704, 1705, 1707, 1709, 1711, 1713, 1715, 1717, 1719, 1720, 1721, 1722, 1723, 1725, 1727, 1729, 1730, 1732, 1734, 1736, 1738, 1739, 1740, 1741, 1742, 1743, 1744, 1745, 1746, 1748, 1750, 1751, 1752, 1754, 1756, 1758, 1760, 1762, 1764, 1766, 1767, 1768, 1769, 1770, 1771, 1772, 1773, 1774, 1775, 1776, 1777, 1778, 1780, 1782, 1784, 1786, 1788, 1790, 1792, 1794, 1796, 1798, 1800, 1802, 1804, 1805, 1806, 1807, 1808, 1809, 1810, 1811, 1812, 1813, 1814, 1815, 1816, 1817, 1818, 1819, 1820, 1821, 1822, 1823, 1824, 1825, 1826, 1827, 1828, 1829, 1830, 1831, 1832, 1833, 1834, 1835, 1836, 1837, 1838, 1839, 1840, 1842, 1843, 1844, 1845, 1846, 1847, 1848, 1850, 1852, 1854, 1856, 1858, 1859, 1860, 1861, 1862, 1863, 1864, 1865, 1866, 1867, 1869, 1870, 1871, 1873, 1875, 1877, 1879, 1881, 1883, 1885, 1887, 1889, 1891, 1893, 1895, 1897, 1899, 1901, 1903, 1905, 1907, 1909, 1911, 1913, 1915, 1917, 1919, 1921, 1923, 1925, 1927, 1929, 1931, 1933, 1935, 1937, 1939, 1941, 1943, 1945, 1947, 1949, 1951, 1953, 1955, 1957, 1959, 1961, 1963, 1965, 1967, 1969, 1971, 1973, 1975, 1977, 1979, 1981, 1983, 1985, 1987, 1989, 1991, 1993, 1995, 1997, 1999, 2001, 2003, 2005, 2007, 2009, 2011, 2013, 2015, 2017, 2019, 2021, 2023, 2025, 2027, 2029, 2030, 2031, 2032, 2033, 2034, 2035, 2036, 2037, 2038, 2039, 2040, 2041, 2042, 2043, 2044, 2045, 2046, 2047, 2048, 2049, 2050, 2051, 2052, 2053, 2054, 2055, 2056, 2057, 2058, 2059, 2060, 2061, 2062, 2063, 2064, 2065, 2066, 2067, 2069, 2070, 2072, 2074, 2076, 2078, 2080, 2081, 2083, 2084, 2085, 2087, 2089, 2091, 2093, 2095, 2097, 2099, 2101, 2103, 2105, 2107, 2109, 2111, 2113, 2114, 2115, 2116, 2117, 2118, 2119, 2120, 2121, 2123, 2125, 2127, 2129, 2131, 2133, 2135, 2136, 2137, 2138, 2139, 2140, 2141, 2142, 2143, 2144, 2146, 2148, 2150, 2152, 2154, 2156, 2158, 2160, 2162, 2164, 2166, 2168, 2170, 2172, 2174, 2176, 2178, 2180, 2182, 2183, 2184, 2185, 2186, 2187, 2188, 2189, 2190, 2191, 2192, 2193, 2194, 2195, 2196, 2197, 2198, 2199, 2200, 2201, 2202, 2203, 2204, 2205, 2206, 2207, 2208, 2209, 2210, 2211, 2212, 2213, 2214, 2215, 2216, 2217, 2218, 2219, 2220, 2221, 2222, 2223, 2224, 2225, 2226, 2227, 2228, 2229, 2230, 2231, 2232, 2233, 2234, 2235, 2236, 2237, 2238, 2239, 2240, 2241, 2242, 2243, 2244, 2245, 2246, 2247, 2248, 2249, 2250, 2251, 2252, 2253, 2254, 2255, 2256, 2257, 2258, 2259, 2260, 2261, 2262, 2263, 2264, 2266, 2268, 2269, 2270, 2271, 2272, 2273, 2274, 2275, 2276, 2277, 2278, 2280, 2282, 2284, 2286, 2288, 2290, 2292, 2294, 2296, 2298, 2300, 2302, 2304, 2306, 2308, 2310, 2312, 2314, 2316, 2318, 2320, 2322, 2323, 2324, 2325, 2326, 2327, 2328, 2329, 2330, 2331, 2332, 2333, 2334, 2335, 2336, 2337, 2338, 2339, 2340, 2341, 2342, 2343, 2344, 2345, 2346, 2347, 2348, 2350, 2352, 2354, 2356, 2358, 2360, 2362, 2364, 2366, 2368, 2370, 2372, 2374, 2375, 2376, 2377, 2378, 2379, 2380, 2381. Examples of nucleic acids encoding SD+EODFR and/or low light-tolerance polypeptides are described herein. The SD+EODFR and/or low light-tolerance polypeptide encoded by a recombinant nucleic acid can be a native SD+EODFR and/or low light-tolerance polypeptide, or can be heterologous to the cell. In some cases, the recombinant construct contains a nucleic acid that inhibits expression of an SD+EODFR and/or low light-tolerance polypeptide, operably linked to a regulatory region. Examples of suitable regulatory regions are described in the section entitled "Regulatory Regions."

Vectors containing recombinant nucleic acid constructs such as those described herein also are provided. Suitable vector backbones include, for example, those routinely used in the art such as plasmids, viruses, artificial chromosomes, BACs, YACs, or PACs. Suitable expression vectors include, without limitation, plasmids and viral vectors derived from, for example, bacteriophage, baculoviruses, and retroviruses. Numerous vectors and expression systems are commercially available from such corporations as Novagen (Madison, Wis.), Clontech (Palo Alto, Calif.), Stratagene (La Jolla, Calif.), and Invitrogen/Life Technologies (Carlsbad, Calif.).

The vectors provided herein also can include, for example, origins of replication, scaffold attachment regions (SARs), and/or markers. A marker gene can confer a selectable phenotype on a plant cell. For example, a marker can confer biocide resistance, such as resistance to an antibiotic (e.g., kanamycin, G418, bleomycin, or hygromycin), or an herbicide (e.g., glyphosate, chlorsulfuron or phosphinothricin). In addition, an expression vector can include a tag sequence designed to facilitate manipulation or detection (e.g., purification or localization) of the expressed polypeptide. Tag sequences, such as luciferase, β-glucuronidase (GUS), green fluorescent protein (GFP), glutathione S-transferase (GST), polyhistidine, c-myc, hemagglutinin, or Flag™ tag (Kodak, New Haven, Conn.) sequences typically are expressed as a fusion with the encoded polypeptide. Such tags can be inserted anywhere within the polypeptide, including at either the carboxyl or amino terminus.

F. Regulatory Regions

The choice of regulatory regions to be included in a recombinant construct depends upon several factors, including, but not limited to, efficiency, selectability, inducibility, desired expression level, and cell- or tissue-preferential expression. It is a routine matter for one of skill in the art to modulate the expression of a coding sequence by appropriately selecting and positioning regulatory regions relative to the coding sequence. Transcription of a nucleic acid can be modulated in a similar manner.

Some suitable regulatory regions initiate transcription only, or predominantly, in certain cell types. Methods for identifying and characterizing regulatory regions in plant genomic DNA are known, including, for example, those described in the following references: Jordano et al., *Plant Cell*, 1:855-866 (1989); Bustos et al., *Plant Cell*, 1:839-854 (1989); Green et al., *EMBO J.*, 7:4035-4044 (1988); Meier et al., *Plant Cell*, 3:309-316 (1991); and Zhang et al., *Plant Physiology*, 110:1069-1079 (1996).

Examples of various classes of regulatory regions are described below. Some of the regulatory regions indicated below as well as additional regulatory regions are described in more detail in U.S. Patent Application Ser. Nos. 60/505,689; 60/518,075; 60/544,771; 60/558,869; 60/583,691; 60/619,181; 60/637,140; 60/757,544; 60/776,307; 10/957,569; 11/058,689; 11/172,703; 11/208,308; 11/274,890; 60/583,609; 60/612,891; 11/097,589; 11/233,726; 11/408,791; 11/414,142; 10/950,321; 11/360,017; PCT/US05/011105; PCT/US05/23639; PCT/US05/034308; PCT/US05/034343; and PCT/US06/038236; PCT/US06/040572; and PCT/US07/62762.

For example, the sequences of regulatory regions p326, YP0144, YP0190, p13879, YP0050, p32449, 21876, YP0158, YP0214, YP0380, PT0848, PT0633, YP0128, YP0275, PT0660, PT0683, PT0758, PT0613, PT0672, PT0688, PT0837, YP0092, PT0676, PT0708, YP0396, YP0007, YP0111, YP0103, YP0028, YP0121, YP0008, YP0039, YP0115, YP0119, YP0120, YP0374, YP0101, YP0102, YP0110, YP0117, YP0137, YP0285, YP0212, YP0097, YP0107, YP0088, YP0143, YP0156, PT0650, PT0695, PT0723, PT0838, PT0879, PT0740, PT0535, PT0668, PT0886, PT0585, YP0381, YP0337, PT0710, YP0356, YP0385, YP0384, YP0286, YP0377, PD1367, PT0863, PT0829, PT0665, PT0678, YP0086, YP0188, YP0263, PT0743 and YP0096 are set forth in the sequence listing of PCT/US06/040572; the sequence of regulatory region PT0625 is set forth in the sequence listing of PCT/US05/034343; the sequences of regulatory regions PT0623, YP0388, YP0087, YP0093, YP0108, YP0022 and YP0080 are set forth in the sequence listing of U.S. patent application Ser. No. 11/172,703; the sequence of regulatory region PR0924 is set forth in the sequence listing of PCT/US07/62762; and the sequences of regulatory regions p530c10, pOsFIE2-2, pOsMEA, pOsYp102, and pOsYp285 are set forth in the sequence listing of PCT/US06/038236.

It will be appreciated that a regulatory region may meet criteria for one classification based on its activity in one plant species, and yet meet criteria for a different classification based on its activity in another plant species.

i. Broadly Expressing Promoters

A promoter can be said to be "broadly expressing" when it promotes transcription in many, but not necessarily all, plant tissues. For example, a broadly expressing promoter can promote transcription of an operably linked sequence in one or more of the shoot, shoot tip (apex), and leaves, but weakly or not at all in tissues such as roots or stems. As another example, a broadly expressing promoter can promote transcription of an operably linked sequence in one or more of the stem, shoot, shoot tip (apex), and leaves, but can promote transcription weakly or not at all in tissues such as reproductive tissues of flowers and developing seeds. Non-limiting examples of broadly expressing promoters that can be included in the nucleic acid constructs provided herein include the p326, YP0144, YP0190, p13879, YP0050, p32449, 21876, YP0158, YP0214, YP0380, PT0848, and PT0633 promoters. Additional examples include the cauliflower mosaic virus (CaMV) 35S promoter, the mannopine synthase (MAS) promoter, the 1' or 2' promoters derived from T-DNA of *Agrobacterium tumefaciens*, the figwort mosaic virus 34S promoter, actin promoters such as the rice actin promoter, and ubiquitin promoters such as the maize ubiquitin-1 promoter. In some cases, the CaMV 35S promoter is excluded from the category of broadly expressing promoters.

ii. Root Promoters

Root-active promoters confer transcription in root tissue, e.g., root endodermis, root epidermis, or root vascular tissues. In some embodiments, root-active promoters are root-preferential promoters, i.e., confer transcription only or predominantly in root tissue. Root-preferential promoters include the YP0128, YP0275, PT0625, PT0660, PT0683, and PT0758 promoters. Other root-preferential promoters include the PT0613, PT0672, PT0688, and PT0837 promoters, which drive transcription primarily in root tissue and to a lesser extent in ovules and/or seeds. Other examples of root-preferential promoters include the root-specific subdomains of the CaMV 35S promoter (Lam et al., *Proc. Natl. Acad. Sci. USA*, 86:7890-7894 (1989)), root cell specific promoters reported by Conkling et al., *Plant Physiol.*, 93:1203-1211 (1990), and the tobacco RD2 promoter.

iii. Maturing Endosperm Promoters

In some embodiments, promoters that drive transcription in maturing endosperm can be useful. Transcription from a maturing endosperm promoter typically begins after fertilization and occurs primarily in endosperm tissue during seed development and is typically highest during the cellularization phase. Most suitable are promoters that are active predominantly in maturing endosperm, although promoters that are also active in other tissues can sometimes be used. Non-limiting examples of maturing endosperm promoters that can be included in the nucleic acid constructs provided herein include the napin promoter, the Arcelin-5 promoter, the phaseolin promoter (Bustos et al., *Plant Cell*, 1(9):839-853 (1989)), the soybean trypsin inhibitor promoter (Riggs et al., *Plant Cell*, 1(6):609-621 (1989)), the ACP promoter (Baerson et al., *Plant Mol. Biol.*, 22(2):255-267 (1993)), the stearoyl-ACP desaturase promoter (Slocombe et al., *Plant Physiol.*, 104(4):167-176 (1994)), the soybean α' subunit of β-conglycinin promoter (Chen et al., *Proc. Natl. Acad. Sci. USA*, 83:8560-8564 (1986)), the oleosin promoter (Hong et al., *Plant Mol. Biol.*, 34(3):549-555 (1997)), and zein promoters, such as the 15 kD zein promoter, the 16 kD zein promoter, 19 kD zein promoter, 22 kD zein promoter and 27 kD zein promoter. Also suitable are the Osgt-1 promoter from the rice glutelin-1 gene (Zheng et al., *Mol. Cell Biol.*, 13:5829-5842 (1993)), the beta-amylase promoter, and the barley hordein promoter. Other maturing endosperm promoters include the YP0092, PT0676, and PT0708 promoters.

iv. Ovary Tissue Promoters

Promoters that are active in ovary tissues such as the ovule wall and mesocarp can also be useful, e.g., a polygalacturonidase promoter, the banana TRX promoter, the melon actin promoter, YP0396, and PT0623. Examples of promoters that are active primarily in ovules include YP0007, YP0111, YP0092, YP0103, YP0028, YP0121, YP0008, YP0039, YP0115, YP0119, YP0120, and YP0374.

v. Embryo Sac/Early Endosperm Promoters

To achieve expression in embryo sac/early endosperm, regulatory regions can be used that are active in polar nuclei and/or the central cell, or in precursors to polar nuclei, but not in egg cells or precursors to egg cells. Most suitable are promoters that drive expression only or predominantly in polar nuclei or precursors thereto and/or the central cell. A pattern of transcription that extends from polar nuclei into early endosperm development can also be found with embryo sac/early endosperm-preferential promoters, although transcription typically decreases significantly in later endosperm development during and after the cellularization phase. Expression in the zygote or developing embryo typically is not present with embryo sac/early endosperm promoters.

Promoters that may be suitable include those derived from the following genes: *Arabidopsis* viviparous-1 (see, GenBank No. U93215); *Arabidopsis* atmyc1 (see, Urao (1996) Plant Mol. Biol., 32:571-57; Conceicao (1994) Plant, 5:493-505); *Arabidopsis* FIE (GenBank No. AF129516); *Arabidopsis* MEA; *Arabidopsis* FIS2 (GenBank No. AF096096); and FIE 1.1 (U.S. Pat. No. 6,906,244). Other promoters that may be suitable include those derived from the following genes: maize MAC1 (see, Sheridan (1996) Genetics, 142:1009-1020); maize Cat3 (see, GenBank No. L05934; Abler (1993) Plant Mol. Biol., 22:10131-1038). Other promoters include the following *Arabidopsis* promoters: YP0039, YP0101, YP0102, YP0110, YP0117, YP0119, YP0137, DME, YP0285, and YP0212. Other promoters that may be useful include the following rice promoters: p530c10, pOsFIE2-2, pOsMEA, pOsYp102, and pOsYp285.

vi. Embryo Promoters

Regulatory regions that preferentially drive transcription in zygotic cells following fertilization can provide embryo-preferential expression. Most suitable are promoters that preferentially drive transcription in early stage embryos prior to the heart stage, but expression in late stage and maturing embryos is also suitable. Embryo-preferential promoters include the barley lipid transfer protein (Ltp1) promoter (*Plant Cell Rep* (2001) 20:647-654), YP0097, YP0107, YP0088, YP0143, YP0156, PT0650, PT0695, PT0723, PT0838, PT0879, and PT0740.

vii. Photosynthetic Tissue Promoters

Promoters active in photosynthetic tissue confer transcription in green tissues such as leaves and stems. Most suitable are promoters that drive expression only or predominantly in such tissues. Examples of such promoters include the ribulose-1,5-bisphosphate carboxylase (RbcS) promoters such as the RbcS promoter from eastern larch (*Larix laricina*), the pine cab6 promoter (Yamamoto et al., *Plant Cell Physiol.*, 35:773-778 (1994)), the Cab-1 promoter from wheat (Fejes et al., *Plant Mol. Biol.*, 15:921-932 (1990)), the CAB-1 promoter from spinach (Lubberstedt et al., *Plant Physiol.*, 104:997-1006 (1994)), the cab1R promoter from rice (Luan et al., *Plant Cell*, 4:971-981 (1992)), the pyruvate orthophosphate dikinase (PPDK) promoter from corn (Matsuoka et al., *Proc. Natl. Acad. Sci. USA*, 90:9586-9590 (1993)), the tobacco Lhcb1*2 promoter (Cerdan et al., *Plant Mol. Biol.*, 33:245-255 (1997)), the *Arabidopsis thaliana* SUC2 sucrose-H+ symporter promoter (Truernit et al., *Planta*, 196:564-570 (1995)), and thylakoid membrane protein promoters from spinach (psaD, psaF, psaE, PC, FNR, atpC, atpD, cab, rbcS). Other photosynthetic tissue promoters include PT0535, PT0668, PT0886, YP0144, YP0380 and PT0585.

viii. Vascular Tissue Promoters

Examples of promoters that have high or preferential activity in vascular bundles include YP0087, YP0093, YP0108, YP0022, and YP0080. Other vascular tissue-preferential promoters include the glycine-rich cell wall protein GRP 1.8 promoter (Keller and Baumgartner, *Plant Cell*, 3(10):1051-1061 (1991)), the Commelina yellow mottle virus (CoYMV) promoter (Medberry et al., *Plant Cell*, 4(2):185-192 (1992)), and the rice tungro bacilliform virus (RTBV) promoter (Dai et al., *Proc. Natl. Acad. Sci. USA*, 101(2):687-692 (2004)).

ix. Inducible Promoters

Inducible promoters confer transcription in response to external stimuli such as chemical agents or environmental stimuli. For example, inducible promoters can confer transcription in response to hormones such as giberellic acid or ethylene, or in response to light or drought. Examples of drought-inducible promoters include YP0380, PT0848, YP0381, YP0337, PT0633, YP0374, PT0710, YP0356, YP0385, YP0396, YP0388, YP0384, PT0688, YP0286, YP0377, PD1367, and PD0901. Examples of nitrogen-inducible promoters include PT0863, PT0829, PT0665, and PT0886. Examples of shade-inducible promoters include PR0924 and PT0678. An example of a promoter induced by salt is rd29A (Kasuga et al. (1999) Nature Biotech 17: 287-291).

x. Basal Promoters

A basal promoter is the minimal sequence necessary for assembly of a transcription complex required for transcription initiation. Basal promoters frequently include a "TATA box" element that may be located between about 15 and about 35 nucleotides upstream from the site of transcription initiation. Basal promoters also may include a "CCAAT box" element (typically the sequence CCAAT) and/or a GGGCG sequence, which can be located between about 40 and about 200 nucleotides, typically about 60 to about 120 nucleotides, upstream from the transcription start site.

xi. Other Promoters

Other classes of promoters include, but are not limited to, shoot-preferential, callus-preferential, trichome cell-preferential, guard cell-preferential such as PT0678, tuber-preferential, parenchyma cell-preferential, and senescence-preferential promoters. Promoters designated YP0086, YP0188, YP0263, PT0758, PT0743, PT0829, YP0119, and YP0096, as described in the above-referenced patent applications, may also be useful.

xii. Other Regulatory Regions

A 5' untranslated region (UTR) can be included in nucleic acid constructs described herein. A 5' UTR is transcribed, but is not translated, and lies between the start site of the transcript and the translation initiation codon and may include the +1 nucleotide. A 3' UTR can be positioned between the translation termination codon and the end of the transcript. UTRs can have particular functions such as increasing mRNA stability or attenuating translation. Examples of 3' UTRs include, but are not limited to, polyadenylation signals and transcription termination sequences, e.g., a nopaline synthase termination sequence.

It will be understood that more than one regulatory region may be present in a recombinant polynucleotide, e.g., introns, enhancers, upstream activation regions, transcription terminators, and inducible elements. Thus, for example, more than one regulatory region can be operably linked to the sequence of a polynucleotide encoding an SD+EODFR and/or low light-tolerance polypeptide.

Regulatory regions, such as promoters for endogenous genes, can be obtained by chemical synthesis or by subcloning from a genomic DNA that includes such a regulatory region. A nucleic acid comprising such a regulatory region can also include flanking sequences that contain restriction enzyme sites that facilitate subsequent manipulation.

IV. Transgenic Plants and Plant Cells

A. Transformation

The invention also features transgenic plant cells and plants comprising at least one recombinant nucleic acid construct described herein. A plant or plant cell can be transformed by having a construct integrated into its genome, i.e., can be stably transformed. Stably transformed cells typically retain the introduced nucleic acid with each cell division. A plant or plant cell can also be transiently transformed such that the construct is not integrated into its genome. Transiently transformed cells typically lose all or some portion of the introduced nucleic acid construct with each cell division such that the introduced nucleic acid cannot be detected in daughter cells after a sufficient number of cell divisions. Both transiently transformed and stably transformed transgenic plants and plant cells can be useful in the methods described herein.

Transgenic plant cells used in methods described herein can constitute part or all of a whole plant. Such plants can be grown in a manner suitable for the species under consideration, either in a growth chamber, a greenhouse, or in a field. Transgenic plants can be bred as desired for a particular purpose, e.g., to introduce a recombinant nucleic acid into other lines, to transfer a recombinant nucleic acid to other species, or for further selection of other desirable traits. Alternatively, transgenic plants can be propagated vegetatively for those species amenable to such techniques. As used herein, a transgenic plant also refers to progeny of an initial transgenic plant provided the progeny inherits the transgene. Seeds produced by a transgenic plant can be grown and then selfed (or outcrossed and selfed) to obtain seeds homozygous for the nucleic acid construct.

Transgenic plants can be grown in suspension culture, or tissue or organ culture. For the purposes of this invention, solid and/or liquid tissue culture techniques can be used. When using solid medium, transgenic plant cells can be placed directly onto the medium or can be placed onto a filter that is then placed in contact with the medium. When using liquid medium, transgenic plant cells can be placed onto a flotation device, e.g., a porous membrane that contacts the liquid medium. A solid medium can be, for example, Murashige and Skoog (MS) medium containing agar and a suitable concentration of an auxin, e.g., 2,4-dichlorophenoxyacetic acid (2,4-D), and a suitable concentration of a cytokinin, e.g., kinetin.

When transiently transformed plant cells are used, a reporter sequence encoding a reporter polypeptide having a reporter activity can be included in the transformation procedure and an assay for reporter activity or expression can be performed at a suitable time after transformation. A suitable time for conducting the assay typically is about 1-21 days after transformation, e.g., about 1-14 days, about 1-7 days, or about 1-3 days. The use of transient assays is particularly convenient for rapid analysis in different species, or to confirm expression of a heterologous SD+EODFR and/or low light-tolerance polypeptide whose expression has not previously been confirmed in particular recipient cells.

Techniques for introducing nucleic acids into monocotyledonous and dicotyledonous plants are known in the art, and include, without limitation, *Agrobacterium*-mediated transformation, viral vector-mediated transformation, electroporation and particle gun transformation, e.g., U.S. Pat. Nos. 5,538,880; 5,204,253; 6,329,571 and 6,013,863. If a cell or cultured tissue is used as the recipient tissue for transformation, plants can be regenerated from transformed cultures if desired, by techniques known to those skilled in the art.

B. Screening/Selection

A population of transgenic plants can be screened and/or selected for those members of the population that have a trait or phenotype conferred by expression of the transgene. For example, a population of progeny of a single transformation event can be screened for those plants having a desired level of expression of an SD+EODFR and/or low light-tolerance polypeptide or nucleic acid. Physical and biochemical methods can be used to identify expression levels. These include Southern analysis or PCR amplification for detection of a polynucleotide; Northern blots, 51 RNase protection, primer-extension, or RT-PCR amplification for detecting RNA transcripts; enzymatic assays for detecting enzyme or ribozyme activity of polypeptides and polynucleotides; and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides. Methods for performing all of the referenced techniques are known. As an alternative, a population of plants comprising independent transformation events can be screened for those plants having a desired trait, such as a modulated level SD+EODFR and/or low light tolerance. Selection and/or screening can be carried out over one or more generations, and/or in more than one geographic location. In some cases, transgenic plants can be grown and selected under conditions which induce a desired phenotype or are otherwise necessary to produce a desired phenotype in a transgenic plant. In addition, selection and/or screening can be applied during a particular developmental stage in which the phenotype is expected to be exhibited by the plant. Selection and/or screening can be carried out to choose those transgenic plants having a statistically significant difference in SD+EODFR and/or low light tolerance level relative to a control plant that lacks the transgene. Selected or screened transgenic plants have an altered phenotype as compared to a corresponding control plant, as described in the "Transgenic Plant Phenotypes" section herein.

C. Plant Species

The polynucleotides and vectors described herein can be used to transform a number of monocotyledonous and dicotyledonous plants and plant cell systems, including species from one of the following families: Acanthaceae, Alliaceae, Alstroemeriaceae, Amaryllidaceae, Apocynaceae, Arecaceae, Asteraceae, Berberidaceae, Bixaceae, Brassicaceae, Bromeliaceae, Cannabaceae, Caryophyllaceae, Cephalotaxaceae, Chenopodiaceae, Colchicaceae, Cucurbitaceae, Dioscoreaceae, Ephedraceae, Erythroxylaceae, Euphorbiaceae, Fabaceae, Lamiaceae, Linaceae, Lycopodiaceae, Malvaceae, Melanthiaceae, Musaceae, Myrtaceae, Nyssaceae, Papaveraceae, Pinaceae, Plantaginaceae, Poaceae, Rosaceae, Rubiaceae, Salicaceae, Sapindaceae, Solanaceae, Taxaceae, Theaceae, or Vitaceae.

Suitable species may include members of the genus *Abelmoschus, Abies, Acer, Agrostis, Allium, Alstroemeria, Ananas, Andrographis, Andropogon, Artemisia, Arundo, Atropa, Berberis, Beta, Bixa, Brassica, Calendula, Camellia, Camptotheca, Cannabis, Capsicum, Carthamus, Catharanthus, Cephalotaxus, Chrysanthemum, Cinchona, Citrullus, Coffea, Colchicum, Coleus, Cucumis, Cucurbita, Cynodon, Datura, Dianthus, Digitalis, Dioscorea, Elaeis, Ephedra, Erianthus, Erythroxylum, Eucalyptus, Festuca, Fragaria, Galanthus, Glycine, Gossypium, Helianthus, Hevea, Hordeum, Hyoscyamus, Jatropha, Lactuca, Linum, Lolium, Lupinus, Lycopersicon, Lycopodium, Manihot, Medicago, Mentha, Miscanthus, Musa, Nicotiana, Oryza, Panicum, Papaver, Parthenium, Pennisetum, Petunia, Phalaris, Phleum, Pinus, Poa, Poinsettia, Populus, Rauwolfia, Ricinus, Rosa, Saccharum, Salix, Sanguinaria, Scopolia, Secale, Solanum, Sorghum, Spartina, Spinacea, Tanacetum, Taxus, Theobroma, Triticosecale, Triticum, Uniola, Veratrum, Vinca, Vitis,* and *Zea.*

Suitable species include *Panicum* spp. or hybrids thereof, *Sorghum* spp. or hybrids thereof, sudangrass, *Miscanthus* spp. or hybrids thereof, *Saccharum* spp. or hybrids thereof, *Erianthus* spp., *Populus* spp., *Andropogon gerardii* (big bluestem), *Pennisetum purpureum* (elephant grass) or hybrids thereof (e.g., *Pennisetum purpureum* x *Pennisetum typhoidum*), *Phalaris arundinacea* (reed canarygrass), *Cynodon dactylon* (bermudagrass), *Festuca arundinacea* (tall fescue), *Spartina pectinata* (prairie cord-grass), *Medicago sativa* (alfalfa), *Arundo donax* (giant reed) or hybrids thereof, *Secale cereale* (rye), *Salix* spp. (willow), *Eucalyptus* spp. (eucalyptus), Triticosecale (triticum—wheat X rye) and bamboo.

In some embodiments, a suitable species can be a wild, weedy, or cultivated sorghum species such as, but not limited to, *Sorghum almum, Sorghum amplum, Sorghum angustum, Sorghum arundinaceum, Sorghum bicolor* (such as bicolor, guinea, caudatum, kafir, and durra), *Sorghum brachypodum, Sorghum bulbosum, Sorghum burmahicum, Sorghum controversum, Sorghum drummondii, Sorghum ecarinatum, Sorghum exstans, Sorghum grande, Sorghum halepense, Sorghum interjectum, Sorghum intrans, Sorghum laxiflorum, Sorghum leiocladum, Sorghum macrospermum, Sorghum matarankense, Sorghum miliaceum, Sorghum* nigrum, *Sorghum nitidum, Sorghum plumosum, Sorghum propinquum, Sorghum purpureosericeum, Sorghum stipoideum, Sorghum sudanensese, Sorghum timorense, Sorghum trichocladum, Sorghum versicolor, Sorghum virgatum, Sorghum vulgare*, or hybrids such as *Sorghum* x *almum, Sorghum* x *sudangrass* or *Sorghum* x *drummondii*.

Suitable species also include *Helianthus annuus* (sunflower), *Carthamus tinctorius* (safflower), *Jatropha curcas* (jatropha), *Ricinus communis* (castor), *Elaeis guineensis* (palm), *Linum usitatissimum* (flax), and *Brassica juncea*.

Suitable species also include *Beta vulgaris* (sugarbeet), and *Manihot esculenta* (cassava).

Suitable species also include *Lycopersicon esculentum* (tomato), *Lactuca sativa* (lettuce), *Musa paradisiaca* (banana), *Solanum tuberosum* (potato), *Brassica oleracea* (broccoli, cauliflower, Brussels sprouts), *Camellia sinensis* (tea), *Fragaria ananassa* (strawberry), *Theobroma cacao* (cocoa), *Coffea arabica* (coffee), *Vitis vinifera* (grape), *Ananas comosus* (pineapple), *Capsicum* annum (hot & sweet pepper), *Allium cepa* (onion), *Cucumis melo* (melon), *Cucumis sativus* (cucumber), *Cucurbita maxima* (squash), *Cucurbita moschata* (squash), *Spinacea oleracea* (spinach), *Citrullus lanatus* (watermelon), *Abelmoschus esculentus* (okra), and *Solanum melongena* (eggplant).

Suitable species also include *Papaver somniferum* (opium poppy), *Papaver orientale, Taxus baccata, Taxus brevifolia, Artemisia annua, Cannabis sativa, Camptotheca acuminate, Catharanthus roseus, Vinca rosea, Cinchona officinalis, Colchicum autumnale, Veratrum californica, Digitalis lanata, Digitalis purpurea, Dioscorea* spp., *Andrographis paniculata, Atropa belladonna, Datura stomonium, Berberis* spp., *Cephalotaxus* spp., *Ephedra sinica, Ephedra* spp *Erythroxylum coca, Galanthus wornorii, Scopolia* spp., *Lycopodium serratum* (=*Huperzia serrata*), *Lycopodium* spp., *Rauwolfia serpentina, Rauwolfia* spp., *Sanguinaria canadensis, Hyoscyamus* spp., *Calendula officinalis, Chrysanthemum parthenium, Coleus forskohlii*, and *Tanacetum parthenium*.

Suitable species also include *Parthenium argentatum* (guayule), *Hevea* spp. (rubber), *Mentha spicata* (mint), *Mentha piperita* (mint), *Bixa orellana*, and *Alstroemeria* spp.

Suitable species also include *Rosa* spp. (rose), *Dianthus caryophyllus* (carnation), *Petunia* spp. (*petunia*) and *Poinsettia pulcherrima* (poinsettia).

Suitable species also include *Nicotiana tabacum* (tobacco), *Lupinus albus* (lupin), *Uniola paniculata* (oats), bentgrass (*Agrostis* spp.), *Populus tremuloides* (aspen), *Pinus* spp. (pine), *Abies* spp. (fir), *Acer* spp. (maple), *Hordeum vulgare* (barley), *Poa pratensis* (bluegrass), *Lolium* spp. (ryegrass) and *Phleum pratense* (timothy).

Thus, the methods and compositions can be used over a broad range of plant species, including species from the dicot genera *Brassica, Carthamus, Glycine, Gossypium, Helianthus, Jatropha, Parthenium, Populus*, and *Ricinus*; and the monocot genera *Elaeis, Festuca, Hordeum, Lolium, Oryza, Panicum, Pennisetum, Phleum, Poa, Saccharum, Secale, Sorghum, Triticosecale, Triticum*, and *Zea*. In some embodiments, a plant is a member of the species *Panicum virgatum* (switchgrass), *Sorghum bicolor* (sorghum, sudangrass), *Miscanthus giganteus* (miscanthus), *Saccharum* sp. (energycane), *Populus balsamifera* (poplar), *Zea mays* (corn), *Glycine max* (soybean), *Brassica napus* (canola), *Triticum aestivum* (wheat), *Gossypium hirsutum* (cotton), *Oryza sativa* (rice), *Helianthus annuus* (sunflower), *Medicago sativa* (alfalfa), *Beta vulgaris* (sugarbeet), or *Pennisetum glaucum* (pearl millet).

In certain embodiments, the polynucleotides and vectors described herein can be used to transform a number of monocotyledonous and dicotyledenous plants and plant cell systems, wherein such plants are hybrids of different species or varieties of a specific species (e.g., *Saccharum* sp. X *Miscanthus* sp., *Panicum virgatum* x *Panicum amarum, Panicum virgatum* x *Panicum amarulum*, and *Pennisetum purpureum* x *Pennisetum typhoidum*).

D. Transgenic Plant Phenotypes

The light in shady environments is enriched in FR wavelengths relative to the light in non-shady environments. Red wavelengths typically range from a photon irradiance of about 630 nm to a photon irradiance of about 700 nm. Far-red wavelengths typically range from a photon irradiance of about 700 nm to a photon irradiance of about 750 nm.

In some embodiments, a plant in which expression of an SD+EODFR and/or low light-tolerance polypeptide is modulated can have increased SD+EODFR and/or low light tolerance. The phenotype of a transgenic plant in which expression of an SD+EODFR and/or low light-tolerance polypeptide is modulated and a corresponding control plant that either lacks the transgene or does not express the transgene can be evaluated under particular environmental conditions that are useful for simulating shade, i.e., Short Day plus End-of-Day Far-Red (SD+EODFR) conditions. SD+EODFR conditions consist of a light period followed by a pulse of far-red-enriched light conditions followed by a 14 hour dark period. The light period is from about 9.0 to about 9.6 hours with a red:far-red ratio of about 5.5, with the following fluence rates: $blue_{450}$=12 μmol/m²/s, $red_{633}$=22 μmol/m²/S, $far\text{-}red_{740}$=4 μmol/m²/s, $PPFD_{400\text{-}700}$=55 μmol/m²/s. The pulse of far-red-enriched light conditions is from about 0.4 to about 1.0 hours with a red:far-red ratio of about 0.14 with the following fluence rates: $blue_{450}$=0.004 μmol/m²/s, $red_{633}$=10 μmol/m²/s, $far\text{-}red_{740}$=70 μmol/m²/s, $PPFD_{400\text{-}700}$=8 μmol/m²/s. Sources of lighting equipment appropriate for producing and maintaining SD+EODFR conditions are known to those in art.

The phenotype of a transgenic plant in which expression of an SD+EODFR and/or low light-tolerance polypeptide is modulated and a corresponding control plant can also be evaluated under conditions of low light irradiance. Low light conditions are conditions under which a plant is exposed to an irradiance of about 0.01 μmol/m²/s of light to about 20 μmol/m²/s of light at room temperature and about 70% relative humidity. For example, conditions under which a plant is exposed to 0.01, 1, 5, 10, 15, or 20 μmol/m²/s of light are low light conditions. Sources of lighting and other equipment appropriate for controlling light conditions are known to those in art.

Low light conditions typically have light of a combination of wavelengths, such as white light. White light can be supplied, e.g., by 32 watt fluorescent bulbs (Sylvania, F032/841/ECO, Danvers, Mass.), providing a red:far-red ratio of 13:1. Red wavelengths typically range from a photon irradiance of about 630 to about 700 nm. Far-red wavelengths typically range from a photon irradiance of about 700 to about 750 nm.

In some embodiments, the phenotype of a transgenic plant is assayed under low light conditions in which there is continuous low light during the light period of a light/dark cycle. Continuous low light conditions can be, for example, 16 hours of irradiance with 0.01 to 20 μmol/m²/s of light alternating with 8 hours of darkness. The phenotype of a transgenic plant is assayed once the plant has been exposed to continuous low light conditions during the light period of the light/dark cycle for seven days.

In some embodiments, the phenotype of a transgenic plant is assayed under red light conditions in which there is continuous red light. Continuous red light conditions can be, for example, continuous irradiance with about ~15 μmol/m$^2$/s of light with a red light to far-red light ratio (R:FR) of about 80. Continuous red light can be supplied by a LED array that can be used to activate and deactivate the plant photoreceptor phytochrome (e.g., SNAP-LITE™ Quantum Devices, WI). The phenotype of a transgenic plant is assayed once the plant has been exposed to continuous red light conditions for about five days.

In some embodiments, the phenotype of a transgenic plant is assayed under far-red light conditions in which there is continuous far-red light. Continuous far-red light conditions can be, for example, continuous irradiance with about 5 μmol/m$^2$/s of light with a R:FR of about 0.10. Continuous far-red light can be supplied by a LED array that can be used to activate and deactivate the plant photoreceptor phytochrome (e.g., SNAP-LITE™ Quantum Devices, WI). The phenotype of a transgenic plant is assayed once the plant has been exposed to continuous far-red light conditions for about five days.

In some embodiments, the phenotype of a transgenic plant is assayed under natural daylight or other broad spectrum light conditions. Natural daylight conditions, can be, for example, full sun or other natural irradiation of green house or field grown transgenic plants. Broad spectrum conditions can be irradiation supplied by a fluorescent lamp with continuous fluence rates of about 12 μmol/m$^2$/s of blue$_{450}$ light, 22 μmol/m$^2$/s of red$_{633}$ light, 4 μmol/m$^2$/s far-red$_{740}$ light, and photosynthetically active radiation (PAR$_{400-700}$) of about 55 μmol/m$^2$/s, with a R:FR of about 5. Other broad spectrum conditions can be, for example, continuous broad-spectrum light during the light period of a light/dark photocycle. In some cases, continuous broad spectrum light can be 16 hours of irradiance of about 15 to 55 μmol/m$^2$/s PAR$_{400-700}$, alternating with 8 hours of darkness, with a dark period of 8 hours, for example. In some cases, continuous broad spectrum light can be 12 hours of irradiance of about 15 to 55 μmol/m$^2$/s PAR$_{400-700}$, alternating with 12 hours of darkness, for example. The phenotype of a transgenic plant is assayed during maturation and/or once the plant has reached maturity.

As compared to a control plant that does not express an SD+EODFR and/or low light-tolerance polypeptide grown under SD+EODFR conditions or low light conditions, a transgenic plant expressing an SD+EODFR and/or low light-tolerance polypeptide can exhibit one or more of the following phenotypes under SD+EODFR conditions or low light conditions: decreases in extension growth, acceleration in leaf development, decreased apical dominance, increased chloroplast development, alterations in flowering and seed/fruit production, and an increase in storage organ deposition.

As compared to a control plant that does not overexpress a red specific light response pathway polypeptide grown under continuous red light or far-red light conditions, a transgenic plant overexpressing a red light specific response pathway polypeptide can exhibit decreases in hypocotyl length under continuous red light or natural daylight conditions, but has similar hypocotyl length under continuous far-red light or dark conditions.

Typically, a difference (e.g., an increase or a decrease) in a morphological feature in a transgenic plant or cell relative to a control plant or cell is considered statistically significant at p<0.05 with an appropriate parametric or non-parametric statistic, e.g., Chi-square test, Student's t-test, Mann-Whitney test, or F-test. In some embodiments, a difference in the dimensions of any individual morphological feature is statistically significant at p<0.01, p<0.005, or p<0.001. A statistically significant difference in, for example, a morphological feature in a transgenic plant compared to the corresponding morphological feature a control plant indicates that expression of the recombinant nucleic acid present in the transgenic plant confers the alteration in the morphological feature.

Examples of a decrease in extension growth include, without limitation, decreased petiole length, decreased hypocotyl length, decreased internode spacing, and decreased leaf elongation in cereals, when comparing a transgenic plant expressing an SD+EODFR and/or low light-tolerance polypeptide grown under SD+EODFR conditions or low light conditions to a control plant that does not express an SD+EODFR and/or low light-tolerance polypeptide grown under SD+EODFR conditions or low light conditions. A decrease in extension growth can be a decrease of from about 0.25% to about 90%, e.g., from about 0.25% to about 15%, from about 5% to about 50%, from about 5% to about 10%, from about 25% to about 50%, from about 1% to about 30%, from about 50% to about 90%, from about 20% to about 40%, from about 1% to about 5%, from about 0.5% to about 2%, from about 15% to about 50%, about 20%, about 25%, about 30%, about 35%, about 40%, about 45%, about 50%, about 55%, about 60%, about 65%, about 70%, about 75%, or about 80%.

One suitable phenotype to measure is hypocotyl length. When wild-type seedlings are grown under SD+EODFR conditions or low light conditions, the hypocotyl length is typically significantly increased relative to the hypocotyl length found in wild-type seedlings grown under control light conditions. Thus, seedlings of a transgenic plant and seedlings of a corresponding control plant that either lacks the transgene or does not express the transgene can be grown under SD+EODFR conditions or low light conditions and at the appropriate time, hypocotyl lengths from seedlings of each group can be measured. Under SD+EODFR conditions or low light conditions, a seedling in which the expression of an SD+EODFR and/or low light-tolerance polypeptide is increased can have a statistically significantly shorter hypocotyl length than a seedling of a corresponding control plant that either lacks the transgene or does not express the transgene. The hypocotyl length can be shorter by at least 20 percent, e.g., 20, 25, 30, 35, 40, 45, 50, 55, 60, 65, 70, 75, or 80 percent, as compared to the hypocotyl length in a corresponding control plant that does not express the transgene.

When wild-type seedlings are grown under continuous red-light conditions, the hypocotyl length is typically significantly decreased relative to the hypocotyl length found in wild-type seedlings grown under continuous far-red light conditions. Thus, seedlings of a transgenic plant and seedlings of a corresponding control plant that either lacks the transgene or does not express the transgene can be grown under continuous red-light conditions or far-red light conditions and at the appropriate time, hypocotyl lengths from seedlings of each group can be measured. Under red light conditions, a seedling in which the expression of a red light specific response pathway polypeptide is increased can have a statistically significantly shorter hypocotyl length than a seedling of a corresponding control plant that either lacks the transgene or does not express the transgene. The hypocotyl length can be shorter by at least 20 percent, e.g., 20, 25, 30, 35, 40, 45, 50, 55, 60, 65, 70, 75, or 80 percent, as compared to the hypocotyl length in a corresponding control plant that does not express the transgene. Under far-red conditions, a seedling in which the expression of a red light specific response pathway polypeptide is increased can have a hypocotyl of similar length to a corresponding control plant that either lacks the transgene or does not express the transgene.

In contrast, a seedling in which the expression of a red light specific response pathway polypeptide is decreased can have a statistically significantly longer hypocotyl length than a seedling of a corresponding control plant that either lacks the transgene or does not express the transgene. The hypocotyl length can be longer by at least 20 percent, e.g., 20, 25, 30, 35, 40, 45, 50, 55, 60, 65, 70, 75, or 80 percent, as compared to the hypocotyl length in a corresponding control plant that does not express the transgene. Under far-red conditions, a seedling in which the expression of a red light specific response pathway polypeptide is decreased can have a hypocotyl of similar length to a corresponding control plant that either lacks the transgene or does not express the transgene.

Another suitable phenotype can be overall plant height of mature plants. When wild-type plants are grown under natural light or other broad spectrum light conditions, the plant height at maturity can be significantly decreased relative to the plant height found in wild-type plants grown under low light conditions. Thus, the transgenic plant and a corresponding control plant that either lacks the transgene or does not express the transgene can be grown under natural light conditions or low light conditions and at maturity, the height of the plants from each group can be measured. Under natural light or other broad spectrum light conditions, a mature plant in which the expression of a red light specific response pathway polypeptide is decreased can have a statistically significantly taller plant than a mature plant of a corresponding control plant that either lacks the transgene or does not express the transgene. The plant height can be taller by at least 20 percent, e.g., 20, 25, 30, 35, 40, 45, 50, 55, 60, 65, 70, or 75 percent, as compared to the height in a corresponding control plant that does not express the transgene.

Another suitable phenotype can be rate of plant growth. The rate of plant growth can be determined by measuring differences in fresh weight (T/acre), or differences in subapical cell expansion, over a period of time, for example. When wild-type plants are grown under natural light or other broad spectrum light conditions, the rate of plant growth can be significantly slower relative to the rate of plant growth found in wild-type plants grown under low light conditions. Thus, the transgenic plant and a corresponding control plant that either lacks the transgene or does not express the transgene can be grown under natural light conditions or low light conditions and during maturation, the rate of plant growth for plants from each group can be measured. Under natural light or other broad spectrum light conditions, a plant in which the expression of a red light specific response pathway polypeptide is decreased can have a statistically significantly increased rate of plant growth, than a plant of a corresponding control plant that either lacks the transgene or does not express the transgene. The rate of growth can be increased by at least 2 percent, e.g., 2, 3, 4, 5, 6, 7, 8, 9, 10, 11, 12, 13, 14, 15, 16, 17, 18, 19, 20, 25, 30, 35, 40, 45, 50, 55, 60, or more than 60 percent, as compared to the growth rate in a corresponding control plant that does not express the transgene. Another suitable phenotype to measure can be dry matter yield of stem parts, or above ground parts, excluding inflorescence and seed parts of a plant. When wild-type plants are grown under natural light or other broad spectrum light conditions, the dry matter yield can be significantly decreased relative to the dry matter yield found in wild-type plants grown under low light conditions. Thus, the transgenic plant and a corresponding control plant that either lacks the transgene or does not express the transgene can be grown under natural light conditions or low light conditions and at harvest, the dry matter yield of the plants from each group can be measured. Under natural light or other broad spectrum light conditions, a mature plant in which the expression of a red light specific response pathway polypeptide is decreased can have a statistically significantly greater dry matter yield than a mature plant of a corresponding control plant that either lacks the transgene or does not express the transgene. Dry matter yield (DMY) yield is calculated using the fresh matter weight (FMW) and a measurement of weight percent moisture (M) in the following equation. $DMY=((100-M)/100)* FMW$. For example, the dry matter yield can be increased by at least 2 percent, e.g., 2, 3, 4, 5, 6, 7, 8, 9, 10, 11, 12, 13, 14, 15, 16, 17, 18, 19, 20, 25, 30, 35, 40, 45, 50, 55, 60, or more than 60 percent, as compared to the dry matter yield level in a corresponding control plant that does not express the transgene.

Another suitable phenotype to measure is petiole length. When wild-type seedlings are grown under SD+EODFR conditions or low light conditions, the petiole length is typically significantly increased relative to the petiole length found in wild-type seedlings grown under control light conditions. Thus, seedlings of a transgenic plant and seedlings of a corresponding control plant that either lacks the transgene or does not express the transgene can be grown under SD+EODFR conditions or low light conditions and at the appropriate time, petiole lengths from seedlings of each group can be measured. Under SD+EODFR conditions or low light conditions, a seedling in which the expression of an SD+EODFR and/or low light-tolerance polypeptide is increased can have a statistically significantly shorter petiole length than a seedling of a corresponding control plant that either lacks the transgene or does not express the transgene. The petiole length can be shorter by at least 20 percent, e.g., 20, 25, 30, 35, 40, 45, 50, 55, 60, 65, 70, or 75 percent, as compared to the petiole length in a corresponding control plant that does not express the transgene.

Examples of acceleration in leaf development include, without limitation, increased leaf thickness and increased leaf area growth when comparing a transgenic plant expressing an SD+EODFR and/or low light-tolerance polypeptide grown under SD+EODFR conditions or low light conditions to a control plant that does not express an SD+EODFR and/or low light-tolerance polypeptide grown under SD+EODFR conditions or low light conditions. Leaf thickness or leaf area growth can be increased by about 0.25% to about 200% (e.g., about 0.25% to about 2%, about 0.5% to about 5%, about 0.5% to about 15%, about 2% to about 10%, about 5% to about 35%, about 10% to about 25%, about 20% to about 80%, about 50% to about 200%, about 100% to about 200%, about 100% to about 150%, about 5%, about 10%, about 20%, about 35%, about 50%, about 70%, about 90%, about 120%, about 180%, or about 200%) in a transgenic plant expressing an SD+EODFR and/or low light-tolerance polypeptide grown under SD+EODFR conditions or low light conditions as compared to a control plant that does not express an SD+EODFR and/or low light-tolerance polypeptide grown under SD+EODFR conditions or low light conditions.

Examples of decreased apical dominance include, without limitation, increased branching and increased tillering when comparing a transgenic plant expressing an SD+EODFR and/or low light-tolerance polypeptide grown under SD+EODFR conditions or low light conditions to a control plant that does not express an SD+EODFR and/or low light-tolerance polypeptide grown under SD+EODFR conditions or low light conditions. Branching and tillering can be increased by about 0.25% to about 200% (e.g., about 0.25% to about 2%, about 0.5% to about 5%, about 0.5% to about 15%, about 2% to about 10%, about 5% to about 35%, about 10% to about 25%, about 20% to about 80%, about 50% to about 200%, about 100% to about 200%, about 100% to about 150%, about 5%, about 10%, about 20%, about 35%, about 50%, about 70%, about 90%, about 120%, about 180%, or about 200%) in a transgenic plant expressing an SD+EODFR and/or low light-tolerance polypeptide grown under SD+EODFR conditions or low light conditions as compared to a control plant that does not express an SD+EODFR and/or low light-tolerance polypeptide grown under SD+EODFR conditions or low light conditions.

Examples of increased apical dominance include, without limitation, decreased branching and decreased tillering when comparing a transgenic plant in which a red light specific response pathway polypeptide is down-regulated to a control plant that either lacks the transgene or does not express the transgene grown natural light or other broad spectrum light conditions. Branching and tillering can be decreased by about 0.25% to about 200% (e.g., about 0.25% to about 2%, about 0.5% to about 5%, about 0.5% to about 15%, about 2% to about 10%, about 5% to about 35%, about 10% to about 25%, about 20% to about 80%, about 50% to about 200%, about 100% to about 200%, about 100% to about 150%, about 5%, about 10%, about 20%, about 35%, about 50%, about 70%, about 90%, about 120%, about 180%, or about 200%) in a transgenic plant in which a red light specific response pathway polypeptide is down-regulated grown under natural light or other broad spectrum light conditions as compared to a control plant that either lacks the transgene or does not express the transgene grown natural light or other broad spectrum light conditions.

Examples of increased chloroplast development include, without limitation, increased chlorophyll synthesis and a change in the chlorophyll a:b ratio when comparing a transgenic plant expressing an SD+EODFR and/or low light-tolerance polypeptide grown under SD+EODFR conditions or low light conditions to a control plant that does not express an SD+EODFR and/or low light-tolerance polypeptide grown under SD+EODFR conditions or low light conditions. Chlorophyll synthesis and/or the chlorophyll a:b ratio can be about 0.25% to about 200% (e.g., about 0.25% to about 2%, 0.25% to about 0.5%, about 0.25% to about 1.5%, about 0.5% to about 1%, about 0.5% to about 5%, about 0.5% to about 15%, about 2% to about 10%, about 5% to about 35%, about 10% to about 25%, about 20% to about 80%, about 50% to about 200%, about 100% to about 200%, about 100% to about 150%, about 5%, about 10%, about 20%, about 35%, about 50%, about 70%, about 90%, about 120%, about 180%, or about 200%) greater in a transgenic plant expressing an SD+EODFR and/or low light-tolerance polypeptide grown under SD+EODFR conditions or low light conditions as compared to a control plant that does not express an SD+EODFR and/or low light-tolerance polypeptide grown under SD+EODFR conditions or low light conditions.

Examples of alterations in flowering and seed/fruit production include, without limitation, a decreased rate of flowering, an increase in seed set, and an increase of fruit development when comparing a transgenic plant expressing an SD+EODFR and/or low light-tolerance polypeptide grown under SD+EODFR conditions or low light conditions to a control plant that does not express an SD+EODFR and/or low light-tolerance polypeptide grown under SD+EODFR conditions or low light conditions. The rate of flowering can be a decreased from about 0.25% to about 90% (e.g., from about 0.25% to about 15%, from about 5% to about 50%, from about 5% to about 10%, from about 25% to about 50%, from about 1% to about 30%, from about 50% to about 90%, from about 20% to about 40%, from about 1% to about 5%, from about 0.5% to about 2%, from about 15% to about 50%, about 20%, about 25%, about 30%, about 35%, about 40%, about 45%, about 50%, about 55%, about 60%, about 65%, about 70%, about 75%, or about 80%) in a transgenic plant expressing an SD+EODFR and/or low light-tolerance polypeptide grown under SD+EODFR conditions or low light conditions as compared to a control plant that does not express an SD+EODFR and/or low light-tolerance polypeptide grown under SD+EODFR conditions or low light conditions. Seed or fruit weight can be increased by about 0.25% to about 200% (e.g., about 0.25% to about 2%, about 0.5% to about 5%, about 0.5% to about 15%, about 2% to about 10%, about 5% to about 35%, about 10% to about 25%, about 20% to about 80%, about 50% to about 200%, about 100% to about 200%, about 100% to about 150%, about 5%, about 10%, about 20%, about 35%, about 50%, about 70%, about 90%, about 120%, about 180%, or about 200%) in a transgenic plant expressing an SD+EODFR and/or low light-tolerance polypeptide grown under SD+EODFR conditions or low light conditions as compared to a control plant that does not express an SD+EODFR and/or low light-tolerance polypeptide grown under SD+EODFR conditions or low light conditions.

The phenotype of a transgenic plant is evaluated relative to a control plant. A plant is said "not to express" a polypeptide when the plant exhibits less than 10%, e.g., less than 9%, 8%, 7%, 6%, 5%, 4%, 3%, 2%, 1%, 0.5%, 0.1%, 0.01%, or 0.001%, of the amount of polypeptide or mRNA encoding the polypeptide exhibited by the plant of interest. Expression can be evaluated using methods including, for example, RT-PCR, Northern blots, 51 RNase protection, primer extensions, Western blots, protein gel electrophoresis, immunoprecipitation, enzyme-linked immunoassays, chip assays, and mass spectrometry. It should be noted that if a polypeptide is expressed under the control of a tissue-preferential or broadly expressing promoter, expression can be evaluated in the entire plant or in a selected tissue. Similarly, if a polypeptide is expressed at a particular time, e.g., at a particular time in development or upon induction, expression can be evaluated selectively at a desired time period.

V. Plant Breeding

Genetic polymorphisms are discrete allelic sequence differences in a population. Typically, an allele that is present at 1% or greater is considered to be a genetic polymorphism. The discovery that polypeptides disclosed herein can modulate SD+EODFR and/or low light tolerance is useful in plant breeding, because genetic polymorphisms exhibiting a degree of linkage with loci for such polypeptides are more likely to be correlated with variation in SD+EODFR and/or low light tolerance. For example, genetic polymorphisms linked to the loci for such polypeptides are more likely to be useful in marker-assisted breeding programs to create lines having SD+EODFR and/or low light tolerance.

Thus, one aspect of the invention includes methods of identifying whether one or more genetic polymorphisms are associated with variation in SD+EODFR and/or low light tolerance. Such methods involve determining whether genetic polymorphisms in a given population exhibit linkage with the locus for one of the polypeptides depicted in FIGS. 1-24 and/or a functional homolog thereof. The correlation is measured between variation in SD+EODFR and/or low light tolerance in plants of the population and the presence of the genetic polymorphism(s) in plants of the population, thereby identifying whether or not the genetic polymorphism(s) are associated with variation for the trait. If the presence of a particular allele is statistically significantly correlated with a desired modulation in SD+EODFR and/or low light tolerance, the allele is associated with variation for the trait and is useful as a marker for the trait. If, on the other hand, the presence of a particular allele is not significantly correlated with the desired modulation, the allele is not associated with variation for the trait and is not useful as a marker.

Such methods are applicable to populations containing the naturally occurring endogenous polypeptide rather than an exogenous nucleic acid encoding the polypeptide, i.e., populations that are not transgenic for the exogenous nucleic acid. It will be appreciated, however, that populations suitable for use in the methods may contain a transgene for another, different trait, e.g., herbicide resistance.

Genetic polymorphisms that are useful in such methods include simple sequence repeats (SSRs, or microsatellites), rapid amplification of polymorphic DNA (RAPDs), single nucleotide polymorphisms (SNPs), amplified fragment length polymorphisms (AFLPs) and restriction fragment length polymorphisms (RFLPs). SSR polymorphisms can be identified, for example, by making sequence specific probes and amplifying template DNA from individuals in the population of interest by PCR. If the probes flank an SSR in the population, PCR products of different sizes will be produced. See, e.g., U.S. Pat. No. 5,766,847. Alternatively, SSR polymorphisms can be identified by using PCR product(s) as a probe against Southern blots from different individuals in the population. See, U. H. Refseth et al., (1997) Electrophoresis 18: 1519. The identification of RFLPs is discussed, for example, in Alonso-Blanco et al. (Methods in Molecular Biology, vol. 82, "*Arabidopsis* Protocols", pp. 137-146, J. M. Martinez-Zapater and J. Salinas, eds., c. 1998 by Humana Press, Totowa, N.J.); Burr ("Mapping Genes with Recombinant Inbreds", pp. 249-254, in Freeling, M. and V. Walbot (Ed.), The Maize Handbook, c. 1994 by Springer-Verlag New York, Inc.: New York, N.Y., USA; Berlin Germany; Burr et al. Genetics (1998) 118: 519; and Gardiner, J. et al., (1993) Genetics 134: 917). The identification of AFLPs is discussed, for example, in EP 0 534 858 and U.S. Pat. No. 5,878,215.

In some embodiments, the methods are directed to breeding a plant line. Such methods use genetic polymorphisms identified as described above in a marker assisted breeding program to facilitate the development of lines that have a desired alteration in SD+EODFR and/or low light tolerance. Once a suitable genetic polymorphism is identified as being associated with variation for the trait, one or more individual plants are identified that possess the polymorphic allele correlated with the desired variation. Those plants are then used in a breeding program to combine the polymorphic allele with a plurality of other alleles at other loci that are correlated with the desired variation. Techniques suitable for use in a plant breeding program are known in the art and include, without limitation, backcrossing, mass selection, pedigree breeding, bulk selection, crossing to another population and recurrent selection. These techniques can be used alone or in combination with one or more other techniques in a breeding program. Thus, each identified plants is selfed or crossed a different plant to produce seed which is then germinated to form progeny plants. At least one such progeny plant is then selfed or crossed with a different plant to form a subsequent progeny generation. The breeding program can repeat the steps of selfing or outcrossing for an additional 0 to 5 generations as appropriate in order to achieve the desired uniformity and stability in the resulting plant line, which retains the polymorphic allele. In most breeding programs, analysis for the particular polymorphic allele will be carried out in each generation, although analysis can be carried out in alternate generations if desired.

In some cases, selection for other useful traits is also carried out, e.g., selection for fungal resistance or bacterial resistance. Selection for such other traits can be carried out before, during or after identification of individual plants that possess the desired polymorphic allele.

VI. Articles of Manufacture

Transgenic plants provided herein have various uses in the agricultural and energy production industries. For example, transgenic plants described herein can be used to make animal feed and food products. Such plants, however, are often particularly useful as a feedstock for energy production.

Transgenic plants described herein often produce higher yields of grain and/or biomass per hectare, relative to control plants that lack the exogenous nucleic acid. In some embodiments, such transgenic plants provide equivalent or even increased yields of grain and/or biomass per hectare relative to control plants when grown under conditions of low light conditions and/or SD+EODFR conditions. Thus, such transgenic plants can be used to provide yield stability under environmentally stressful conditions such as low light conditions and/or SD+EODFR conditions. By providing higher yields under environmentally stressful conditions such as low light conditions and/or SD+EODFR conditions, the transgenic plants described herein improve profitability for farmers and processors as well as decrease costs to consumers.

Seeds from transgenic plants described herein can be conditioned and bagged in packaging material by means known in the art to form an article of manufacture. Packaging material such as paper and cloth are well known in the art. A package of seed can have a label, e.g., a tag or label secured to the packaging material, a label printed on the packaging material, or a label inserted within the package, that describes the nature of the seeds therein.

VII. Other Polypeptides, Nucleic Acids, Plant Cells, Plants, and Methods

In some cases, this document provides methods and materials involved in plant UV-B tolerance. For example, this document provides seeds and plants having cells comprising an exogenous nucleic acid encoding a polypeptide having UV-B tolerance activity as described in U.S. Patent Application Publication No. 2010-0192261 (U.S. patent application Ser. No. 12/373,134), which is incorporated by reference herein in its entirety. In some cases, a plant can include a polypeptide or nucleic acid or can be made to include a polypeptide or nucleic acid such that the sequence of such a polypeptide or nucleic acid is as set forth in one of the identified sequences of U.S. Patent Application Publication No. 2010-0192261 (U.S. patent application Ser. No. 12/373,134) (e.g., SEQ ID NOs:1-119 of U.S. Patent Application Publication No. 2010-0192261 (U.S. patent application Ser. No. 12/373,134)), or is a homolog or ortholog thereof as described in U.S. Patent Application Publication No. 2010-0192261 (U.S. patent application Ser. No. 12/373,134), or has at least 80% sequence identity (e.g., at least 80%, 85%, 90%, 95%, 97%, 98%, or 99% sequence identity) to an identified sequence of U.S. Patent Application Publication No. 2010-0192261 (U.S. patent application Ser. No. 12/373,134), as set forth in U.S. Patent Application Publication No. 2010-0192261 (U.S. patent application Ser. No. 12/373,134). SEQ ID NOs:1-119 of U.S. Patent Application Publication No. 2010-0192261 (U.S. patent application Ser. No. 12/373,134), together with the identified activities for each of SEQ ID NOs:1-119, the described homologs and orthologs of SEQ ID NOs:1-119 and their associated activities, the sequences having at least 80% sequence identity (e.g., at least 80%, 85%, 90%, 95%, 97%, 98%, or 99% sequence identity) to SEQ ID NOs:1-119 and their associated activities, the phenotypes of plants containing any one of SEQ ID NOs:1-119 or the described homologs of SEQ ID NOs:1-119 or the described orthologs of SEQ ID NOs:1-119 or the described sequences having at least 80% sequence identity to any one of SEQ ID NOs:1-119, and the working examples and data set forth in Examples 1-6 of U.S. Patent Application Publication No. 2010-0192261 (U.S. patent application Ser. No. 12/373,134) are incorporated by reference herein.

In some cases, this document provides methods and materials involved in tolerance of plants to low light conditions. For example, this document provides transgenic plants and seeds comprising nucleic acids encoding polypeptides that confer tolerance to conditions of low light irradiance as described in U.S. Patent Application Publication No. 2010-0205688 (U.S. patent application Ser. No. 14/513,086), which is incorporated by reference herein in its entirety. In some cases, a plant can include a polypeptide or nucleic acid or can be made to include a polypeptide or nucleic acid such that the sequence of such a polypeptide or nucleic acid is as set forth in one of the identified sequences of U.S. Patent Application Publication No. 2010-0205688 (U.S. patent application Ser. No. 14/513,086) (e.g., SEQ ID NOs:1-149 of U.S. Patent Application Publication No. 2010-0205688 (U.S. patent application Ser. No. 12/513,086)), or is a homolog or ortholog thereof as described in U.S. Patent Application Publication No. 2010-0205688 (U.S. patent application Ser. No. 12/513,086), or has at least 80% sequence identity (e.g., at least 80%, 85%, 90%, 95%, 97%, 98%, or 99% sequence identity) to an identified sequence of U.S. Patent Application Publication No. 2010-0205688 (U.S. patent application Ser. No. 12/513,086), as set forth in U.S. Patent Application Publication No. 2010-0205688 (U.S. patent application Ser. No. 12/513,086). SEQ ID NOs:1-149 of U.S. Patent Application Publication No. 2010-0205688 (U.S. patent application Ser. No. 12/513,086), together with the identified activities for each of SEQ ID NOs:1-149, the described homologs and orthologs of SEQ ID NOs:1-149 and their associated activities, the sequences having at least 80% sequence identity (e.g., at least 80%, 85%, 90%, 95%, 97%, 98%, or 99% sequence identity) to SEQ ID NOs:1-149 and their associated activities, the phenotypes of plants containing any one of SEQ ID NOs:1-149 or the described homologs of SEQ ID NOs:1-149 or the described orthologs of SEQ ID NOs:1-149 or the described sequences having at least 80% sequence identity to any one of SEQ ID NOs:1-149, and the working examples and data set forth in Examples 1-8 of U.S. Patent Application Publication No. 2010-0205688 (U.S. patent application Ser. No. 14/513,086) are incorporated by reference herein.

In some cases, this document provides methods and materials involved in shade tolerance in plants. For example, this document provides plants having increased shade tolerance as well as materials and methods for making plants having increased shade tolerance and plant products derived from plants having increased shade tolerance as described in U.S. Patent Application Publication No. 2010-0199378 (U.S. patent application Ser. No. 12/515,687), which is incorporated by reference herein in its entirety. In some cases, a plant can include a polypeptide or nucleic acid or can be made to include a polypeptide or nucleic acid such that the sequence of such a polypeptide or nucleic acid is as set forth in one of the identified sequences of U.S. Patent Application Publication No. 2010-0199378 (U.S. patent application Ser. No. 12/515,687) (e.g., SEQ ID NOs:1-171 of U.S. Patent Application Publication No. 2010-0199378 (U.S. patent application Ser. No. 14/515,687)), or is a homolog or ortholog thereof as described in U.S. Patent Application Publication No. 2010-0199378 (U.S. patent application Ser. No. 14/515,687), or has at least 80% sequence identity (e.g., at least 80%, 85%, 90%, 95%, 97%, 98%, or 99% sequence identity) to an identified sequence of U.S. Patent Application Publication No. 2010-0199378 (U.S. patent application Ser. No. 12/515,687), as set forth in U.S. Patent Application Publication No. 2010-0199378 (U.S. patent application Ser. No. 12/515,687). SEQ ID NOs:1-171 of U.S. Patent Application Publication No. 2010-0199378 (U.S. patent application Ser. No. 14/515,687), together with the identified activities for each of SEQ ID NOs:1-171, the described homologs and orthologs of SEQ ID NOs:1-171 and their associated activities, the sequences having at least 80% sequence identity (e.g., at least 80%, 85%, 90%, 95%, 97%, 98%, or 99% sequence identity) to SEQ ID NOs:1-171 and their associated activities, the phenotypes of plants containing any one of SEQ ID NOs:1-171 or the described homologs of SEQ ID NOs:1-171 or the described orthologs of SEQ ID NOs:1-171 or the described sequences having at least 80% sequence identity to any one of SEQ ID NOs:1-171, and the working examples and data set forth in Examples 1-11 of U.S. Patent Application Publication No. 2010-0199378 (U.S. patent application Ser. No. 14/515,687) are incorporated by reference herein.

In some cases, this document provides methods and materials involved in tolerance of plants to low light conditions. For example, this document provides transgenic plants and seeds comprising nucleic acids encoding polypeptides that confer tolerance to conditions of low light irradiance as described in U.S. Patent Application Publication No. 2010-0119688 (U.S. patent application Ser. No. 12/307,561), which is incorporated by reference herein in its entirety. In some cases, a plant can include a polypeptide or nucleic acid or can be made to include a polypeptide or nucleic acid such that the sequence of such a polypeptide or nucleic acid is as set forth in one of the identified sequences of U.S. Patent Application Publication No. 2010-0119688 (U.S. patent application Ser. No. 12/307,561) (e.g., SEQ ID NOs:1-146 of U.S. Patent Application Publication No. 2010-0119688 (U.S. patent application Ser. No. 12/307,561)), or is a homolog or ortholog thereof as described in U.S. Patent Application Publication No. 2010-0119688 (U.S. patent application Ser. No. 12/307,561), or has at least 80% sequence identity (e.g., at least 80%, 85%, 90%, 95%, 97%, 98%, or 99% sequence identity) to an identified sequence of U.S. Patent Application Publication No. 2010-0119688 (U.S. patent application Ser. No. 12/307,561), as set forth in U.S. Patent Application Publication No. 2010-0119688 (U.S. patent application Ser. No. 12/307,561). SEQ ID NOs:1-146 of U.S. Patent Application Publication No. 2010-0119688 (U.S. patent application Ser. No. 12/307,561), together with the identified activities for each of SEQ ID NOs:1-146, the described homologs and orthologs of SEQ ID NOs:1-146 and their associated activities, the sequences having at least 80% sequence identity (e.g., at least 80%, 85%, 90%, 95%, 97%, 98%, or 99% sequence identity) to SEQ ID NOs:1-146 and their associated activities, the phenotypes of plants containing any one of SEQ ID NOs: 1-146 or the described homologs of SEQ ID NOs:1-146 or the described orthologs of SEQ ID NOs:1-146 or the described sequences having at least 80% sequence identity to any one of SEQ ID NOs:1-146, and the working examples and data set forth in Examples 1-22 of U.S. Patent Application Publication No. 2010-0119688 (U.S. patent application Ser. No. 12/307,561) are incorporated by reference herein.

In some cases, this document provides methods and materials involved in modulating biomass levels in plants. For example, this document provides plants having increased biomass levels as well as materials and methods for making plants and plant products having increased biomass levels as described in International Patent Application Publication No. WO 2010/033564 and U.S. patent application Ser. No. 13/119,572, which are incorporated by reference herein in their entireties. In some cases, a plant can include a polypeptide or nucleic acid or can be made to include a polypeptide or nucleic acid such that the sequence of such a polypeptide or nucleic acid is as set forth in one of the identified sequences of International Patent Application Publication No. WO 2010/033564 and U.S. patent application Ser. No. 13/119,572 (e.g., SEQ ID NOs:1-638 of International Patent Application Publication No. WO 2010/033564 and U.S. patent application Ser. No. 13/119,572), or is a homolog or ortholog thereof as described in International Patent Application Publication No. WO 2010/033564 and U.S. patent application Ser. No. 13/119,572, or has at least 80% sequence identity (e.g., at least 80%, 85%, 90%, 95%, 97%, 98%, or 99% sequence identity) to an identified sequence of International Patent Application Publication No. WO 2010/033564 and U.S. patent application Ser. No. 13/119,572, as set forth in International Patent Application Publication No. WO 2010/033564 and U.S. patent application Ser. No. 13/119,572. SEQ ID NOs:1-638 of International Patent Application Publication No. WO 2010/033564 and U.S. patent application Ser. No. 13/119,572, together with the identified activities for each of SEQ ID NOs:1-638, the described homologs and orthologs of SEQ ID NOs:1-638 and their associated activities, the sequences having at least 80% sequence identity (e.g., at least 80%, 85%, 90%, 95%, 97%, 98%, or 99% sequence identity) to SEQ ID NOs:1-638 and their associated activities, the phenotypes of plants containing any one of SEQ ID NOs:1-638 or the described homologs of SEQ ID NOs:1-638 or the described orthologs of SEQ ID NOs:1-638 or the described sequences having at least 80% sequence identity to any one of SEQ ID NOs:1-638, and the working examples and data set forth in Examples 1-11 of International Patent Application Publication No. WO 2010/033564 and U.S. patent application Ser. No. 13/119,572 are incorporated by reference herein.

The invention will be further described in the following examples, which do not limit the scope of the invention described in the claims.

VIII. Examples

Example 1—Transgenic *Arabidopsis* Plants

The following symbols are used in the Examples with respect to *Arabidopsis* transformation: $T_1$: first generation transformant; $T_2$: second generation, progeny of self-pollinated $T_1$ plants; $T_3$: third generation, progeny of self-pollinated $T_2$ plants; $T_4$: fourth generation, progeny of self-pollinated $T_3$ plants. Independent transformations are referred to as events.

Nucleic acids were isolated from *Arabidopsis thaliana* plants, and cloned into a Ti plasmid vector, CRS338 or CRS 811, under the control of a 35S promoter. Each construct contained a phosphinothricin acetyltransferase gene which confers Finale™ resistance to transformed plants. Wild-type *Arabidopsis thaliana* ecotype Wassilewskija (Ws) plants were transformed separately with each construct. The transformations were performed essentially as described in Bechtold et al., *C.R. Acad. Sci. Paris*, 316:1194-1199 (1993).

Transgenic *Arabidopsis* lines containing SEQ ID NO:1, SEQ ID NO:69, SEQ ID NO:127, SEQ ID NO:315, SEQ ID NO:335, SEQ ID NO:454, SEQ ID NO:537, SEQ ID NO:568, SEQ ID NO:604, SEQ ID NO:632, SEQ ID NO:642, SEQ ID NO:848, SEQ ID NO:905, SEQ ID NO:951, SEQ ID NO:1023, SEQ ID NO:1045, SEQ ID NO:1150, SEQ ID NO:1276, SEQ ID NO:1345, SEQ ID NO:1456, SEQ ID NO:1496, SEQ ID NO:1539, SEQ ID NO:1586, SEQ ID NO:1629, or SEQ ID NO:1634 were designated, ME05268, ME06120, ME09503, ME10007, ME10852, ME11939, ME12006, ME12596, ME12899, ME13456, ME15935, ME16594, ME16597, ME16630, ME17128, ME17578, ME18158, ME18314, ME18408, ME19304, ME19738, ME19971, ME20871, ME21199, or ME21508, respectively. The presence of each vector containing a nucleic acid described above in the respective transgenic *Arabidopsis* line transformed with the vector was confirmed by Finale™ resistance, PCR amplification from green leaf tissue extract, and/or sequencing of PCR products.

Example 2—Identification of Transgenic Plants Tolerant to Low Light Conditions

Wild-type and transgenic seeds were sterilized, plated on solid 0.5×MS medium containing 5 g/L sucrose, and stratified at 4° C. in the dark for three days. After stratification, plates containing the seeds were allowed to reach room temperature. The plates were then transferred to a Conviron walk-in growth chamber (Controlled Environments Inc., Pambina, N. Dak.) at 22° C. and 70% humidity with a 16:8 hour light:dark cycle. Lighting was supplied by 32 watt fluorescent bulbs (Sylvania, F032/841/ECO, Danvers, Mass.), providing a red:far-red ratio of 13:1. The plates were covered with three layers of shade cloth (New York wire, charcoal fiberglass screen, 857650; Home Depot, Atlanta, Ga.) such that the irradiance was about 10 µmol/m²/s. The plates were rotated daily and monitored for changes in hypocotyl elongation. After 48 hours, the plates were scored for late germinators, which were eliminated from consideration as candidate plants having reduced hypocotyl elongation under low light conditions. Each seedling was transplanted to an 8×8 cm well of a flat containing a total of 18 wells (three wells by six wells) and measuring 24 cm by 48 cm in size.

Seedlings maintained under conditions of irradiance with about 10 µmol/m$^2$/s of light for seven days at 22° C. were analyzed for hypocotyl length. The hypocotyls of individual seedlings were determined to be "long" or "short" based on qualitative observation (see, for example, FIG. 28).

Example 3—Identification of Transgenic Plants Tolerant to Short Day Plus End-of-Day-Far-Red (SD+EODFR) Conditions A Short Day plus End-of-Day-Far-Red (SD+EODFR) assay was carried out on seedlings in order to evaluate the effect of SD+EODFR conditions on hypocotyl length. For the SD+EODFR assay, seeds were plated on 0.5% sucrose, 1×MS media (PhytoTech) agar plates, cold-treated for 3-4 days at 4° C., then germinated for 2 days under continuous white light at about 60 µmol/m$^2$/s in walk-in Conviron growth chambers. Seedlings were then exposed to SD+EODFR conditions for 4 days. SD+EODFR conditions were 9.5 hours light, followed by a 30 minute pulse of far-red light at the end of each light cycle, alternating with 14 hours of darkness. Two Gro-Lux (Sylvania, 24660) and two Cool White (Phillips) lights at about 60 µmol/m$^2$ PPFD, with a red:far-red ratio of about 5.5, were used for the light cycle; the fluence rates under these conditions were: blue$_{450}$=12 µmol/m$^2$/s, red$_{633}$=22 µmol/m$^2$/s, far-red$_{740}$=4 µmol/m$^2$/s, PPFD$_{400-700}$=55 µmol/m$^2$/s. The far-red pulse was generated by 3 SNAP-LITE Far-red light boxes (Quantum devices, SL1515-670-735) at about 8 µmol/m$^2$/s PPFD, with a red:far-red ratio of about 0.14; the fluence rates under these conditions were: blue$_{450}$=0.004 µmol/m$^2$/s, red$_{633}$=10 µmol/m$^2$/s, far-red$_{740}$=70 µmol/m$^2$/s, PPFD$_{400-700}$=8 µmol/m$^2$/s. Control seedlings were cultured exactly as above except that they did not receive the far-red pulse; that is, following germination, they were exposed for two days to a cycle of 10 hours of light alternating with 14 hours of darkness under 2 Gro-Lux and 2 Cool white lights at about 60 µmol/m$^2$/s PPFD, with a red:far-red ratio of about 5.5. Plates were rotated on the third day after plating and hypocotyl length was characterized on the fourth day after plating. The hypocotyls of individual seedlings were determined to be "long" or "short" based on qualitative observation (see, for example, FIG. 28).

Seedlings were then sprayed with sterile Finale® (concentration=0.63%), on two subsequent days, then allowed to grow for 24 hours before chlorophyll fluorescence imaging was done to determine the Finale® resistant:Finale® sensitive ratio. Finale® sensitivity was determined by placing plates of Finale® treated seedlings in a chlorophyll fluorescence imager (CF Imager, Technologica Limited, UK). Finale® resistant seedlings appeared red and Finale® sensitive seedlings appeared blue. Hypocotyl lengths from Finale® resistant seedlings and Finale® sensitive seedlings were then subjected to a Chi-squared analysis to determine statistical significance.

Example 4—Results for ME05268, ME06120, ME09503, ME10007, ME10852, ME11939, ME13456, ME15935, ME16594, ME16597, ME16630, ME17128, ME17578, ME18158, ME18314, ME19304, ME19738, ME20871, ME21199, and ME21508 Events T$_3$ and T$_4$ seed from event -03 of ME05268, T$_2$ and T$_3$ seed from event -04 of ME05268, T$_2$ and T$_3$ seed from events -11 and -12 of ME06120, T$_2$ and T$_3$ seed from events -03 and -07 of ME09503, T$_2$ and T$_3$ seed from events -02 and -05 of ME10007, T$_2$ and T$_3$ seed from events -03 and -04 of ME10852, T$_2$ and T$_3$ seed from events -01, -02, and -03 of ME11939, T$_2$ and T$_3$ seed from events -02 and -05 of ME13456, T$_2$ and T$_3$ seed from events -03 and -04 of ME15935, T$_3$ and T$_4$ seed from events -02 and -05 of ME16594, T$_2$ and T$_3$ seed from events -01, -04, and -06 of ME16597, T$_2$ and T$_3$ seed from events -01, -02, and -04 of ME16630, T$_2$ and T$_3$ seed from events -02, -03, and -03 of ME17128, T$_2$ and T$_3$ seed from events -01 and -03 of ME17578, T$_2$ and T$_3$ seed from events -01, -03, and -04 of ME18158, T$_2$ and T$_3$ seed from events -01, -02, -03, and -04 of ME18314, T$_2$ and T$_3$ seed from events -07 and -08 of ME19304, T$_2$ and T$_3$ seed from events -02 and -05 of ME19738, T$_2$ and T$_3$ seed from events -03, -05, and -10 of ME20871, T$_2$ and T$_3$ seed from events -01, -03 and -05 of ME21199, T$_2$ and T$_3$ seed from events -01 and -05 of ME21508 was grown under low light conditions and evaluated for hypocotyl length as described in Example 2.

A Chi-square test was performed to compare transgenic seedlings and corresponding non-transgenic segregants having a short or a long hypocotyl. A hypocotyl having a length similar to the hypocotyl length typically exhibited by wild-type *Arabidopsis* seedlings grown under normal light conditions (e.g., about 100 µmol/m$^2$/s of white light) was considered a short hypocotyl, whereas a hypocotyl having a length similar to that typically exhibited by wild-type *Arabidopsis* seedlings grown under low light conditions (e.g., about 10 µmol/m$^2$/s of white light) was considered a long hypocotyl. Wild-type *Arabidopsis* seeds grown for seven days at 22° C. under conditions of irradiance with about 100 µmol/m$^2$/s of white light and a 16:8 hour light:dark cycle typically form hypocotyls that are about 1-3 mm in length. Under conditions of irradiance with about 10 µmol/m$^2$/s of white light, the hypocotyls typically are about 5-7 mm in length.

Seedlings from event -03 of ME05268; event -04 of ME05268; events -11 and -12 of ME06120; events -03 and -07 of ME09503; events -02 and -05 of ME10007; events -03 and -04 of ME10852; events -01, -02, and -03 of ME11939; events -02 and -05 of ME13456; events -03 and -04 of ME15935; events -02 and -05 of ME16594; events -01, -04, and -06 of ME16597; events -01, -02, and -04 of ME16630; events -02, -03, and -03 of ME17128; events -01 and -03 of ME17578; events -01, -03, and -04 of ME18158; events -01, -02, -03, and -04 of ME18314; events -07 and -08 of ME19304; events -02 and -05 of ME19738; events -03, -05, and -10 of ME20871; events -01, -03 and -05 of ME21199; and events -01 and -05 of ME21508 displayed a short hypocotyl under low light conditions in both the T$_2$ and T$_3$ generations, and the transgene was linked to the short hypocotyl phenotype with a confidence level of $p<0.05$ (Tables 1-23).

T$_3$ or T$_4$ data designated with -99 are data obtained from seed pooled from multiple individual plants of the indicated generation and event.

TABLE 1

Hypocotyl length in seedlings from ME05268

| Plants | Short Hypo-cotyl | Long Hypo-cotyl | Chi-Square | p-value |
|---|---|---|---|---|
| T$_3$ seedlings from event -03-99 of ME05268 | 32 | 6 | 54.35 | 1.68E−13 |
| T$_3$ non-transgenic segregants of event -03-99 of ME05268 | 0 | 37 | | |
| T$_4$ seedlings from event -03-99-99 of ME05268 | 69 | 3 | 53.00 | 1.68E−13 |

TABLE 1-continued

Hypocotyl length in seedlings from ME05268

| Plants | Short Hypo-cotyl | Long Hypo-cotyl | Chi-Square | p-value |
|---|---|---|---|---|
| $T_4$ non-transgenic segregants of event -03-99-99 of ME05268 | 0 | 7 | | |
| $T_2$ seedlings from event -04 of ME05268 | 55 | 9 | 17.98 | 2.23E−05 |
| $T_2$ non-transgenic segregants of event -04 of ME05268 | 0 | 4 | | |
| $T_3$ seedlings from event -04-99 of ME05268 | 52 | 8 | 40.81 | 1.68E−10 |
| $T_3$ non-transgenic segregants of event -04-99 of ME05268 | 0 | 14 | | |

TABLE 2

Hypocotyl length in seedlings from ME06120

| Plants | Short Hypo-cotyl | Long Hypo-cotyl | Chi-Square | p-value |
|---|---|---|---|---|
| $T_2$ seedlings from event -11 of ME06120 | 26 | 4 | 16.89 | 3.96E−05 |
| $T_2$ non-transgenic segregants of event -11 of ME05268 | 1 | 7 | | |
| $T_3$ seedlings from event -11-99 of ME06120 | 52 | 3 | 37.89 | 7.48E−10 |
| $T_3$ non-transgenic segregants of event -11-99 of ME06120 | 4 | 13 | | |
| $T_2$ seedlings from event -12 of ME06120 | 27 | 2 | 14.43 | 1.45E−04 |
| $T_2$ non-transgenic segregants of event -12 of ME06120 | 0 | 2 | | |
| $T_3$ seedlings from event -12-99 of ME ME06120 | 46 | 0 | 39.93 | 2.63E−10 |
| $T_3$ non-transgenic segregants of event -12-99 of ME ME06120 | 1 | 4 | | |

TABLE 3

Hypocotyl length in seedlings from ME09503

| Plants | Short Hypo-cotyl | Long Hypo-cotyl | Chi-Square | p-value |
|---|---|---|---|---|
| $T_2$ seedlings from event -03 of ME09503 | 34 | 4 | 35.47 | 2.59E−09 |
| $T_2$ non-transgenic segregants of event -03 of ME09503 | 1 | 16 | | |
| $T_3$ seedlings from event -03-99 of ME09503 | 55 | 0 | 68.85 | 1.06E−16 |
| $T_3$ non-transgenic segregants of event -03-99 of ME09503 | 1 | 18 | | |
| $T_2$ seedlings from event -07 of ME09503 | 46 | 1 | 44.94 | 2.03E−11 |
| $T_2$ non-transgenic segregants of event -07 of ME09503 | 2 | 12 | | |
| $T_3$ seedlings from event -07-99 of ME09503 | 72 | 1 | 56.91 | 4.56E−14 |
| $T_3$ non-transgenic segregants of event -07-99 of ME09503 | 1 | 6 | | |

TABLE 4

Hypocotyl length in seedlings from ME10007

| Plants | Short Hypo-cotyl | Long Hypo-cotyl | Chi-Square | p-value |
|---|---|---|---|---|
| $T_2$ seedlings from event -02 of ME10007 | 57 | 3 | 42.15 | 8.45E−11 |
| $T_2$ non-transgenic segregants of event -02 of ME10007 | 5 | 15 | | |
| $T_3$ seedlings from event -02-99 of ME10007 | 50 | 8 | 40.30 | 2.18E−10 |
| $T_3$ non-transgenic segregants of event -02-99 of ME10007 | 2 | 19 | | |
| $T_2$ seedlings from event -05 of ME10007 | 58 | 0 | 37.14 | 1.10E−09 |
| $T_2$ non-transgenic segregants of event -05 of ME10007 | 9 | 11 | | |
| $T_3$ seedlings from event -05-99 of ME10007 | 49 | 6 | 39.36 | 3.53E−10 |
| $T_3$ non-transgenic segregants of event -05-99 of ME10007 | 3 | 18 | | |

TABLE 5

Hypocotyl length in seedlings from ME10852

| Plants | Short Hypo-cotyl | Long Hypo-cotyl | Chi-Square | p-value |
|---|---|---|---|---|
| $T_2$ seedlings from event -03 of ME10852 | 57 | 1 | 48.97 | 2.59E−12 |
| $T_2$ non-transgenic segregants of event -03 of ME10852 | 5 | 15 | | |
| $T_3$ seedlings from event -03-99 of ME10852 | 55 | 0 | 35.66 | 2.59E−09 |
| $T_3$ non-transgenic segregants of event -03-99 of ME10852 | 11 | 13 | | |
| $T_2$ seedlings from event -04 of ME10852 | 57 | 0 | 71.00 | 3.57E−17 |
| $T_2$ non-transgenic segregants of event -04 of ME10852 | 0 | 14 | | |
| $T_3$ seedlings from event -04-99 of ME10852 | 63 | 3 | 57.75 | 2.97E−14 |
| $T_3$ non-transgenic segregants of event -04-99 of ME10852 | 0 | 11 | | |

TABLE 6

Hypocotyl length in seedlings from ME11939

| Plants | Short Hypo-cotyl | Long Hypo-cotyl | Chi-Square | p-value |
|---|---|---|---|---|
| $T_2$ seedlings from event -01 of ME13 | 32 | 6 | 29.39 | 5.93E−08 |
| $T_2$ non-transgenic segregants of event -01 of ME11939 | 0 | 13 | | |
| $T_3$ seedlings from event -01-99 of ME11939 | 47 | 0 | 52.88 | 3.55E−13 |
| $T_3$ non-transgenic segregants of event -01-99 of ME11939 | 2 | 14 | | |
| $T_2$ seedlings from event -02 of ME11939 | 42 | 5 | 23.34 | 1.35E−06 |
| $T_2$ non-transgenic segregants of event -02 of ME11939 | 4 | 11 | | |
| $T_3$ seedlings from event -02-99 of ME11939 | 46 | 2 | 44.94 | 2.03E−11 |
| $T_3$ non-transgenic segregants of event -02-99 of ME11939 | 1 | 12 | | |
| $T_2$ seedlings from event -05 of ME11939 | 45 | 8 | 27.72 | 1.40E−07 |
| $T_2$ non-transgenic segregants of event -05 of ME11939 | 4 | 16 | | |

TABLE 6-continued

Hypocotyl length in seedlings from ME11939

| Plants | Short Hypocotyl | Long Hypocotyl | Chi-Square | p-value |
|---|---|---|---|---|
| $T_3$ seedlings from event -05-99 of ME11939 | 33 | 0 | 27.59 | 1.50E−07 |
| $T_3$ non-transgenic segregants of event -05-99 of ME11939 | 3 | 7 | | |

TABLE 7

Hypocotyl length in seedlings from ME13456

| Plants | Short Hypocotyl | Long Hypocotyl | Chi-Square | p-value |
|---|---|---|---|---|
| $T_2$ seedlings from event -02 of ME13456 | 18 | 1 | 12.28 | 4.58E−04 |
| $T_2$ non-transgenic segregants of event -02 of ME13456 | 3 | 6 | | |
| $T_3$ seedlings from event -02-99 of ME13456 | 47 | 3 | 34.55 | 4.16E−09 |
| $T_3$ non-transgenic segregants of event -02-99 of ME13456 | 1 | 8 | | |
| $T_2$ seedlings from event -05 of ME13456 | 14 | 2 | 13.13 | 2.91E−04 |
| $T_2$ non-transgenic segregants of event -05 of ME13456 | 0 | 5 | | |
| $T_3$ seedlings from event -05-99 of ME13456 | 21 | 3 | 23.42 | 1.30E−06 |
| $T_3$ non-transgenic segregants of event -05-99 of ME13456 | 1 | 13 | | |

TABLE 8

Hypocotyl length in seedlings from ME15935

| Plants | Short Hypocotyl | Long Hypocotyl | Chi-Square | p-value |
|---|---|---|---|---|
| $T_2$ seedlings from event -03 of ME15935 | 44 | 2 | 33.90 | 5.81E−09 |
| $T_2$ non-transgenic segregants of event -03 of ME15935 | 2 | 12 | | |
| $T_3$ seedlings from event -03-99 of ME15935 | 53 | 3 | 51.86 | 5.97E−13 |
| $T_3$ non-transgenic segregants of event -03-99 of ME15935 | 1 | 15 | | |
| $T_2$ seedlings from event -04 of ME15935 | 23 | 0 | 33.00 | 9.22E−09 |
| $T_2$ non-transgenic segregants of event -04 of ME15935 | 0 | 10 | | |
| $T_3$ seedlings from event -04-99 of ME15935 | 58 | 0 | 41.24 | 1.34E−10 |
| $T_3$ non-transgenic segregants of event -04-99 of ME15935 | 2 | 4 | | |

TABLE 9

Hypocotyl length in seedlings from ME16594

| Plants | Short Hypocotyl | Long Hypocotyl | Chi-Square | p-value |
|---|---|---|---|---|
| $T_2$ seedlings from event -02 of ME16594 | 16 | 0 | 37.14 | 1.10E−09 |
| $T_2$ non-transgenic segregants of event -02 of ME16594 | 12 | 52 | | |

TABLE 9-continued

Hypocotyl length in seedlings from ME16594

| Plants | Short Hypocotyl | Long Hypocotyl | Chi-Square | p-value |
|---|---|---|---|---|
| $T_3$ seedlings from event -02-99 of ME16594 | 46 | 10 | 10.18 | 1.42E−03 |
| $T_3$ non-transgenic segregants of event -02-99 of ME16594 | 4 | 7 | | |
| $T_2$ seedlings from event -05 of ME16594 | 35 | 2 | 52.10 | 5.28E−13 |
| $T_2$ non-transgenic segregants of event -05 of ME16594 | 4 | 33 | | |
| $T_3$ seedlings from event -05-99 of ME16594 | 41 | 11 | 5.14 | 2.34E−02 |
| $T_3$ non-transgenic segregants of event -05-99 of ME16594 | 5 | 6 | | |

TABLE 10

Hypocotyl length in seedlings from ME16597

| Plants | Short Hypocotyl | Long Hypocotyl | Chi-Square | p-value |
|---|---|---|---|---|
| $T_2$ seedlings from event -01 of ME16597 | 18 | 6 | 16.99 | 3.77E−05 |
| $T_2$ non-transgenic segregants of event -01 of ME16597 | 0 | 11 | | |
| $T_3$ seedlings from event -01-99 of ME16597 | 69 | 3 | 55.76 | 8.20E−04 |
| $T_3$ non-transgenic segregants of event -01-99 of ME16597 | 0 | 8 | | |
| $T_2$ seedlings from event -04 of ME16597 | 25 | 3 | 21.88 | 2.91E−06 |
| $T_2$ non-transgenic segregants of event -04 of ME16597 | 0 | 7 | | |
| $T_3$ seedlings from event -04-99 of ME16597 | 54 | 5 | 32.49 | 1.20E−08 |
| $T_3$ non-transgenic segregants of event -04-99 of ME16597 | 3 | 11 | | |
| $T_2$ seedlings from event -04 of ME16597 | 44 | 5 | 34.14 | 5.12E−09 |
| $T_2$ non-transgenic segregants of event -04 of ME16597 | 4 | 17 | | |
| $T_3$ seedlings from event -04-99 of ME16597 | 49 | 4 | 43.99 | 3.30E−11 |
| $T_3$ non-transgenic segregants of event -04-99 of ME16597 | 3 | 18 | | |

TABLE 11

Hypocotyl length in seedlings from ME16630

| Plants | Short Hypocotyl | Long Hypocotyl | Chi-Square | p-value |
|---|---|---|---|---|
| $T_2$ seedlings from event -01 of ME16630 | 49 | 7 | 49.26 | 2.24E−12 |
| $T_2$ non-transgenic segregants of event -01 of ME16630 | 0 | 20 | | |
| $T_3$ seedlings from event -01-99 of ME16630 | 59 | 1 | 55.63 | 8.75E−14 |
| $T_3$ non-transgenic segregants of event -01-99 of ME16630 | 0 | 6 | | |
| $T_2$ seedlings from event -02 of ME16630 | 32 | 9 | 25.13 | 5.36E−07 |
| $T_2$ non-transgenic segregants of event -02 of ME16630 | 4 | 22 | | |
| $T_3$ seedlings from event -02-99 of ME16630 | 43 | 6 | 33.59 | 6.79E−09 |

TABLE 11-continued

Hypocotyl length in seedlings from ME16630

| Plants | Short Hypo-cotyl | Long Hypo-cotyl | Chi-Square | p-value |
|---|---|---|---|---|
| T$_3$ non-transgenic segregants of event -02-99 of ME16630 | 2 | 15 | | |
| T$_2$ seedlings from event -04 of ME16630 | 60 | 9 | 19.53 | 9.89E−06 |
| T$_2$ non-transgenic segregants of event -04 of ME16630 | 0 | 4 | | |
| T$_3$ seedlings from event -04-99 of ME16630 | 65 | 9 | 12.14 | 4.94E−04 |
| T$_3$ non-transgenic segregants of event -04-99 of ME16630 | 0 | 2 | | |

TABLE 12

Hypocotyl length in seedlings from ME17128

| Plants | Short Hypo-cotyl | Long Hypo-cotyl | Chi-Square | p-value |
|---|---|---|---|---|
| T$_2$ seedlings from event -02 of ME17128 | 31 | 0 | 38.00 | 7.07E−10 |
| T$_2$ non-transgenic segregants of event -02 of ME17128 | 0 | 7 | | |
| T$_3$ seedlings from event -02-99 of ME17128 | 68 | 0 | 70.78 | 4.00E−17 |
| T$_3$ non-transgenic segregants of event -02-99 of ME17128 | 1 | 10 | | |
| T$_2$ seedlings from event -03 of ME17128 | 21 | 11 | 11.05 | 8.86E−04 |
| T$_2$ non-transgenic segregants of event -03 of ME17128 | 0 | 8 | | |
| T$_3$ seedlings from event -03-99 of ME17128 | 74 | 0 | 80.00 | 3.74E−19 |
| T$_3$ non-transgenic segregants of event -03-99 of ME17128 | 0 | 6 | | |
| T$_2$ seedlings from event -04 of ME17128 | 28 | 4 | 18.06 | 2.14E−05 |
| T$_2$ non-transgenic segregants of event -04 of ME17128 | 1 | 7 | | |
| T$_3$ seedlings from event -04-99 of ME17128 | 62 | 0 | 39.42 | 3.41E−10 |
| T$_3$ non-transgenic segregants of event -04-99 of ME17128 | 7 | 9 | | |

TABLE 13

Hypocotyl length in seedlings from ME17578

| Plants | Short Hypocotyl | Long Hypocotyl | Chi-Square | p-value |
|---|---|---|---|---|
| T$_2$ seedlings from event-01 of ME17578 | 32 | 1 | 32.42 | 1.24E−08 |
| T$_2$ non-transgenic segregants of event-01 of ME17578 | 0 | 6 | | |
| T$_3$ seedlings from event-01-99 of ME17578 | 63 | 0 | 69.06 | 9.56E−17 |
| T$_3$ non-transgenic segregants of event-01-99 of ME17578 | 1 | 12 | | |
| T$_2$ seedlings from event-03 of ME17578 | 20 | 0 | 30.00 | 4.32E−08 |
| T$_2$ non-transgenic segregants of event-03 of ME17578 | 0 | 10 | | |
| T$_3$ seedlings from event-03-99 of ME17578 | 29 | 4 | 19.26 | 1.14E−05 |
| T$_3$ non-transgenic segregants of event-03-99 of ME17578 | 14 | 24 | | |

TABLE 14

Hypocotyl length in seedlings from ME18158

| Plants | Short Hypocotyl | Long Hypocotyl | Chi-Square | p-value |
|---|---|---|---|---|
| T$_2$ seedlings from event-01 of ME18158 | 23 | 2 | 22.31 | 2.33E−06 |
| T$_2$ non-transgenic segregants of event-01 of ME18158 | 2 | 11 | | |
| T$_3$ seedlings from event-01-99 of ME18158 | 61 | 0 | 54.93 | 1.25E−13 |
| T$_3$ non-transgenic segregants of event-01-99 of ME18158 | 1 | 5 | | |
| T$_2$ seedlings from event-02 of ME18158 | 25 | 5 | 7.62 | 5.78E−03 |
| T$_2$ non-transgenic segregants of event-02 of ME18158 | 0 | 2 | | |
| T$_3$ seedlings from event-02-99 of ME18158 | 70 | 0 | 7.88 | 5.01E−03 |

TABLE 14-continued

Hypocotyl length in seedlings from ME18158

| Plants | Short Hypocotyl | Long Hypocotyl | Chi-Square | p-value |
|---|---|---|---|---|
| $T_3$ non-transgenic segregants of event-02-99 of ME18158 | 8 | 1 | | |
| $T_2$ seedlings from event-04 of ME18158 | 22 | 3 | 27.17 | 1.86E−07 |
| $T_2$ non-transgenic segregants of event-04 of ME18158 | 0 | 13 | | |
| $T_3$ seedlings from event-04-99 of ME18158 | 22 | 3 | 49.13 | 2.40E−12 |
| $T_3$ non-transgenic segregants of event-04-99 of ME18158 | 0 | 13 | | |

TABLE 15

Hypocotyl length in seedlings from ME18314

| Plants | Short Hypocotyl | Long Hypocotyl | Chi-Square | p-value |
|---|---|---|---|---|
| $T_2$ seedlings from event-01 of ME18314 | 13 | 14 | 5.72 | 1.67E−02 |
| $T_2$ non-transgenic segregants of event-01 of ME18314 | 1 | 11 | | |
| $T_3$ seedlings from event-01-99 of ME18314 | 62 | 0 | 47.75 | 4.85E−12 |
| $T_3$ non-transgenic segregants of event-01-99 of ME18314 | 2 | 5 | | |
| $T_2$ seedlings from event-02 of ME18314 | 16 | 9 | 4.48 | 3.43E−02 |
| $T_2$ non-transgenic segregants of event-02 of ME18314 | 0 | 3 | | |
| $T_3$ seedlings from event-02-99 of ME18314 | 56 | 0 | 46.67 | 8.41E−12 |
| $T_3$ non-transgenic segregants of event-02-99 of ME18314 | 4 | 10 | | |
| $T_2$ seedlings from event-03 of ME18314 | 18 | 6 | 4.78 | 2.88E−02 |
| $T_2$ non-transgenic segregants of event-03 of ME18314 | 6 | 9 | | |
| $T_3$ seedlings from event-03-99 of ME18314 | 37 | 0 | 42.00 | 9.13E−11 |
| $T_3$ non-transgenic segregants of event-03-99 of ME18314 | 0 | 5 | | |
| $T_2$ seedlings from event-04 of ME18314 | 24 | 3 | 20.84 | 4.99E−06 |
| $T_2$ non-transgenic segregants of event-04 of ME18314 | 2 | 11 | | |
| $T_3$ seedlings from event-04-99 of ME18314 | 67 | 0 | 79.00 | 6.21E−19 |
| $T_3$ non-transgenic segregants of event-04-99 of ME18314 | 0 | 12 | | |

TABLE 16

Hypocotyl length in seedlings from ME19304

| Plants | Short Hypocotyl | Long Hypocotyl | Chi-Square | p-value |
|---|---|---|---|---|
| $T_2$ seedlings from event-07 of ME19304 | 28 | 1 | 29.22 | 6.48E−08 |
| $T_2$ non-transgenic segregants of event-07 of ME19304 | 1 | 9 | | |
| $T_3$ seedlings from event-07-99 of ME19304 | 57 | 0 | 40.51 | 1.95E−10 |
| $T_3$ non-transgenic segregants of event-07-99 of ME19304 | 8 | 12 | | |
| $T_2$ seedlings from event-08 of ME19304 | 18 | 11 | 7.67 | 5.62E−03 |
| $T_2$ non-transgenic segregants of event-08 of ME19304 | 0 | 6 | | |

TABLE 16-continued

| | Hypocotyl length in seedlings from ME19304 | | | |
|---|---|---|---|---|
| Plants | Short Hypocotyl | Long Hypocotyl | Chi-Square | p-value |
| $T_3$ seedlings from event-08-99 of ME19304 | 69 | 0 | 63.61 | 1.52E−15 |
| $T_3$ non-transgenic segregants of event-08-99 of ME19304 | 2 | 9 | | |

TABLE 17

| | Hypocotyl length in seedlings from ME19738 | | | |
|---|---|---|---|---|
| Plants | Short Hypocotyl | Long Hypocotyl | Chi-Square | p-value |
| $T_2$ seedlings from event-02 of ME19738 | 32 | 0 | 20.84 | 4.99E−06 |
| $T_2$ non-transgenic segregants of event-02 of ME19738 | 0 | 7 | | |
| $T_3$ seedlings from event-02-99 of ME19738 | 68 | 0 | 80.00 | 3.74E−19 |
| $T_3$ non-transgenic segregants of event-02-99 of ME19738 | 0 | 12 | | |
| $T_2$ seedlings from event-05 of ME19738 | 22 | 6 | 15.76 | 7.20E−05 |
| $T_2$ non-transgenic segregants of event-05 of ME19738 | 1 | 10 | | |
| $T_3$ seedlings from event-05-99 of ME19738 | 65 | 1 | 66.48 | 3.54E−16 |
| $T_3$ non-transgenic segregants of event-05-99 of ME19738 | 0 | 9 | | |

TABLE 18

| | Hypocotyl length in seedlings from ME20871 | | | |
|---|---|---|---|---|
| Plants | Short Hypocotyl | Long Hypocotyl | Chi-Square | p-value |
| $T_2$ seedlings from event-03 of ME20871 | 27 | 8 | 10.03 | 1.54E−03 |
| $T_2$ non-transgenic segregants of event-03 of ME20871 | 0 | 4 | | |
| $T_3$ seedlings from event-03-99 of ME20871 | 51 | 10 | 12.35 | 4.41E−04 |
| $T_3$ non-transgenic segregants of event-03-99 of ME20871 | 0 | 3 | | |
| $T_2$ seedlings from event-05 of ME20871 | 32 | 0 | 40.00 | 2.54E−10 |
| $T_2$ non-transgenic segregants of event-05 of ME20871 | 0 | 8 | | |
| $T_3$ seedlings from event-05-99 of ME20871 | 61 | 0 | 68.52 | 1.26E−16 |
| $T_3$ non-transgenic segregants of event-05-99 of ME20871 | 1 | 13 | | |
| $T_2$ seedlings from event-10 of ME20871 | 26 | 0 | 27.24 | 1.80E−07 |
| $T_2$ non-transgenic segregants of event-10 of ME20871 | 1 | 6 | | |
| $T_3$ seedlings from event-10-99 of ME20871 | 52 | 1 | 48.91 | 2.68E−12 |
| $T_3$ non-transgenic segregants of event-10-99 of ME20871 | 1 | 9 | | |

TABLE 19

Hypocotyl length in seedlings from ME21199

| Plants | Short Hypocotyl | Long Hypocotyl | Chi-Square | p-value |
|---|---|---|---|---|
| $T_2$ seedlings from event-01 of ME21199 | 29 | 0 | 29.83 | 4.72E−08 |
| $T_2$ non-transgenic segregants of event-01 of ME21199 | 1 | 6 | | |
| $T_3$ seedlings from event-01-99 of ME21199 | 62 | 0 | 78.00 | 1.03E−18 |
| $T_3$ non-transgenic segregants of event-01-99 of ME21199 | 0 | 16 | | |
| $T_2$ seedlings from event-03 of ME21199 | 19 | 0 | 9.44 | 2.12E−03 |
| $T_2$ non-transgenic segregants of event-03 of ME21199 | 7 | 5 | | |
| $T_3$ seedlings from event-03-99 of ME21199 | 68 | 0 | 55.03 | 1.19E−13 |
| $T_3$ non-transgenic segregants of event-03-99 of ME21199 | 3 | 8 | | |
| $T_2$ seedlings from event-05 of ME21199 | 26 | 0 | 20.41 | 6.26E−06 |
| $T_2$ non-transgenic segregants of event-05 of ME21199 | 4 | 7 | | |
| $T_3$ seedlings from event-05-99 of ME21199 | 31 | 1 | 17.88 | 2.35E−05 |
| $T_3$ non-transgenic segregants of event-05-99 of ME21199 | 5 | 7 | | |

TABLE 20

Hypocotyl length in seedlings from ME21508

| Plants | Short Hypocotyl | Long Hypocotyl | Chi-Square | p-value |
|---|---|---|---|---|
| $T_2$ seedlings from event-01 of ME21508 | 20 | 5 | 15.76 | 7.19E−05 |
| $T_2$ non-transgenic segregants of event-01 of ME21508 | 2 | 12 | | |
| $T_3$ seedlings from event-01-99 of ME21508 | 74 | 0 | 80.00 | 3.74E−19 |
| $T_3$ non-transgenic segregants of event-01-99 of ME21508 | 0 | 6 | | |
| $T_2$ seedlings from event-05 of ME21508 | 23 | 8 | 15.71 | 7.85E−05 |
| $T_2$ non-transgenic segregants of event-05 of ME21508 | 0 | 9 | | |
| $T_3$ seedlings from event-05-99 of ME21508 | 65 | 0 | 78.00 | 1.03E−18 |
| $T_3$ non-transgenic segregants of event-05-99 of ME21508 | 0 | 13 | | |

There were no observable or statistically significant differences between $T_2$ ME05268, ME06120, ME09503, ME10007, ME10852, ME11939, ME13456, ME15935, ME16594, ME16597, ME16630, ME17128, ME17578, ME18158, ME18314, ME19304, ME19738, ME20871, ME21199, and ME21508 plants and control plants in germination, onset of flowering, rosette area, fertility, and general morphology/architecture.

Example 5—Results for ME12006, ME12596, and ME12899 Events $T_2$ and $T_3$ seed from events -03, -02, and -03 of ME12006, $T_2$ and $T_3$ seed from events -08 and -09 of ME12596, and $T_2$ and $T_3$ seed from events -05 and -06 of ME12899 was grown under SD+EODFR conditions and evaluated for hypocotyl length as described in Example 3.

Seedlings from events -03, -02, and -03 of ME12006; events -08 and -09 of ME12595; and events -05 and -06 of ME12899 displayed a short hypocotyl under SD+EODFR conditions in both the $T_2$ and $T_3$ generations, and the transgene was linked to the short hypocotyl phenotype with a confidence level of p<0.05 (Tables 21-23).

TABLE 21

Hypocotyl length in seedlings from ME12006

| Plants | Short Hypocotyl | Long Hypocotyl | Chi-Square | p-value |
|---|---|---|---|---|
| $T_2$ seedlings from event-01 of ME12006 | 22 | 2 | 8.89 | 2.87E−03 |
| $T_2$ non-transgenic segregants of event-01 of ME12006 | 8 | 8 | | |
| $T_3$ seedlings from event-01-03 of ME12006 | 27 | 3 | 7.50 | 6.17E−03 |
| $T_3$ non-transgenic segregants of event-01-03 of ME12006 | 5 | 5 | | |
| $T_2$ seedlings from event-02 of ME12006 | 20 | 20 | 12.23 | 4.70E−04 |
| $T_2$ non-transgenic segregants of event-02 of ME12006 | 6 | 10 | | |
| $T_3$ seedlings from event-02-01 of ME12006 | 23 | 4 | 12.61 | 3.84E−04 |
| $T_3$ non-transgenic segregants of event-02-01 of ME12006 | 2 | 7 | | |
| $T_2$ seedlings from event-03 of ME12006 | 24 | 4 | 7.94 | 4.83E−03 |
| $T_2$ non-transgenic segregants of event-03 of ME12006 | 4 | 6 | | |
| $T_3$ seedlings from event-03-04 of ME12006 | 19 | 2 | 8.82 | 2.99E−03 |
| $T_3$ non-transgenic segregants of event-03-04 of ME12006 | 2 | 4 | | |

TABLE 22

Hypocotyl length in seedlings from ME12596

| Plants | Short Hypocotyl | Long Hypocotyl | Chi-Square | p-value |
|---|---|---|---|---|
| $T_2$ seedlings from event-08 of ME12596 | 22 | 4 | 18.75 | 1.487E−05 |
| $T_2$ non-transgenic segregants of event-08 of ME12596 | 2 | 12 | | |
| $T_3$ seedlings from event-08-01 of ME12596 | 18 | 4 | 10.21 | 1.40E−04 |
| $T_3$ non-transgenic segregants of event-08-01 of ME12596 | 4 | 10 | | |
| $T_2$ seedlings from event-09 of ME12596 | 21 | 5 | 8.12 | 4.39E−03 |
| $T_2$ non-transgenic segregants of event-09 of ME12596 | 5 | 9 | | |
| $T_3$ seedlings from event-09-01 of ME12596 | 20 | 4 | 5.08 | 2.42E−02 |
| $T_3$ non-transgenic segregants of event-09-01 of ME12596 | 8 | 8 | | |

TABLE 23

Hypocotyl length in seedlings from ME12899

| Plants | Short Hypocotyl | Long Hypocotyl | Chi-Square | p-value |
|---|---|---|---|---|
| $T_2$ seedlings from event-05 of ME12899 | 24 | 4 | 10.98 | 9.23E−04 |
| $T_2$ non-transgenic segregants of event-05 of ME12899 | 4 | 8 | | |
| $T_3$ seedlings from event-05-99 of ME12899 | 27 | 3 | 7.5 | 6.17E−03 |
| $T_3$ non-transgenic segregants of event-05-99 of ME12899 | 5 | 5 | | |
| $T_2$ seedlings from event-06 of ME12899 | 26 | 2 | 23.22 | 1.445E−06 |
| $T_2$ non-transgenic segregants of event-06 of ME12899 | 2 | 10 | | |

TABLE 23-continued

Hypocotyl length in seedlings from ME12899

| Plants | Short Hypocotyl | Long Hypocotyl | Chi-Square | p-value |
|---|---|---|---|---|
| $T_3$ seedlings from event-06-99 of ME12899 | 21 | 3 | 6.77 | 9.264E−03 |
| $T_3$ non-transgenic segregants of event-06-99 of ME12899 | 8 | 8 | | |

There were no observable or statistically significant differences between $T_2$ ME12006, ME12596, and ME12899 plants and control plants in germination, onset of flowering, rosette area, fertility, and general morphology/architecture.

Example 6—Results for ME18408 and ME19971 Events $T_2$ and $T_3$ seed from events -01, -02, and -03 of ME18408, and $T_2$ and $T_3$ seed from events -01, -02, -03, and -05 of ME19971 was grown under low light conditions and SD+EODFR conditions as described in Examples 2 and 3, respectively, and evaluated for hypocotyl length.

Seedlings from events -01, -02, and -03 of ME18408, and events -01, -02, -03, and -05 of ME19971 displayed a short hypocotyl under SD+EODFR conditions in both the $T_2$ and $T_3$ generations, and the transgene was linked to the short hypocotyl phenotype with a confidence level of $p<0.05$ (Tables 24 and 26). Seedlings from events -01, and -02 of ME18408, and events -01, -02, -03, and -05 of ME19971 displayed a short hypocotyl under SD+EODFR conditions in both the $T_2$ and $T_3$ generations, and the transgene was linked to the short hypocotyl phenotype with a confidence level of $p<0.05$ (Tables 25 and 27).

TABLE 24

Hypocotyl length in seedlings from ME18408 grown under low light conditions

| Plants | Short Hypocotyl | Long Hypocotyl | Chi-Square | p-value |
|---|---|---|---|---|
| $T_2$ seedlings from event-01 of ME18408 | 63 | 2 | 44.58 | 2.44E−11 |
| $T_2$ non-transgenic segregants of event-01 of ME18408 | 0 | 4 | | |
| $T_3$ seedlings from event-01-99 of ME18408 | 40 | 6 | 35.90 | 2.08E−09 |
| $T_3$ non-transgenic segregants of event-01-99 of ME18408 | 1 | 16 | | |
| $T_2$ seedlings from event-02 of ME18408 | 38 | 7 | 28.67 | 8.58E−08 |
| $T_2$ non-transgenic segregants of event-02 of ME18408 | 3 | 17 | | |
| $T_3$ seedlings from event-02-99 of ME18408 | 39 | 17 | 10.98 | 9.20E−04 |
| $T_3$ non-transgenic segregants of event-02-99 of ME18408 | 5 | 14 | | |
| $T_2$ seedlings from event-03 of ME18408 | 30 | 1 | 25.76 | 3.86E−07 |
| $T_2$ non-transgenic segregants of event-03 of ME18408 | 7 | 15 | | |
| $T_3$ seedlings from event-03-99 of ME18408 | 23 | 5 | 21.74 | 3.12E−06 |
| $T_3$ non-transgenic segregants of event-03-99 of ME18408 | 11 | 32 | | |

TABLE 25

Hypocotyl length in seedlings from ME18408 grown under SD + EODFR conditions

| Plants | Short Hypocotyl | Long Hypocotyl | Chi-Square | p-value |
|---|---|---|---|---|
| $T_2$ seedlings from event-01 of ME18408 | 22 | 5 | 6.18 | 1.29E−02 |
| $T_2$ non-transgenic segregants of event-01 of ME18408 | 5 | 7 | | |
| $T_3$ seedlings from event-01-99 of ME18408 | 19 | 8 | 10.71 | 1.06E−03 |
| $T_3$ non-transgenic segregants of event-01-99 of ME18408 | 1 | 9 | | |

TABLE 25-continued

Hypocotyl length in seedlings from ME18408 grown under SD + EODFR conditions

| Plants | Short Hypocotyl | Long Hypocotyl | Chi-Square | p-value |
|---|---|---|---|---|
| $T_2$ seedlings from event-02 of ME18408 | 25 | 5 | 4.44 | 3.50E−02 |
| $T_2$ non-transgenic segregants of event-02 of ME18408 | 5 | 5 | | |
| $T_3$ seedlings from event-02-99 of ME18408 | 22 | 3 | 6.8 | 9.13E−03 |
| $T_3$ non-transgenic segregants of event-02-99 of ME18408 | 7 | 7 | | |

TABLE 26

Hypocotyl length in seedlings from ME19971 grown under low light conditions

| Plants | Short Hypocotyl | Long Hypocotyl | Chi-Square | p-value |
|---|---|---|---|---|
| $T_2$ seedlings from event-01 of ME19971 | 8 | 0 | 18.00 | 2.21E−05 |
| $T_2$ non-transgenic segregants of event-01 of ME19971 | 0 | 10 | | |
| $T_3$ seedlings from event-01-99 of ME19971 | 37 | 0 | 61.00 | 5.71E−15 |
| $T_3$ non-transgenic segregants of event-01-99 of ME19971 | 0 | 24 | | |
| $T_2$ seedlings from event-02 of ME19971 | 16 | 2 | 19.64 | 9.37E−06 |
| $T_2$ non-transgenic segregants of event-02 of ME19971 | 0 | 9 | | |
| $T_3$ seedlings from event-02-99 of ME19971 | 36 | 0 | 29.19 | 6.56E−08 |
| $T_3$ non-transgenic segregants of event-02-99 of ME19971 | 1 | 3 | | |
| $T_2$ seedlings from event-03 of ME19971 | 14 | 1 | 19.08 | 1.25E−05 |
| $T_2$ non-transgenic segregants of event-03 of ME19971 | 0 | 8 | | |
| $T_3$ seedlings from event-03-99 of ME19971 | 34 | 0 | 46.00 | 1.18E−11 |
| $T_3$ non-transgenic segregants of event-03-99 of ME19971 | 0 | 12 | | |
| $T_2$ seedlings from event-05 of ME19971 | 26 | 0 | 29.00 | 7.24E−08 |
| $T_2$ non-transgenic segregants of event-05 of ME19971 | 0 | 3 | | |
| $T_3$ seedlings from event-05-99 of ME19971 | 42 | 0 | 47.94 | 4.39E−12 |
| $T_3$ non-transgenic segregants of event-05-99 of ME19971 | 3 | 16 | | |

TABLE 27

Hypocotyl length in seedlings from ME19971 grown under SD + EODFR conditions

| Plants | Short Hypocotyl | Long Hypocotyl | Chi-Square | p-value |
|---|---|---|---|---|
| $T_2$ seedlings from event-01 of ME19971 | 30 | 2 | 30.00 | 4.32E−08 |
| $T_2$ non-transgenic segregants of event-01 of ME19971 | 0 | 8 | | |
| $T_3$ seedlings from event-01-04 of ME19971 | 22 | 0 | 32.00 | 1.542E−08 |
| $T_3$ non-transgenic segregants of event-01-04 of ME19971 | 0 | 10 | | |
| $T_2$ seedlings from event-02 of ME19971 | 24 | 4 | 17.60 | 2.721E−05 |
| $T_2$ non-transgenic segregants of event-02 of ME19971 | 2 | 10 | | |

TABLE 27-continued

Hypocotyl length in seedlings from ME19971 grown under SD + EODFR conditions

| Plants | Short Hypocotyl | Long Hypocotyl | Chi-Square | p-value |
|---|---|---|---|---|
| T$_3$ seedlings from event-02-04 of ME19971 | 22 | 6 | 16.16 | 5.811E−05 |
| T$_3$ non-transgenic segregants of event-02-04 of ME19971 | 0 | 8 | | |
| T$_2$ seedlings from event-03 of ME19971 | 28 | 0 | 40.00 | 2.54E−10 |
| T$_2$ non-transgenic segregants of event-03 of ME19971 | 0 | 12 | | |
| T$_3$ seedlings from event-03-06 of ME19971 | 24 | 0 | 17.49 | 2.895E−05 |
| T$_3$ non-transgenic segregants of event-03-06 of ME19971 | 4 | 6 | | |
| T$_2$ seedlings from event-05 of ME19971 | 24 | 2 | 24.35 | 8.034E−07 |
| T$_2$ non-transgenic segregants of event-05 of ME19971 | 2 | 12 | | |
| T$_3$ seedlings from event-05-02 of ME19971 | 25 | 4 | 6.13 | 1.33E−02 |
| T$_3$ non-transgenic segregants of event-05-02 of ME19971 | 3 | 4 | | |

There were no observable or statistically significant differences between T$_2$ ME18408 and ME19971 plants and control plants in germination, onset of flowering, rosette area, fertility, and general morphology/architecture.

Example 7—Determination of Functional Homologs by Reciprocal BLAST

A candidate sequence was considered a functional homolog of a reference sequence if the candidate and reference sequences encoded proteins having a similar function and/or activity. A process known as Reciprocal BLAST (Rivera et al., *Proc. Natl. Acad. Sci. USA*, 95:6239-6244 (1998)) was used to identify potential functional homolog sequences from databases consisting of all available public and proprietary peptide sequences, including NR from NCBI and peptide translations from Ceres clones.

Before starting a Reciprocal BLAST process, a specific reference polypeptide was searched against all peptides from its source species using BLAST in order to identify polypeptides having BLAST sequence identity of 80% or greater to the reference polypeptide and an alignment length of 85% or greater along the shorter sequence in the alignment. The reference polypeptide and any of the aforementioned identified polypeptides were designated as a cluster.

The BLASTP version 2.0 program from Washington University at Saint Louis, Mo., USA was used to determine BLAST sequence identity and E-value. The BLASTP version 2.0 program includes the following parameters: 1) an E-value cutoff of 1.0e-5; 2) a word size of 5; and 3) the -postsw option. The BLAST sequence identity was calculated based on the alignment of the first BLAST HSP (High-scoring Segment Pairs) of the identified potential functional homolog sequence with a specific reference polypeptide. The number of identically matched residues in the BLAST HSP alignment was divided by the HSP length, and then multiplied by 100 to get the BLAST sequence identity. The HSP length typically included gaps in the alignment, but in some cases gaps were excluded.

The main Reciprocal BLAST process consists of two rounds of BLAST searches; forward search and reverse search. In the forward search step, a reference polypeptide sequence, "polypeptide A," from source species SA was BLASTed against all protein sequences from a species of interest. Top hits were determined using an E-value cutoff of $10^{-5}$ and a sequence identity cutoff of 35%. Among the top hits, the sequence having the lowest E-value was designated as the best hit, and considered a potential functional homolog or ortholog. Any other top hit that had a sequence identity of 80% or greater to the best hit or to the original reference polypeptide was considered a potential functional homolog or ortholog as well. This process was repeated for all species of interest.

In the reverse search round, the top hits identified in the forward search from all species were BLASTed against all protein sequences from the source species SA. A top hit from the forward search that returned a polypeptide from the aforementioned cluster as its best hit was also considered as a potential functional homolog.

Functional homologs were identified by manual inspection of potential functional homolog sequences. Representative functional homologs for SEQ ID NO:3, SEQ ID NO:70, SEQ ID NO:129, SEQ ID NO:317, SEQ ID NO:337, SEQ ID NO:456, SEQ ID NO:538, SEQ ID NO:570, SEQ ID NO:606, SEQ ID NO:634, SEQ ID NO:644, SEQ ID NO:850, SEQ ID NO:907, SEQ ID NO:953, SEQ ID NO:1024, SEQ ID NO:1047, SEQ ID NO:1151, SEQ ID NO:1277, SEQ ID NO:1347, SEQ ID NO:1457, SEQ ID NO:1497, SEQ ID NO:1540, SEQ ID NO:1587, SEQ ID NO:1630, and SEQ ID NO:1635 are shown in FIGS. 1-24, respectively.

Example 8—Determination of Functional Homologs by Hidden Markov Models

Hidden Markov Models (HMMs) were generated by the program HMMER 2.3.2. To generate each HMM, the default HMMER 2.3.2 program parameters, configured for glocal alignments, were used.

An HMM was generated using the sequences shown in FIG. 1 as input. These sequences were fitted to the model and a representative HMM bit score for each sequence is shown in the Sequence Listing. Additional sequences were fitted to the model, and representative HMM bit scores for any such additional sequences are shown in the Sequence Listing. The results indicate that these additional sequences are functional homologs of SEQ ID NO:3.

The procedure above was repeated and an HMM was generated for each group of sequences shown in FIGS. 2-24, using the sequences shown in each Figure as input for that HMM. A representative bit score for each sequence is shown in the Sequence Listing. Additional sequences were fitted to certain HMMs, and representative HMM bit scores for such additional sequences are shown in the Sequence Listing. The results indicate that these additional sequences are functional homologs of the sequences used to generate that HMM.

Example 9—Identification of Transgenic Plants Exhibiting a Red Light-Specific Short Hypocotyl Phenotype Wild type and transgenic seeds were surface-sterilized, plated on solid 0.5×MS medium containing 5 g/L sucrose, 0.5 g/L MES, 7 g/L Agar (adjusted to pH 5.7), and stratified at 4° C. in the dark for three to four days. After stratification, plates were acclimated to room temperature, wrapped in micropore tape, and exposed to continuous white light having a fluence rate of ~60 µmol/m$^2$/s PAR, and a red:far-red ratio (R:FR) of ~5.3. After 24 hours, plates from wild type controls and transgenic lines were moved to one of three light conditions: (1) white light conditions at a lower fluence rate (~15 µmol/m$^2$/s PAR, R:FR=~5.0), (2) red-light conditions (SNAP-LITE™ Red/Far-Red light box (Quantum Devices), at ~15 µmol/m$^2$/s PAR, R:FR=~80), or (3) far-red conditions (SNAP-LITE™ Red/Far-red light box, at ~15 µmol/m$^2$/s PAR, R:FR=~0.10). Seedlings were maintained under continuous light conditions for five days. The hypocotyls of individual seedlings were determined to be "tall" or "short" based on qualitative observation.

A hypocotyl having a length similar to the hypocotyl length typically exhibited by wild-type *Arabidopsis* seedlings grown under the same light conditions was considered a tall hypocotyl. A hypocotyl having reduced length relative to the hypocotyl length typically exhibited by wild-type *Arabidopsis* seedlings grown under the same light conditions was considered a short hypocotyl. Transgenic seedlings from ten Ceres SEEDLINE ID nos. failed to germinate, or germinated poorly, under continuous red light (ME10007, ME10852, ME11961, ME15935, ME17128, ME18158, ME18314, ME19304, ME20871, and ME21508).

Transgenic seedlings from eight Ceres SEEDLINE ID nos. (ME11939, ME16630, ME19971, ME05268, ME13456, ME13629, ME16597, and ME17578) exhibited short hypocotyls when grown under continuous red light. Transgenic seedlings from three of these (ME11939, ME16630, and ME19971) exhibited tall hypocotyls under continuous far-red light exposure, indicating that the short hypocotyl phenotype was red-light specific in these three seed lines. In contrast, the other five seedlings (ME05268, ME13456, ME13629, ME16597, and ME17578) exhibited a short-hypocotyl phenotype when grown under far-red light, indicating that the short-hypocotyl phenotype exhibited by ME05268, ME13456, ME13629, ME16597, and ME17578 was not red-light specific (See, e.g., Parks and Spaulding, *Proc. Natl. Acad. Sci.*, 96: 14142-14146 (1999) describing different molecular mechanisms for suppression of hypocotyl elongation under continuous red and far-red light conditions).

A similar red light-dependent short hypocotyl phenotype has been observed in transgenic plants overexpressing the photochemically and biologically functional photoreceptor, Phytochrome B (Phy B) (Wagner et al., Plant Cell, 3: 1275-1288 (1991)). Phy B null mutants exhibit a long hypocotyl seedling phenotype and increased plant height (Kebrom and Brutnell, *J Exp. Bot.*, 58: 3079-3089 (2007)). These observations suggest that transgene modulation of light response pathways can produce plants exhibiting either increased grain yield, or increased biomass. See Pennell et al., U.S. Pat. App. Ser. No. 61/097,789, "Transgenic Plants Having Increased Biomass," filed Sep. 17, 2008, incorporated by reference herein. Thus, transgenic plants comprising nucleic acid sequences that down-regulate expression of a At5g14370 polypeptide (SEQ ID NO: 456) (FIG. 6), a At1g13360 polypeptide (SEQ ID NO: 953) (FIG. 11), a At2g35940 polypeptide (SEQ ID NO: 1540) (FIG. 21), and sequences identified as functional homologs of these sequences (see FIGS. 6, 11, 21 and sequence listing) are predicted to exhibit a tall hypocotyl phenotype under conditions of normal or low light.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

---

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11174491B2). An electronic copy of the "Sequence Listing" will also be available from the USPTO upon request and payment of the fee set forth in 37 CFR 1.19(b)(3).

What is claimed is:

1. A method of modulating a trait in a plant, said method comprising
introducing into a plant cell an exogenous nucleic acid, said exogenous nucleic acid comprising a regulatory region operably linked to a nucleotide sequence encoding a polypeptide comprising the amino acid sequence of SEQ ID NO:1540;
producing a plant from said plant cell; and
selecting a plant for short hypocotyl under low light or SD+EODFR as compared to a control plant that does not comprise said nucleic acid;
wherein said plant otherwise comprises the morphology of a control plant that does not comprise said nucleic acid.

2. The method of claim 1, wherein said nucleotide sequence comprises the nucleotide sequence of SEQ ID NO:1537, SEQ ID NO:1538, or SEQ ID NO:1539.

3. The method of claim 1, wherein said nucleotide sequence comprises the nucleotide sequence of SEQ ID NO:1537.

4. The method of claim 1, wherein said nucleotide sequence comprises the nucleotide sequence of SEQ ID NO:1538.

5. The method of claim 1, wherein said nucleotide sequence comprises the nucleotide sequence of SEQ ID NO:1539.

* * * * *